(12) United States Patent
Tarleton et al.

(10) Patent No.: US 8,329,411 B2
(45) Date of Patent: Dec. 11, 2012

(54) DIAGNOSTIC ASSAY FOR TRYPANOSOMA CRUZI INFECTION

(75) Inventors: Rick L. Tarleton, Watkinsville, GA (US); Ronald D. Etheridge, Jr., Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 12/670,993

(22) PCT Filed: Jul. 30, 2008

(86) PCT No.: PCT/US2008/009174
§ 371 (c)(1),
(2), (4) Date: Jun. 10, 2010

(87) PCT Pub. No.: WO2009/017736
PCT Pub. Date: Feb. 5, 2009

(65) Prior Publication Data
US 2010/0323909 A1 Dec. 23, 2010

Related U.S. Application Data

(63) Continuation-in-part of application No. 11/587,283, filed as application No. PCT/US2005/013777 on Apr. 22, 2005, now Pat. No. 7,888,135.

(60) Provisional application No. 60/962,498, filed on Jul. 30, 2007, provisional application No. 60/564,804, filed on Apr. 23, 2004, provisional application No. 60/623,299, filed on Oct. 29, 2004.

(51) Int. Cl.
*G01N 33/53* (2006.01)

(52) U.S. Cl. ........................................ 435/7.1

(58) Field of Classification Search .................. None
See application file for complete search history.

(56) References Cited

U.S. PATENT DOCUMENTS

| | | | |
|---|---|---|---|
| 5,232,844 A | 8/1993 | Horowitz et al. | |
| 5,756,662 A * | 5/1998 | Reed | 530/300 |
| 6,368,827 B1 | 4/2002 | Tarleton et al. | |
| 6,403,103 B1 | 6/2002 | Paranhos-Baccala et al. | |
| 6,419,933 B1 | 7/2002 | Reed et al. | |
| 6,875,584 B1 | 4/2005 | Tarleton et al. | |
| 7,888,135 B2 | 2/2011 | Tarleton et al. | |
| 2004/0241729 A1 | 12/2004 | Liew | |
| 2005/0158347 A1 | 7/2005 | Tarleton et al. | |
| 2005/0244505 A1 | 11/2005 | Higbee et al. | |
| 2006/0228300 A1 | 10/2006 | Chang et al. | |
| 2008/0019995 A1 | 1/2008 | Tarleton et al. | |

FOREIGN PATENT DOCUMENTS

WO WO 2005/111622 A2 11/2005

OTHER PUBLICATIONS

Luhrs et al. (Vaccine, 21:3058-3069, 2003).*
Mezzasoma et al. (Clin. Chem., 48:121-130, Jan. 2002).*
He et al. (Clin. Diag. Lab. Immunol., 7:899-903, 2000).*
Atwood et al., "The *Trypanosoma cruzi* proteome," *Science*, 2005, 309(5733):473-476.
Avila et al., "Detection of *Trypanosoma cruzi* in Blood Specimens of Chronic Chagasic Patients by Polymerase Chain Reaction Amplification of Kinetoplast Minicircle DNA: Comparison with Serology and Xenodiagnosis". 1993, *J. Clin Microbiol* 31:2421-2426.
Bahia-Oliveira et al., "Immunological and Clinical Evaluation of Chagasic Patients Subjected to Chemotherapy during the Acute Phase of *Trypanosoma cruzi* Infection 14-30 Years Ago". 2000. *J. Infect Dis.* 182:634-638.
Bio-Plex System and Suspension Array Technology. Bio-Rad Laboratories. Available online [retrieved Apr. 18, 2005]. Retrieved from the Internet: <http://www.biorad.com/B2B/BioRad/product/br_category.jsp?BV_SessionID=@@@@0429302147.
1179497201@@@@&BV_
EngineID=ccchaddkmhhmfjkcfngcfkmdhldcdflm.0
&categoryPath=%2fCatalogs%2fLife+Science+Resear
ch%2fMultiplex+Suspension+Array+System%2fBio-
Plex+System+and+Suspension+Array+Technology&catLevel=4
&divName=Corporate&loggedIn=false&lang=English
&country=HQ&catOID=-24083&isPA=false
&serviceLevel=Lit+Request>; 5 pgs.
Bio-Plex Workstation and Software. Bio-Rad Laboratories. Available online [retrieved Apr. 18, 2005]. Retrieved from the Internet: <http://www.biorad.corn/B2B/BioRad/product/br_category.jsp?BV_SessionID=@@@@0429302147.1179497201@@@@&BV_
EngineID=ccchaddkmhhmfjkcfngefkmdhkkdflm.0&
divName=Life+Science+Research&categoryPath=%
2fCatalogs%2fLife+Science+Research%2fMultiplex+Suspension+
Array+System%2fBio-Plex+Workstation+and+Software
&loggedIn=false&lang=English&catLevel=4&country=HQ
&catOID=-24084&isPA=false&serviceLevel=Lit+Request>; 3 pgs.
Caballero et al., "Evaluation of Serological Tests to Identify *Trypanosoma cruzi* Infection in Humans and Determine Cross-Reactivity with *Trypanosoma rangeli* and *Leishmania* spp". 2007. *Clin Vaccine Immunol.* 14(8):1045-1049.
Castro et al. "Blood culture and polymerase chain reaction for the diagnosis of the chronic phase of human infection with *Trypanosoma cruzi*". 2002. *Parasitol Res.* 88:894-900.
Chang et al. "Evaluation of a prototype *Trypanosoma cruzi* antibody assay with recombinant antigens on a fully automated chemiluminescence analyzer for blood donor screening". 2006. *Transfusion* 46:1737-1744.
Cooley et al., "High Throughput Selection of Effective Serodiagnostics for *Trypanosoma cruzi* infection," 2008. *PLOS.* vol. 2, Issue 10, e316. pp. 1-12.
da Silveira et al., "Chagas disease: recombinant *Trypanosoma cruzi* antigens for serological diagnosis," 2001, *Trends Parasitol.*, 17(6):286-291.
Davies et al. "Proteome-wide analysis of the serological response to vaccinia and smallpox". 2007. *Proteomics* 7:1678-1686.
Dias et al., "The Evolution of Chagas Disease (American Trypanosomiasis) Control after 90 Years since Carlos Chagas Discovery," 1999, *Mem. Inst. Oswaldo Cruz*, 94:Suppl.1:103-121.
Donnelly et al., "DNA Vaccines," *Ann.Rev.Immunol.* 15:617-648, 1997.

(Continued)

*Primary Examiner* — Brian J Gangle
(74) *Attorney, Agent, or Firm* — Mueting Raasch & Gebhardt, P.A.

(57) ABSTRACT

A sensitive, multicomponent diagnostic test for infection with *T. cruzi*, the causative agent of Chagas disease, including methods of making and methods of use. Also provided is a method for screening *T. cruzi* polypeptides to identify antigenic polypeptides for inclusion as components of the diagnostic test, as well as compositions containing antigenic *T. cruzi* polypeptides.

20 Claims, 22 Drawing Sheets

OTHER PUBLICATIONS

Duarte et al. "Assessment of chemiluminescence and PCR effectiveness in relation to conventional serological tests for the diagnosis of Chagas' disease". 2006. *Rev Soc. Bras. Med. Trop.* 39(4):385-387.

El-Sayed et al. "The Genome Sequence of *Trypanosoma cruzi*, Etiologic Agent of Chagas Disease". 2005. *Science.* 309:409-415.

Endresz et al., "Induction of human cytomegalovirus (HCMV)-glycoprotein B (gB)pspecific neutralizing antibody and phosphoprotein 65 (pp65)-specific cytotoxic T lymphocyte responses by naked DNA immunization," 1999, *Vaccine*, 17:50-58.

Etheridge and Tarleton "What is wrong with this test: A high throughput screening of *Trypanosoma cruzi* antigens for seroligical diagnosis." Poster. Woods Hole ImmunoParasitology Conference: Woods Hole, MA. Apr. 25-28, 2004. 1 page; Abstract printed in meeting program.

Fabbro et al. "Trypanocide treatment among adults with chronic Chagas disease living in Santa Fe City (Argentina), over a mean follow-up of 21 years: parasitological, serological and clinical evolution". 2007. *Rev Soc Bras Med Trop.* 40(1):1-10.

Ferreira et al., "Enzyme-Linked Immunosorbent Assay for Serological Diagnosis of Chagas' Disease Employing a *Trypanosoma cruzi* Recombinant Antigen that Consists of Four Different Peptides," 2001, *J Clin.Micro.*, 39(12):4390-4395.

Fifis et al., "Size-Dependent Immunogenicity: Therapeutic and Protective Properties of Nano-Vaccines against Tumors," 2004, *J. Immunol.*, 173:3148-3154.

Fifis et al., "Short peptide sequences containing MHC Class I and/or Class II epitopes linked to nano-beads induce strong immunity and inhibition of growth of antigen-specific tumor challenge in mice," 2004, *Vaccine*, 23:258-266.

Gateway® Cloning. Premier Biosoft International TechNotes. Available online [retrieved Apr. 15, 2005]. Retreived from the Internet: <http://www.premierbiosoft.com/tech_notes/Gateway_Cloning.html>; 6 pgs.

Giovanni, "NIAID Genomics Initiatives," Internet Article 2004. Retrieved from http://www.niaid.nih.gov/dmid/genomes/brc/PDF/gen_init., entire document.

Gutierrez et al. "Comparison of four serological tests for the diagnosis of Chagas disease in a Colombian endemic area". 2004. (4). 129:439-444.

Ho et al. "Synthetic Protein Transduction Domains: Enhanced Transduction Potential in Vitro and in Vivo". 2001. *Cancer Research* 61:474-477.

Hoffman et al., "Toward clinical trials of DNA vaccines against malaria," 1997, *Immunol. Cell Biol.* 75:376-381.

Jones et al., "Synthetic oligodeoxynucleotides containing CpG motifs enhance immunogenicity of a peptide malaria vaccine in Aotus monkeys," 1999, *Vaccine*, 17:3065-3071.

Kartalov et al. "High-throughput multi-antigen microfluidic fluorescence immunoassays". 2006. *Biotechniques* 40(1):85-90.

Kirchhoff et al. "Cryptic Epitope Explains the Failure of a Monoclonal Antibody to Bind to Certain Isolates of *Trypanosoma Cruzi*". 1984. J. Immunol. 133(5):2731-2735.

Krautz et al., "Human Antibody Responses to *Trypanosoma Cruzi* 70-kD Heat-Shock Proteins". 1998. *Am J. Trop Med Hyg* 58(2):137-143.

Laucella et al., "Frequency of Interferon-γ-Producing T Cells Specific for *Trypanosoma cruzi* I nversely correlates with disease severity in chronic human Chagas Disease," 2004, *J. Infect. Dis.* Mar. 1;189(5):909-918.

LeBorgne et al., "In Vivo Induction of Specific Cytotoxic T Lumphocytes in Mice and Rhesus Macaques Immunized with DNA Vector Encoding an HIV Epitope Fused with Hepatitis B Surface Antigen," 1998, *Virology*. 240:304-315.

Luchtan et al., "TcruziDB: an integrated *Trypanosoma cruzi* genome," Nucleic Acids, Res., vol. 32, 2004, pp. D344-D346.

Marcon et al. "Use of a nested polymerase chain reaction (N-PCR) to detect *Trypanosoma cruzi* in blood samples from chronic chagasic patients and patients with doubtful serologies". 2002. *Diagn Microbiol Infect Dis.* 43:39-43.

McCluskie et al., "Route and Method of Delivery of DNA Vaccine Influence Immune Responses in Mice and Non-Human Primates," 1999, *Mol. Med.* 5287-5300.

MMWR Morb Mortal Wkly Report. 2001, Mar 15:51(10):210-2.

"MultiSite Gateway® Three-Fragment Vector Construction Kit." Instruction Manuel. Invitrogen life technologies. Catalog No. 12537-023. Version C; updated Nov. 29, 2004. Available online [retrieved Apr. 15, 2005]. Retrieved from the Internet: <http://www.invitrogen.com/content/sfs/manuals/multisite_gateway_man.pdf>; 68 pgs.

Nagahara et al., "Transduction of full-length TAT fusion proteins into mammalian cells: TAT-p27$^{Kip1}$ induces cell migration". 1998. *Nature Medicine.* 4(12):1449-1452.

Nakazawa et al., "Excretory-Secretory Antigens of *Trypanosoma cruzi* are Potentially Useful for Serodiagnosis of Chronic Chagas' Disease," 2001, *Clin. Diag. Lab. Immunol.*, 8:1024-1027.

Picka et al., "Definition of a Diagnostic Routine in Individuals with Inconclusive Serology for Chagas Disease". 2007. *Braz J. Infect Dis* 11(2):226-233.

Pirard et al., "The validity of serologic tests for *Trypanosoma cruzi* and the effectiveness of transfusional screening strategies in a hyperendemic region". 2005. *Transfusion* 45(4):554-561.

Plebanski et al., "Size-Dependent Immunogenicity: Therapeutic and Protective Properties of Nano-Vaccines against Tumors". 2004. *J. Immunol.* 173(5):3148-3154.

Salomone et al., "Prevalence of Circulating *Trypanosoma cruzi* Detected by Polymerase Chain Reaction in Patients with Chagas' Cardiomyopathy". 2000. *Am J. Cardiol.* 85:1274-1276.

Salomone et al., "*Trypanosoma cruzi* in Persons without Serologic Evidence of Disease, Argentina," 2003, *Emerg. Infect. Dis.* Dec;9(12):1558-1562.

Sanchez Negrette et al. "Serological Evaluation of Specific-Antibody Levels in Patients Treated for Chronic Chagas' Disease". 2008. *Clin Vaccine Immunol.* 15(2):297-302.

Schutze-Redelmeier et al., "Introduction of Exogenous Antigens into the MHC Class 1 Processing and Presentation Pathway by *Drosophila* Antennapedia Homeodomain Primes Cytotoxic T Cells in Vivo," 1996, *J. Immunol.* 157:650-655.

Schwarze et al., "In Vivo Protein Transduction: Delivery of a Biologically Active Protein into the Mouse," 1999, *Science*, 285:1569-1572.

Silveira-Lacerda et al., "Chagas' disease: application of TESA-blot in inconclusive sera from a Brazilian blood bank". 2004. *Vox Sanguinis* 87:204-207.

Soen et al., "Detection and Characterization of Cellular Immune Responses Using Peptide-MHC Microarrays," 2003, *PloS. Biol.*, 1:429-438.

Solari et al. "Treatment of *Trypanosoma cruzi*-infected children with nifurtimox: a 3 year follow-up by PCR". 2001. *J. Antimicrob Chemother* 48:515-519.

Sosa et al., "Efficacy of Chemotherapy with Benznidazole in Children in the Indeterminate Phase of Chagas' Disease". 1998. *Am J. Trop Med Hyg.* 59(4):526-529.

Stone et al., "HLA-restricted epitope identification and detection of functional T cell responses by using MHC-peptide and costimulatory microarrays," 2005, *PNAS USA*, 102:3744-3749.

Sundaresh et al., "Identification of humoral immune responses in protein microarrays using DNA microarray data analysis techniques". 2006. *Bioinformatics* 22(14):1760-1766.

Sundaresh et al. "From protein microarrays to diagnostic antigen discovery: a study of the pathogen *Francisella tularensis*". 2007. *Bioformatics.* 23:i508-i518.

Tacket et al., "Phase 1 safety and immune response studies of a DNA vaccine encoding hepatitis B surface antigen delivered by a gene delivery device," 1999, *Vaccine*, 17:2826-2829.

"TcruziDB: An integrated *Trypanosoma cruzi* Genome Resource." Online Database [retrieved May 17, 2007]. Funded by the American Heart Association. Last updated Nov. 7, 2006. Retrieved from the Internet: <http://www.tcruzidb.org/tcruzidb/>; 2 pgs.

TcruziDB Gene: Tc00.1047053506563.40 (old ID No. 6998. t00004). Encoding eta-tubulin, putative. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053506563.40>; 4 pgs.

TcruziDB Gene: Tc00.1047053411235.9 (old ID No. 11788. t00001). Encoding alpha-tubulin, putative. Available online

[retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053411235.9>; 4 pgs.

TcruziDB Gene: Tc00.1047053508299.60 (old ID No. 5568.t00006). Encoding 60S ribosomal protein L2, putative. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053508299.60>; 4 pgs.

TcruziDB Gene: Tc00.1047053506529.460 (old ID No. 6986.t00046). Encoding hypothetical protein, conserved. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053506529.460>; 4 pgs.

TcruziDB Gene: Tc00.1047053506529.360 (old ID No. 6986.t00036). Encoding Cytochrome C oxidase subunit IV, putative. Available online [retrieved May 18, 2007]. Retrieved from the Internet: <http://wvvw.tcruzidb.org/tcruzidb/showRecord.do?name=GeneRecordClasses.GeneRecordClass&project_id=&primary_key=Tc00.1047053506529.360>; 3 pgs.

TcruziDB Gene: Tc00.1047053506529.610 (old ID No. 6986.t00061). Encoding hypothetical protein. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053506529.610>; 3 pgs.

TcruziDB Gene: Tc00.1047053510887.50 (old ID No. 6003.t00005). Encoding hypothetical protein, conserved. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053510887.50>; 4 pgs.

TcruziDB Gene: Tc00.1047053509775.40 (old ID No. 5781.t00004). Encoding iron superoxide dismutase, putative. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053509775.40>; 3 pgs.

TcruziDB Gene: Tc00.1047053503583.40 (old ID No. 4650.t00004). Encoding trans-splicing factor, putative. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053503583.40>; 3 pgs.

TcruziDB Gene: Tc00.1047053506297.270 (old ID No. 6890.t00027). Encoding 60S ribosomal protein L28, putative. Available online [retrieved May 18, 2007]. Retrieved from the Internet: <http://wwvv.tcruzidb.org/tcruzidb/showRecord.do?name=GeneRecordClasses.GeneRecordClass&project_id=&primary_key=Tc00.1047053506297.270>; 4 pgs.

TcruziDB Gene: Tc00.1047053508441.20 (old ID No. 7730.t00002). Encoding glycosomal phosphoenolpyruvate carboxykinase (Phosphoenolpyruvate Carboxylkinase 9Pepck)), putative. Available online [retrieved May 18, 2007]. Retrieved from the Internet: <http://www.tcruzidb.org/tcruzidb/showRecord.do?name=GeneRecordClasses.GeneRecordClass&projectid=&primary_key=Tc00.1047053508441.20>; 4 pgs.

TcruziDB Gene: Tc00.1047053508355.250 (old ID No. 7695.t00025). Encoding 60S acidic ribosomal subunit protein, putative (Calmodulin-ubiquitin Associated Protein CUB2.8). Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053508355.250>; 4 pgs.

TcruziDB Gene: Tc00.1047053506391.30 (old ID No. 6925.t00003). Encoding ef-hand protein 5, putative. Available online [retrieved May 18, 2007]. Retrieved from the Internet: <http://wwvv.tcruzidb.org/tcruzidb/showRecord.do?name=GeneRecordClasses.GeneRecordClass&project_id=&primary_key=Tc00.1047053506391.30>; 3 pgs.

TcruziDB Gene: Tc00.1047053509617.20 (old ID No. 8152.t00002). Encoding paraflagellar rod protein 3, putative. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053509617.20>; 4 pgs.

TcruziDB Gene: Tc00.1047053510955.40 (old ID No. 8553.t00004). Encoding axoneme central apparatus protein, putative. Available online [retrieved May 18, 2007]. Retrieved from the Internet: <http://www.tcruzidb.org/tcruzidb/showRecord.do?name=GeneRecordClasses.GeneRecordClass&projectid=&primary_key=Tc00.1047053510955.40>; 4 pgs.

TcruziDB Gene: Tc00.1047053509695.220 (old ID No. 8171.t00022). Encoding serine carboxypeptidase (CBP1), putative. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053509695.220>; 4 pgs.

TcruziDB Gene: Tc00.1047053511289.30 (old ID No. 8647.t00003). Encoding aminopeptidase, putative. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053511289.30>; 4 pgs.

TcruziDB Gene: Tc00.1047053510163.20 (old ID No. 8322.t00002). Encoding elongation factor-1 gamma, putative. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053510163.20>; 4 pgs.

TcruziDB Gene: Tc00.1047053506531.20 (old ID No. 6987.t00002). Encoding hypothetical protein, conserved. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053506531.20>; 5 pgs.

TcruziDB Gene: Tc00.1047053506489.30 (old ID No. 6967.t00003). Encoding hypothetical protein, conserved. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053506489.30>; 3 pgs.

Tobler et al. "Evaluation of a new enzyme-linked immunosorbent assay for detection of Chagas antibody in US blood donors". 2007. *Transfusion* 47(1):90-96.

Umezawa et al., Evaluation of Recombinant Antigens for Serodiagnosis of Chagas' Disease in South and Central American, 1999, *J. Clin. Micro.*, 37:1554-1560.

Umezawa et al., "An improved serodiagnostic test for Chagas' disease employing a mixture of *Trypanosoma cruzi* recombinant antigens," 2003, *Transfusion*, 43:91-97.

Viotti et al., "Treatment of chronic Chagas' disease with benznidazole: clinical and serologic evolution of patients with long-term follow-up". 1994. *Am Heart Journal*. 127:151-162.

Viotti et al., "Long-Term Cardiac Outcomes of Treating Chronic Chagas Disease with Benznidazole versus No Treatment". 2006. *Ann Intern Med*. 144(10):724-734.

Wang et al., "Simultaneous Induction of Multiple Antigen-Specific Cytotoxic T Lymphocytes in Nonhuman Primates by Immunization with a Mixture of Four Plasmodium falciparum DNA Plas mids," 1998, *Infect. Immun.* 66:4193-4202.

Wang et al., Induction of Antigen-Specific Cytotoxic T Lymphocytes in Humans by a Malaria DNA Vaccine, 1998, *Science*, 282(5388):476-480.

Waterboer et al., "Suppression of non-specific binding in serological Luminex assays". 2006. *J. Immunol Methods*. 309:200-204.

Wincker et al. "Use of a Simplified Polymerase Chain Reaction Procedure to Detect *Trypanosoma Cruzi* in Blood Samples from Chronic Chagasic Patients in a Rural Endemic Area". 1994. *Am J. Trop Med Hyg* 51(6):771-777.

Wincker et al. "High correlation between Chagas' disease serology and PCR-based detection of *Trypanosoma cruzi* kinetoplast DNA in Bolivian children living in an endemic area". 1994. FEMS Microbiol Lett. 124:419-423.

Zarate-Blades et al., "Diagnostic performance of tests based on *Trypanosoma cruzi* excreted-secreted antigens in an endemic area for Chagas' disease in Bolivia". 2007. *Diagn. Microbiol Infect Dis* 57:229-232.

\* cited by examiner

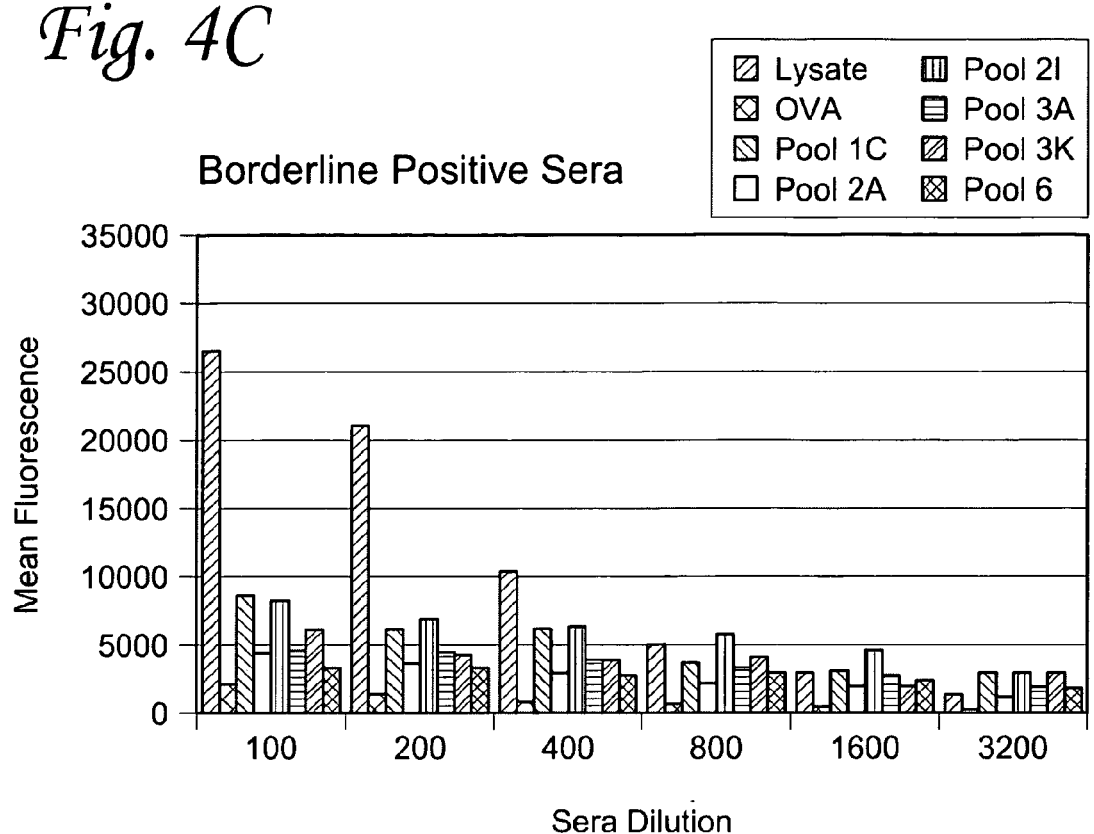
Fig. 4C  Borderline Positive Sera
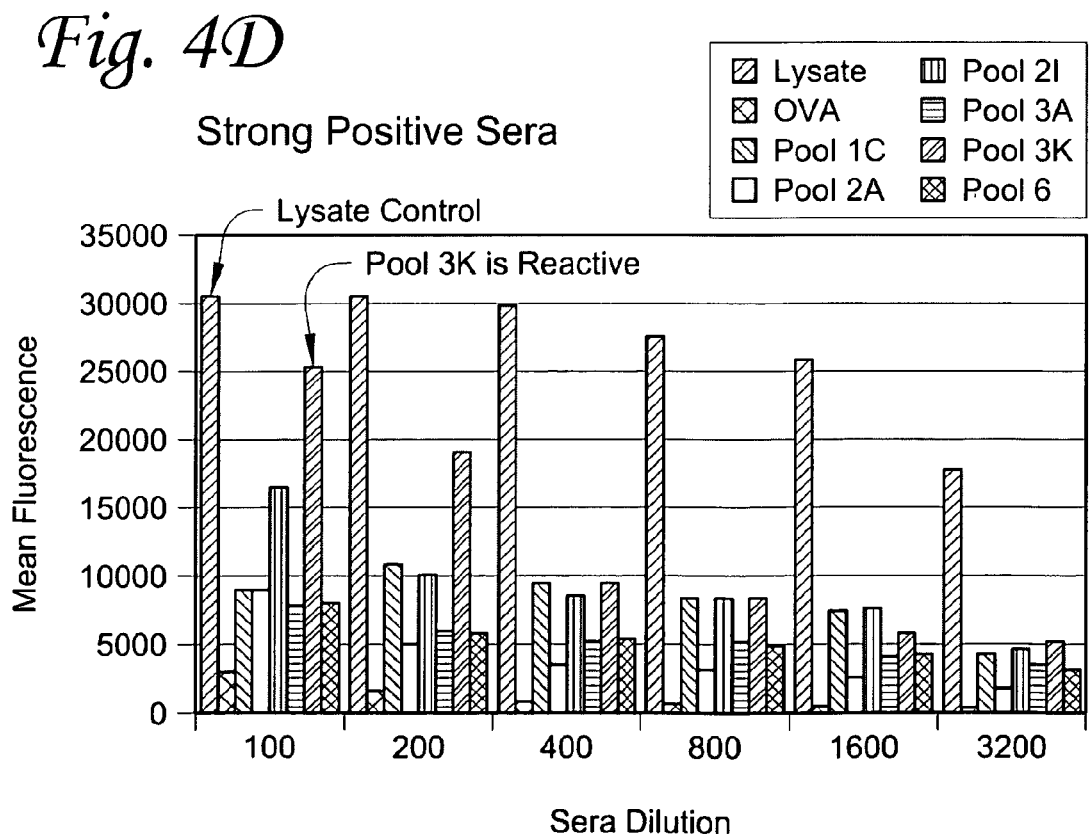
Fig. 4D  Strong Positive Sera

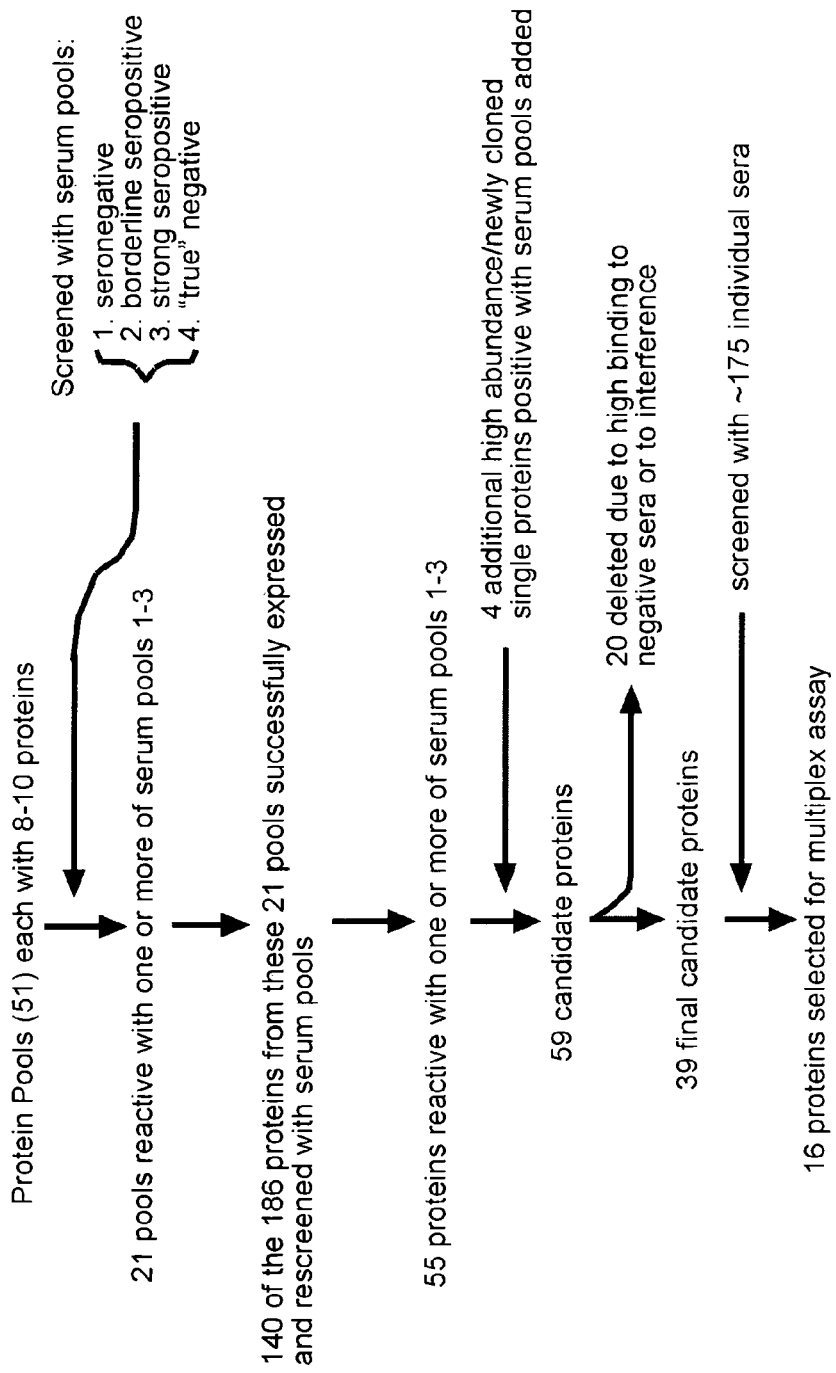

*Fig. 13A*
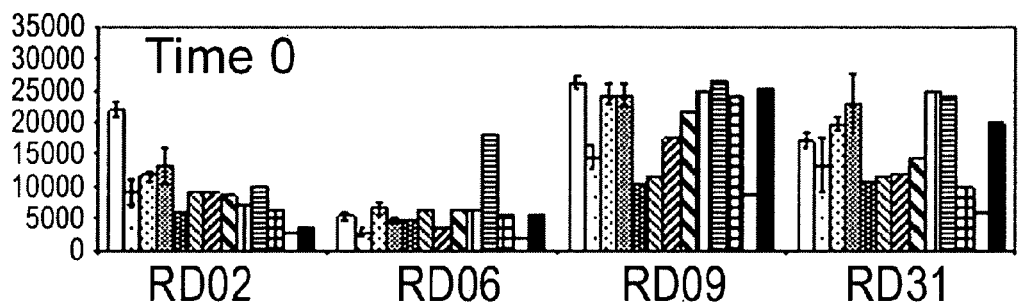
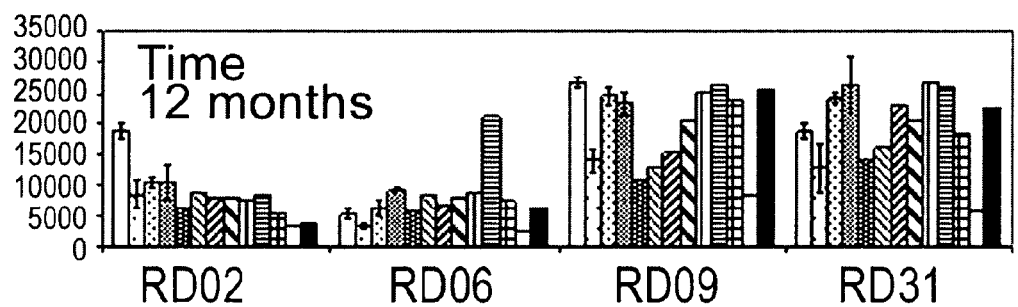
▫ kn107-ptd4 (24)
▫ kn109-ptd4 (26)
▫ kn117-ptd4 (28)
▫ kn122-ptd4 (30)
■ AnoB-E09-ptd4 (32)
▫ AnoD-B06-ptd4 (34)
▫ AnoF-F10-ptd4 (36)
▫ AnoH-E01-ptd4 (38)
▫ AnoH-G10-ptd4 (50)
■ AnoL-E02-ptd4 (52)
▫ FAB-A04-ptd4 (54)
▫ OVA-ptd4 (58)
■ T.c. lysate (15)

DIAGNOSTIC ASSAY FOR *TRYPANOSOMA CRUZI* INFECTION

CROSS-REFERENCE TO RELATED APPLICATIONS

This application is a 371 of PCT/US08/09174, filed on Jul. 30, 2008, which claims the benefit of U.S. Provisional Application Ser. No. 60/962,498, filed Jul. 30, 2007, and is a continuation-in-part application of U.S. Ser. No. 11/587,283, filed Aug. 2, 2007 (now issued as U.S. Pat. No. 7,888,135), which is a U.S. National Stage Application of international application PCT/US2005/013777, filed Apr. 22, 2005, which claims the benefit of U.S. Provisional Application Ser. No. 60/564,804, filed 23 Apr. 2004, and U.S. Provisional Application Ser. No. 60/623,299, filed 29 Oct. 2004, each of which is incorporated herein by reference in its entirety.

STATEMENT OF GOVERNMENT RIGHTS

This invention was made with government support under Program Project P01 AI0449790 awarded by the National Institutes of Health. The United States Government has certain rights in the invention.

BACKGROUND OF THE INVENTION

*Trypanosoma cruzi* is an obligate intracellular protozoan parasite. In mammalian hosts *T. cruzi* cycles between a trypomastigote stage which circulates in the blood and the amastigote stage which replicates in the cytoplasm of infected host cells (primarily muscle).

*T. cruzi* is the etiological agent of Chagas disease and is ranked as the most serious parasitic disease in the Americas, with an economic impact far outranking the combined effects of other parasitic diseases such as malaria, schistosomiasis, and *leishmania* (Dias et al., Mem. Inst. Oswaldo Cruz, 1999, 94:Suppl.1:103). Chagas Disease affects up to 20 million individuals primarily in the Americas where the insect vectors are present and where zoonotic transmission cycles guarantee a steady source of parasites. *T. cruzi* infection has its greatest human impact in areas of Latin America where housing conditions bring people, infected animals, and vector insects into close proximity. More than 90 million are at risk of infection in endemic areas, and roughly 50,000 children and adults die of chronic Chagas disease every year due to lack of effective treatments. Additionally, 2-5% of fetus carried by infected mothers in endemic areas are either aborted or born with congenital Chagas disease. Loss of revenue in terms of productivity lost due to sickness and medical costs have an overwhelming effect on economic growth of these countries.

Recently, increasing travel and immigration have brought *T. cruzi* infection into the spotlight globally, even in areas where transmission has previously been absent or very low. *T. cruzi* has spread beyond the borders of Latin America and has been detected in Europe, Asia, and the United States (Ferreira et al., J. Clin. Micro., 2001, 39:4390). In the U.S., 50-100 thousand serologically positive persons progressing to the chronic phase of Chagas disease are present, and the number of infected immigrants in developed countries is increasing. It is expected that, due to the exponential increase in emigration from Latin America, Chagas disease may become a serious health issue in North America and Europe in the next decade.

Congenital and transfusion/transplantation-related transmissions are thus becoming increasingly recognized as significant threats. As the number of infected individuals grows, transmission of *T. cruzi* to non-infected individuals through blood transfusion and organ transplants from the infected immigrant donors is emerging as a route for *T. cruzi* transmission in more developed nations (Umezawa et. al. J. Clin. Micro., 1999, 37:1554; Silveira et. al. Trends Parasitol., 2001, 17; Chagas disease after organ transplantation—United States, 2001; MMWR Morb Mortal Wkly Rep. 2002 Mar. 15; 51(10):210-2). Each year, 15 million units of blood are transfused and approximately 23,000 organ transplants are performed in the United States alone, and presently almost none of the blood supply is tested for *T. cruzi*. A few cases of infection by *T. cruzi* through organ donation have already been reported to United States Centers for Disease Control since 2001. It has therefore become apparent that the screening of blood and organ donors is necessary not only in Latin America but also in developed countries that receive immigrants from endemic areas.

Diagnosis of *T. cruzi* infection is challenging for a number of reasons. The initial infection is seldom detected except in cases where infective doses are high and acute symptoms very severe, as in localized outbreaks resulting from oral transmissions. Classical signs of inflammation at proposed sites of parasite entry (e.g. "Romahia's sign") or clinical symptoms other than fever, are infrequently reported. As a result, diagnosis is very rarely sought early in the infection, when direct detection of parasites may be possible. In the vast majority of human cases, *T. cruzi* infection evolves undiagnosed into a well-controlled chronic infection wherein circulating parasites or their products are difficult to detect even with the use of amplification techniques. A "conclusive" diagnosis of *T. cruzi* infection is often reached only after multiple serological tests and in combination with epidemiological data and (occasionally) clinical symptoms. Further complicating matters, some researchers have reported positive PCR and clinical disease in patients with negative serology. Salomone et al. Emerg Infect Dis. 2003 December; 9(12):1558-62.

Unfortunately, multiple studies from geographically distinct areas and utilizing a wide range of tests and test formats have shown current diagnostics to be far from dependable (Pirard et al., 2005, Transfusion 45: 554-561; Salomone et al., 2003, Emerg Infect Dis 9: 1558-1562; Avila et al., 1993, J Clin Microbiol 31: 2421-2426; Castro et al., 2002, Parasitol Res 88: 894-900; Caballero et al., 2007, Clin Vaccine Immunol. 14:1045-1049; Silveira-Lacerda et al., 2004, Vox Sang 87: 204-207; Wincker et al., 1994, Am J Trop Med Hyg 51: 771-777; Gutierrez et al., 2004, Parasitology 129: 439-444; Marcon et al., 2002, Diagn Microbiol Infect Dis 43: 39-43; Picka et al., 2007, Braz J Infect Dis 11: 226-233; Zarate-Blades et al., 2007, Diagn Microbiol Infect Dis 57: 229-232). Many of the most widely employed serological tests, including one recently licensed by the United States Food and Drug Administration for use as a blood screening test in the U.S. (Tobler et al., 2007, Transfusion 47: 90-96), use crude or semi-purified parasite preparations, often derived from parasite stages present in insects but not in infected humans. The most widely accepted serological tests for *T. cruzi* infection utilize antigens from either whole to semi-purified parasite lysates from epimastigotes that react with anti-*T. cruzi* IgG antibodies. These tests show a degree of variability due to a lack of standardization of procedures and reagents between laboratories, and a number of inconclusive and false positive results occur due to cross-reactivity with antibodies developed against other parasites (Nakazawa et. al. Clin. Diag. Lab. Immunol., 2001, 8:1024).

Other tests have incorporated more defined parasite components, including multiple fusion proteins containing epitopes from various parasite proteins, which, individually have shown some promise as diagnostics (Caballero et al., 2007, Clin Vaccine Immunol. 14:1045-1049; da Silveira J F et al., 2001, Trends Parasitol 17: 286-291; Chang et al., 2006, Transfusion 46: 1737-1744). Unfortunately, in the absence of a true gold standard, the sensitivity of new tests is generally determined using sera that have been shown to be unequivocally positive on multiple other serologic tests, but rarely with sera that are borderline or equivocal on one or more tests, an approach that assures only that the test being evaluated is no worse, but not necessarily any more sensitive, than the existing tests.

SUMMARY OF THE INVENTION

The present invention provides new tools for diagnosing and treating *T. cruzi* infections in people and animals. In one aspect, the invention provides a method of screening for antigenic *T. cruzi* polypeptides. First and second substrates are provided that each include a plurality of individually addressable candidate antigens derived from *T. cruzi*. The antigens present on the first and second substrate are substantially the same in order to facilitate comparison. The candidate antigens of the first substrate are contacted with a body fluid of a first mammal known to be positive for *T. cruzi* infection. The candidate antigens of the second substrate are contacted with a body fluid from a second mammal known or reasonably believed to be unexposed to *T. cruzi* infection. At least one antigenic *T. cruzi* polypeptide is then identified using a process in which the antigenic *T. cruzi* polypeptide binds to an antibody present in the body fluid of the first mammal but exhibits little or no binding to an antibody present in the body fluid of the second mammal. Optionally, the first and second mammals may be humans.

Positive evidence of *T. cruzi* infection in the first mammal may, for example, be based on a detection method such as a T cell assay, polymerase chain reaction (PCR), hemoculture or a xenodiagnostic technique. Evidence of negative serology in the second mammal is preferably shown by a negative result when the mammal is tested for *T. cruzi* infection utilizing a conventional serodiagnostic test that relies on antigens from whole or semi-purified parasite lysates from *T. cruzi*, such as, for example, from a *T. cruzi* epimastigote lysate.

More than two substrates that include a plurality of individually addressable candidate antigens may be used. Each substrate is contacted with the body fluid from a mammal which exhibits a different level of serological reaction to *T. cruzi* using a conventional serodiagnostic test that relies on antigens from whole or semi-purified parasite lysates from *T. cruzi*. The method optionally further includes the step of preparing the polypeptide antigens from an expression vector including a nucleotide sequence from *T. cruzi*.

Optionally, the screening method may further include a preliminary screening step. The preliminary screening step includes providing a first and a second substrate comprising a plurality of individually addressable antigen pools derived from *T. cruzi* in which the antigen pools present on the first and second substrate are substantially the same. The first substrate is contacted with a body fluid of a first mammal known to be positive for *T. cruzi* infection and the second substrate is contacted with a body fluid from a second mammal known or reasonably believed to be unexposed to *T. cruzi* infection. An antigen pool is then identified that binds to an antibody present in the body fluid of the first mammal but exhibits little or no binding to an antibody present in the body fluid of the second mammal.

In another aspect, the present invention provides an article that includes a substrate and a plurality of individually addressable antigenic *T. cruzi* polypeptides. The antigenic polypeptides can be selected from the polypeptides identified in Table 1, 2 and/or 4, and include antigenic analogs or subunits thereof. In some embodiments, some or all of the polypeptides are selected from the polypeptides listed in Table 2 and/or Table 4, with the proviso that at least one of the polypeptides selected from Table 2 and/or Table 4 is a polypeptide that is not listed in Table 1. The polypeptides are immobilized onto a surface of the substrate. Optionally, the article may include at least one antigenic *T. cruzi* polypeptide identified according to the screening method described above, or antigenic analogs or subunits thereof, immobilized onto the surface of the substrate. In embodiment, the polypeptides are immobilized on the substrate surface to form a microarray. In another embodiment, the substrate includes at least one nanoparticle, with the polypeptides being immobilized on the surface of the nanoparticle.

The present invention also provides a kit for diagnosis of *T. cruzi* infection that includes an article that includes a substrate and a plurality of individually addressable antigenic *T. cruzi* polypeptides selected from the polypeptides identified in Table 1, 2 and/or 4, in which the polypeptides are immobilized onto a surface of the substrate. In some embodiments, some or all of the polypeptides are selected from the polypeptides listed in Table 2 and/or Table 4, with the proviso that at least one of the polypeptides selected from Table 2 and/or Table 4 is a polypeptide that is not listed in Table 1. The kit also includes packaging materials and instructions for use. Optionally, the kit may include at least on antigenic *T. cruzi* polypeptide identified by the screening method described above and immobilized onto the surface of the substrate. The kit may be formulated for medical or veterinary use.

The present invention also provides a diagnostic method for obtaining information about a known or suspected *T. cruzi* infection in a mammal, or for determining whether a mammal is or has been infected by *T. cruzi*. Execution of the method involves obtaining a biological sample from the mammal, contacting the biological sample with a plurality of individually addressable antigenic *T. cruzi* polypeptides selected from the polypeptides identified in Table 1, 2, and/or 4, or antigenic analogs or subunits thereof, and evaluating the presence, absence, intensity or pattern of interaction of components of the biological sample with the antigenic *T. cruzi* polypeptides. In some embodiments, some or all of the polypeptides are selected from the polypeptides listed in Table 2 and/or Table 4, with the proviso that at least one of the polypeptides selected from Table 2 and/or Table 4 is a polypeptide that is not listed in Table 1. Optionally, an antigenic *T. cruzi* polypeptide identified according to the screening method described herein, or antigenic analogs or subunits thereof, can be included in the plurality of antigenic *T. cruzi* polypeptides. In a preferred embodiment, the biological sample is contacted with an article that includes a substrate and a plurality of individually addressable antigenic *T. cruzi* polypeptides immobilized onto a surface of the substrate. Information that can be obtained according to the method includes, for example, the presence or absence of *T. cruzi* infection, the identity of the infective strain, the length of the infection, the stage of the infection, whether the infection is still present or the mammal has been cured, the vaccination status of the mammal, the success of treatment, or any combination thereof. The method can, for example, be a serodiagnostic method, wherein the biological sample component that interacts with an antigenic *T. cruzi* polypeptide is an antibody from the mammal. Alternatively, the method may be embodied by a cellular assay method where the biological sample component that interacts with an antigenic *T. cruzi* polypeptide is T cell from the mammal. Like all diagnostic methods described herein, the method can be implemented as a multiplexed assay in which the biological sample is contacted simultaneously with the plurality of antigenic *T. cruzi* polypeptides. The biological sample can, for example, be obtained from a person suspected of having or being exposed to disease, or obtained from an actual or potential blood donor or transplant donor. Alternatively, the biological sample is obtained from a pooled blood product supply intended for use in transfusions or research.

Also provided by the invention is a method for detecting a *T. cruzi* infection, particularly a maternally transmitted *T. cruzi* infection, in an infant born to a mother who is known to have, or suspected of having, a *T. cruzi* infection. A biological sample is obtained from the infant and contacted with a plurality of individually addressable antigenic *T. cruzi* polypeptides, or antigenic analogs or subunits thereof. The biological sample is preferably a bodily fluid, more preferably blood, plasma or serum. The timing for obtaining the sample from the infant is important, as enough time should have elapsed after the birth such that antibodies produced by the infant can be detected. The sample can be obtained from the infant at about two or three months after birth but is preferably obtained about 4, 5 or 6 months after birth, or later. Preferably, at least one polypeptide is selected from the polypeptides listed in Table 1, Table 2 and/or Table 4. The presence, absence, intensity or pattern of interaction of components of the biological sample, particularly antibodies, with the antigenic *T. cruzi* polypeptides is evaluated to determine whether the infant exhibits an antibody response that exceeds background levels.

The method optionally further includes comparing the infant's antibody response to the plurality of antigenic *T. cruzi* polypeptides with the antibody response of the infant's mother to the same or similar panel of *T. cruzi* polypeptides. Comparison with the mother's antibody response is especially useful when the infant's antibody response is higher than background level. A biological sample is obtained from the infant's mother and contacted with the plurality of individually addressable antigenic *T. cruzi* polypeptides, or antigenic analogs or subunits thereof. The biological sample of the mother can be obtained prior to birth, during birth, or after birth. The presence, absence, intensity or pattern of interaction of components of the mother's biological sample with the antigenic *T. cruzi* polypeptides is compared to the presence, absence, intensity or pattern of interaction of components of the infant's biological sample with the antigenic *T. cruzi* polypeptides, to determine whether the infant's antibody response differs from the mother's antibody response. A difference in antibody responses, where the infant's response is above background levels, indicates that the infant may have a *T. cruzi* infection. Similar antibody responses for mother and infant indicate that maternal antibodies may still be present in the infant's bodily fluids. In that event, the comparison is optionally repeated using a biological sample can be obtained from the infant at a later date.

Additionally or alternatively, the method further optionally includes comparing the infant's antibody response to the plurality of antigenic *T. cruzi* polypeptides with the infant's antibody response to the same or similar panel of *T. cruzi* polypeptides as measured earlier, i.e., shortly after birth. Shortly after birth, the infant's antibody response is expected to mirror the mother's antibody response, reflecting the presence of maternal antibodies in the infant's bodily fluids. A biological sample is obtained from the infant shortly after birth, contacted with the plurality of individually addressable antigenic *T. cruzi* polypeptides, or antigenic analogs or subunits thereof, and the presence, absence, intensity or pattern of interaction of components of the infant's earlier biological sample with the antigenic *T. cruzi* polypeptides is compared to the presence, absence, intensity or pattern of interaction of components of the infant's later biological sample, or of the mother's biological sample, or both, with the antigenic *T. cruzi* polypeptides, to determine whether the infant's later antibody response differs from the mother's antibody response, wherein a difference in antibody responses indicates that the infant may have a *T. cruzi* infection.

In instances wherein the method identifies an infant having or suspected of having a *T. cruzi* infection, the method further optionally includes treating the infant for a *T. cruzi* infection, for example by administering a therapeutic agent to the infant.

In another aspect, the present invention provides a method for detecting contamination of a blood product supply with *T. cruzi*. The method of detecting contamination includes selecting a sample from the blood supply, contacting the sample with a plurality of individually addressable antigenic *T. cruzi* polypeptides selected from the polypeptides identified in Table 1, 2 and/or 4, or antigenic analogs or subunits thereof, and evaluating the presence, absence, intensity or pattern of interaction of components of the sample with the antigenic *T. cruzi* polypeptides to determine whether the blood supply is contaminated with *T. cruzi*. In some embodiments, some or all of the polypeptides are selected from the polypeptides listed in Table 2 and/or Table 4, with the proviso that at least one of the polypeptides selected from Table 2 and/or Table 4 is a polypeptide that is not listed in Table 1. Optionally, an antigenic *T. cruzi* polypeptide identified according to the screening method described herein, or antigenic analogs or subunits thereof, can be included in the plurality of antigenic *T. cruzi* polypeptides. In a preferred embodiment, the blood supply sample is contacted with an article that includes a substrate and a plurality of individually addressable antigenic *T. cruzi* polypeptides immobilized onto a surface of the substrate.

Blood products that can be tested include whole blood, a blood product, or a blood fraction. For example, a cellular blood component, a liquid blood component, a blood protein, or mixtures thereof, or a red blood cell concentrate, a leukocyte concentrate, a platelet concentrate, plasma, serum, a clotting factor, an enzymes, albumin, plasminogen, or a immunoglobulin, or mixtures of thereof, can be tested for contamination according to the method.

The method of detecting contamination can be a serodiagnostic method, wherein the sample component that interacts with an antigenic *T. cruzi* polypeptide is an antibody. Alternatively, the method can take the form of a cellular assay method, wherein the sample component that interacts with an antigenic *T. cruzi* polypeptide is T cell.

In yet another aspect, the present invention provides a multicomponent vaccine. In one embodiment, the vaccine includes a plurality of immunogenic *T. cruzi* polypeptides selected from the *T. cruzi* polypeptides listed in Table 1, 2, and/or 4, or immunogenic subunits or analogs thereof. In some embodiments, some or all of the polypeptides are selected from the polypeptides listed in Table 2 and/or Table 4, with the proviso that at least one of the polypeptides selected from Table 2 and/or Table 4 is a polypeptide that is not listed in Table 1. The multicomponent polypeptide vaccine optionally includes at least one immunogenic *T. cruzi* polypeptide identified according to the screening method described herein, or immunogenic subunit or analog thereof. In another embodiment, the multicomponent vaccine includes one or more polynucleotides operably encoding a plurality of immunogenic *T. cruzi* polypeptides selected from the *T. cruzi* polypeptides listed in Table 1, 2, and/or 4 or immunogenic subunits or analogs thereof. In some embodiments, some or all of the polypeptides are selected from the polypeptides listed in Table 2 and/or Table 4, with the proviso that at least one of the polypeptides selected from Table 2 and/or Table 4 is a polypeptide that is not listed in Table 1. The multicomponent polynucleotide vaccine optionally includes a polynucleotide operably encoding a polypeptide identified according to the screening method, or immunogenic subunit or analog thereof. The multicomponent vaccine may be a therapeutic or prophylactic vaccine.

BRIEF DESCRIPTION OF THE DRAWINGS

FIG. 7 is a schematic showing a screening process for the high-throughput selection of diagnostic proteins for detection of *T. cruzi* infection.

DETAILED DESCRIPTION OF ILLUSTRATIVE EMBODIMENTS

Figure 1C:
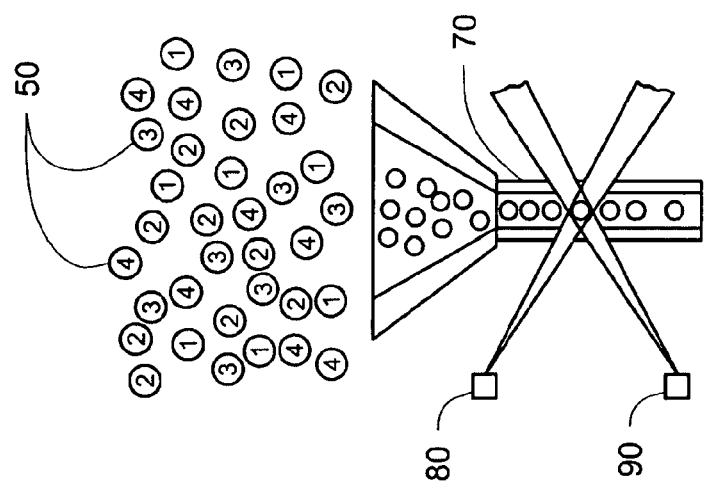
FIG. 1 provides a pictoral overview of the BIO-PLEX array analysis method; A) shows the protein-antibody-microsphere complex used by the BIO-PLEX method, B) shows multiple complexes in the well of a microplate substrate, and C) shows laser excitation of the complexes as they flow through a flow cytometer.
Figure 1B:
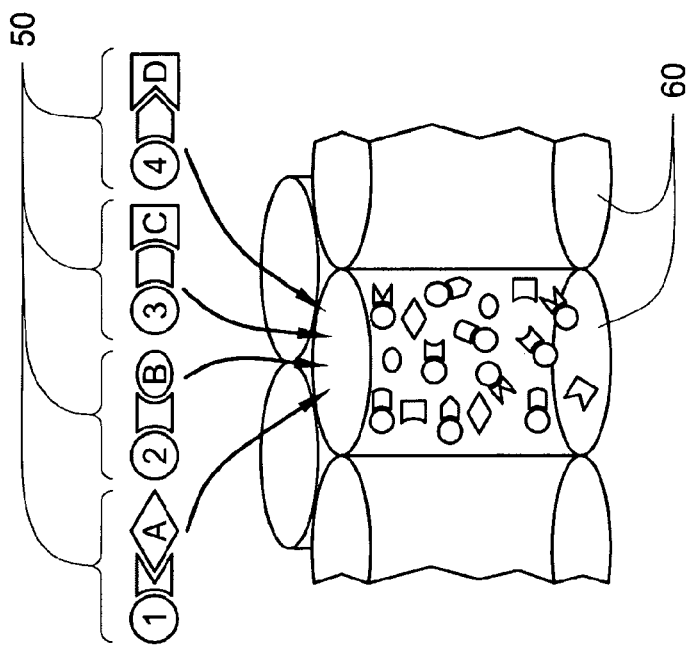
Figure 1A:
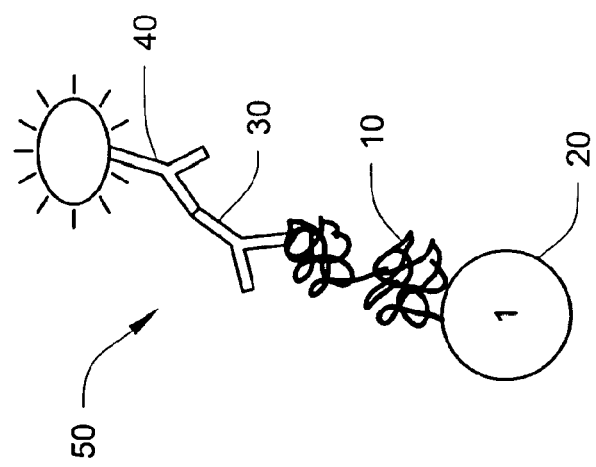

In one aspect, the present invention is directed to the detection of *T. cruzi* infection in a mammal, particularly a human. A plurality of *T. cruzi* polypeptides, or subunits or analogs thereof, that are detectable by antibodies present in a bodily fluid, such as blood, plasma or serum, of at least some individuals that are infected with *T. cruzi* are included in a multicomponent panel for use in a diagnostic assay, which may be a serodiagnostic assay or a cellular assay. The term "serodiagnostic" is used because the assay is typically performed on a blood component such as whole blood, plasma or serum, but it should be understood that any bodily fluid that may provide evidence of an immune response to *T. cruzi* can be assayed using the serodiagnostic test of the invention.

The panel components are contacted with a bodily fluid of an individual such as blood, plasma, serum, urine, saliva or tears and the like, and the presence of absence of evidence of an immune response to *T. cruzi* in the individual is evaluated. The body fluid that is tested can be that of an individual patient to be screened, or it can be a body fluid that is part of a blood or plasma supply, for example, pooled or unpooled, that is available for transfusion and/or research.

An immune response indicative of *T. cruzi* infection may be evidenced by the binding of antibodies in the biological fluid to panel components. The panel components can likewise be used to assess the presence of a T cell response in the subject.

In a preferred embodiment, the diagnostic test is highly specific for *T. cruzi* infection and sufficiently sensitive to detect infection in subjects considered negative with conventional serological assays based on *T. cruzi* lysates due to a poor or inconsistent B cell response to infection. Optionally the test can include, as specificity controls, polypeptide antigens that are recognized when other infections are present.

The diagnostic test can detect the presence or absence of *T. cruzi* infection. In some embodiments, and depending on the antigenic polypeptides selected for including in the multicomponent panel, the pattern of antigen recognition may provide additional information such as the stage of infection or the severity of disease. The antigen recognition pattern may also be useful to discriminate among patients with active or latent infections, and those who have been cured or vaccinated.

The multicomponent diagnostic assay (also referred to herein as a multiplexed assay) has advantages over conventional serodiagnostic methods. For example, the multiplexed assay of the invention consistently detects infection, whereas conventional assays are plagued by high failure rates and inconsistent performance. The Examples below show that infected subjects produce individual patterns of antibody responses that differ from one another, rendering serodiagnostics based on a single antigen a less effective diagnostic than a multiplexed assay. There are numerous examples of the failure of conventional serology to detect infection, and parasitological tests are also unreliable. Individuals who are seropositive in the multiplex assay of the invention are likely to be infected with *T. cruzi*, particularly if they exhibit antibodies to at least 4, more preferably 6, and even more preferably 8 different recombinant *T. cruzi* proteins, and/or were born in endemic areas and/or have evidence of heart disease. Such individuals are likely to be infected with *T. cruzi* even if they exhibit negative results with conventional serologic assays.

Additionally, the multiplexed serodiagnostic assay of the invention provides a better measure of the efficacy and effectiveness of therapeutic treatment than conventional serological or parisitological assays. Most subjects are negative by parasitological assays prior to treatment and remain positive by conventional serology for long periods of time after treatment. However a multiplexed assay using a selected set of recombinant proteins as described herein can detect changes in antibody levels upon completion of treatment. The use of multiple targets allows serologic changes to be detected following treatment when similar changes are not consistently observed using conventional serologic tests.

Also, the *T. cruzi* proteins identified herein for use in the multiplexed assays of the invention (both serodiagnostic and cellular) are expected to be effective diagnostics for different *T. cruzi* strains in different regions, since many of them are unique to *T. cruzi* and/or highly abundant proteins, such as "housekeeping" proteins, that are expected to show little variation among the different strains.

The invention is applicable to human disease but also has veterinary applications. For example, a diagnostic assay developed according to the invention can be used to diagnose *T. cruzi* infection in farm animals or pets, such as dogs.

Antigenic Polypeptides

A *T. cruzi* polypeptide, or subunit or analog thereof, that is suitable for inclusion in the panel is one that reacts to antibodies in the sera of individuals infected with *T. cruzi*. Such a polypeptide is referred to herein as an antigenic polypeptide or a polypeptide antigen.

A preferred antigenic polypeptide, or antigenic subunit or analog thereof, is one that detectably binds antibodies in a bodily fluid of a subject who is known to be infected or to have been infected by *T. cruzi*, but whose bodily fluid is seronegative when assayed by conventional means. A bodily fluid that is seronegative when assayed by conventional means is one that, for example, does not show a positive reaction (antibody binding) when exposed to antigens from either whole or semi-purified parasite lysates, for example those from epimastigotes, in conventional diagnostic tests. A subject who shows evidence of *T. cruzi* infection using, for example, a T cell assay, polymerase chain reaction (PCR), hemoculture, or xenodiagonstic techniques, is considered to known to be infected or to have been infected by *T. cruzi*, even if the subject shows a negative response to a conventional serodiagnostic test.

Another preferred polypeptide, or subunit or analog thereof, is one that detectably binds antibodies in a bodily fluid of a subject who is seropositive when assayed by conventional means, regardless of whether the polypeptide also exhibits detectable binding to antibodies in a bodily fluid of a subject who is known to be infected or to have been infected by *T. cruzi*, but whose bodily fluid is seronegative when assayed by conventional means.

The antigenic *T. cruzi* polypeptides, and antigenic subunits and analogs thereof, bind antibodies in a bodily fluid of a subject, such as blood, plasma or sera, thereby providing evidence of exposure to *T. cruzi*. These antigenic polypeptides, and antigenic subunits and analogs thereof, may also be immunogenic; i.e., they may also, when delivered to a subject in an appropriate manner, cause an immune response (either humoral or cellular or both) in the subject. Immunogenic *T. cruzi* polypeptides, as well as immunogenic subunits and analogs thereof, are therefore expected to be useful in vaccines, as described below.

It should be understood that the term "polypeptide" as used herein refers to a polymer of amino acids and does not refer to a specific length of a polymer of amino acids. Thus, for example, the terms peptide, oligopeptide, and protein are included within the definition of polypeptide.

An antigenic *T. cruzi* polypeptide according to the invention is not limited to a naturally occurring antigenic *T. cruzi* polypeptide; it can include an antigenic subunit or antigenic analog of a *T. cruzi* polypeptide. Likewise the antigenic polypeptide can be a multivalent construct that includes epitopes obtained from different antigenic polypeptides of *T. cruzi*. An antigenic analog of an antigenic *T. cruzi* polypeptide is a polypeptide having one or more amino acid substitutions, insertions, or deletions relative to an antigenic *T. cruzi* polypeptide, such that antigenicity is not entirely eliminated. Substitutes for an amino acid are preferably conservative and are selected from other members of the class to which the amino acid belongs. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free —OH is maintained; and Gln for Asn to maintain a free $NH_2$. Antigenic subunits of an antigenic *T. cruzi* polypeptide are antigenic *T. cruzi* polypeptides that are truncated at either or both of the N-terminus or C-terminus, without eliminating their ability to detect serum antibodies against *T. cruzi*. Preferably, an antigenic subunit contains an epitope recognized by a host B cell or T cell. Fragments of an antigenic *T. cruzi* protein contain at least about eight amino acids, preferably at least about 12 amino acids, more preferably at least about 20 amino acids.

Examples of antigenic *T. cruzi* polypeptides suitable for inclusion in the multicomponent panel of the invention are listed in Tables 1, 2 and 4 in the Examples, below. The "Gene ID Numbers" represent gene numbers assigned by annotators of the *T. cruzi* genome and are accessed via the *T. cruzi* genome database on the worldwide web at "*TcruziDB*.org".

Furthermore, as described below, the present invention also includes a method for identifying additional antigenic polypeptides indicative of *T. cruzi* infection. The use of the additional *T. cruzi* polypeptides thus identified, or antigenic subunit or analog thereof, alone or in combination with each other, with the antigenic *T. cruzi* polypeptides of Table 1, 2 and 4, and/or with other known antigens, in diagnostic and therapeutic applications relating to *T. cruzi* infection as described is also envisioned. It should be understood that the antigenic *T. cruzi* polypeptides described herein or identified using the screening method described herein are generally useful in any of diagnostic and/or therapeutic applications relating to *T. cruzi* infection.

Antigenic polypeptides used in the multicomponent panel of the invention preferably include polypeptides that are abundant during the two stages (amastigote and trypomastigote) that are prevalent in the life cycle of the parasite in mammals. In a mammalian host, *T. cruzi* cycles between a dividing intracellular stage (the amastigote) and a non-replicative extracellular trypomastigote form which circulates in the blood. The presence of two developmental stages of *T. cruzi* in mammalian hosts provides two anatomically and (to some degree) antigenically distinct targets of immune detection—the trypomastigotes in the bloodstream and the amastigotes in the cytoplasm of infected cells. The intracellular location of amastigotes of *T. cruzi* has long been considered a "hiding place" for the parasite wherein it is not susceptible to immune recognition and control. Notably, most current serological tests for *T. cruzi* are based upon antigens from epimastigotes, the form of *T. cruzi* present in insects but not humans. Thus, in a preferred embodiment, an antigenic polypeptide for use in a *T. cruzi* diagnostic test or vaccine according to the invention can be one that is expressed by *T. cruzi* in the extracellular (trypomastigote) stage, in the intracellular (amastigote) stage, or during both stages of the life cycle.

Diagnostic Method

The diagnostic of the invention utilizes a multicomponent panel to assess the presence of an immune response (e.g., the presence of antibodies or reactive T cells) in the subject to multiple antigenic *T. cruzi* polypeptides, or antigenic subunits or analogs thereof. The panel may contain a number of antigenic *T. cruzi* polypeptides, or antigenic subunits or analogs thereof, wherein said number is between 5 and 50 or even more, depending on the embodiment and the intended application. For example, the panel may contain 5, 8, 10, 12, 15, 18, 20, 25, 30, 40 or more antigenic *T. cruzi* polypeptides. A typical multicomponent panel may contain 10 to 20 antigenic *T. cruzi* polypeptides. Preferably, some or all of the antigenic *T. cruzi* polypeptides used in the multicomponent panel are selected from those listed in one or more of Tables 1, 2 or 4. Conveniently, the *T. cruzi* polypeptides that are used in the multicomponent diagnostic test can be recombinant polypeptides; however they can be naturally occurring polypeptides or polypeptides that have been chemically or enzymatically synthesized, as well.

In one embodiment, the diagnostic test takes the form of a serodiagnostic assay, which detects a humoral (antibody) immune response in the subject. The binding of an antibody that is present in a biological fluid, such as a serum antibody, to any of the various components of the panel is determined. The threshold for a diagnosis of *T. cruzi* infection can be readily determined by the scientist, medical personnel, or clinician, for example based upon the response of known infected and control sera to the particular panel being used. For example, diagnosis criteria can be based on the number of "hits" (i.e., positive binding events) or they can represent a more quantitative determination based, for example, on the intensity of binding and optional subtraction of background. As an illustrative example, the multicomponent panel could contain 15 to 20 antigenic polypeptides, or antigenic analogs or subunits thereof, and a positive diagnosis could be interpreted as, say, 5 or more positive responses. Optionally, the serodiagnostic test could be further refined to set quantitative cutoffs for positive and negative based upon the background response to each individual panel component. So, for example, the response to each polypeptide could be set to be >2 standard deviations above the response of "pooled normal," sera and an individual would have to have responses to a minimum of 5 out of 20 polypeptides.

The serodiagnostic assay of the invention can take any convenient form. For example, standard immunoassays such as indirect immunofluorescence assays (IFA), enzyme-linked immunosorbent assay (ELISA), radioimmunoassay (RIA), fluorescent bead technology and Western blots can be employed. Detection can be by way of an enzyme label, radiolabel, chemical label, fluorescent label, chemiluminescent label, a change in spectroscopic or electrical property, and the like.

In another embodiment, the diagnostic method can take the form of a cellular assay. In this embodiment, a multicomponent panel of antigenic *T. cruzi* polypeptides as described herein is used to assess T cell responses in a mammalian subject, thereby providing another method for evaluating the presence or absence (or stage, etc.) of *T. cruzi* infection. Individuals are known who are serologically negative (based upon conventional tests) but who have T cells reactive with parasite antigens (usually a lysate of trypomastigotes and epimastigotes—but in some cases also against specific *T. cruzi* polypeptides). This suggests that T cell responses may be a sensitive way to assess infection, or to determine the stage of infection or exposure.

Recombinant antigenic *T. cruzi* polypeptides can be readily produced, for example, as histidine-tagged polypeptides. These His-tagged polypeptides can be purified onto a nickel-coated substrate, then added to a blood fraction comprising peripheral blood lymphocytes (e.g., a peripheral blood mononuclear cell, PBMC, fraction). The ability of the T cells to make IFN-gamma is then assessed, for example using an ELISPOT assay (e.g., Laucella et al., J Infect Dis. 2004 Mar. 1; 189(5):909-18). As another example, antigenic *T. cruzi* polypeptides, or antigenic analogs or subunits thereof, can be bound to major histocompatibility complex (MHC) tetramers and presented to T cells, for example in a composition of peripheral blood lymphocytes, in a microarray format. In this assay, smaller polypeptides, for example antigenic peptide subunits of antigenic *T. cruzi* polypeptides described herein, are preferred as they are more readily bound to the MHC tetramers and recognized by the T cells. Antigenic subunits of antigenic *T. cruzi* polypeptides can be predicted using various computer algorithms, and are amenable to chemical synthesis. Binding of T cells to the spots containing MHC-polypeptide complexes indicates recognition and hence *T. cruzi* infection. See, for example, Stone at al (Proc. Nat'l. Acad. Sci. USA, 2005, 102:3744) and Soen et al. (PLoS. Biol, 2003, 1:429) for a description of the general technique.

In a multiplexed assay, multiple analytes are simultaneously measured. Each polypeptide antigen is positioned such that it is individually addressable. For example, the polypeptide antigens can be immobilized in a substrate. In a preferred embodiment, the multiplexed serodiagnostic assay of the invention is performed using a bioassay such as the Luminex system (Luminex Corporation, Austin, Tex.). The Luminex system, which utilizes fluorescently labeled microspheres, allows up to 100 analytes to be simultaneously measured in a single microplate well, using very small sample volumes. However, other multiplex platforms such as protein microarrays can also be used, and the invention is not intended to be limited by the type of multiplex platform selected.

The panel components can be assembled on any convenient substrate, for example on a microtiter plate, on beads, or in a microarray on a microchip. A microarray format is advantageous because it is inexpensive and easy to read using a standard fluorescence microscope. In this format, one might just use the total number of spots (proteins) positive for each test patient to make a positive or negative diagnosis. In addition, the diagnostic test of the invention is well-suited to adaptation for use with commercially available high-throughput devices and immunoassay protocols, for example those available from Abbott Laboratories and Applied Biosystems, Inc. The serodiagnostic assay can also take the form of an immunochromatographic test, in the form of a test strip loaded with the panel components. The bodily fluid can be wicked up onto the test strip and the binding pattern of antibodies from the fluid can be evaluated.

Detection of *T. cruzi* Infection in Infants

In another aspect, the invention provides method for determining whether an infant has a *T. cruzi* infection. In situations where the infant's mother is infected with *T. cruzi*, the method facilitates early detection of a maternally transmitted infection. A maternally transmitted infection can be transmitted prior to or during birth (a congenital infection), or it may be transmitted after birth, as through breastfeeding.

At birth and for a period shortly thereafter, the antibody response of an infant born to an infected mother mirrors the antibody response of the infant's infected mother, reflecting the presence of maternal antibodies in the baby's fluids. With time, however, if the infant is infected, the infant will begin producing its own antibodies, and the pattern of response will begin to differentiate from that of the mother. Eventually, typically by about six months after birth, the antibody response of the infant will either diminish to near background levels (if the infant is not infected), or will appear distinct from that of the mother, indicating possible infection.

The method for detecting *T. cruzi* infection in an infant, particularly an infant born to a mother with a known or suspected *T. cruzi* infection, therefore includes analyzing at least one biological sample obtained from the infant. Preferably the biological sample is a body fluid such as blood, plasma or serum. The sample is obtained at a time after birth by which the infant's antibody response to the antigentic *T. cruzi* polypeptides, if the infant is infected, is detectably different from the mother's antibody response. Preferably the sample is obtained from the infant at about 6 months of age, but the sample can be obtained earlier, for example at about 5 months, 4 months, 3 months or 2 months. Likewise, the sample can be obtained later since after 6 months the baby is expected to be producing its own antibodies at a detectable level. Analysis is preferably performed using the multiplexed assay of the invention.

An infant that exhibits a background level antibody response to *T. cruzi* antigens in the multiplexed assay is unlikely to be infected with *T. cruzi*. However, an antibody response that exceeds background levels indicates possible infection. Optionally, the method therefore also includes administering a therapeutic agent an infant suspected of having a *T. cruzi* infection.

In a preferred embodiment of the method, the infant's antibody response to the *T. cruzi* antigen panel is first analyzed shortly after birth. When a neonate's antibody response is measured shortly after birth (preferably no later than one month after birth, more preferably no later then two months after birth), the neonate's antibody response will parallel that of its mother, due to the presence of maternal antibodies. Optionally, the mother's antibody response to the antigen panel is thus analyzed. The infant's antibody response at the later time point (when its own antibodies have begun to be produced) is compared to the antibody response of the mother, and/or to its own antibody response at a time shortly after birth. Comparison of the antibody response of the later infant sample with the antibody response of the earlier neonate sample and/or with the antibody response of the mother (preferably using a sample obtained from the mother at about the same time as the sample or samples are obtained from the infant, although the sample from the mother can be obtained at any convenient time as it is expected to be fairly stable) is preferred, as it facilitates the determination as to whether the infant's own antibody response is sufficiently different from the mother's to support the diagnosis of *T. cruzi* infection.

It should be understood that in this method, as in all methods involving the use of the multiplexed assay of the invention, the panel of serodiagnostic targets can include any antigenic *T. cruzi* polypeptide described herein, or subsequently discovered using the screening assay of the invention. Preferably, multiple *T. cruzi* polypeptide antigens are selected from those listed in Tables 1, 2 and/or 4 and used to assess the infant's antibody response in a multiplexed assay.

It should also be noted that the method of detecting *T. cruzi* infection in an infant according to the invention can take the form of either a serodiagnostic method, wherein the sample components that interact with an antigenic *T. cruzi* polypeptides are antibodies, or a cellular assay method, and wherein the sample components that interact with the antigenic *T. cruzi* polypeptides are T cells.

Blood Supply Screening

The diagnostic test of the invention can be used to detect the presence of *T. cruzi* infection in blood and blood products or fractions include whole blood as well as such as cellular blood components, including red blood cell concentrates, leukocyte concentrates, and platelet concentrates and extracts; liquid blood components such as plasma and serum; and blood proteins such as clotting factors, enzymes, albumin, plasminogen, and immunoglobulins, or mixtures of cellular, protein and/or liquid blood components. Details regarding the make-up of blood, the usefulness of blood transfusions, cell-types found in blood and proteins found in blood are set forth in U.S. Pat. No. 5,232,844. Techniques regarding blood plasma fractionation are generally well known to those of ordinary skill in the art and an excellent survey of blood fractionation also appears in Kirk-Othmer's Encyclopedia of Chemical Technology, Third Edition, Interscience Publishers, Volume 4.

A sample is contacted with a multicomponent panel of the invention, and a positive or negative response is detected as described above for clinical use of the assay in patients suspected of having *T. cruzi* infection. Advantageously, the diagnostic test is readily automated, for example using microchip technology, for the processing of large numbers of samples.

Prophylactic and Therapeutic Immunization

In another aspect, the present invention is directed to both prophylactic and therapeutic immunization against *T. cruzi* infection and the chronic disease state, known as Chagas disease, that often eventually follows initial *T. cruzi* infection. Antigenic *T. cruzi* polypeptides described herein, or identified using a screening method described herein, may be immunogenic. That is, they may elicit a humoral (B cell) response and/or a cell-mediated immune response (i.e., a "T cell" response) in the subject. A cell-mediated response can involve the mobilization helper T cells, cytotoxic T-lymphocytes (CTLs), or both. Preferably, an immunogenic polypeptide elicits one or more of an antibody-mediated response, a $CD4^+$ Th1-mediated response (Th1: type 1 helper T cell), and a $CD8^+$ T cell response. Therapeutic administration of the polynucleotide or polypeptide vaccine to infected subjects is expected to be effective to delay or prevent the progression of the *T. cruzi* infection to a chronic disease state, and also to arrest or cure the chronic disease state that follows *T. cruzi* infection. Prophylactic administration of the polynucleotide or polypeptide vaccine to uninfected subjects is expected to be effective to reduce either or both if the morbidity and mortality associated with infection by *T. cruzi*. Further, if an uninfected, vaccinated subject is subsequently infected with *T. cruzi*, the vaccine is effective to prevent progression of the initial infection to a chronic disease state. As discussed in more detail hereinbelow, the vaccine can contain or encode a single immunogenic polypeptide or multiple immunogenic polypeptides. Methods for identifying nucleotide sequences encoding such polypeptides from a *T. cruzi* genomic library using, for example, expression library immunization (ELI) or DNA microarray analysis are described below.

Advantages of a Genetic Vaccine

The choice of polynucleotide delivery as an immunization technique offers several advantages over other vaccine or antigen delivery systems. Vaccines containing genetic material are favored over traditional vaccines because of the ease of construction and production of the vectors, the potential for modification of the sequences by site-directed mutagenesis to enhance the antigenic potency of the individual epitopes or to abolish epitopes that may trigger unwanted response, in the case of DNA vaccines, the stability of DNA, the lack of the dangers associated with live and attenuated vaccines, their ability to induce both humoral and cell mediated immunity and, in particular, $CD8^+$ T cell responses, and the persistence of the immune responses. Successful induction of humoral and/or cellular immune responses to plasmid-encoded antigens using various routes of gene delivery have been shown to provide partial or complete protection against numerous infectious agents including influenza virus, bovine herpes virus I, human hepatitis B virus, human immunodeficiency virus-1, as well as parasitic protozoans like *Plasmodium* and *Leishmania* (Donnelly et al., Ann. Rev. Immunol. 15:617-648, 1997). Representative papers describing the use of DNA vaccines in humans and primates include Endresz et al. (Vaccine 17:50-58, 1999), McCluskie et al. (Mol. Med. 5:287-300, 1999), Wang et al. (Infect. Immun: 66:4193-202, 1998), Le Borgne et al. (Virology 240:304-315, 1998), Tacket et al. (Vaccine 17:2826-9, 1999), Jones et al. (Vaccine 17:3065-71, 1999) and Wang et al. (Science 282(5388):476-80, 1998). The ability to enhance the immune response by the co-delivery of genes encoding cytokines is also well-established.

Polynucleotide Vaccine

The polynucleotide vaccine of the invention includes at least one, preferably at least two, nucleotide coding regions, each coding region encoding an immunogenic polypeptide component from *T. cruzi* as identified herein and/or using the screening method described herein. When it contains two or more nucleotide coding regions, the polynucleotide vaccine is referred to herein as a "multicomponent" polynucleotide vaccine. It is desirable to minimize the number of different immunogenic polypeptides encoded by the nucleotide coding regions in the polynucleotide vaccine; however, it is nonetheless contemplated that a polynucleotide vaccine that generates the highest level of protection will encode 10 or more immunogenic polypeptides.

The polynucleotide vaccine can contain DNA, RNA, a modified nucleic acid, or any combination thereof. Preferably, the vaccine comprises one or more cloning or expression vectors; more preferably, the vaccine comprises a plurality of expression vectors each capable of autonomous expression of a nucleotide coding region in a mammalian cell to produce at least one immunogenic polypeptide or cytokine, as further described below. An expression vector preferably includes a eukaryotic promoter sequence, more preferably the nucleotide sequence of a strong eukaryotic promoter, operably linked to one or more coding regions. A promoter is a DNA fragment that acts as a regulatory signal and binds RNA polymerase in a cell to initiate transcription of a downstream (3' direction) coding sequence; transcription is the formation of an RNA chain in accordance with the genetic information contained in the DNA. A promoter is "operably linked" to a nucleic acid sequence if it is does, or can be used to, control or regulate transcription of that nucleic acid sequence. The invention is not limited by the use of any particular eukaryotic promoter, and a wide variety are known; preferably, however, the expression vector contains a CMV or RSV promoter. The promoter can be, but need not be, heterologous with respect to the host cell. The promoter used is preferably a constitutive promoter.

A vector useful in the present invention can be circular or linear, single-stranded or double stranded and can be a plasmid, cosmid, or episome but is preferably a plasmid. In a preferred embodiment, each nucleotide coding region (whether it encodes an immunogenic polypeptide or a cytokine) is on a separate vector; however, it is to be understood that one or more coding regions can be present on a single vector, and these coding regions can be under the control of a single or multiple promoters.

There are numerous plasmids known to those of ordinary skill in the art useful for the production of polynucleotide vaccines. Preferred embodiments of the polynucleotide vaccine of the invention employ constructs using the plasmids VR1012 (Vical Inc., San Diego Calif.), pCMVI.UBF3/2 (S. Johnston, University of Texas) or pcDNA3.1 (INVITROGEN Corporation, Carlsbad, Calif.) as the vector. Plasmids VR1012 and pCMVI.UBF3/2 are particularly preferred. In addition, the vector construct can contain immunostimulatory sequences (ISS), such as unmethylated dCpG motifs, that stimulate the animal's immune system. Other possible additions to the polynucleotide vaccine constructs include nucleotide sequences encoding cytokines, such as granulocyte macrophage colony stimulating factor (GM-CSF), interleukin-12 (IL-12) and co-stimulatory molecules such B7-1, B7-2, CD40. The cytokines can be used in various combinations to fine-tune the response of the animal's immune system, including both antibody and cytotoxic T lymphocyte responses, to bring out the specific level of response needed to control or eliminate the T. cruzi infection.

The polynucleotide vaccine can also encode a fusion product containing the antigenic polypeptide and a molecule, such as CTLA-4, that directs the fusion product to antigen-presenting cells inside the host. Plasmid DNA can also be delivered using attenuated bacteria as delivery system, a method that is suitable for DNA vaccines that are administered orally. Bacteria are transformed with an independently replicating plasmid, which becomes released into the host cell cytoplasm following the death of the attenuated bacterium in the host cell.

An alternative approach to delivering the polynucleotide to an animal involves the use of a viral or bacterial vector. Examples of suitable viral vectors include adenovirus, polio virus, pox viruses such as vaccinia, canary pox, and fowl pox, herpes viruses, including catfish herpes virus, adenovirus-associated vector, and retroviruses. Exemplary bacterial vectors include attenuated forms of *Salmonella, Shigella, Edwardsiella ictaluri, Yersinia ruckerii,* and *Listeria monocytogenes*. Preferably, the polynucleotide is a vector, such as a plasmid, that is capable of autologous expression of the nucleotide sequence encoding the immunogenic polypeptide.

Preferably, the polynucleotide vaccine further includes at least one nucleotide coding region encoding a cytokine. Preferred cytokines include interleukin-12 (IL-12), granulocyte-macrophage colony-stimulating factor (GM-CSF), interleukin-6 (IL-6), interleukin-18 (IL-18), γ-interferon, α,β(3-interferons, and chemokines. Especially preferred cytokines include IL-12 and GM-CSF.

Plasmids and other delivery systems are made using techniques well-known in the art of molecular biology. The invention should be understood as including methods of making and using the polynucleotide vaccine.

Polypeptide Vaccine

The polypeptide vaccine of the invention includes at least one, preferably at least two, immunogenic polypeptides from T. cruzi as described herein and/or as identified using the screening method described herein. As with the polynucleotide vaccine, it is desirable to minimize the number of different immunogenic polypeptides supplied in the vaccine; however, it is nonetheless contemplated that a polypeptide vaccine that generates the highest level of protection will contain 10 or more immunogenic polypeptides.

Because a $CD8^+$ T cell response cannot normally be directly triggered by the administration of a conventional protein subunit vaccine, the immunogenic polypeptides contained in the polypeptide vaccine preferably include one or more membrane transporting sequences (MTS) fused to their N-terminus or C-terminus or both. A membrane transporting sequence allows for transport of the immunogenic polypeptide across a lipid bilayer, allowing it to be delivered to the inside of a mammalian cell. In a particularly preferred embodiment, the immunogenic polypeptides are shocked with urea, as described further in Example VIII, prior to administration as a vaccine. From there, portions of the polypeptide can be degraded in the proteasome, and the resulting peptides can be displayed as class I MHC-peptide complexes on the cell surface. In this way, a polypeptide vaccine can stimulate a CD8+ T cell immune response. In another preferred embodiment, the immunogenic polypeptides are attached to nanoparticles and administered to a subject (e.g., Plebanski et al., J. Immunol. 2004, 173:3148; Plebanski et al., Vaccine, 2004, 23:258). A polypeptide vaccine of the invention is optionally adjuvanted using any convenient and effective adjuvant, as known to one of skill in the art.

The invention should be understood as including methods of making and using the polypeptide vaccine.

Pharmaceutical Compositions

The polynucleotide and polypeptide vaccines of the invention are readily formulated as pharmaceutical compositions for veterinary or human use. The pharmaceutical composition optionally includes excipients or diluents that are pharmaceutically acceptable as carriers and compatible with the genetic material. The term "pharmaceutically acceptable carrier" refers to a carrier(s) that is "acceptable" in the sense of being compatible with the other ingredients of a composition and not deleterious to the recipient thereof. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, salts, and/or adjuvants which enhance the effectiveness of the immune-stimulating composition. Methods of making and using such pharmaceutical compositions are also included in the invention.

Administration of the Polynucleotide Vaccine

The polynucleotide vaccine of the invention can be administered to the mammal using any convenient method, such as intramuscular injection, topical or transdermal application to the mammal's skin, or use of a gene gun, wherein particles coated with the polynucleotide vaccine are shot into the mammal's skin. The amount of polynucleotide administered to the mammal is affected by the nature, size and disease state of the mammal as well as the delivery method; for example, typically less DNA is required for gene gun administration than for intramuscular injection. Further, if a polynucleotide encoding a cytokine is co-delivered with nucleotide coding regions encoding the immunogenic polypeptide from T. cruzi, the amount of polynucleotide encoding the immunogenic polypeptide from T. cruzi in the vaccine is optionally reduced.

Hundreds of publications have now reported the efficacy of DNA vaccines in small and large animal models of infectious diseases, cancer and autoimmune diseases (Donnelly et al., Rev. Immunol. 15:617, 1997). Vaccine dosages for humans can be readily extended from the murine models by one skilled in the art of genetic immunization, and a substantial literature on genetic immunization of humans is now available to the skilled practitioner. For example, Wang et al. (Science 282:476-480, 1998) vaccinated humans with plasmid DNA encoding a malaria protein, and the same group has developed a plan for manufacturing and testing the efficacy of a multigene *Plasmodium falciparum* liver-stage DNA vaccine in humans (Hoffman et al., Immunol. Cell Biol. 75:376, 1997). In general, the polynucleotide vaccine of the invention is administered in dosages that contain the smallest amount of polynucleotide necessary for effective immunization. It is typically administered to human subjects in dosages containing about 20 μg to about 2500 μg plasmid DNA; in some instances 500 μg or more of plasmid DNA may be indicated. Typically the vaccine is administered in two or more injections at time intervals, for example at four week intervals.

Administration of the Polypeptide Vaccine.

Like the polynucleotide vaccine, the polypeptide vaccine can be administered to the mammal using any convenient method, such as intramuscular or intraperitoneal injection, topical administration, oral or intranasal administration, inhalation, perfusion and the like. The amount of polypeptide administered to the mammal is affected by the nature, size and disease state of the mammal, as well as by the delivery method. Intraperitoneal injection of 25 to 50 ug of polypeptide containing a membrane transducing sequence has been shown to result in import of the protein into nearly 100% of murine blood and spleen cells within 20 minutes (Schwarze et al., Science 285:1569-1572, 1999) and the sensitization of cytotoxic T cells (Schutze-Redelmeier et al., J. Immunol. 157:650-655, 1996). Useful dosages of the polypeptide vaccine for humans can be readily determined by evaluating its activity in vivo activity in mice.

Administration of a Combination of Polynucleotide Vaccine and Polypeptide Vaccine.

The invention contemplates administration of both a polynucleotide vaccine and a polypeptide vaccine to a mammal in a serial protocol. For example, a plasmid-based DNA vaccine may be administered to a mammal to "prime" the immune system, followed by the one or more administrations of a polypeptide vaccine or a viral vaccine (e.g., vaccinia vector carrying the genes that encode the immunogenic polypeptides and, optionally, cytokines) to further stimulate the mammal's immune system. The order of administration of the different types of vaccines, and the nature of the vaccines administered in any given dose (e.g., polypeptide vaccine, plasmid vaccine, viral vector vaccine) can be readily determined by one of skill in the art to invoke the most effective immune response in the mammal.

Screening Method for Identification of Antigenic *T. cruzi* Polypeptides

In another aspect, the invention provides high-throughput method to screen putative *T. cruzi* polypeptides for diagnostic potential. The antigenic polypeptides thus identified can be incorporated into a diagnostic test for *T. cruzi* as described herein.

*T. cruzi* polypeptides that are preferred candidates for screening, either individually or as part of a pool, have one or more of the following characteristics or features. The *T. cruzi* polypeptides may be abundant in the trypomastigote and/or amastigote stages of the *T. cruzi* life cycle in mammals, as described in more detail above. Additionally or alternatively, the *T. cruzi* polypeptides may be, or may be likely to be, surface-associated or secreted. Surface associated-antigenic polypeptides include, for example, *T. cruzi* proteins that are anchored to the plasma membrane by glycosylphosphotidylinositols, or GPIs, and those that have transmembrane domains or are otherwise embedded in the plasma membrane. This property can be evaluated, for example, by analyzing the polypeptide sequence for the presence of an N-terminal leader sequence which directs the polypeptide to the cell membrane; by analyzing the polypeptide sequence for the presence of a known GPI sequence that facilitates attachment of the polypeptide to the cell surface; and/or by analyzing the polypeptide sequence for the presence of a transmembrane domain. Another preferred feature is that the polypeptide is unique to *T. cruzi* and not expressed in other organisms, including other kinetoplastids. This can be determined by performing BLAST searches of GenBank entries for other organisms and/or comparative genomics with *T. brucei* and *Leishmania major*. This feature enhances the specificity of the diagnostic test.

Another preferred feature is that the *T. cruzi* polypeptide be one that is less likely than others to be highly variant. For example, members of large gene families that appear to undergo rearrangements that create new variants are generally not preferred. However, pools of large gene family members (such as the trans-sialidase family, the Mucin-assocated surface protein (MASP) family, and other smaller families of genes can be cloned and tested using degenerate primers. In that case, rather than a bead or a spot in the diagnostic test containing only one gene family member, it may have ten or hundreds, thereby circumventing the problem of recombination and variation in these families, and providing a better representation of the family than a single (possibly variant) protein.

The screening method involves providing two substrates that include a plurality of individually addressable candidate antigens derived from *T. cruzi*, in which the antigens present on both substrates are substantially the same. A substrate, as defined herein, is a surface of unreactive material that can be used to contain the individually addressable candidate antigens in isolation from one another. For example, a multi-welled array system such as a 96 well microplate is a substrate useful in the method of screening for serodiagnostic *T. cruzi* antigens. Individually addressed candidate antigens refers to potentially serodiagnostic *T. cruzi* antigens that have been positioned and/or labeled in such a way that differing antigens can be discretely identified using methods known to those skilled in the art. For example, antigens obtained directly or indirectly from *T. cruzi*, labeled with a fluorescent label with a different wavelength sensitivity from other fluorescent labels used with other antigens and positioned within a specific well or set of wells on a multi-welled array system, are individually addressed candidate antigens.

Candidate antigens immobilized on the first substrate are contacted with a body fluid from an organism known to be positive for *T. cruzi* infection based on a detection method such as a T cell assay, polymerase chain reaction (PCR), hemoculture or xenodiagonstic techniques. The organism is preferably a mammal, more preferably a dog or a human. Preferably, the organism exhibits negative serology when tested for *T. cruzi* infection utilize conventional serodiagnostic tests that rely on antigens from either whole to semi-purified parasite lysates, for example from epimastigotes, that react with anti-*T. cruzi* IgG antibodies.

Candidate antigens immobilized on the first substrate are contacted with the second substrate with a body fluid from an organism known or reasonably believed to be unexposed to *T. cruzi* infection. The second substrate serves as a control. The organism does not exhibit a strong positive serological signal indicating infection by *T. cruzi*. Preferably, the organism shows no evidence of *T. cruzi* infection by any other diagnostic test as well. Optionally, the screening method includes testing of additional substrates using body fluids that are strongly, weakly and/or borderline seropositive using conventional tests for *T. cruzi*, as described in more detail below.

The body fluid may be any fluid found within the body of an organism that is capable of containing components of *T. cruzi* or immune system components prepared in response to exposure to *T. cruzi*. For example, an immune system component may be an antibody that specifically binds to a *T. cruzi* antigen. Such body fluids include, for example, blood, plasma, serum, urine, saliva, tears, lymphatic fluid, and the like.

The organism itself may be any organism that can be infected by *T. cruzi*, including vector organisms. For example, organisms may include insect vectors of Chagas disease belonging to the Hemiptera order, Reduviidae family, and Triatominae subfamily. The organism can also be a vertebrate reservoir of *T. cruzi* infection. Mammals are most susceptible to infection with *T. cruzi*, with approximately 150 species known to serve as reservoirs. Birds, amphibians, and reptiles are naturally resistant to infection. In the domestic cycle, frequently infected mammals, besides humans, are dogs, cats, mice, rats, guinea pigs, and rabbits. Pigs, goats, cattle, and horses can be infected by *T. cruzi*, but generally only manifest transitory parasitemia. Humans are a preferred organism due to the importance of diagnosing *T. cruzi* infection in humans.

Antigens that exhibit binding to antibodies present in the bodily fluid contacted with the first substrate but little or no binding to antibodies present in the control bodily fluid contacted with the second substrate are identified as antigenic *T. cruzi* polypeptides for use in the multicomponent diagnostic assay. The binding of an antigen to an antibody can be detected by various means known to those skilled in the art. For example, the association may be detected using flow cytometry, or by enzyme immunoassay (EIA) or enzyme-linked immunoassay (ELISA). Preferably, the association of one or more antibodies with multiple antigens is detected using a multiplex analysis system such as the BIO-PLEX multiplex analysis system commercially available from, for example, Bio-Rad® Laboratories (Hercules, Calif.).

The BIO-PLEX suspension array system is a biomarker assay system that includes a flow-based 96-well fluorescent microplate assay reader integrated with specialized software, automated validation and calibration protocols, and assay kits. The multiplex analysis system utilizes up to 100 fluorescent color-coded bead sets, each of which can be conjugated with a different specific antigen. The term “multiplexing” refers to the ability to analyze many different antigens essentially simultaneously. To perform a multiplexed assay, sample and reporter antibodies are allowed to react with the conjugated bead mixture in microplate wells. The constituents of each well are drawn up into the flow-based BIO-PLEX array reader, which identifies each specific reaction based on bead color and quantitates it. The magnitude of the reaction is measured using fluorescently labeled reporter antibodies specific for each antibody that may associate with the antigen being tested.

The BIO-PLEX suspension array system uses a liquid suspension array of about 100 sets of micrometer-sized beads, each internally dyed with different ratios of two spectrally distinct fluorophores to assign it a unique spectral address. The overall operation of the BIO-PLEX array system is illustrated in FIGS. 1A through 1C. As shown in FIG. 1A, polypeptide antigen 10 is bound to a microsphere bead 20 by, for example, a histidine tag. The polypeptide antigen 10 is then contacted with a sample of sera containing an antibody; for example, an anti-*T. cruzi* antibody 30. This antibody, in turn, is contacted with a fluorescently labeled reporter antibody 40 to form a microsphere-antigen-antibody complex 50. As shown in FIG. 1B, since the microsphere beads 20 provide a large variety of different colors, and the microsphere beads 20 were earlier attached only to specific polypeptide antigens 10, a number of microsphere-antigen-antibody complexes 50 may be present in a microplate well 60. The complexes 50 are then run through a flow cytometry apparatus 70 that includes a classifying laser 70 and a reporting laser 80. The reporting laser 80 determines the amount of a particular antigen present, based on the amount of fluorescently labeled reporter antibody 40. The classifying laser 90, on the other hand, determines the frequency of fluorescence provided by the microsphere bead 20, and based on this frequency, the identity of the polypeptide antigen 10 can be determined.

In the embodiment used in this invention, the BIO-PLEX assay utilizes dyed beads containing nickel to capture the His-tagged *T. cruzi* polypeptides produced in the host bacterial cells. Each spectrally addressed bead captures a different protein. The protein-conjugated beads are allowed to react with a sample, and biomolecules in the sample (typically antibodies) bind to the bound protein antigens as further described in the Examples.

It should be understood that the invention is not limited to multiplexing as employed in the BIO-PLEX assay; other multiplexed approaches can readily be used. For example, protein arrays can be placed on a matrix, and the response to the individual proteins on the solid-phase array can be assayed.

An important advantage of using a multiplexed method is that a plurality of serodiagnostic antigens may be identified during a single run of the analysis. For example, serological responses to as many as a 100 individual proteins can be screened at one time, and the pattern of responsiveness to all 100, or any subset thereof, can be used to make or assist in making a diagnosis. Tests in current use employ crude antigen preparations from *T. cruzi* itself (an undefined composition thus not very reproducible), or utilize an individual recombinant protein (i.e., a single target thus not very robust) or a string of three portions of three different proteins combined in one synthetic protein. In the latter case, there is more than one target, but still the response to only a single entity is measured, thus the assay lacks robustness.

Optionally, the method of the invention can utilize more than two substrates that include a plurality of individually addressed candidate antigens. These additional substrates can be used, for example, to evaluate the body fluids from organisms classified as providing a very high positive sera response, intermediate positive sera response, very low positive sera response or a borderline positive sera response. When used to supplement data obtained on sera from control (uninfected) organisms and organisms that are or have been infected but show little or no positive serological response, these substrates can provide additional information on candidate *T. cruzi* antigens that may be used as serodiagnostic antigens. Measuring the pattern of responses to many antigens is also useful for evaluating other aspects of the *T. cruzi* infection such as the stage of the disease, its severity, or the particular strain of *T. cruzi* involved.

The method of screening for serodiagnostic *T. cruzi* antigens can also be done at the less specific level of an antigen pool, rather than specific antigens. An antigen pool, as defined herein, is a plurality of antigens in a mixture. Antigen pools may be used either as a means of evaluating a wide number of antigens more rapidly, as a means of evaluating mixtures of antigens for possible interactions, or simply out of necessity when the identify of specific antigens is not known. The method of screening antigen pools can be done either as an independent analysis method, or it may be an optional preliminary step to the screening of individual *T. cruzi* antigens for potential as serodiagnostic antigens. In either case, the method of analyzing antigen pools includes providing two substrates that include a plurality of individually addressable antigen pools derived from *T. cruzi*, where the antigen pools present on the two substrates are substantially the same. The first substrate is then contacted with a body fluid from an organism known to be serologically positive for *T. cruzi* infection, while the second substrate is then contacted with a body fluid from an organism known to be not serologically positive for *T. cruzi* infection. Antigen pools that associate with an antibody present in the body fluid from an organism known to be serologically positive but that are absent or present to a lesser degree in the body fluid of an organism known to be not serologically positive for *T. cruzi* infection are thereby identified as serodiagnostic antigen pools that may be used by themselves or further evaluated to determine that specific antigens involved.

The candidate antigens derived from *T. cruzi* that are screened by the method of the invention can include antigens formed from polypeptides, polysaccharides, polynucleotides, or other substances present in *T. cruzi* that are capable of being specifically bound by antibodies. As polypeptides are known by those skilled in the art to be the most common and diverse antigens, the method of the invention preferably identifies polypeptide antigens. Polypeptide antigens can be obtained directly from *T. cruzi* using biochemical separation technology, particularly protein purification methods. More preferably, the polypeptide antigens are obtained using recombinant DNA technology. Using recombinant DNA technology, nucleotide sequences from *T. cruzi* are inserted into a host organism where they are used to direct product of a polypeptide that may contain one or more antigens that may be detected by the screening method.

The smallest useful peptide sequence contemplated to provide an antigen is generally on the order of about 6 amino acids in length. Thus, this size will generally correspond to the smallest polypeptide antigens that are screened for by the method of the invention. It is proposed that short peptides that incorporate a species-specific amino acid sequence will provide advantages in certain circumstances, for example, in the preparation of vaccines or for use in methods of detecting *T. cruzi*. Exemplary advantages of shorter peptides include the ease of preparation and purification, and the relatively low cost and improved reproducibility of production. However, the size of polypeptide antigens may be significantly larger. Longer polypeptide antigens identified by the method may be on the order of 15 to 50 amino acids in length, or may represent an entire protein, including modified proteins such as fusion proteins.

Preparation of the polypeptide antigens will generally include the use of an expression vector. An expression vector is a cloning vector that contains the necessary regulatory sequences to allow transcription and translation of a cloned gene or genes. An expression vector preferably includes a promoter sequence operably linked to one or more coding regions. A promoter is a DNA fragment that acts as a regulatory signal and binds RNA polymerase in a cell to initiate transcription of a downstream (3' direction) coding sequence; transcription is the formation of an RNA chain in accordance with the genetic information contained in the DNA. A promoter is "operably linked" to a nucleic acid sequence if it is does, or can be used to, control or regulate transcription of that nucleic acid sequence. The invention is not limited by the use of any particular promoter. A wide variety of promoters are known by those skilled in the art.

A vector useful in the present invention can be circular or linear, single-stranded or double stranded and can be a plasmid, cosmid, or episome but is preferably a plasmid. In a preferred embodiment, each nucleotide coding region encoding an antigenic polypeptide is on a separate vector; however, it is to be understood that one or more coding regions can be present on a single vector, and these coding regions can be under the control of a single or multiple promoters.

There are numerous expression vectors known to those of ordinary skill in the art useful for the production of polypeptide antigens. A preferred expression vector is an expression vector formed using the GATEWAY cloning method. The GATEWAY cloning method is a universal cloning technique that allows transfer of DNA fragments between different cloning g vectors while maintaining the reading frame, and has effectively replaced the use of restriction endonucleases and ligases. The steps involved in the GATEWAY cloning method are shown in FIG. 2. First, a gene is selected for cloning. For the present invention, this would be a gene selected from *T. cruzi*. The gene is then provided with primers and amplified using PCR technology with the help of an attB tagged primer pair, as readily practiced by those skilled in the art. The PCR fragment then combined with a donor vector (pDONR™) that includes attP sites to provide an entry clone, using the BP reaction. An integration reaction between the attB and the attP sites combines the PCR fragment with the donor vector. The resulting entry clone contains the gene of interest flanked by attL sites. The LR reaction is then used to combine the entry clone with a destination vector to produce an expression vector. In the LR reaction, a recombination reaction is used to link the entry clone with the destination vector (pDEST™) using the attL and attR sites and a CLONASE enzyme. The attL sites are already found in the entry clone, while the destination vector includes the attR sites. The LR reaction is carried out to transfer the sequence of interest into one or more destination vectors in simultaneous reactions, making the technology high throughput. For example, as this method allows multiple genes to be transferred to one or more vectors in one experiment, this method readily allows multiple antigenic polypeptides to be prepared that can then be screened by the method of the invention, potentially revealing a plurality of serodiagnostic antigens.

The *T. cruzi* genes are cloned into expression vectors, as described, which are then expressed in a host cell, such as a bacterial cell, yeast cell, insect cell, protozoan call, or mammalian cell. A preferred host cell is a bacterial cell, for example an *E. coli* cell. Another preferred cell is a protozoan cell, more preferably a kinetoplastid cell, most preferably a *Crithidia* cell (U.S. Pat. No. 6,368,827; Apr. 9, 2002). Proteins are isolated from the host cell, purified, and analyzed. Preferably, the proteins are purified onto beads that are then used in a Bio-Plex assay; as described. Various serum samples (e.g., negative, mildly positive, strongly positive) can be efficiently screened for reactivity with a large number of gene products to identify those gene products that are associated with *T. cruzi* infection, for example those indicative of the existence of and, optionally, the extent and/or stage of *T. cruzi* infection. Typically, the identified antigens elicit an antibody response *T. cruzi* in a mammal. The genes and gene products thus identified are useful in diagnostic assays for *T. cruzi.*

The Examples that follow provide representative data from a screening of more than 350 *T. cruzi* gene products. Following FIGS. 4-6 in the Examples, a procedure including a preliminary screening of antigen pools, followed by screening for specific antigens, is described. Four different substrates were used to provide data for the reactivity of the antigens in sera with various levels of reactivity to *T. cruzi* antigens. One pool, labeled "3K" on FIG. 4D, was selected for further analysis because it showed good reactivity with the positive sera. The "3K" pool was broken down into individual constituent gene products, and four of the gene products (antigens) were identified as potential candidates for diagnostic use. The "top" antigens identified this way can be combined into a single, robust diagnostic assay for *T. cruzi*; see, for instance, Example 9. Examples of gene products identified in accordance with the invention are also described.

The method of screening is also capable of identifying antigens that do not consistently elicit a strong B cell response. The majority of conventional and commercially available serological methods for diagnosis and blood screening of *T. cruzi* infection utilize either crude or semi-purified parasite lysates typically from epimastigotes. However the complex nature of molecules in these lysates creates a test that routinely gives false positive diagnosis. Research to improve serological diagnosis techniques has focused on the identification, characterization and cloning of particular *T. cruzi* antigens that elicit a strong B cell response. Experiments have demonstrated that some individuals declared negative by current serological tests in fact respond to parasite lysate by producing IFN-gamma in ELISPOT assays. These individuals therefore have T cells that have been exposed to parasite antigen but have a poor B cell antibody response to the antigens in the serological tests that use parasite lysate. The present invention is capable of detecting components present in the sera of such individuals, as shown in FIG. 6.

It is to be understood that other screening methods are applicable to the identification of antigenic *T. cruzi* polypeptides to be included in the multicomponent panel for the diagnostic test. For example, U.S. Pat. No. 6,875,584, issued Apr. 5, 2005, describes screening methods that can be used to identify additional antigenic *T. cruzi* polypeptides for use in a diagnostic test and/or as vaccine components. As another example, a nickel-coated substrate, such as a nanoparticle array, can be used to immobilize His-tagged candidate antigens which can then be contacted with serum or other blood product (in the case of the serodiagnostic test) or MHC-peptide complexes (in the case of the cellular test) to detect evidence of an immune response in the serum.

It is to be understood that any of the diagnostic, therapeutic or laboratory methods described herein can be performed with one or more protein antigens as set forth in Table 1, Table 3 and/or Table 4 herein; or as elsewhere described in the specification.

The present invention is illustrated by the following examples. It is to be understood that the particular examples, materials, amounts, and procedures are to be interpreted broadly in accordance with the scope and spirit of the invention as set forth herein.

EXAMPLES

The majority of current serological tests for *T. cruzi* infection utilize whole to semi-purified parasite lysates and are often inconclusive or result in false positives. Recent studies have identified individuals who are seronegative for *T. cruzi* infection by standard tests but are positive by PCR (Salomone et. al. Emerg. Infect. Disease, 2003, 9:1558) or have demonstrable cellular immune responses to *T. cruzi*. With respect to the latter, our lab has recently demonstrated that some individuals declared negative by current serological tests in fact have demonstrable T cell responses to parasite lysate as seen in ELISPOT assays. These individuals therefore have T cells which have been exposed to parasite antigen but have a poor B cell antibody response to the mix of antigens in the serological test. It is apparent that the use of lysates is a poor test for *T. cruzi* infection and we expect that screening with multiple recombinant proteins will be able to reduce the number of false positives, and more importantly false negatives.

We have therefore developed a high-throughput method to screen large numbers of recombinantly expressed *T. cruzi* proteins for their serodiagnosis potential. Specifically, we combined a set of putative *T. cruzi* genes cloned into the GATEWAY with the BIO-PLEX LIQUICHIP bead technology to screen large numbers of recombinantly expressed proteins for their antigenicity using only a small volume of sample (<100 µl). So far, we have produced 34 pools of approximately 10 proteins each and screened them for antigenicity. From the preliminary testing, 11 pools were found to bind readily detectable amounts of antibodies in the sera of *T. cruzi*-infected subjects. These pools were then broken down and each gene was expressed individually and tested. From these 81 genes we have been able to define more than 15 proteins with serodiagnostic potential.

Our method utilizes a blind screening process that has identified several known antigens as well as previously unidentified antigenic proteins from within pools containing multiple non-antigenic proteins. The use of the BIO-PLEX technology is not limited to antigen screening but its full potential may be realized as a novel method of blood donor screening. The highly antigenic proteins we discovered, and expect to continue to discover, with this method can be used to create a highly sensitive and specific test for *T. cruzi* infection.

Example 1

Buffer and Medium Preparation

A variety of buffers were used in the BIO-PLEX multiplex analysis. The buffers were prepared as follows. To prepare 1 liter of PBS/BSA (10 mM $NaH_2PO_4$, 150 mM NaCl, and 0.1% (w/v) BSA), 8.77 g NaCl (MW 58.44 g/mol) and 1.4 g $NaH_2PO_4$—$H_2O$ (MW 137.99 g/mol) were dissolved in 900 ml $H_2O$ and the pH was adjusted to 7.4 using NaOH. Then, dissolve 1 gram of BSA and adjust the volume to 1 liter. Before use, filter the buffer using a 0.45 µM filter. Sodium Azide should be added to 0.5% when storing the PBS/BSA buffer for long term. Azide should not be used with Carboxy Beads.

To prepare 1 liter of coupling buffer (50 mM MES), 11.67 g MES (MW 233.2 g/mol) was dissolved in 900 ml $H_2O$ and the pH was adjusted to 5.0 using NaOH. The volume was then adjusted to 1 liter using additional $H_2O$. Before use, the buffer should be filtered using a 0.45 µM filter.

To prepare 1 liter of activation buffer (100 mM $NaH_2PO_4$), 13.80 g $NaH_2PO_4$—$H_2O$ (MW 137.99 g/mol) was dissolved in 900 ml $H_2O$ and the pH was adjusted to 6.3 using NaOH. The volume was then adjusted to 1 liter using additional $H_2O$. Before use, the buffer should be filtered using a 0.45 µM filter.

To prepare Buffer Z, 8 M urea, 20 mM Hepes, and 100 mM NaCl are combined and dissolved in deionized water to form a solution. The pH of the solution is adjusted to 8.0, and the solution is filtered through a 0.45 µm filter and stored at room temperature. Imidazole (the side chain molecule in histidine) is added to Buffer Z at varying concentrations to either prevent the cobalt resin from binding non-specifically to something other than the histidine tag, or to out-competing the binding of the histidine tag and thus causing the protein to elute off the resin.

To prepare LB (*Luria-Bertani*) Medium, 10 g tryptone, 5 g yeast extract, and 10 g. NaCl were dissolved in 1 L deionized water and autoclaved for 25 minutes. For plates, 15 grams of agarose were also dissolved into the water prior to autoclaving.

Example 2

Production of Protein Pools or Individual Proteins

To provide a large set of *T. cruzi* proteins, over 350 proteins in pools of approximately 10 proteins each were prepared. The proteins were prepared using the GATEWAY universal cloning technique developed by INVITROGEN. The procedure can be carried out by cloning a pool of several genes together, which results in a pool of proteins, or by cloning an individual gene, resulting in the preparation of an individual protein. For preparation of an individual protein, a gene that codes for a desired *T. cruzi* protein is first selected for cloning. This gene is amplified from *T. cruzi* genomic DNA using gene specific primers flanked by lambda phage recombination sites, attB1 (5') and attB2 (3') and polymerase chain reaction. Gel purification of the att-flanked PCR produced was carried out by separating the PCR reaction product on a 1% agarose gel using electrophoresis. The particular gene is identified by comparison with a DNA standard containing bands of known size. The band of the gene of interest is cut out of the gel and purified using Sigma-Aldrich's GenElute Minus EtBr Spin Columns (Catalog No. 5-6501).

The GATEWAY BP reaction is then used to insert the att-flanked *T. cruzi* gene fragment with a pDONR™201 vector (Catalog No. 11798-014, INVITROGEN Corp., Carlsbad, Calif.). The BP reaction is conducted by adding the 5 μl of gel-purified attB-flanked PCR product (40-100 fmoles), 1 μl of the pDONR™201 vector (supercoiled, 150 ng/μl), and 2 μl 5×BP CLONASE Reaction Buffer (Catalog No. 11789-013) to obtain a final volume of 8 μl. The BP CLONASE enzyme mix (Catalog No. 11789-013, INVITROGEN Corp., Carlsbad, Calif.) is mixed gently, and then 2 μl of the enzyme mix was added to the BP reaction mixture and mixed well. The reaction was then incubated at (room temperature) 25° C. overnight. Next, 1 μl of Proteinase K solution (Catalog No. 11789-013, INVITROGEN Corp., Carlsbad, Calif. 2 μg/μl) was added, and the mixture was allowed to incubate for 10 minutes at 37° C. Five microliters of the BP reaction are transformed by heat shock into chemical competent DH5α cells and grown up overnight at 37° C. shaking at 280 RPM in 5 mL of LB with 50 mg/L kanamycin to select for pDONR201-transformed cells. The plasmid is then purified from the culture using a QIAprep Spin Miniprep Kit (Catalog No. 27106, Qiagen Inc., Valencia, Calif.).

For the next step of protein production, the GATEWAY recombination reaction was used to insert the gene of interest in pDONR201 into a destination vector to provide the final expression clone. The destination vector in this case is a modified version of INVITROGEN's pRSET (Catalog No. V351-20), called pDEST-PTD4. First, the pDEST-PTD4 was linearized by restriction digest of a novel site (PvuII) within the cell death cassette. The linearized plasmid was purified using QIAquick Gel Extraction Kit (Catalog No. 28207, Qiagen Inc., Valencia, Calif.). The LR reaction between the gene of interest in the pDONR™201 vector and the desired pDEST-PTD4 expression vector was then set up. First, 300 ng of the pDONR entry clone (prepared above), 300 ng of linearized pDEST-PTD4 (INVITROGEN Corp., Carlsbad, Calif.), and 2 μl LR CLONASE Reaction Buffer (Catalog No. 11791-019, INVITROGEN Corp., Carlsbad, Calif.), 2 μl LR CLONASE Enzyme Mix, and deionized water are combined to obtain a final volume of 10 μl and mixed thoroughly by flicking the tube. The reaction was then incubated overnight at 25° C. Next, 2 μl proteinase K solution (2 μg/μl) was added and the mix was allowed to incubate for 10 minutes at 37° C. DH5α cells were then transformed by heat shock with 6 μl of LR reaction products, and plated onto LB agar plates containing 150 mg/L ampicillin and incubated overnight at 37° C. to select for ampicillin-resistant expression clones.

Next, all of the colonies were scraped clean with a clean sterile spatula, and used to inoculate a tube of 5 mL LB containing 150 mg/L ampicillin, and grown overnight at 37° C., 280 RPM. The pDEST-PTD4 containing the gene of interest is purified from the culture using a QIAprep Spin Miniprep Kit (Catalog No. 27106, Qiagen Inc., Valencia, Calif.). The miniprep preparation should contain copies of each gene of the pool from the desired pDEST vector. Three microliters of purified pDEST-PTD4 containing the gene of interest was then transformed into BL21(DE3)pLysS chemical competent cells. The culture was then directly inoculated into 10 ml LB/ampicillin (Amp)/chloramphenicol (CAM) (100 mg/L)/(34 mg/L) and grown overnight, shaking at 37° C. at 280 RPM.

On the fifth day, a 10 ml starter culture was inoculated into 500 ml LB/Amp/CAM and grown to an OD600 of 0.4. Protein expression was then induced with 0.3 mM concentration of IPTG (isopropyl-β-D-thiogalactopyranoside), using 150 μl of 1M IPTG in 500 ml culture. The cells were spun down at 5,000 rpm for 8 minutes and 10 mL Buffer Z (8M urea, 20 mM Hepes, 100 mM NaCl) containing 15 mM imidazole was added. The cells were then sonicated three times for 25 seconds at an amplitude of 40. The samples were spun down at 13,000 rpm for 10 minutes and the supernatant is combined with 1 ml settled BD TALON™ Metal Affinity Resin (BD Biosciences Clontech, Catalog No 635502) and rocked overnight at 4° C.

The resin/cell lysate slurry is then placed into an empty 0.8×4 cm chromatography column and the resin bed is allowed to settle. The liquid was allowed to run through and the resin bed was washed with 10 bed volumes (10 mL) of Buffer Z containing 15 mM imidazole. Once the 10 mL wash has run through, the His-tag protein was eluted with 3 bed volumes (3 mL) of Buffer Z containing 250 mM imidazole. The resulting sample contained the purified protein of interest. The sample was then desalted into Buffer Z (without imidazole) using a PD-10 desalting column (Amersham Biosciences, Catalog No. 17-0851-01). The resulting imidazole-free sample is quantified and diluted to a concentration of 10 μg/mL which is ready to be used to bind to BIO-PLEX beads for testing.

Example 3

Preparation of BIO-PLEX Beads

LIQUICHIP Ni-NTA beads (Qiagen Inc., Valencia, Calif.) were used to bind His-tagged purified proteins in the BIO-PLEX assay, but had to be prepared before use. First, the protein samples were desalted into Buffer Z that does not contain Imidazole using Amersham PD-10 desalting columns (Amersham Biosciences Corp, Piscataway, N.J.). The protein was then quantified using a BCA assay and diluted to a concentration of 10 μg/ml with Buffer Z. The LIQUICHIP Ni-NTA Bead stock was then vortexed for 30 seconds at full speed. Next, 50 µl of bead suspension was pipetted out and placed into a 1.5 ml microcentrifuge tube. His-tagged protein dilution (50 µl) was then added to the 50 µl LIQUICHIP Bead suspension. The beads were then incubated at 4° C. in the dark from at least 4 hours to overnight. Buffer (900 µl PBS/BSA (10 mM $NaH_2PO_4$, 150 mM NaCl, 0.1% BSA pH 7.4)) was then added to the protein-coupled LIQUICHIP Bead suspension, adding 0.5% azide as a preservative.

Example 4

Preparation of Positive Controls

Positive and negative controls were used in the BIO-PLEX analysis of *T. cruzi* antigens. The positive control consists of proteins from a *T. cruzi* lysate coupled to LIQUICHIP Carboxy Beads. The beads thus contain a mix of *T. cruzi* proteins bound to their surface, and function as a general antigen mix. The LIQUICHIP Carboxy Beads bind to the proteins in a random manner, forming covalent bonds to amine groups in lysine side chains. The first step in the preparation of positive controls was the activation of Carboxy Beads using EDC/NHS. First, approximately 10 mg each of EDC (N-(3-dimethylaminopropyl)-N'-ethylcarbodiimide (Fluka catalog No. 03449)) and NHS (N-hydroxysulfosuccinimide (Fluka catalog No. 56485)) were weighed into two microcentrifuge tubes. The LIQUICHIP CarboxyBead suspension (1 ml) was then centrifuged for 5 minutes at 10,000 rpm in a microcentrifuge. The supernatant was removed with a 200 µl pipette and discarded. The beads were then washed twice by adding 80 µl of activation buffer and centrifuged for 5 minutes at 10,000 rpm. The supernatant was then carefully removed. Activation buffer (80 µl) was then added to the bead pellet at the bottom of the tube. The pellet should not be resuspended. The pellet in activation buffer was then vortexed for at least 2 minutes. De-ionized water was then added to the weighed EDC and NHS aliquots to provide solutions with a concentration of 50 mg/ml. NHS solution (10 µl) and EDC solution (10 µl) were then added to the bead suspension, which was then incubated for 20 minutes in the dark. Finally, the beads were centrifuged for 5 minutes at 10,000 rpm, after which the supernatant was removed and discarded.

The activated beads were then coupled to the *T. cruzi* lysate. First, the *T. cruzi* pellet was freeze/thawed about 5 times. Insoluble particles were removed by centrifugation. The protein stock was then diluted with coupling buffer to a concentration of 100 µg/ml and a volume of 500 µl. Any foreign protein, azide, glycine, Tris, or other reagent containing primary amine groups present in the protein preparation should be removed by dialysis or gel filtration. Coupling buffer (500 µl) was then added to the beads, which were then resuspended by vortexing. The beads were then washed twice by adding 500 µl of coupling buffer, centrifuging for 5 minutes at 10,000 rpm, removing the supernatant, and then repeating the process. Diluted protein solution (500 µl), prepared earlier, was then added. Next, the tube containing the activated beads and the protein solution was gently agitated on a shaker for 2 hours in the dark at room temperature. The beads were then washed twice with PBS/BSA buffer. The beads were then resuspended in 500 µl PBS/BSA, and 0.5% azide was added as a preservative. The bead number was then adjusted to provide the desired concentration per microliter.

Example 5

BIO-PLEX Analysis of Proteins

At the start of the analysis, a dilution series of the serum to be tested was prepared on a MILLIPORE 96 well filtration plate. The BIO-PLEX Bead/Protein preparation, prepared according to Example 3, was then added to the wells on a MILLIPORE 96 well filtration plate. When preparing beads according to the normal protocol, 10 µl of bead suspension is sufficient to make a useful data point. However when testing beads in which multiple proteins are bound to an individual bead, it may be necessary to combine the beads into a single tube and distribute them to wells so that enough of each bead is present in a given well to give an accurate data point. Controls are preferably included for each sample (sera/protein) being analyzed. For example, the BIO-PLEX analysis for *T. cruzi* antigens included a bead coated with ovalbumin (OVA) as a negative control and with *T. cruzi* lysate as a positive control.

To prepare for the BIO-PLEX analysis, 30 µl of PBS/BSA buffer and 10 µl of an individual bead suspension (or a predetermined volume containing multiple beads each with different proteins bound) were added to the MILLIPORE 96 well filtration plate. The filtration plate was then placed on the vacuum manifold and the sample liquid was pulled through the plate. Next, 50 µl of PBS/BSA and 50 µl of serum dilution were added. The beads were then incubated for 1 hour at room temperature while being shaken on a plate shaker. Each well was then washed four times with 200 µl PBS/BSA to remove any unbound IgG antibodies from the well. PBS/BSA buffer (90 µl) was then added to each well and beads that had settled to the bottom of the filtration plate well due to washing were resuspended. An aliquot (10 µl) of the secondary reporter molecule was then added. This provided a 1:30 dilution (0.5 mg/ml) of antibody. A higher dilution may be used, but a 1:30 dilution makes sure that secondary antibody is not limited by residual unbound IgG. The solution was then incubated for 1 hour at room temperature while being shaken.

The assay solution was then drawn into the BIO-PLEX array reader, which illuminates and reads the sample. When a red diode "classification" laser (635 nm) in the BIO-PLEX array reader illuminates a dyed bead, the bead's fluorescent signature identifies it as a member of one of the 100 possible sets. BIO-PLEX Manager software correlates each bead set to the assay reagent that has been coupled to it. In this way the BIO-PLEX system can distinguish between the different assays combined within a single microplate well. A green "reporter" laser (532 nm) in the array reader simultaneously excites a fluorescent reporter tag (phycoerythrin, or PE) bound to the detection antibody used in the assay. The amount of green fluorescence is proportional to the amount of analyte captured in the immunoassay. Extrapolating to a standard curve allowed quantitation of the analyte in each sample. The results for specific proteins are described in Example 8, and shown in FIGS. 4-6.

Example 6

BIO-PLEX Assay of VV-Ovalbumin Sera

Figure 3A:
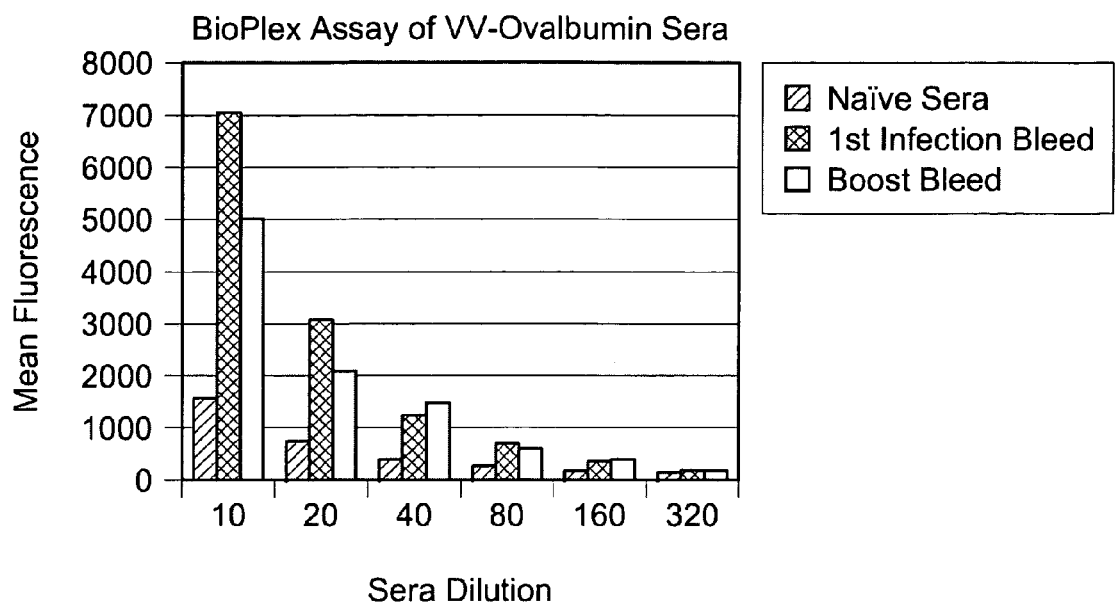
FIG. 3 shows assay development using varicella voster (VV)-ovalbumin sera; A, BIO-PLEX assay; B, ELISA assay.

Ovalbumin (OVA) chosen as the protein antigen to develop the BIO-PLEX method. Mice were infected with Vaccinia virus (VV) containing the OVA gene in order to raise serum antibodies to the protein. Sera was collected at 7 days post infection, followed by a boost and an additional sera collection 7 more days later. OVA protein was expressed in *E. coli* and purified using a His-tag and bound to BIO-PLEX beads via a Ni-NTA residue and adsorbed to an ELISA plate for analysis. The sera was diluted and tested using the BIO-PLEX Assay described in Example 5. The results are shown in FIG. 3A. The results obtained were very comparable to those obtained using ELISA, as described in Example 7.

Example 7

ELISA Assay of VV-Ovalbumin Sera

Figure 3B:
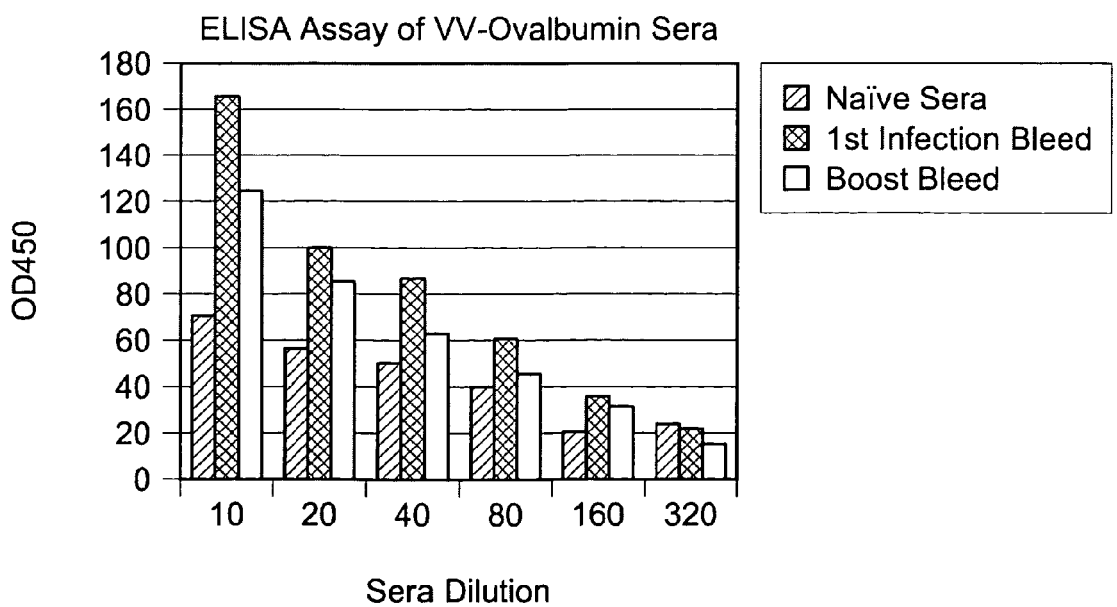

A comparison assay on the ovalbumin of mice infected with Vaccinia virus was run using the ELISA (Enzyme-linked Immunosorbent Assay) method. First, a 96-well polystyrene Immunolon microtiter plate (Dynex Technologies, Chantilly, Va.) was coated with 100 µl of 10 µg/ml ovalbumin (OVA) in PBS overnight at 4° C. or 2 hours at 37° C. The wells were then washed three times with PBS-T (PBS-TWEEN 20 buffer) and then blocked with 1% BSA for 2 hours. Serum dilutions were then added to each well and the wells were incubated for 2 hours at room temperature or overnight at 4° C. After incubation, the wells were washed five times with PBST. Biotinylated secondary mouse antibody (1:100 dilution) was then added and the wells were allowed to set for 1 hour at room temperature. The wells were then washed again for five times with PBST. Horseradish peroxidase-conjugated streptavidin was then added for 30 minutes at room temperature at a 1:100 dilution. The wells were then washed again five times with PBST. Finally, a developing reagent (2,2'-azido-di-[3-ethylbenzthiazoline sulfonate], ABTS) was added. The results of the ELISA assay of ovalbumin sera are shown in FIG. 3B.

Example 8

BIO-PLEX Assay Results for Pooled and Specific Proteins

Using the method of protein production described in Example 2, over 350 proteins in pools of approximately 10 proteins each were prepared. Each of the pools were screened for antigenicity using the BIO-PLEX technology, as described in Example 5. From the preliminary testing, 11 pools were found to bind readily detectable amounts of antibodies in the sera of *T. cruzi*-infected subjects. These pools were then broken down and each gene was expressed individually and tested. From the over 80 genes expressed, 15 proteins have been confirmed as having serodiagnostic potential.

A Hemagen® Diagnostics Chagas Disease Test Kit (Hemagen Diagnostics, Inc., Columbia, Md.) was used to evaluate and confirm the presence of anti-*T. cruzi* antibodies in sera from areas of active transmission in Argentina. Sera from non-endemic uninfected in-house sera served as the negative controls. Sera from 4 individuals from areas of active transmission, all of which have tested seronegative using standard assays but 1 of which tests positive for T cell reactivity to *T. cruzi*, were used for the very low positive control. Sera from 5 individuals that were borderline positive/negative using standard serological assays were used to make up the borderline positive control and sera from 7 individuals that were consistently seropositive using standard serological assays make up the strong positive control.

Figure 2:
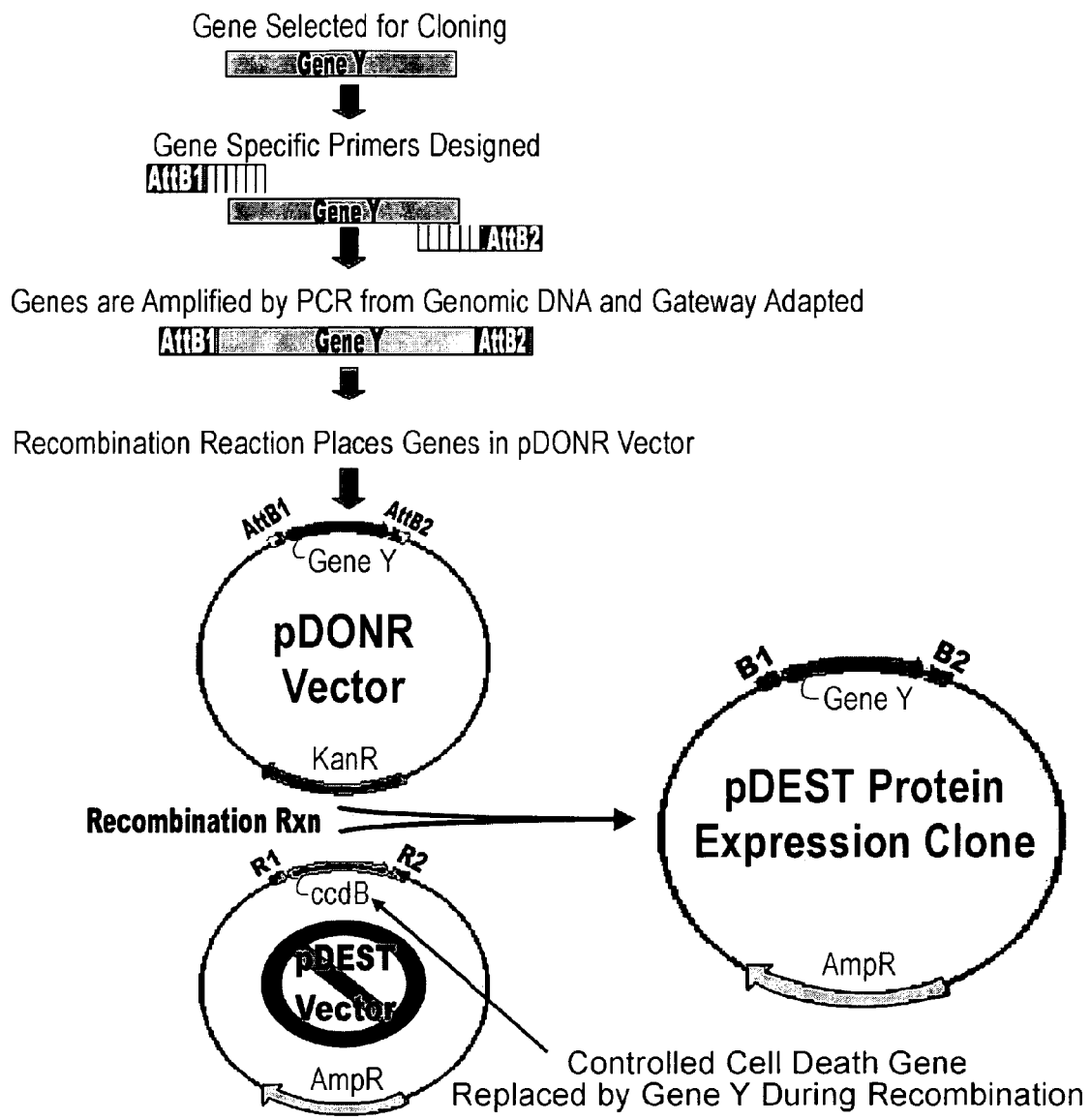
FIG. 2 provides a pictoral overview of the GATEWAY cloning method used to provide an expression vector used for the preparation of *T. cruzi* polypeptide antigens in one embodiment of the invention.
Figure 4A:
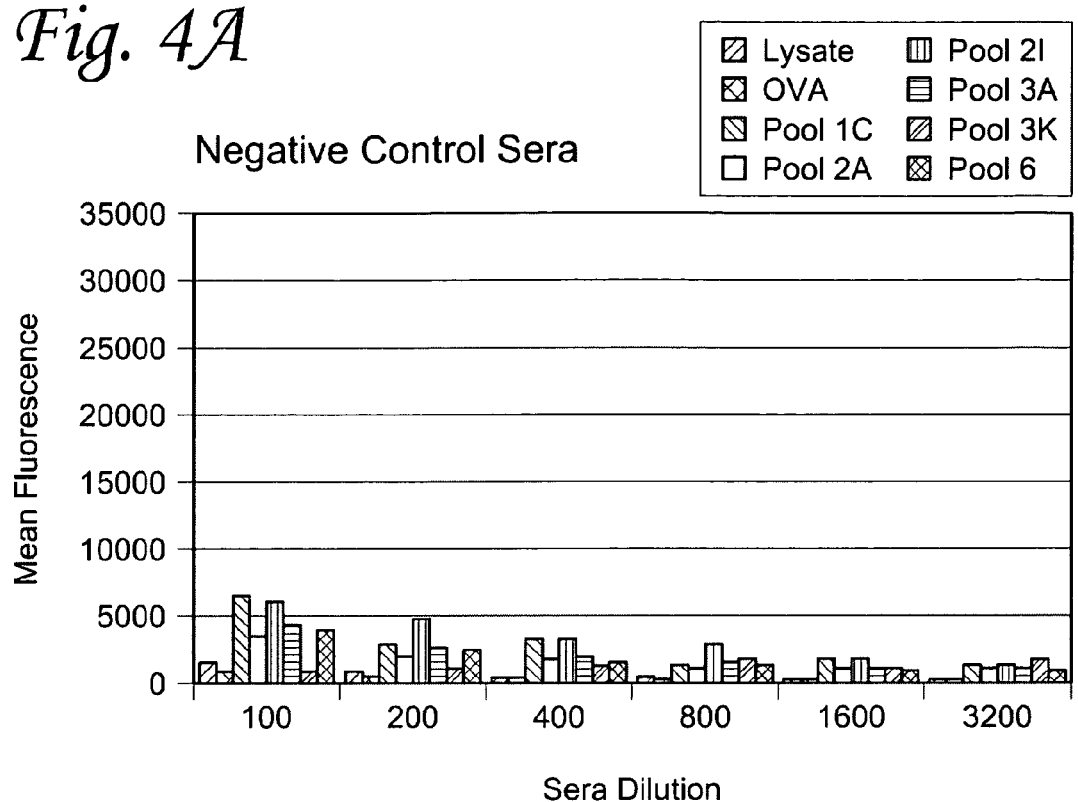
FIG. 4 shows testing of protein pools for antigenic potential using A, negative control sera; B, very low positive sera; C, borderline positive sera; and D, strong positive sera. From left to right, in each panel at each of the sera dilutions, the tested samples are: lysate control, ovalbumin, pool 1C, pool 2A, pool 2I, pool 3A, pool 3K and pool 6. Pool 3K reacted with antibodies from infected individuals and was a candidate for further testing.
Figure 4B:
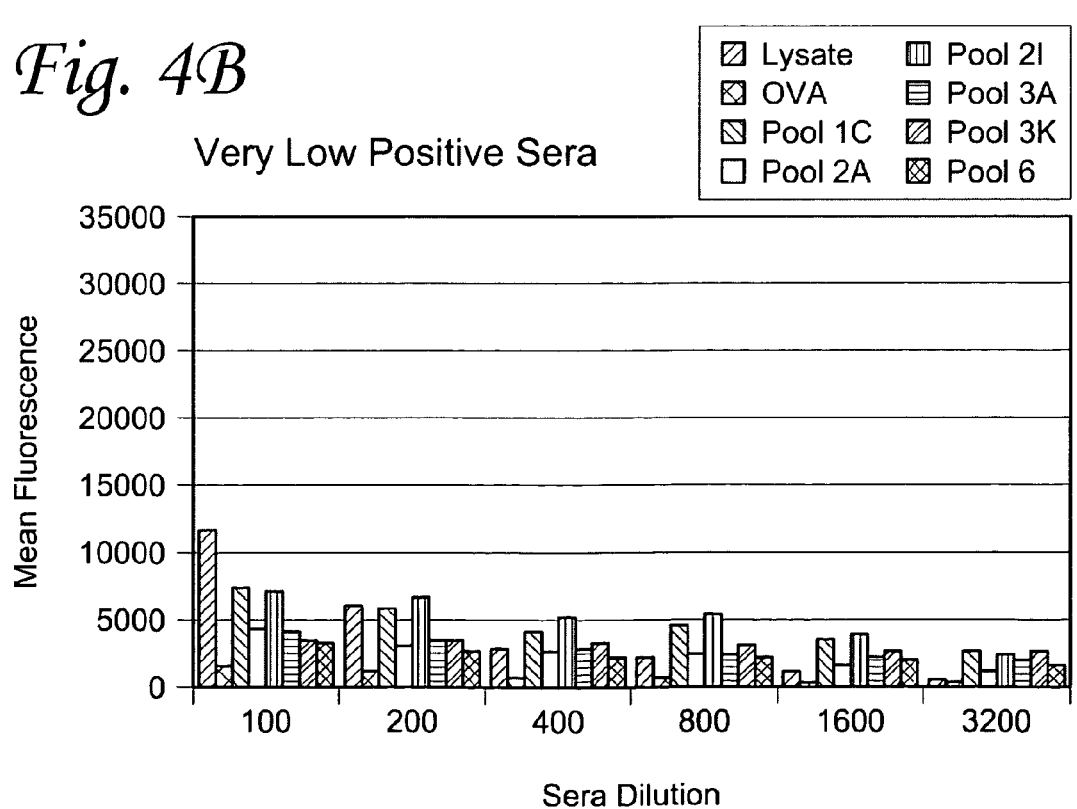

Genes of interest were first cloned into the GATEWAY holding vectors (pDONR™ vector) and archived as single vectors or are placed into pools. Pools of genes in pDONR™ vectors can be moved simultaneously into either DNA vaccination vectors or protein expression vectors without the loss of individual genes in the pool. The resulting pools were expressed in *E. coli* strain BL21(DE3)pLysS cells, minimizing the possible toxic effects of individual genes. The protein pools are purified and tested using the BIO-PLEX bead technology for antigenicity. The results from analysis of the protein pools using the BIO-PLEX analysis method are shown in FIGS. 4A-2D. The headings in the figures indicate the type of sera being tested, based on the four categories (negative, very low positive, borderline positive, and strong positive) resulting from the evaluation using the Hemagen® Test Kit. As indicated by the arrow, FIG. 4D demonstrates a pool that shows high fluorescence, and hence contains a high level of protein that binds to *T. cruzi*-specific antibodies.

Figure 5A:
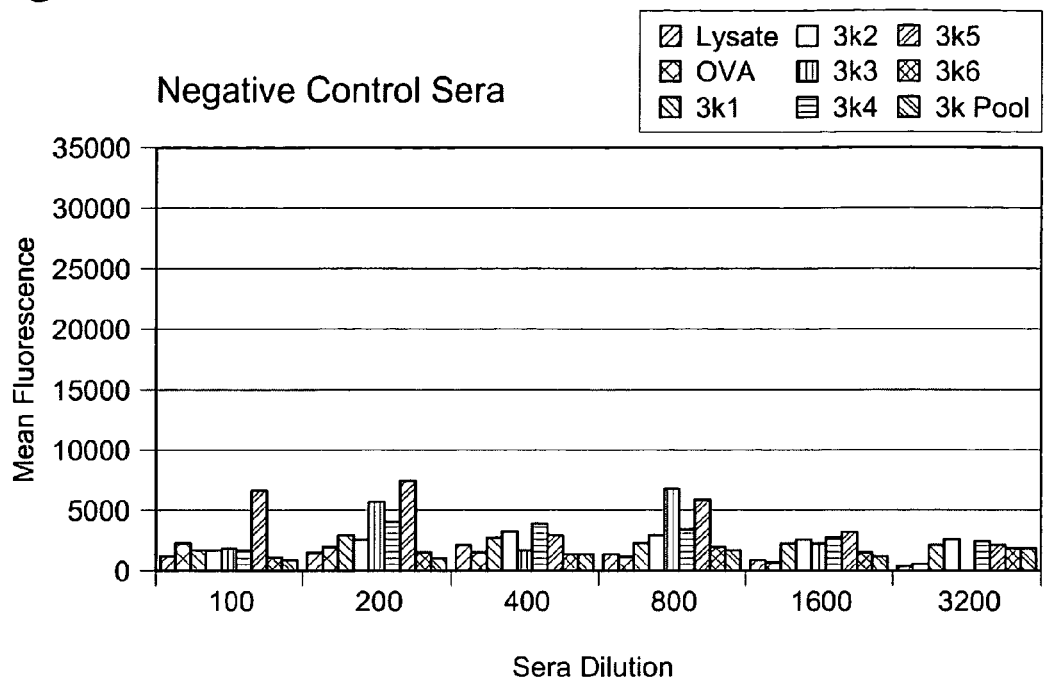
FIG. 5 shows testing of the component proteins of pool 3K for antigenic potential using A, negative control sera; B, very low positive sera; C, borderline positive sera; and D, strong positive sera. From left to right, in each panel at each of the sera dilutions, the tested samples are: lysate control, ovalbumin, protein 3K-1, 3K-2, 3K-3, 3K-4, 3K-5 and 3K-6, and pool 3K. Proteins 3K-1, 3K-2, 3K-3 and 3K-5 demonstrated varying degrees of reactivity to antibodies in sera from infected individuals.
Figure 5B:
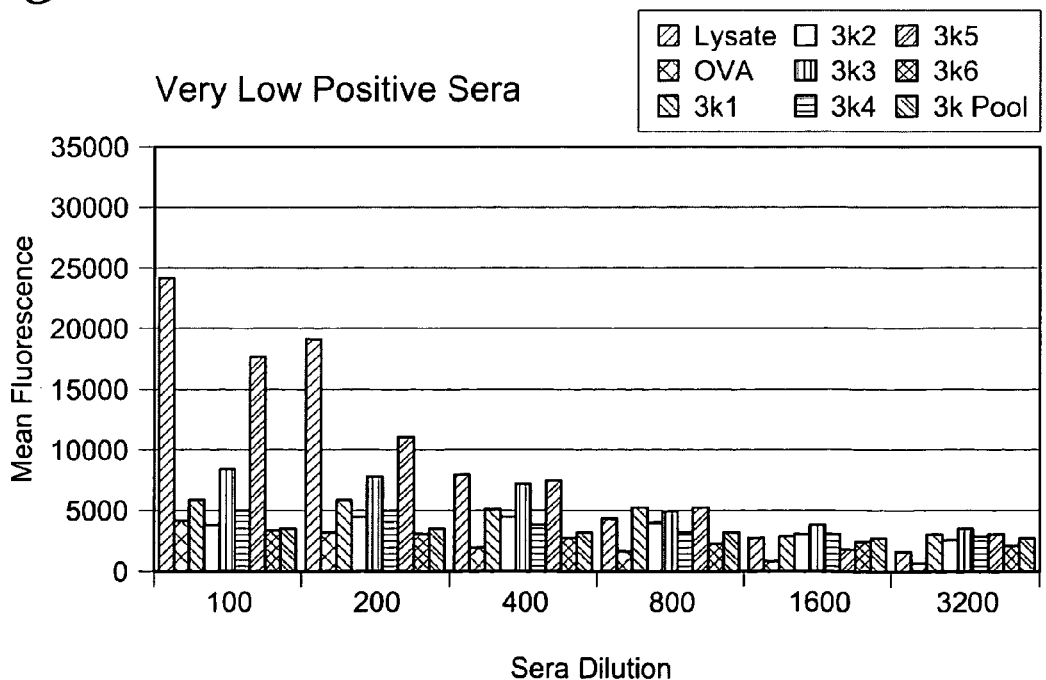
Figure 5C:
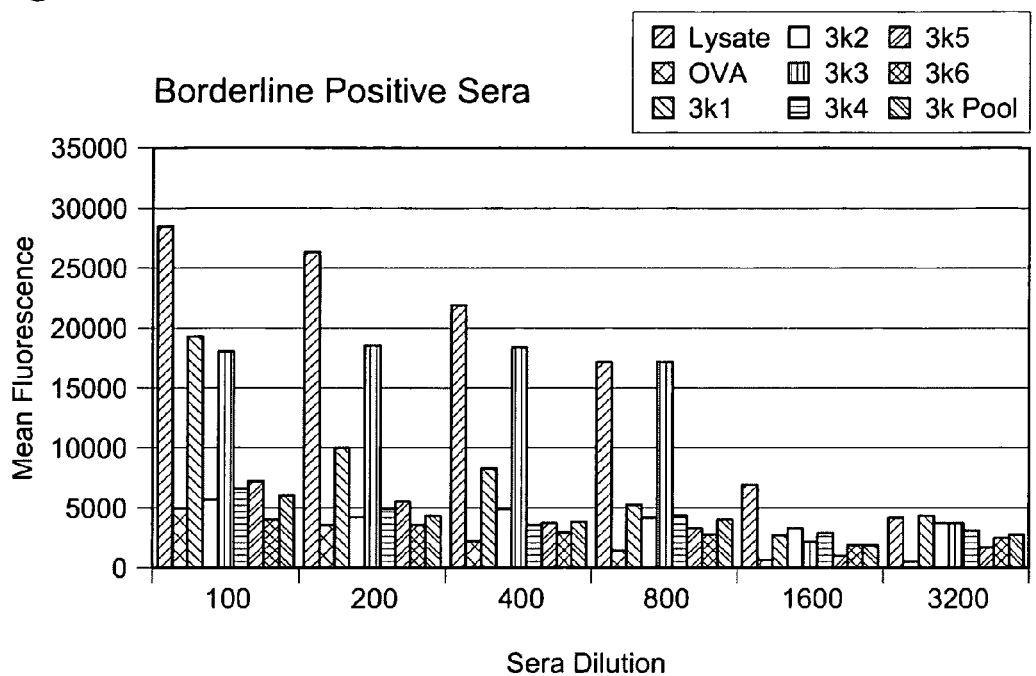
Figure 5D:
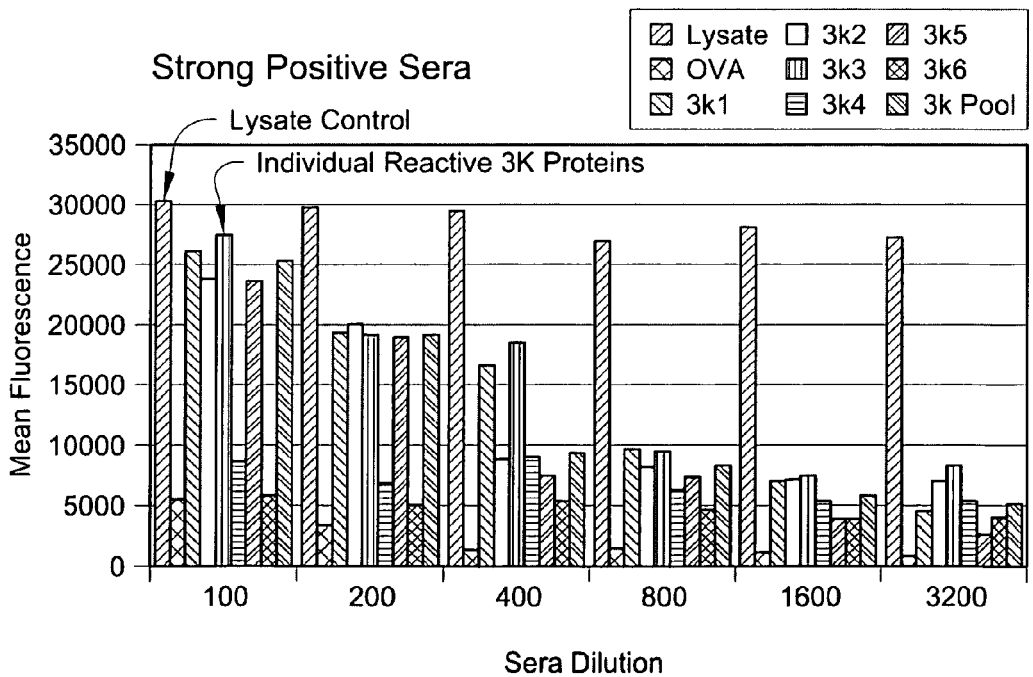
Figure 6A:
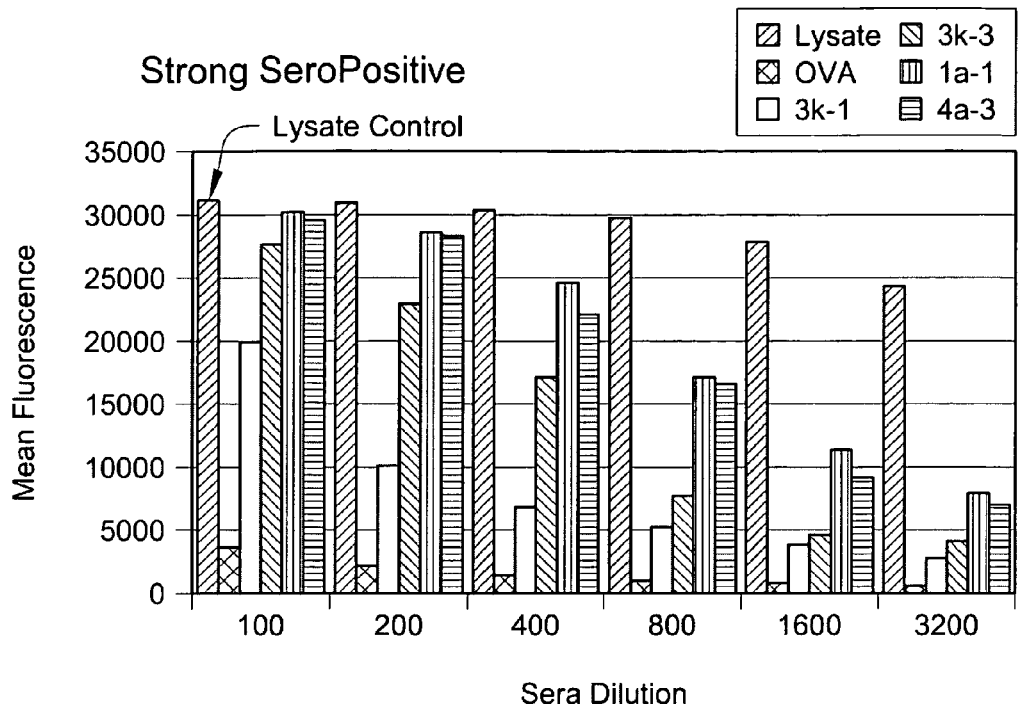
FIG. 6 shows testing of four different serum samples using a panel of serodiagnostic proteins; A, strong seropositive serum; B, Subject 58: T cell reactive/seronegative serum; C, Subject 44: T cell non-reactive/seronegative serum; D, Subject 60: T cell non-reactive/seronegative. From left to right, in each panel at each of the sera dilutions, the test proteins are: lysate control, ovalbumin, protein 3K-1, 3K-3, 1A-1 and 4A-3, and pool 3K. Subject 58, declared seronegative by standard serological assay but exhibiting T cell reactivity to *T. cruzi* antigens, is of particular interest because antibodies are detected that recognize the recombinant *T. cruzi* antigens but not the parasite lysate.
Figure 6B:
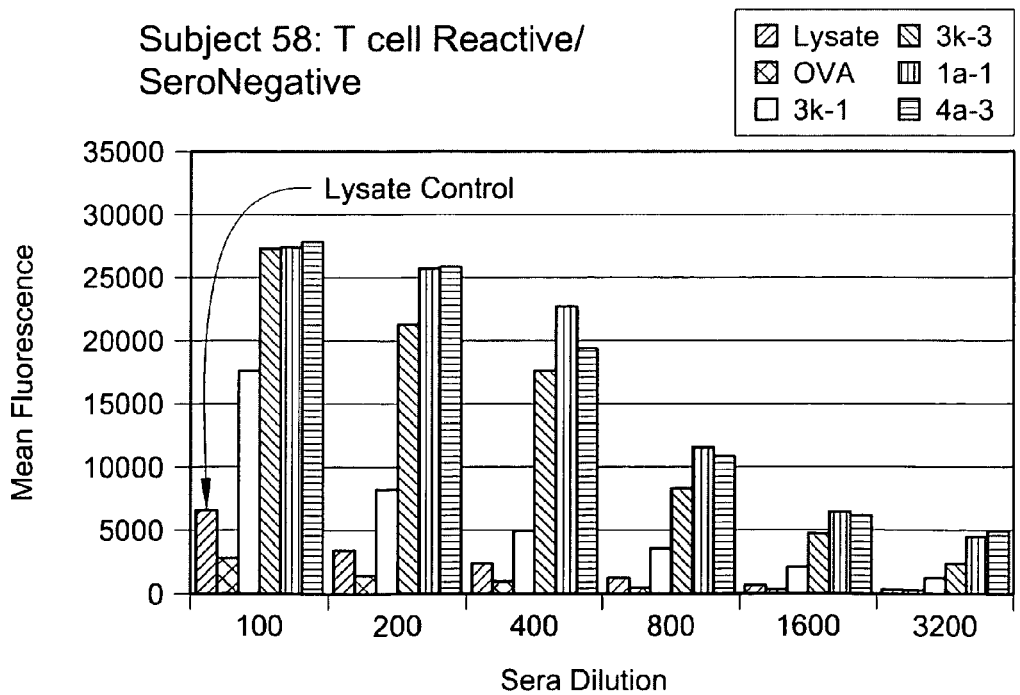
Figure 6C:
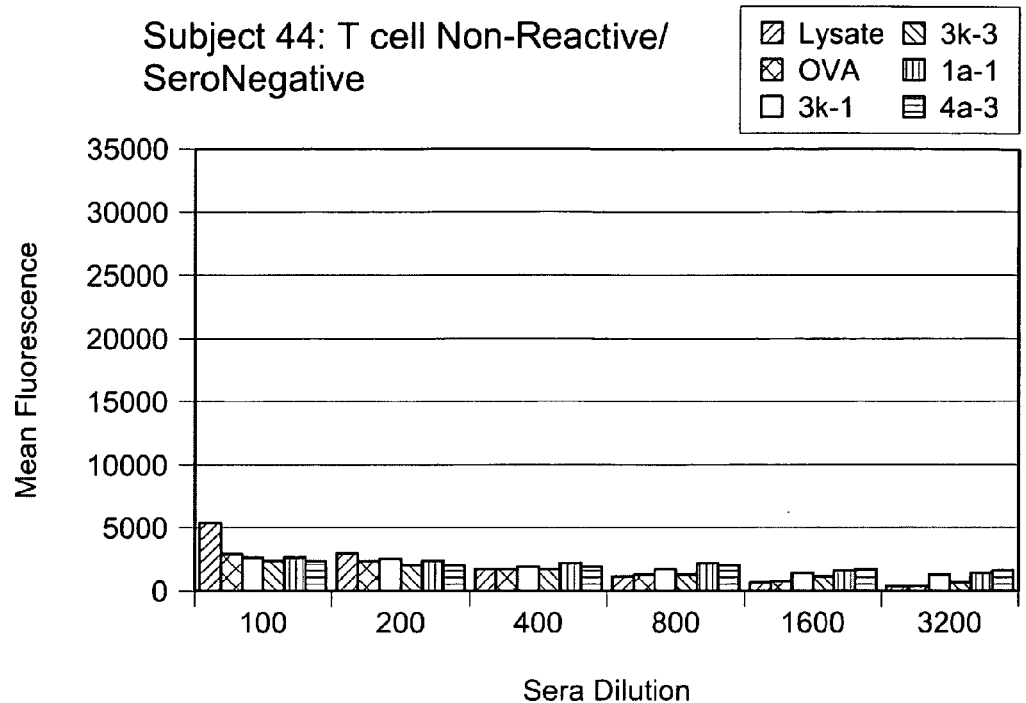
Figure 6D:
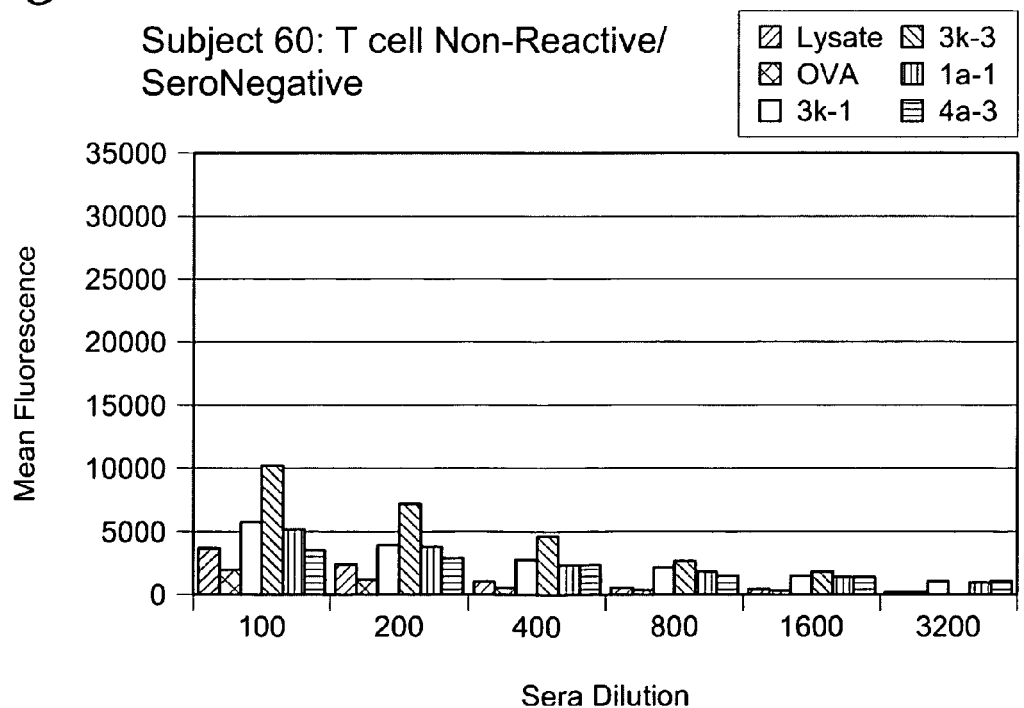

Once a pool of proteins was identified using the BIO-PLEX screening method as having possible antigenic properties, the individual genes in the pool were examined and tested to find which ones provided reactive antigens. The genes were first moved individually from the pDONR holding vector into an expression vector, followed by expression, purification and testing. Those proteins that exhibit binding to antibodies in infected individuals were then retested for confirmation and identified. The results of screening the pools for individual proteins is shown in FIGS. 5A-5D. The arrow in FIG. 5D shows a particular protein that reacted strongly with anti-*T. cruzi* antibodies present in strong positive sera.

From the proteins that were screened, many that showed antigenic activity were proteins that had been previously characterized as *T. cruzi* antigens. This provides a level of proof to the capacity of this technique to discover single antigens in pools. Selected ribosomal proteins, ubiquitin, calcium binding proteins, and paraflagellar rod proteins have all been described previously as being possible targets for serological diagnosis of *T. cruzi* infection. A list of the individual proteins identified as *T. cruzi* antigens using the BIO-PLEX screening method are shown below. The "Gene ID numbers" represent gene numbers assigned by annotators of the *T. cruzi* genome and are accessed via the *T. cruzi* genome database on the worldwide web at "*Tcruzi*DB.org."

TABLE 1

| Assay Protein ID | Protein | T. Cruzi database accession numbers | Gene ID numbers | SEQ ID No: |
|---|---|---|---|---|
| 1a-1 | Tc beta-tubulin | Tc00.1047053506563.40 | 6998.t00004 | 1 |
| 1a-5 | Tc alpha tubulin | Tc00.1047053411235.9 | 11788.t00001 | 2 |
| 1c-3 | 60S ribosomal protein L2, putative | Tc00.1047053508299.60 | 5568.t00006 | 3 |
| 2b-3 | hypothetical protein, conserved | Tc00.1047053506529.460 | 6986.t00046 | 4 |
| 2c-1 | cytochrome C oxidase subunit IV, putative | Tc00.1047053506529.360 | 6986.t00036 | 5 |
| 2c-9 | hypothetical protein | Tc00.1047053506529.610 | 6986.t00061 | 6 |
| 2i-1 | hypothetical protein, conserved | Tc00.1047053510887.50 | 6003.t00005 | 7 |
| 3d-3 | iron superoxide dismutase, putative | Tc00.1047053509775.40 | 5781.t00004 | 8 |
| 3d-4 | trans-splicing factor, putative | Tc00.1047053503583.40 | 4650.t00004 | 9 |

TABLE 1-continued

| Assay Protein ID | Protein | T. Cruzi database accession numbers | Gene ID numbers | SEQ ID No: |
|---|---|---|---|---|
| 3j-1 | 60S ribosomal protein L28, putative | Tc00.1047053506297.270 | 6890.t00027 | 10 |
| 3k-1 | glycosomal phosphoenolpyruvate carboxykinase, putative (Phosphoenolpyruvate Carboxykinase (Pepck)) | Tc00.1047053508441.20 | 7730.t00002 | 11 |
| 3k-2 | ubiquitin-fusion protein, putative (polyubiquitin/ribosomal protein CEP52) | none | 7355.t00001 | 12 |
| 3k-3 | 60S acidic ribosomal subunit protein, putative (Calmodulin-ubiquitin associated protein CUB2.8) | Tc00.1047053508355.250 | 7695.t00025 | 13 |
| 3k-5 | ef-hand protein 5, putative | Tc00.1047053506391.30 | 6925.t00003 | 14 |
| 4a-3 | paraflagellar rod protein 3 | Tc00.1047053509617.20 | 8152.t00002 | 15 |
| B1 | axoneme central apparatus protein, putative | Tc00.1047053510955.40 | 8553.t00004 | 16 |
| B2 | serine carboxypeptidase (CBP1), putative | Tc00.1047053509695.220 | 8171.t00022 | 17 |
| B5 | aminopeptidase, putative | Tc00.1047053511289.30 | 8647.t00003 | 18 |
| B7 | elongation factor-1 gamma, putative | Tc00.1047053510163.20 | 8322.t00002 | 19 |
| B8 | hypothetical protein, conserved | Tc00.1047053506531.20 | 6987.t00002 | 20 |
| D3 | hypothetical protein, conserved | Tc00.1047053506489.30 | 6967.t00003 | 21 |

Research to improve serological diagnosis techniques has focused on the identification, characterization and cloning of particular *T. cruzi* antigens that elicit a strong B cell response. The use of *T. cruzi* specific antigens in a serological test gives a high level of specificity to a serological test, eliminating the problems that arise due to cross-reactivity to a parasite lysate. However using only a single antigen may not be sensitive enough to detect all individuals that are infected, and thus the use of multiple antigens is preferred. Recent evidence demonstrates that some individuals declared negative by current serological tests in fact respond to parasite lysate by producing IFN-γ in ELISPOT assays. These individuals therefore have T cells that have been exposed to parasite antigen, but have a poor B cell antibody response to the antigens in the serological tests that use parasite lysate. The ability to evaluate the T cell reactivity of individual proteins to sera from various subjects using the BIO-PLEX analysis is shown in FIG. 6A-6D.

Example 9

High Throughput Selection of Effective Serodiagnostics for *T. cruzi* Infection and Multiplex Diagnostic for Chagas Disease As noted above, diagnosis of *T. cruzi* infection by direct pathogen detection is complicated by the low parasite burden in subjects persistently infected with this agent of human Chagas disease. In this study, we sought to improve upon current diagnostics for *T. cruzi* infection by screening for diagnostic candidates that displayed the ability to detect infection in subjects that went undetected or gave discordant results using other conventional serologic tests. We screened more than 400 recombinant proteins of *T. cruzi*, including randomly selected and those known to be highly expressed in the parasite stages present in mammalian hosts, for the ability to detect anti-parasite antibodies in the sera of subjects with confirmed or suspected *T. cruzi* infection. A set of 16 protein groups were then incorporated into a multiplex bead array format which detected 100% of more than 100 confirmed positive sera and also documented consistent, strong and broad responses in samples undetected or discordant using conventional serologic tests. Each serum had a distinct but highly stable reaction pattern. The end result was thus the identification of a panel of recombinant proteins that more reliably detects *T. cruzi* infection than do a combination of existing conventional tests. Additionally, we show that a multiplex assay utilizing this diagnostic panel has utility in monitoring drug treatment efficacy in chronic Chagas disease. These results substantially extend the variety and quality of diagnostic targets for Chagas disease and offer a useful tool for determining treatment success or failure.

Methods

Parasites, gene selection and cloning. *T. cruzi* epimastigotes of the Sylvio, C L Brenner, Brazil, C L, Tulahuen, M83, M91 and Chapulin isolates were maintained in logarithmic phase growth (Kirchhoff et al., 1984, J Immunol 133: 2731-2735) and used as a source of genomic DNA. Primer sets incorporating lambda phage recombination sites flanking the 18-21 base gene-specific sequence (excluding both start and stop codons), were designed for each gene of interest, the genes cloned by PCR from the pooled DNA of the 8 *T. cruzi* isolates and GATEWAY adapted gene product inserted into the pDONR-201 plasmid (INVITROGEN, Carlsbad, Calif.). To speed the cloning process while improving our chances of cloning full-length non-mutated genes, at least 10 clones positive for the appropriate sized insert were pooled for each gene. *T. cruzi* lysate from Brazil strain amatigote and trypomastigotes was prepared as previously described (Laucella et al., 2004, J Infectious Diseases 189:909-918).

pDEST-PTD construction. The pDEST-PTD protein expression vector was created from pTAT_HA (Nagahara et al., 1998, Nat Med 4: 1449-1452) by replacing the BamHI-flanked TAT sequence with a BamHI-flanked PTD-4 encoding sequence (Ho et al., 2001, Cancer Res 61: 474-477), followed by GATEWAY (INVITROGEN)—adaptation of the plasmid utilizing the NcoI and XhoI cloning sites. The GATEWAY cloning cassette was PCR amplified from pDEST-YFP (gift from Dr. Boris Striepen, University of Georgia, Ga.).

Protein production and purification. Genes in pDONR plasmids were transferred to pDEST-PTD4 via a GATEWAY LR reaction and the proteins expressed in BL21(DE3)pLysS cells were extracted by sonication in 8M urea, 20 mM HEPES, 100 mM NaCl, pH 8.0 containing 15 mM imidazole. The lysate was then applied to TALON Metal Affinity Resin (BD Biosciences Clonetech, Palo Alto, Calif.) and bound protein was eluted with 250 mM imidazole. Imidazole was removed on PD-10 desalting columns (GE Healthcare, Piscataway, N.J.) and protein concentration was estimated using a modified Bradford assay. Proteins were diluted to 10 μg/mL (in 8M urea) and stored in 1 mL aliquots at −20 C until use.

Human sera. Sera were obtained from individuals living in areas of Santiago del Estero, Argentina endemic for *Trypanosoma cruzi* and were analyzed using conventional serologic tests (e.g. immunofluorescence assay (IFI), hemagglutination (HAI), and ELISA) performed at the Diagnostic Department of the Instituto Nacional de Parasitologia "Dr. Mario Fatala Chabén" and in our laboratory by a commercial ELISA serodiagnostic kit (Hemagen Diagnostics, Columbia, Md.). The latter assay was carried out as per the manufacturer's instructions with a positive response defined as 10% above the cutoff (0.250+mean of negative control absorbencies). Three serum pools were created: a "sero-negative" pool consists of 4 sera negative on all assays; a "borderline positive" pool made up of 5 sera with a response at or just above the equivocal zone of the Hemagen test (between cutoff and below cutoff+10%); a "strong positive" pool containing 7 sera that gave unequivocally positive responses on all tests. True negative controls were obtained from volunteer donors who were not from endemic areas. Sera used for subsequent analysis of individual proteins were obtained from *T. cruzi*-infected adult volunteers aged 29 to 61 recruited through the Chagas Disease Section of the Cardiology Department, Hospital Interzonal General de Agudos "Eva Perón", Buenos Aires, Argentina and infection status was determined serologically as described above. In some cases, subjects treated by a 30 day course of benznidazole as previously described (Viotti et al., 2006, Ann Intern Med 144: 724-734) donated serum samples prior to treatment and at regular intervals following treatment. The protocols were approved by the IRBs of the University of Georgia and the Hospital Interzonal General de Agudos "Eva Perón" and signed informed consent was obtained from all individuals prior to inclusion in the study.

Multiplex assay. Recombinant proteins were attached to LIQUICHIP Ni-NTA beads (Qiagen) or Beadlyte Nickel Beads (Upstate Biotechnology) by overnight incubation at 4° C. in the dark. The sets of distinct addressable beads, each with a different protein attached, were pooled in equal volumes along with positive and negative control beads, consisting respectively of LIQUICHIP Carboxy Beads (Qiagen) coupled to *T. cruzi* lysate and LIQUICHIP Ni-NTA beads coated with recombinant HIS-tagged green fluorescent protein (GFP). Sera at 1:500 dilutions were added and the multiplex assays conducted using standard procedures (Waterboer et al., 2006, J Immunol Methods 309: 200-204). Antibody binding to individual beads was detected with goat anti-human IgG conjugated to phycoerythrin (Jackson ImmunoResearch, West Grove, Pa.) and quantified on a BIO-PLEX Suspension Array System (BioRad).

Statistical analysis. Serum samples were assayed in duplicate and the weighted mean fluorescence intensity (MFI) was calculated for a minimum of 30 beads per determination. The ratio of the specific MFI for each antigen to the MFI of the negative control (GFP- or OVA-coupled) protein was then calculated for each serum and antigen in the assay. Values above the mean plus 4 standard deviations of a minimum of sixteen true negative sera run in the same assay, and individually determined for each antigen, were considered positive.

Results

As part of a vaccine discovery effort, nearly 1500 genes from *T. cruzi* have been cloned into GATEWAY entry vector plasmids that allow them to be easily moved into a range of other plasmids. Genes were selected for cloning using a variety of criteria, initially including known expression in *T. cruzi* lifecycle stages that are present throughout infection in mammals (e.g. trypomastigotes and amastigotes), high likelihood of being surface expressed or secreted and expected presence in the genome at low copy number. With the completion of the *T. cruzi* genome sequencing project (El-Sayed et al., 2005, Science 309: 409-415) and whole organism proteome analysis (Atwood et al., 2005, Science 309: 473-476) the additional criterion of being relatively high in abundance in the proteomes of trypomastigotes and amastigotes was added as a basis for selection. Recombinant proteins produced in *E. coli* had N-terminal tags carrying the 6×His-, PTD (Ho et al., 2001, Cancer Res 61: 474-477) and HA—tags for purification, protein translocation, and identification, respectively were captured by Ni-coupled Luminex beads for use in a multiplex bead array assay.

Figure 8:
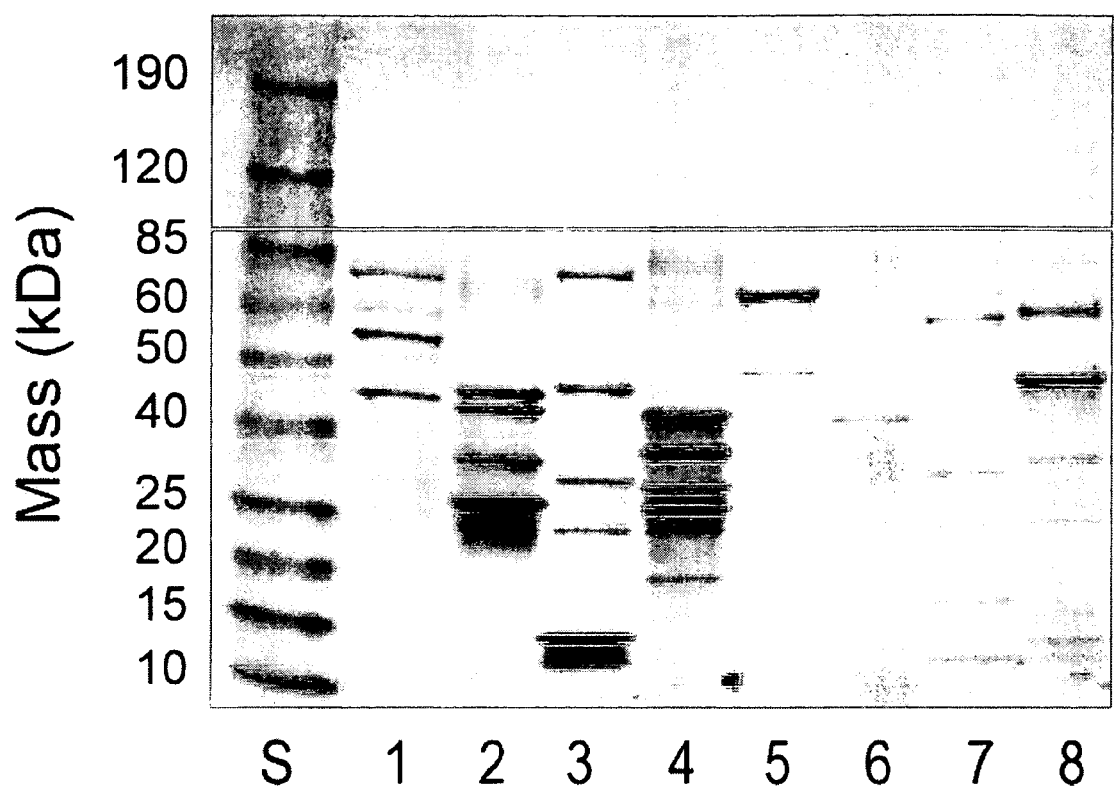
FIG. 8

Selection of the diagnostic panel. The initial selection screen (FIG. 7) used approximately 420 proteins produced in pools of 8-10 proteins each. Production of pooled proteins was accomplished by moving sets of genes in batch into the PTD-4 expression plasmid and was confirmed by SDS-PAGE analysis (FIG. 8). In addition to the individual or pooled recombinant *T. cruzi* proteins, each screening experiment included negative control recombinant protein (ovalbumin or GFP) expressed from the PTD-4 plasmid as well as a lysate of trypomastigotes and amastigotes of *T. cruzi* that had been chemically coupled to BIO-PLEX beads.

To screen the pooled proteins we also took a pooling approach by assembling sera from subjects with and without documented infection with *T. cruzi*. Screening of 51 protein pools revealed 21 pools that were reactive with one or more of the serum pools 1-3 (FIG. 7). Reactive pools were then broken down into their individual constituent proteins; a total of 140 proteins were successfully expressed and individually rescreened with the serum pools, ultimately resulting in the selection of 55 proteins with serodiagnostic potential (FIG. 7 and Table 2). An additional 22 proteins that were either identified as high-abundance proteins using proteome analysis (Atwood et al., 2005, Science 309: 473-476) and/or as being unique to *T. cruzi* (and thus not encoded in the *T. brucei* or *Leishmania major* genomes) were then screened using the pooled sera, and 4 of these 22 were found to be reactive with one or more serum pools. Of the resulting 59 candidate proteins recognized by antibodies in the serum of *T. cruzi*-infected subjects, a substantial number were subsequently excluded from further testing either because they exhibited significant reactivity with sera from the true negative pool, or because they interfered with other beads in the multibead assays, perhaps because of protein-protein interactions. Preference was also given to *T. cruzi* proteins that detected antibodies in sera from the "borderline" pools. Ultimately 39 proteins (in bold and italics in Table 2) were selected for extensive further testing with a wider array of individual subject sera.

TABLE 2

The 59 candidate diagnostic proteins screened independently with individual (non-pooled) sera.

| Gene Id | Gene name(s) | Notes | % reactive with 121 known positive sera | SEQ ID No: |
|---|---|---|---|---|
| Tc00.1047053506391.10,and | calmodulinandATPasebetasubunit | high abundance | 32.23% | 22 |
| Tc00.1047053509233.180 | | | | 23 |
| Tc00.1047053507029.30 | heatshock70kDaprotein,mitochondrialprecursor,putative | high abundance | 52.89% | 24 |
| Tc00.1047053510955.40 | axonemecentralapparatusprotein,putative | | 42.15% | 16 |
| Tc00.1047053511215.119 | 69kDaparaflagellarrodprotein,putative | | 23.97% | 25 |
| Tc00.1047053511271.10 | dispersedgenefamily1fragment4 | unique to *T. cruzi* | 5.08% | 26 |
| Tc00.1047053506529.610 | hypotheticalprotein | | 17.27% | 6 |
| Tc00.1047053506391.30 | EF-handprotein5 | | 2.48% | 14 |
| Tc00.1047053506635.130 | hypotheticalprotein,conserved | high abundance | 68.60% | 27 |
| Tc00.1047053511265.10 | dispersedgenefamily1fragment5 | unique to *T. cruzi* | 8.62% | 28 |
| Tc00.1047053511289.30 | aminopeptidase,putative | | 11.57% | 18 |
| Tc00.1047053506195.110 | malatedehydrogenase,putative | high abundance | 24.79% | 29 |
| Tc00.1047053508461.140 | poly(A)-bindingprotein | high abundance | 34.17% | 30 |
| Tc00.1047053508441.20 | glycosomalphosphoenolpyruvatecarboxykinase,putative | high abundance | 59.29% | 11 |
| Tc00.1047053508355.250 | 60Sacidicribosomalsubunitprotein,putative | high abundance | 75.21% | 13 |
| Tc00.1047053511633.79 | microtubule-associatedproteinhomolog | high abundance | 74.38% | 31 |
| Tc00.1047053510433.20,and | TolTproteins | unique to *T. cruzi* | 74.38% | 32 |
| Tc00.1047053504277.11,and | | | | 33 |
| Tc00.1047053504157.130 | | | | 34 |
| *Tc00.1047053411235.9* | *alpha tubulin* | | | 2 |
| *Tc00.1047053510877.30* | *hypothetical protein, conserved* | | | 35 |
| *Tc00.1047053509695.220* | *serine carboxypeptidase (CBP1), putative* | | | 17 |
| *Tc00.1047053510887.50* | *hypothetical protein, conserved* | | | 7 |
| *Tc00.1047053509141.40* | *hypothetical protein, conserved* | | | 36 |
| *Tc00.1047053506247.220* | *histidine ammonia-lyase* | | | 37 |
| *Tc00.1047053509998.10* | *60S ribosomal protein L4, putative* | | | 38 |
| *Tc00.1047053504163.50* | *fructose-bisphosphate aldolase, glycosomal putative* | | | 39 |
| *Tc00.1047053507089.270* | *dihydrolipoyl dehydrogenase, putative* | | | 40 |
| *Tc00.1047053511019.90* | *iron superoxide dismutase, putative* | | | 41 |
| *Tc00.1047053509017.20* | *hypothetical protein, conserved* | | | 42 |
| *Tc00.1047053506529.360* | *cytochrome C oxidas subunit IV, putative* | | | 5 |
| Tc00.1047053510187.50 | tyrosine aminotransferase, putative | | | 43 |
| Tc00.1047053505989.110 | hypothetical protein, conserved | | | 44 |
| Tc00.1047053508209.140 | protein disulfide isomerase, putative | | | 45 |
| *Tc00.1047053506531.20* | *hypothetical protein, conserved* | | | 20 |
| Tc00.1047053504153.280 | hypothetical protein, conserved | | | 46 |
| Tc00.1047053509233.180 | ATPase beta subunit, putative | | | 47 |
| *Tc00.1047053506563.40* | *beta tubulin* | | | 1 |
| *Tc00.1047053506459.290* | *elongation factor-1-gamma, putative* | | | 48 |
| Tc00.1047053508707.200 | nucleoside diphosphate kinase, putative | | | 49 |
| *Tc00.1047053506529.460* | *hypothetical protein, conserved* | | | 4 |
| *Tc00.1047053506297.270* | *60S ribosomal protein L28, putative* | | | 10 |
| *Tc00.1047053511527.34* | *60S ribosomal protein L2, putative* | | | 50 |
| *Tc00.1047053507483.4* | *polyubiquitin, putative* | | | 51 |
| Tc00.1047053509053.70 | p22 protein precursor, putative | | | 52 |
| *Tc00.1047053506585.40* | *glucose-regulated protein 78, putative* | | | 53 |
| Tc00.1047053511185 | dispersed gene family 1 fragment 8 | | | 54 |
| Tc00.1047053511589.130 | 14-3-3 protein, putative | | | 55 |
| Tc00.1047053511167.90 | 14-3-3 protein, putative | | | 56 |
| Tc00.1047053507241.30 | arginine kinase, putative | | | 57 |
| Tc00.1047053510579.70 | nascent polypeptide associated complex subunit, putative | | | 58 |
| Tc00.1047053506925.300 | cyclophilin a | | | 59 |
| *Tc00.1047053509775.40* | *iron superoxide dismutase, putative* | | | 8 |
| *Tc00.1047053503583.40* | *trans-splicing factor, putative* | | | 9 |
| Tc00.1047053510099.120 | d-isomer specific 2-hydroxyacid dehydrogenase-protein, putative | | | 60 |
| Tc00.1047053507093.300 | hypothetical protein, conserved | | | 61 |
| Tc00.1047053508479.340 | succinyl-CoA synthetase alpha subunit, putative | | | 62 |
| Tc00.1047053509815.120 | dispersed gene family 1 fragment 9 | | | 63 |
| Tc00.1047053511727.270 | RNA-binding protein, putative | | | 64 |
| Tc00.1047053503781.80 | universal minicircle sequence binding protein (UMSBP), putative | | | 65 |
| Tc00.1047053506201.39 | translation elongation factor 1-beta, putative | | | 66 |
| *Tc00.1047053506815.20* | *hypothetical protein* | | | 67 |

Note:
Tc00 numbers indicate closest homologue(s) present in the *T. cruzi* CL Brener sequence database (TcruziDb.org) based upon sequencing of the genes (for top 16) or predicted based upon primer sequences used in cloning. Because some primers for PCR cloning were designed prior to the release of the *T. cruzi* CL Brener sequence and the cloning involved the pooling of multiple clone derived from the PCR of a mixture of *T. cruzi* strains (see Material and Methods), some proteins were derived from mixtures of genes (e.g. numbers 1 and 16) and/or had a percent sequence identity <100% relative to the CL Brener strain (range 94.7 to 100%). In some cases (e.g. # 5 and 9) genes >2 kb in length were cloned in ~2 kb fragments in order to facilitate cloning and protein production. Items listed in bold type were selected for screening using >100 individual sera. Items underlined were selected to be part of the final 16 set bead array for screening of discordant sera or sera from subjects post-treatment with benznidazole.

Figure 9:
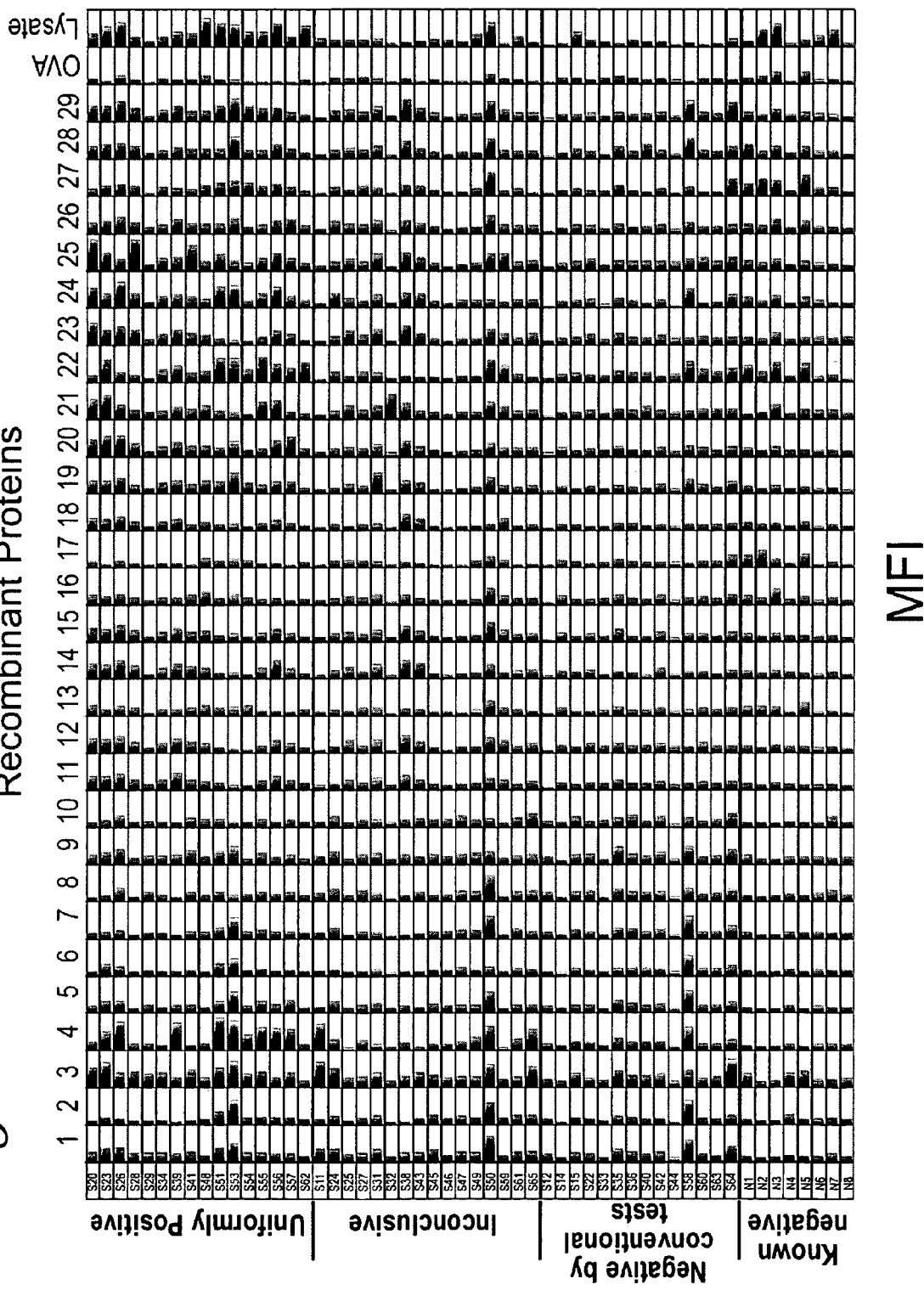

Although the Luminex bead array technology theoretically accommodates up to 100 distinct, addressable beads in a single well—and thus the ability to assay up to 100 individual proteins—at the time of this work only 17 distinct beads were available with the ability to capture his-tagged proteins. Thus our goal in the second part of the screen was to identify a set of the 16 best *T. cruzi* proteins (allowing a bead for a control non-*T. cruzi* protein). The 39 candidate diagnostic proteins were tested in sets of 8-15, with each protein on a separate bead and with a negative control bead (HIS-tagged ovalbumin (OVA)) and a positive control bead (*T. cruzi* lysate) included in each assay sample. Between 38 and 48 individual sera from endemic subjects were used to test each protein. These sera are grouped as "uniformly positive" (reactive on all conventional serological tests), "inconclusive" (positive on at least one, but not all, conventional serologic tests), and "negative by conventional tests", and "known negative" (from residents of North America). FIG. 9 shows a representative set of 29 proteins tested with 54 individual sera and indicates the range of reactivities of both sera and proteins. In addition to providing the basis on which to select the top proteins, this analysis also revealed that among the 30 sera that were inconclusive or negative on conventional tests, nearly half (14 of 30) had substantial reactivity to 3 or more recombinant *T. cruzi* proteins but not with the control OVA protein.

Following repeated screening, 16 proteins were selected to be part of the diagnostic panel (underlined in Table 2). DNA sequencing and mass spectrometric analysis confirmed the identity of each gene and protein and determined that one of the preparations contained two distinct proteins (Cahnodulin and an ATPase) and a second contained a mixture of related TolT proteins. This protein set was then used to screen a larger set of sera, most from chronically infected subjects living in Buenos Aires, and the percentage of these proteins reactive with 121 sera from well-characterized subjects was determined (Table 2). A serum was determined to be positive for any particular test antigen if the average luminescence (MFI) was >4 standard deviations above that of a set of true negative sera run in the same assay. Across all experiments, for the 19 true negative sera assayed multiple times (142 sample runs tested on 16 protein preparations for a total of 2272 determinations), none had S.D. >4 and only 17 of the 2272 determinations were >3 S.D. above the average negative serum values (and 9 of these 17 were from one serum sample reactive with the same antigen in multiple tests). Thus this was a highly stringent cutoff. Sera from all 121 of the confirmed chronically infected subjects reacted with at least 1 of the 16 recombinant protein preparations at the >4 S.D. cutoff and all but 7 reacted with >1 protein. As shown in Table 2, 6 of the 16 of the antigens each detected >50% of the sera and 3 antigens approached a 75% detection rate. Of the 121 sera tested, 118 would have been detected as positive using only 4 of the antigens and 100% would be detected using as few as 7 antigens.

Borderline samples. We then used our 16 bead multiplex test to attempt to resolve questionable infection status in subjects due to discordant results on conventional tests (Table 3). In this analysis, a cutoff for reactivity for each protein in the panel was set at the MFI plus 4 SD above the mean of a set of 16 negative sera. For comparison, the result of multiplex analysis of a pool of strongly positive sera assayed on different days is also shown. The strong positive serum pool showed excellent cross-assay consistency with 11 of the 16 protein preparations positive on each of 8 assays and consistent negative reactivity with 3 of 16. Antibodies to the remaining 2 proteins were also detected but at a lower level that sometimes fell below the strict cutoff of 4 S.D. above the mean. The sera classified as "conventional seronegative with no other evidence of infection" broke into 2 groups based upon the results of the multiplex test. Eight of the 16 failed to react with any of the 16 protein panel (although several reacted with the *T. cruzi* lysate) while the remaining 8 reacted with from 2-4 proteins. A similar nearly 50/50 split was observed in the group of 12 conventional seronegatives who were born in an endemic region, and in 5 individuals who had cardiopathologies consistent with Chagas disease. Lastly, testing in the multiplex assay of sera classified as "positive discordant" (based upon reactivity on 2 of the 3 conventional serologic tests but negative on the $3^{rd}$ test) confirmed the positive diagnosis in all 7 cases with reactivity evident on 2-6 recombinant proteins by each serum. Without a clear gold standard diagnostic it is not possible certify on a case-by-case basis that the multiplex assay more accurately detects infection than does conventional serology—particularly in cases where there is reactivity to only 1 or 2 proteins and near the >4 S.D. cutoff. And while the birth place and presence of heart disease my support a positive diagnostic test, these criteria do not appear to distinguish between those likely to have reactivity with one or more recombinant proteins in the selected panel and those who do not react. However it is clear that conventional serological tests fail to detect a substantial number of individuals, many with antibodies to multiple *T. cruzi* antigens. It is noteworthy that screening of sera with a parasite lysate also routinely fails to detect sera that exhibit reactivity to multiple recombinant *T. cruzi* proteins. The set of 4 most frequently recognized proteins detected all 7 of the discordant positive samples as well as 13 of the 15 discordant negative or negative samples that reacted with at least 1 protein. Expanding the panel to the 7 proteins that detected all of the seropositive samples (see above) allowed us to detect all of these 15 questionable "negative" samples.

TABLE 3

Reactivity of negative, borderline or discordant sera in the 16 protein multiplex assay.

| | Sera | Serology | HAI | ELISA | IFI | 1 | 2 | 3 | 4 | 5 | 6 | 7 | 8 | 9 | 10 | 11 | 12 | 13 | 14 | 15 | 16 | lysate | # > 4 SD |
|---|---|---|---|---|---|---|---|---|---|---|---|---|---|---|---|---|---|---|---|---|---|---|---|
| Pooled sera from strongly reactive | | | | | | 9.70 | 19.26 | 24.42 | 7.17 | -0.12 | nd | 2.54 | 23.83 | -0.37 | 5.48 | 5.68 | 17.55 | 8.79 | 15.94 | 23.91 | 42.37 | 12.58 | 12 |
| | | | | | | 7.63 | 18.83 | 18.08 | 5.48 | 0.06 | nd | 2.19 | 31.80 | -0.51 | 6.64 | 4.41 | 23.57 | 33.21 | 7.02 | 16.64 | 57.60 | 15.97 | 14 |
| | | | | | | 8.47 | 16.74 | 16.65 | 5.46 | 0.04 | 5.91 | 3.18 | 35.79 | nd | 4.00 | 3.63 | 20.01 | nd | 10.47 | 31.26 | 38.01 | 12.91 | 13 |
| | | | | | | 7.33 | 17.46 | 15.47 | 3.63 | -0.39 | 8.21 | 1.82 | 27.18 | -0.49 | 4.30 | 4.35 | 15.60 | 20.38 | 13.70 | 17.22 | 44.23 | 11.83 | 14 |
| | | | | | | 7.23 | 18.87 | 14.06 | 11.59 | 0.38 | 7.67 | 1.80 | 29.61 | 8.93 | 4.16 | 3.52 | 20.81 | 23.22 | 13.41 | 28.35 | 45.36 | 11.11 | 13 |
| | | | | | | 17.64 | 46.65 | 30.56 | 7.84 | nd | 7.01 | 2.91 | 94.71 | -0.05 | 12.30 | 9.57 | 45.06 | 10.81 | 22.94 | 22.01 | 95.05 | 20.28 | 13 |
| | | | | | | 13.14 | 39.82 | 28.91 | 4.10 | nd | 6.35 | 2.12 | 72.56 | -0.59 | 10.07 | 5.03 | 21.23 | 6.60 | 16.63 | 30.29 | 91.38 | 13.71 | 13 |
| | | | | | | 9.03 | 31.25 | 20.79 | 3.92 | nd | 12.59 | 2.68 | 39.70 | -0.08 | 4.31 | 3.51 | 27.05 | 6.67 | 10.11 | 70.18 | 27.91 | 19.22 | 11 |
| Non-infected based upon conventional serology | | | | | | | | | | | | | | | | | | | | | | | |
| no other hard evidence | Fc383 | neg | nr | nr | nr | 0.41 | -0.71 | -0.16 | -1.50 | 0.43 | 0.90 | -1.22 | 0.47 | -0.35 | 0.11 | -0.45 | 0.73 | 0.65 | 1.61 | 0.78 | -0.51 | 4.80 | 0 |
| | Fc323 | neg | nr | nr | nr | -1.07 | -0.50 | 0.42 | -1.94 | -1.81 | -1.37 | -1.26 | -0.49 | 0.16 | -0.50 | -0.84 | -0.71 | -1.32 | -0.58 | -0.36 | 2.89 | -0.73 | 0 |
| | Fc438 | neg | nr | nr | nr | -1.13 | -0.32 | 0.41 | 0.52 | -0.61 | 0.93 | -0.12 | -0.08 | -1.15 | 0.15 | -0.79 | -0.88 | -1.13 | 0.51 | 0.32 | -0.77 | -0.33 | 0 |
| | Fc410 | neg | nr | nr | nr | 0.45 | -0.11 | 0.66 | -1.81 | 1.02 | -0.68 | -1.16 | 1.21 | -0.25 | -0.37 | -0.97 | -0.43 | -0.86 | 0.97 | 0.99 | 1.08 | -1.16 | 0 |
| | Fc411 | neg | nr | nr | nr | 0.03 | 0.40 | 0.42 | -0.21 | 0.05 | 2.88 | 0.13 | 0.44 | 1.84 | -0.29 | 1.01 | -0.07 | 2.96 | 0.67 | 1.65 | 0.55 | 9.19 | 0 |
| | Fc453 | neg | nr | 0.024 | nr | 1.53 | 0.59 | -0.68 | 1.51 | 1.24 | -0.22 | 0.58 | 0.00 | 0.45 | 0.34 | 0.85 | 0.61 | -0.24 | -0.48 | -0.06 | 2.09 | 0.10 | 0 |
| | Fc408 | discord | 32 | nr | nr | 0.55 | -0.11 | -0.18 | 0.39 | 0.94 | -0.38 | 0.40 | 1.72 | -0.04 | 0.02 | -0.45 | 0.12 | 0.99 | 0.46 | 2.08 | 1.16 | 1.93 | 0 |
| | Fc409 | discord | 32 | nr | nr | -0.39 | 1.42 | 1.61 | 0.65 | -0.64 | 2.35 | 0.09 | 1.59 | 0.55 | 0.37 | 2.36 | 1.47 | 3.14 | 0.20 | 1.96 | 2.81 | 0.35 | 0 |
| | Fc437 | neg | nr | nr | nr | -0.09 | 2.96 | 1.90 | 11.99 | 0.55 | nd | 0.07 | 1.73 | -0.78 | -1.02 | 1.13 | 1.11 | 4.05 | 2.29 | 2.73 | 0.91 | -0.24 | 2 |
| | Fc436 | neg | nr | nr | nr | 1.26 | 5.11 | 1.41 | -0.10 | 0.28 | 2.57 | 0.07 | 1.40 | 0.59 | 2.05 | -0.81 | 4.38 | 3.05 | 1.30 | 1.40 | 3.10 | 0.58 | 2 |
| | Fc415 | neg | nr | nr | nr | 1.70 | 8.14 | 4.12 | 0.22 | 1.20 | 0.61 | 0.17 | 1.92 | 2.27 | 2.01 | 1.69 | 1.24 | 1.42 | 2.71 | 2.84 | 2.38 | -0.27 | 2 |
| | Fc324 | neg | nr | nr | nr | -0.50 | 0.03 | 9.62 | 0.18 | -0.69 | 0.50 | -0.11 | -0.84 | -1.66 | 2.55 | -0.79 | -0.35 | -0.64 | 5.32 | -0.76 | -0.54 | -0.24 | 2 |
| | Fc426 | discord | nr | 0.088 | 32 | -1.39 | 2.45 | 2.01 | 0.77 | -2.06 | -0.89 | 0.08 | 2.24 | -0.81 | -1.42 | -1.15 | -0.98 | 2.19 | 4.32 | 4.55 | 0.07 | -0.06 | 2 |
| | Fc320 | neg | nr | nr | nr | -0.79 | 0.76 | 5.19 | -1.84 | 0.92 | 1.56 | -1.67 | -0.16 | 2.41 | -0.49 | 3.86 | 1.28 | 4.75 | 0.63 | 5.05 | 17.82 | 3.63 | 4 |
| | Fc434 | neg | nr | 0.038 | nr | 8.46 | 1.78 | 6.73 | -0.43 | 7.10 | 2.04 | -0.73 | 2.82 | 3.18 | 4.87 | 1.82 | 1.58 | 2.69 | 0.48 | 1.91 | 3.56 | 0.82 | 4 |
| | Fc439 | neg | nr | nr | nr | -1.31 | -0.84 | 6.29 | 4.56 | 1.18 | 8.31 | 0.95 | 0.88 | -1.09 | 0.17 | -0.44 | -0.97 | 0.80 | 4.76 | 1.23 | 1.18 | 0.43 | 4 |

TABLE 3-continued

Reactivity of negative, borderline or discordant sera in the 16 protein multiplex assay.

| | | | | | | | | | | | | | | | | | | | | |
|---|---|---|---|---|---|---|---|---|---|---|---|---|---|---|---|---|---|---|---|---|
| En- | Fc423 | neg | nr | 0.023 | nr | -2.05 | 0.25 | 0.27 | 1.03 | -0.21 | 0.95 | -1.14 | -0.72 | -0.86 | -0.84 | 2.02 | -1.87 | 0.25 | -1.16 | -0.98 | -0.91 | 0 |
| demic | Fc444 | neg | nr | 0.059 | nr | -1.44 | -0.91 | -1.90 | 0.76 | -1.68 | -0.14 | -1.55 | -0.96 | -1.01 | -0.75 | -0.45 | -2.41 | 0.02 | -1.67 | -2.76 | -0.69 | 0 |
| Born | PP048 | neg | nr | 0.096 | nr | 1.92 | -0.56 | -0.94 | -1.18 | 0.50 | -1.24 | -0.69 | 0.02 | -0.56 | 0.40 | 1.84 | -1.30 | -0.62 | 0.13 | -0.33 | 7.94 | 0 |
| | PP035 | neg | nr | nr | nr | -0.40 | -1.86 | -1.39 | -1.65 | 2.71 | -1.68 | -1.83 | 0.19 | -1.11 | 0.18 | -0.07 | -1.80 | 1.11 | -1.61 | -1.43 | 1.52 | 0 |
| | RD46 | neg | nr | 0.041 | nr | -0.01 | 0.81 | -0.43 | -0.44 | 0.01 | -0.17 | 0.53 | -0.15 | -0.36 | 0.05 | 2.63 | -0.08 | 1.11 | 1.11 | -0.09 | -0.14 | 0 |
| | Fc319 | neg | nr | nr | nr | 0.27 | 0.50 | 1.80 | -0.45 | 17.18 | 0.16 | 0.89 | -0.98 | -0.01 | -0.47 | -0.32 | 0.43 | 3.49 | 1.75 | 1.69 | 0.23 | 1 |
| | PP050 | neg | nr | 0.04 | nr | 0.38 | -2.44 | -2.10 | -1.23 | -0.67 | -0.88 | -2.25 | -2.25 | 0.47 | 1.21 | -2.03 | -1.06 | 40.29 | -2.62 | -4.10 | -0.77 | 1 |
| | PP177 | discord | 16 | 0.15 | 128 | 1.70 | -0.99 | 0.21 | -0.85 | -1.46 | -1.00 | -0.32 | 2.08 | 2.47 | -0.99 | 5.92 | -0.79 | 0.80 | 0.00 | 0.57 | 2.21 | 1 |
| | Fc389 | discord | nr | nr | 32 | -0.45 | 0.22 | 0.42 | -0.61 | -0.86 | -0.62 | -0.48 | 0.19 | 0.10 | -0.82 | 2.67 | 0.12 | 5.14 | 1.02 | 1.16 | 0.34 | 1 |
| | Fc464 | neg | nr | 0.019 | nr | 2.55 | 0.10 | 1.03 | -1.00 | 1.49 | -1.01 | 1.99 | 1.98 | 4.07 | 4.17 | 0.29 | 4.92 | 2.59 | 1.19 | 3.35 | 4.05 | 3 |
| | Fc448 | neg | nr | 0.018 | nr | 2.72 | 0.32 | 1.91 | 0.62 | 8.82 | -0.54 | 0.58 | 1.02 | 2.59 | 1.20 | 3.54 | 79.63 | 61.34 | 1.00 | 2.24 | 2.10 | 3 |
| | PP020 | discord | nr | 0.073 | 64 | 0.66 | 7.76 | 0.14 | -0.61 | -0.05 | -0.40 | 19.64 | 1.22 | -1.19 | 1.76 | 0.40 | 5.64 | 1.52 | 4.28 | -0.01 | 7.25 | 4 |
| Heart | Fc560 | neg | nr | 0.041 | nr | -0.27 | -1.01 | -1.18 | -0.66 | -0.14 | 0.04 | -0.09 | -0.60 | -1.03 | -0.94 | -0.45 | -0.66 | -1.02 | 0.83 | -1.70 | 0.68 | 0 |
| Dis- | Fc559 | neg | nr | 0.014 | nr | 0.06 | -1.34 | 3.41 | 0.60 | 1.43 | -0.46 | -0.30 | -0.82 | -0.31 | 0.22 | -0.34 | 0.27 | 0.25 | 0.69 | 0.22 | 0.81 | 0 |
| ease | Fc587 | neg | nr | 0.05 | nr | 2.03 | 4.23 | 6.11 | -0.07 | 7.06 | -1.37 | 22.75 | 0.24 | 0.24 | -0.57 | 11.29 | 2.83 | 3.48 | 37.83 | 28.10 | 4.41 | 8 |
| | Fc565 | neg | nr | 0.056 | nr | -0.24 | 2.40 | -0.28 | -0.28 | -0.74 | -0.69 | 5.21 | 0.29 | 0.69 | 0.57 | 2.04 | 2.18 | 4.61 | 5.60 | 3.17 | 3.92 | 3 |
| | Fc569 | neg | nr | 0.043 | nr | 2.42 | 4.29 | 5.44 | -0.83 | -0.06 | -1.21 | 12.25 | -0.09 | 0.23 | -0.25 | 4.86 | 12.80 | 4.44 | 11.70 | 11.58 | 1.66 | 8 |

Infected based upon conventional serology

| | | | | | | | | | | | | | | | | | | | | |
|---|---|---|---|---|---|---|---|---|---|---|---|---|---|---|---|---|---|---|---|---|
| posi- | Fc273 | discord + | 32 | nr | 128 | -0.34 | 1.53 | 0.07 | -0.35 | 1.60 | -0.67 | 0.77 | 1.12 | -0.27 | 0.80 | 0.58 | 1.27 | 0.05 | 23.11 | 38.34 | 8.36 | 2 |
| tive | Fc404 | discord + | ND | 1.15 | 32 | 1.60 | -0.32 | -0.37 | 1.54 | -1.27 | -0.28 | -0.14 | 2.91 | 1.26 | -0.09 | 0.87 | 1.06 | 14.22 | 6.40 | 3.15 | -0.16 | 2 |
| dis- | Fc331 | discord + | nr | 0.078 | nr | -0.72 | 13.44 | 0.85 | 0.23 | -2.09 | 5.46 | 0.24 | -1.35 | 0.61 | -0.81 | -0.52 | -0.48 | 2.82 | 4.64 | 10.53 | 2.90 | 4 |
| cor- | Fc428 | discord + | nr | 0.238 | 128 | 1.01 | 0.80 | -0.16 | -0.01 | 0.15 | -0.58 | 3.76 | -0.57 | -0.71 | -1.32 | 0.07 | 52.71 | 9.30 | 4.03 | 12.36 | 2.40 | 4 |
| dant | Fc440 | discord + | nr | 0.213 | 32 | 2.14 | 0.53 | 1.21 | 1.32 | 4.69 | -0.66 | 0.51 | 1.85 | 1.86 | 0.43 | 0.07 | 9.06 | 15.31 | 7.30 | 116.71 | 3.35 | 5 |
| | PP178 | discord + | 64 | 0.135 | 32 | 5.95 | 13.82 | 3.73 | 1.15 | 17.71 | 2.23 | 2.59 | -1.04 | 5.05 | 0.99 | nd | 3.83 | 51.95 | 0.61 | 4.45 | 3.61 | 6 |
| | PP080 | discord + | 32 | 0.15 | 32 | 1.04 | 4.26 | 3.87 | 4.55 | 2.55 | 3.98 | 3.64 | 0.42 | 1.34 | 0.53 | 15.35 | 4.45 | 70.78 | 4.99 | 3.88 | 8.60 | 6 |

Sera judged cumulatively as "seronegative" based upon conventional serology were grouped into negative but "no other evidence" of exposure (16 sera), those "born in an endemic area" (12), those with evidence of "heart disease" consistent with Chagas disease (5) and compared to (top) pools of strongly positive sera (high reactivity in all serological tests) and to (bottom) sera from subjects who were negative on at least one of the three conventional serologic tests (discordant positive).
Reactivity in the conventional serological tests (HAI, ELISA and IFI) and the summary consensus of these tests (neg = below cut-off for all three tests; discord + = positive on 2 of the 3 tests), as well as reactivity to the 16 recombinant protein sets and the T. cruzi lysate are shown.
Cutoffs for a positive ELISA is an O.D. > 0.200 and for IFA and HAI is a dilution > 1/32 (a reaction at 1/16 is considered "reactive but negative" and < 1/16 non-reactive (nr)).
The metric for reactivity of each protein is expressed as the number of standard deviations that the ratio of the MFI of the reactive serum to the MFI for GFP was above the average ratios of sixteen true negative sera run in the same assay. Values > 4 S.D. above this "background" reactivity are considered reactive and are highlighted. The total number of reactive recombinant proteins for each serum is indicated in the right-most column.
nd = not determined (insufficient numbers of beads detected in this sample)

Figure 10A:
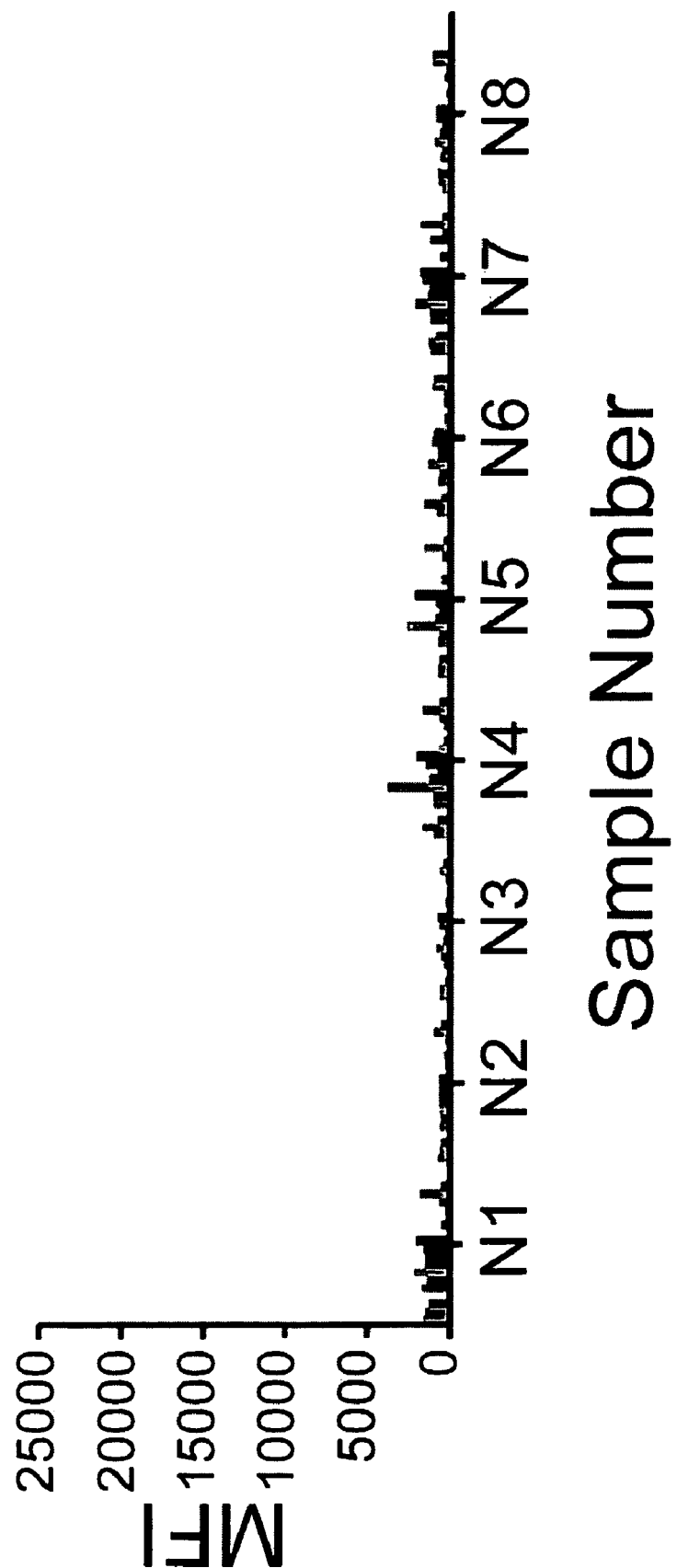
Figure 10B:
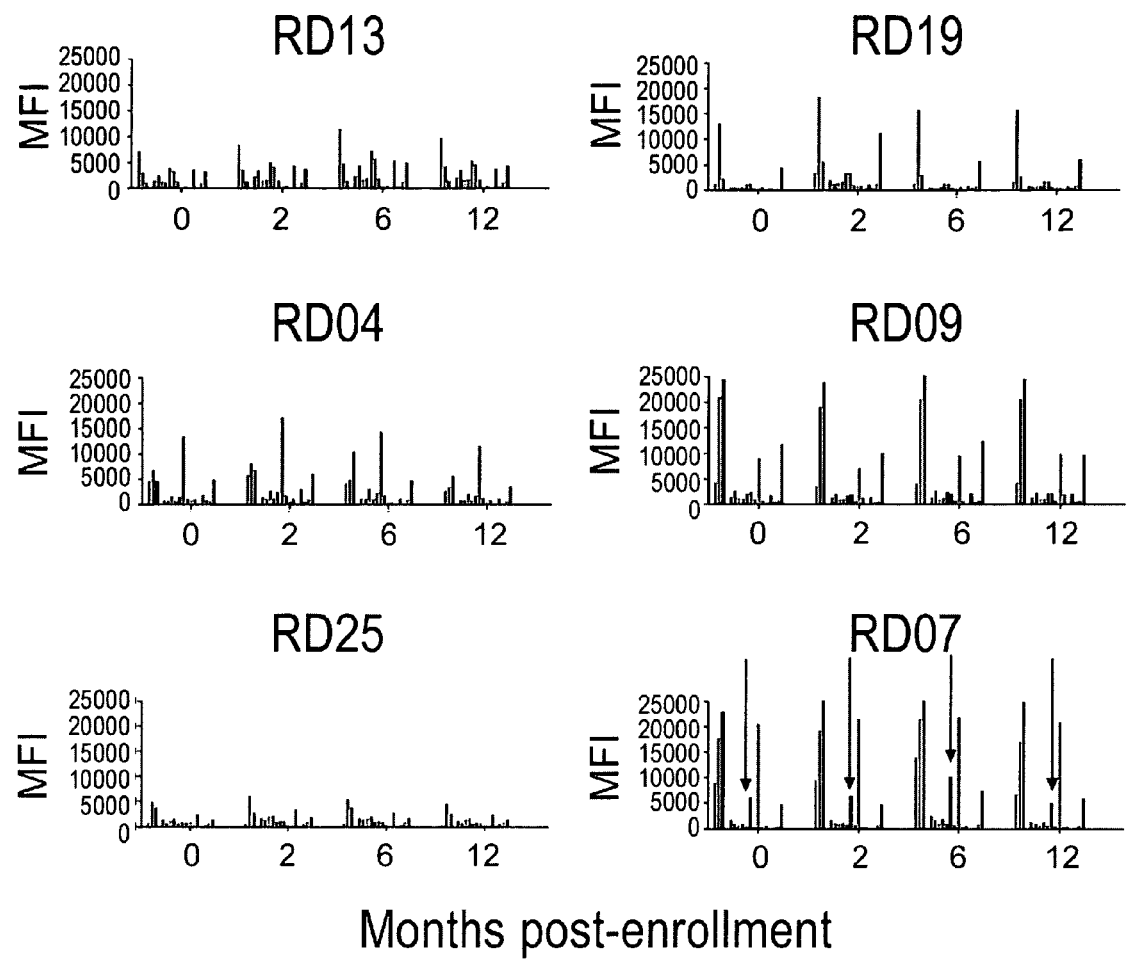
Figure 11A:
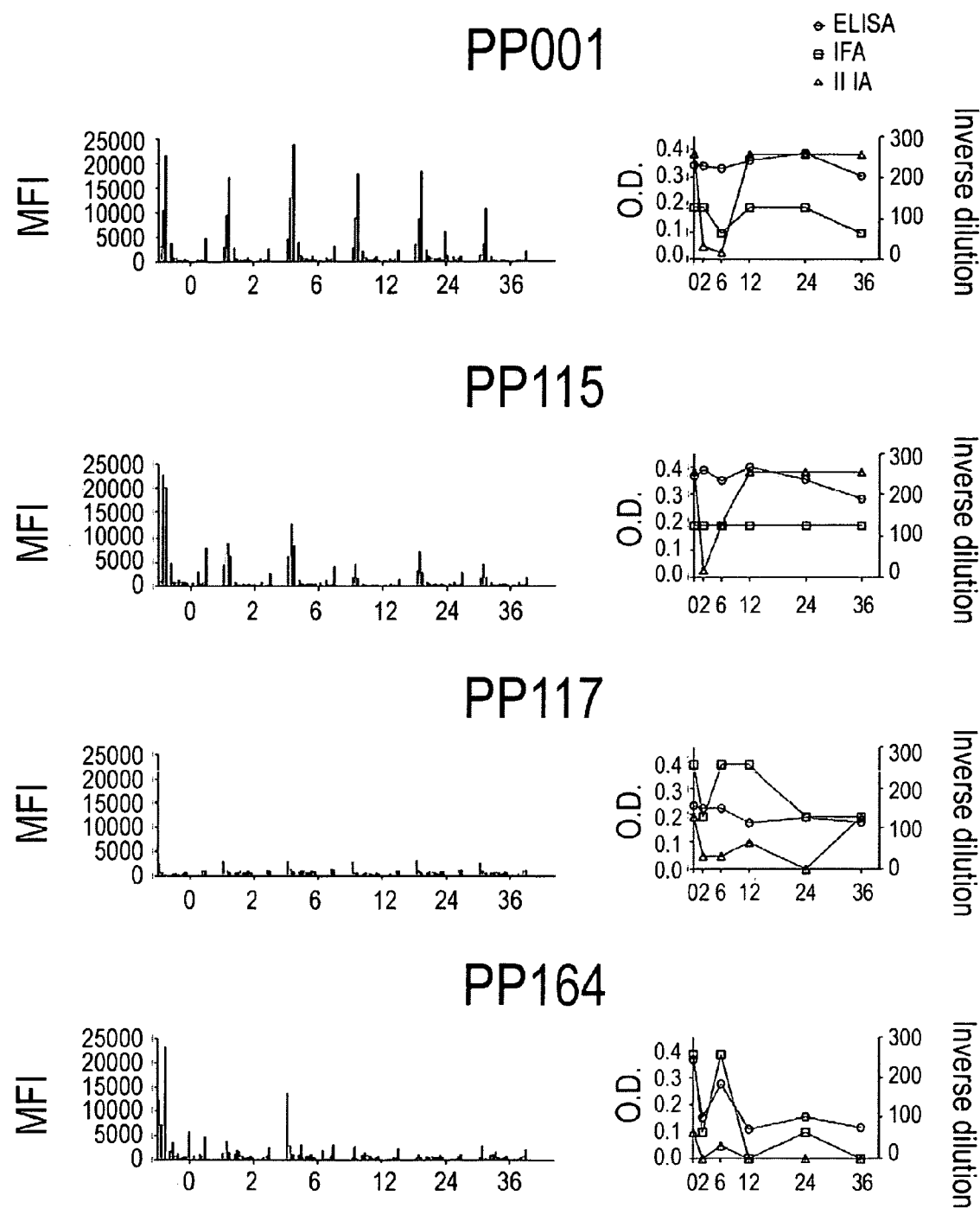
Figure 11B:
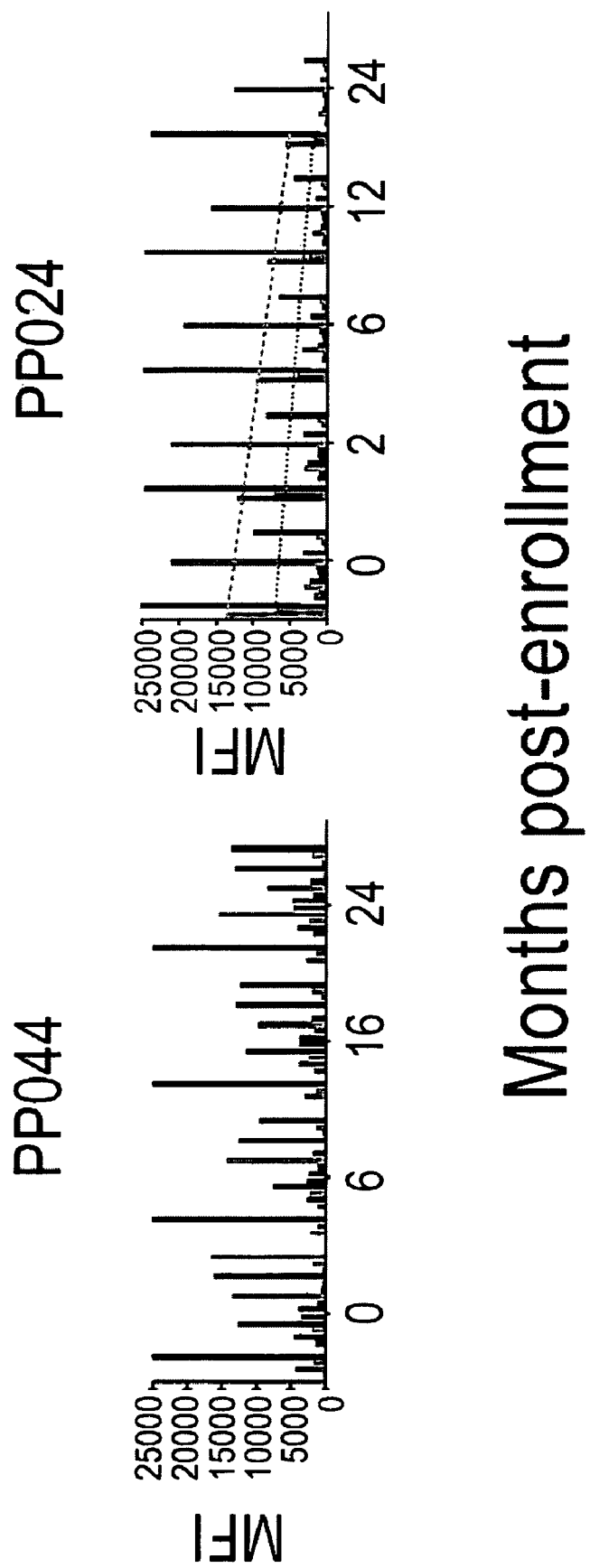

Monitoring treatment efficacy. There is a pressing need for a means to assess treatment efficacy in Chagas disease so we next used the multiplex assay to monitor changes in serology over time in subjects treated with benznidazole (BZ). Representative data from a set of 16 non-endemic normals (FIG. 10A) demonstrates the background level of detection of responses in uninfected individuals, displayed as the MFI for each protein. To establish the stability of serological responses over time in the absence of treatment, serial serum samples were obtained from chronically infected, seropositive subjects, all without clinical disease; a representative set of 6 subjects screened at 4 times points for up to 21 months is shown in FIG. 10B. Each subject exhibits a distinct pattern of serological responses and both the pattern and the potency of those responses are remarkably stable over time. In contrast, a representative set of 4 (from a total of 38) subjects followed for up to 36 months after treatment with BZ shows that some subjects exhibit a post-treatment decrease in the strength of responses to most *T. cruzi* antigens tested (FIG. 11A). In many cases this fall is evident by 2 months post-treatment (e.g. PP001, PP115, PP164) and is followed by a transient increase at 6 months. Interestingly, this early drop in antibody levels following treatment is also sometimes evident, although less consistently so, with conventional serological tests, particularly with indirect hemagglutination (FIG. 11A). Subject PP117 has borderline positive serology in both the multiplex and the conventional serologic assays, and is representative of a case in which documenting changes following treatment would be difficult. FIG. 11A). FIG. 11B presents 2 other patterns of responses following treatment. PP044 shows essentially no change in the pattern or potency of antibody responses up to 24 months post-treatment. Subject PP024 is similar in that responses to the several prominently detected proteins are relatively stable over time. However the MFI reading for numerous other antigens falls consistently over the 24 month monitoring period. Thus, although it might take more time and additional assays to determine treatment efficacy in these two subjects, a preliminary assessment would be that treatment failed in the case of PP044 but was successful for subject PP024.

Discussion

The poor quality of diagnostics for *T. cruzi* infection is a major impediment to coping with a disease that affects as many as 20 million people. Without quality diagnostics, the statistic of the disease burden is at best a guess, the ability to conclusively identify who should be treated, or should be allowed to donate blood or tissues is greatly compromised and the effectiveness of interventions to limit transmission or drugs to treat those infected is impossible to determine with any certainty.

In the early stages of *T. cruzi* infection, parasites can often be detected in blood. However, as immunity develops, even amplification techniques such as xenodiagnosis, hemaculture, and PCR, despite being repeated multiple times, routinely fail to detect infection (Castro et al., 2002, Parasitol Res 88: 894-900; Picka et al., 2007, Braz J Infect Dis 11: 226-233; Salomone et al., 2000, Am J Cardiol 85: 1274-1276; Duarte et al., 2006, Rev Soc Bras Med Trop 39: 385-387). Consequently, determination of infection status is largely dependent on the consensus results of multiple tests with different formats (e.g. ELISA, indirect fluorescent antibody, indirect hemaglutination, complement fixation). However the unreliability of these tests is well documented (Pirard et al., 2005, Transfusion 45: 554-561; Salomone et al., 2003, Emerg Infect Dis 9: 1558-1562; Avila et al., 1993, J Clin Microbiol 31: 2421-2426; Castro et al., 2002, Parasitol Res 88: 894-900; Caballero et al., 2007, Clin Vaccine Immunol. 14:1045-1049; Silveira-Lacerda et al., 2004, Vox Sang 87: 204-207; Wincker et al., 1994, Am J Trop Med Hyg 51: 771-777; Gutierrez et al., 2004, Parasitology 129: 439-444; Marcon et al., 2002, Diagn Microbiol Infect Dis 43: 39-43; Picka et al., 2007, Braz J Infect Dis 11: 226-233; Zarate-Blades et al., 2007, Diagn Microbiol Infect Dis 57: 229-232). Many of these tests, including one recently licensed by the United States Food and Drug Administration for use as a blood screening test in the U.S. (Tobler et al., 2007, Transfusion 47: 90-96), use crude or semi-purified parasite preparations derived from parasite stages present in the insect vector but not in infected humans. Recently a number of recombinant parasite proteins or peptides have also come into limited use for diagnosis (da Silveira et al., 2001, Trends Parasitol 17: 286-291; Chang et al., 2006, Transfusion 46: 1737-1744; Kirchhoff et al., 1984, J Immunol 133: 2731-2735; Laucella et al., 2004, J Infectious Diseases 189:909-918).

A subject whose serum is consistently positive on multiple of the currently used tests is relatively easily determined to be infected. But the infection status of individuals positive on only one test (as in blood bank screening) is unclear and detection of parasites in subjects who are negative using multiple conventional serologic tests (Salomone et al., 2003, Emerg Infect Dis 9: 1558-1562; Gutierrez et al., 2004, Parasitology 129: 439-444; Marcon et al., 2002, Diagn Microbiol Infect Dis 43: 39-43; Picka, et al., 2007, Braz J Infect Dis 11: 226-233; Wincker et al., 1994, FEMS Microbiol Lett 124: 419-423) or who are positive by alternative but not widely available serological tests (Caballero et al., 2007, Clin Vaccine Immunol. 14:1045-1049; Zarate-Blades et al., 2007, Diagn Microbiol Infect Dis 57: 229-232) is not uncommon. Furthermore, currently available tests are inadequate for monitoring treatment efficacy (Sanchez Negrette et al., 2008, Clin Vaccine Immunol 15: 297-302; Bahia-Oliveira et al., 2000, J Infect Dis 182: 634-638; Solari et al., 2001, J Antimicrob Chemother 48: 515-519) and thus may also give inaccurate measurements of the effectiveness of other interventions.

With these deficits in mind, we set out to identify parasite proteins that would more effectively detect *T. cruzi* infection and provide a tool for monitoring changes in infection status over time. Development of a repository of nearly 1500 *T. cruzi* genes cloned into GATEWAY entry vectors provided a relatively straightforward approach to producing a large number and diversity of *T. cruzi* proteins appropriate for high-throughput screening of diagnostics. Adding the targeted approach of selecting proteins documented for high level expression in trypomastigote and amastigote stages of *T. cruzi* allowed us to also focus on the proteins that would be predicted to elicit the strongest antibody response in infected humans. The Luminex-based multiplex bead array system permitted us to screen many proteins simultaneously with very low requirements for serum. The production of histidine-tagged proteins also made it relatively uncomplicated to attach the recombinant proteins to Luminex beads. This latter point is not trivial as the proteins could be coupled to the assay beads directly from the denaturing urea-based lysis buffer without the requirement of movement to a non-denaturing buffer, wherein many of the proteins precipitated. The strong response detected using proteins prepared in this way suggests either that natively folded proteins are not required for the detection of these antibodies or that re-folding of the proteins attached to the Luminex beads during buffer exchange resulted in the formation of native conformational epitopes.

In addition to its utility for screening of a large number of proteins, the Luminex system also excels as a platform for multiplex analysis of antibodies to a relatively large set of targets. We were restricted in this work by the number of Luminex bead sets manufactured with Ni+2 and thus sought to identify a maximum of 16 independent *T. cruzi* proteins that gave informative results from a large set of human sera. The ultimate panel selected by the screen included at least one protein previously identified as a potential diagnostic, the mitochondrial HSP-70 (Krautz et al., 1998, Am J Trop Med Hyg 58: 137-143). It is possible that other proteins revealed in our screen have been studied previously. However since the identity of some of these previously assayed proteins is somewhat cryptic (da Silveira et al., 2001, Trends Parasitol 17: 286-291) and few have been associated with annotated genes in the sequenced *T. cruzi* genome, this is difficult to determine. Also, over half of the antigens selected in our screen were among the 50 most abundant proteins in the trypomastigote and amastigote proteomes (Atwood et al., 2005, Science 309: 473-476). Two hypothetical proteins and 2 proteins unique to *T. cruzi* among the sequenced kinetoplastids, including 2 fragments from the very large and multicopy dispersed gene family protein, were among the proteins selected. Proteins that are unique to *T. cruzi* could be particularly useful in a serological screen as they are absent from *Leishmania*, one of the potentially confounding infections in terms of diagnosis of *T. cruzi*. However the dispersed gene family fragments were among the worst performers in the large scale screen—with only 5-9% of all confirmed positive sera having detectable antibodies to these. Similarly, other gene family proteins, including trans-sialidases, mucins and mucin-associated proteins (MASPS) were part of the screen but failed to make even the initial selection cuts in our assays, presumably because only a small fraction of their diversity would be represented in the recombinant proteins screened.

A multiplex approach like the Luminex also provided a more detailed examination of responses than is possible using a single target consisting of either an individual protein or a protein/peptide mixture. Each individual was seen clearly to have a distinct pattern of responses to the protein panel and that this pattern was impressively stable over time (several years). This is both interesting scientifically and serves as further validation of the quality and consistency of the data generated using this multiplex methodology. This heterogeneity of responses to pathogens among individuals appears to be more the norm than the exception, as similar results have been reported for individuals infected or immunized with viral (vaccinia), bacterial (*Francisella tularensis*) and protozoal (*Plasmodium falciparum*) pathogens (Davies et al., 2007, Proteomics 7: 1678-1686; Sundaresh et al., 2006, Bioinformatics 22: 1760-1766; Sundaresh et al., 2007, Bioinformatics 23: i508-518). Thus serodiagnostics in general are likely to need to move toward multiplex assays, as single antigens that are recognized by all individuals infected by any pathogen appear to be rare (Davies et al., 2007, Proteomics 7: 1678-1686).

The ability to simultaneously and independently assess antibody responses to multiple targets was instrumental to our success in addressing the issues of the detection of serological responses in subjects who are negative by conventional serology and the relatively rapid detection of changes in selected responses following drug treatment. The multiplex assay detected 100% of 121 samples consistently positive by conventional serology, and 100% of samples positive on 2 out of 3 conventional tests. In addition, however, we also detected antibodies specific for one or more recombinant proteins in 18 of 33 subjects judged as negative by conventional serology. Other investigators have documented cases of conventional seronegative subjects being seropositive on alternative tests or even parasite positive (Salomone et al., 2003, Emerg Infect Dis 9: 1558-1562; Caballero et al., 2007, Clin Vaccine Immunol. 14:1045-1049; Gutierrez et al., 2004, Parasitology 129: 439-44; Marcon et al., 2002, Diagn Microbiol Infect Dis 43: 39-43; Picka et al., 2007, Braz J Infect Dis 11: 226-233; Zarate-Blades et al., 2007, Diagn Microbiol Infect Dis 57: 229-232; Wincker et al., 1994, FEMS Microbiol Lett 124: 419-423) although these previous reports of "infected seronegatives" have been somewhat anecdotal—presumably because investigators rarely screen for parasites in seronegative subjects. However in some studies parasite-positive conventional seronegatives are very well documented. For example Picka et al. (Braz J Infect Dis 11: 226-233, 2007) reported on one subject who was negative by up to 5 replicates of 4 different conventional serological tests yet was positive by a combined hemaculture-PCR approach. The multiple examples of failed conventional serology to detect infection in combination with the well-documented unreliability of parasitological tests, supports the conclusion that individuals who are seropositive in our multiplex assay are likely to be infected with *T. cruzi*. This conclusion is further supported by on-going studies demonstrating *T. cruzi*—specific T cell responses in subjects who are negative by conventional serology but positive in our multiplex assays. Without more sensitive parasitological tests we cannot conclusively determine if the subjects who are negative by conventional serology but positive in our multiplex assay are infected or possibly "exposed" but not still infected with *T. cruzi*. And without additional extensive validation, we cannot exclude the possibility that other infections or immunological conditions resulted in some of the multiplex positive responses, although standard clinical analysis failed to detect other complicating infections in these subjects. However, especially for subjects who have antibodies to up to 8 different recombinant *T. cruzi* proteins and were born in endemic areas and/or have evidence of heart disease, it is reasonable to conclude that they are indeed infected with *T. cruzi* despite their negative results with conventional serologic assays. Overall these studies support the already documented conclusion that current serological tests can misdiagnose infection—perhaps to a significant extent.

A second issue we addressed using the multiplex serological assay for *T. cruzi* infection was that of efficacy of therapeutic treatment. Because most subjects are negative by parasitological assays prior to treatment (making a negative result after treatment uninformative) and remain positive by conventional serology for extensive periods of time after treatment, assessing whether treatment actually achieved cure) has been problematic. When combined with other evidence of treatment failures and the adverse effects of the drugs, the absence of a method to detect treatment efficacy has resulted in a very low rate of treatment in chronic Chagas disease. This absence of a reliable and timely test for treatment efficacy is also a major impediment to the development and testing of new drugs—an area that has been at a virtual standstill for decades.

Herein we show that the multiplex assay using the selected set of recombinant proteins can detect significant changes in antibody levels, in some cases as early as the first post-treatment assay point (2 months post-treatment completion). These changes are not evident in all cases—an outcome that is not surprising given that treatment failure is common (Viotti et al., 1994, Am Heart J 127: 151-162). Our ability to assess responses to multiple targets on an individual basis appears to be crucial to the success of detection of serologic changes following treatment, as similar changes are not consistently observed using conventional serologic tests. Previous studies have suggested that various recombinant antigens may provide better assessment of treatment efficacy relative to conventional serology (Sanchez Negrette et al., 2008, Clin Vaccine Immunol 15: 297-302; Sosa Estani et al., 1998, Am J Trop Med Hyg 59: 526-529).

In conclusion, we define a set of diagnostic targets and an assay approach that we believe is a significant improvement upon current diagnostic tests for *T. cruzi* infection both for more consistently detecting infection and for assessing the effectiveness of treatment. Additional validation of these targets and the general methodology will require analysis of a larger set of subjects, a process that is currently on-going. Herein we have also not addressed the question of whether the antigens we identify would be useful throughout the wide endemic range for *T. cruzi*. Heterogeneity among different parasites strains in distinct regions could present a challenge. However here again this is a concern that a multiplex assay might rather easily address—it seems unlikely that all 16 proteins in our pool, most of which are abundant housekeeping proteins, would vary substantially among parasites in various regions. The problem of infection confirmation by detection of parasites or parasite products is likely to continue to be a roadblock to full acceptance of the results of this test, or any other, when they conflict with conventional serologic tests—despite the proven inadequacy of these "standard" tests. A downside of the Luminex system for multiplex analysis is the reagent expense as well as the requirement for specialized equipment to "read" the results. However, other multiplex platforms such as protein microarrays could be more cost conservative and require less infrastructure (Davies et al., 2007, Proteomics 7: 1678-1686; Kartalov et al., 2006, Biotechniques 40: 85-90). Also, our results suggest that the number of proteins in the analysis could be reduced without substantial loss of sensitivity and the possibility exists for additional improvements in sensitivity by the inclusion of *T. cruzi* proteins previously validated by others, or that could be detected in additional screens like that described herein. At a minimum, these results begin to lay the groundwork for the removal of one of the major impediments to the development and effective implementation of treatments for *T. cruzi* infection.

Example 10

Preliminary Panel of Serodiagnostic Proteins

In a preliminary study that eventually resulted in the serodiagnostic proteins described in Example 9, 53 diagnostic proteins was selected (Table 4) from a group of 59 candidate proteins identified through screening with serum pools and individual sera. The preliminary serodiagnostic panel selected for further study consisted of the top 16 proteins in Table 4.

TABLE 4

Protein antigens

| Current panel constituents | Published as antigens? | Common Name | Annotated gene or Tc00 id of closest homolog | SEQ ID No: |
|---|---|---|---|---|
| 1 | | hypothetical protein | Tc00.1047053508767.10 | 68 |
| 2 | | hypothetical protein, conserved | Tc00.1047053506635.130 | 69 |
| 3 | 1, 3 (ribosomal P protein, TcP0?) | 60S acidic ribosomal subunit protein, putative | Tc00.1047053508355.250 | 13 |
| 4 | 1-2 (flagellar CaBP, 1F8) | flagellar calcium-binding protein, putative | Tc00.1047053507491.151 | 70 |
| 5 | 1, 3 (MAP) | microtubule-associated protein, putative | Tc00.1047053511633.79 | 31 |
| 6 | 1 (heat shock) | heat shock 70 kDa protein, mitochondrial precursor, putative | Tc00.1047053507029.30 | 24 |
| 7 | 1 (paraflagellar assoc. prot) | 69 kDa paraflagellar rod protein, putative | Tc00.1047053511215.119 | 25 |
| 8 | | EF-hand protein 5 | Tc00.1047053506391.30 | 14 |
| 9 | | aminopeptidase, putative | Tc00.1047053511289.30 | 18 |
| 10 | | axoneme central apparatus protein, putative | Tc00.1047053510955.40 | 16 |
| 11 | | hypothetical protein | Tc00.1047053506529.610 | 6 |
| 12 | | glycosomal phosphoenolpyruvate carboxykinase, putative | Tc00.1047053508441.20 | 11 |
| 13 | | dispersed gene family protein 1 fragment | Tc00.1047053511271.10 | 26 |
| 14 | | malate dehydrogenase, putative | Tc00.1047053506195.110 | 29 |
| 15 | | dispersed gene family protein 1 fragment | Tc00.1047053511265.10 | 28 |
| 16 | | poly(A)-binding protein | Tc00.1047053508461.140 | 30 |
| | | Understudy - ranked by approximate potential | | |
| 17 | 1 (cytoskeleton assoc?) | beta tubulin | Tc00.1047053506563.40 | 1 |
| 18 | 1 (cytoskeleton assoc?) | alpha tubulin | Tc00.1047053411235.9 | 2 |
| 19 | 1 (ribosomal prot) | 60S ribosomal protein L28, putative | Tc00.1047053506297.270 | 10 |
| 20 | 1 (ribosomal prot) | polyubiquitin (pseudogene), putative | Tc00.1047053507483.4 | 51 |
| 21 | | iron superoxide dismutase, putative | Tc00.1047053511019.90 | 41 |
| 22 | | iron superoxide dismutase, putative | Tc00.1047053509775.40 | 71 |
| 23 | | elongation factor-1 gamma, putative | Tc00.1047053506459.290 | 48 |
| 24 | | hypothetical protein, to be annotated | Tc00.1047053507515.4 | 72 |
| 25 | | dispersed gene family protein 1 fragment | Tc00.1047053509815.120 | 63 |
| 26 | | hypothetical protein, conserved | Tc00.1047053504153.280 | 46 |
| 27 | | p22 protein precursor, putative | Tc00.1047053509053.70 | 52 |
| 28 | | 25 kDa translation elongation factor 1-beta, putative | Tc00.1047053506201.39 | 66 |
| 29 | | universal minicircle sequence binding protein (UMSBP), putative | Tc00.1047053503781.80 | 65 |
| 30 | | hypothetical protein, conserved | Tc00.1047053510877.30 | 35 |
| 31 | | d-isomer specific 2-hydroxyacid dehydrogenase-protein, putative | Tc00.1047053510099.120 | 60 |
| 32 | | RNA-binding protein, putative | Tc00.1047053511727.270 | 64 |
| 33 | | stress-induced protein sti1, putative | Tc00.1047053506321.290 | 73 |
| 34 | | glutamamyl carboxypeptidase, putative | Tc00.1047053510837.20 | 74 |
| 35 | 1 (trans-sialidase) | chunk of conserved hypothetical protein | Tc00.1047053509099.160 | 75 |

TABLE 4-continued

Protein antigens

| Current panel constituents | Published as antigens? | Common Name | Annotated gene or Tc00 id of closest homolog | SEQ ID No: |
|---|---|---|---|---|
| 36 | | centrin, putative | Tc00.1047053506559.380 | 76 |
| 37 | | possible salivary proline-rich protein rp15 | Tc00.1047053506835.110 | 77 |
| 38 | | tuzin | Tc00.1047053507485.140 | 78 |
| 39 | 1 (trans-sialidase) | chunk of putative trans-sialidase | Tc00.1047053507997.14 | 79 |
| 40 | 4 (cruzipain) | cysteine peptidase, putative | Tc00.1047053507603.270 | 80 |
| 41 | 1 (heat shock) | Tc 85 kDa antigen with homology to heat shock proteins | Tc00.1047053509643.130 | 81 |
| 42 | 1 (heat shock) | Tc hsp 70 | Tc00.1047053511211.170 | 82 |
| 43 | | serine carboxypeptidase (CBP1), putative | Tc00.1047053509695.220 | 17 |
| 44 | | hypothetical protein, conserved | Tc00.1047053510887.50 | 7 |
| 45 | | hypothetical protein, conserved | Tc00.1047053509141.40 | 36 |
| 46 | | dihydrolipoyl dehydrogenase, putative | Tc00.1047053507089.270 | 40 |
| 47 | | hypothetical protein, conserved | Tc00.1047053506529.460 | 4 |
| 48 | | trans-splicing factor, putative | Tc00.1047053503583.40 | 9 |
| 49 | | GTP-biNDing nuclear protein rtb2, putative | Tc00.1047053503539.30 | 83 |
| 50 | | 14-3-3 protein, putative | Tc00.1047053511167.90 | 56 |
| 51 | | nascent polypeptide associated complex subunit, putative | Tc00.1047053510579.70 | 58 |
| 52 | | hypothetical protein, conserved | Tc00.1047053507093.300 | 61 |
| 53 | | succinyl-CoA synthetase alpha subunit, putative | Tc00.1047053508479.340 | 62 |

[1] da Silveira, et al., TRENDS in Parasitology Vol. 17 No. 6 June 2001, p.286-291
2 Umezawa, et al., TRANSFUSION Volume 43, January 2003, p. 91-97
3 Umezawa, et al., JOURNAL OF CLINICAL MICROBIOLOGY, January 2004, p. 449-452
4 Martinez, et al., INFECTION AND IMMUNITY, November 1991, p. 4275-4277

Figure 12A:
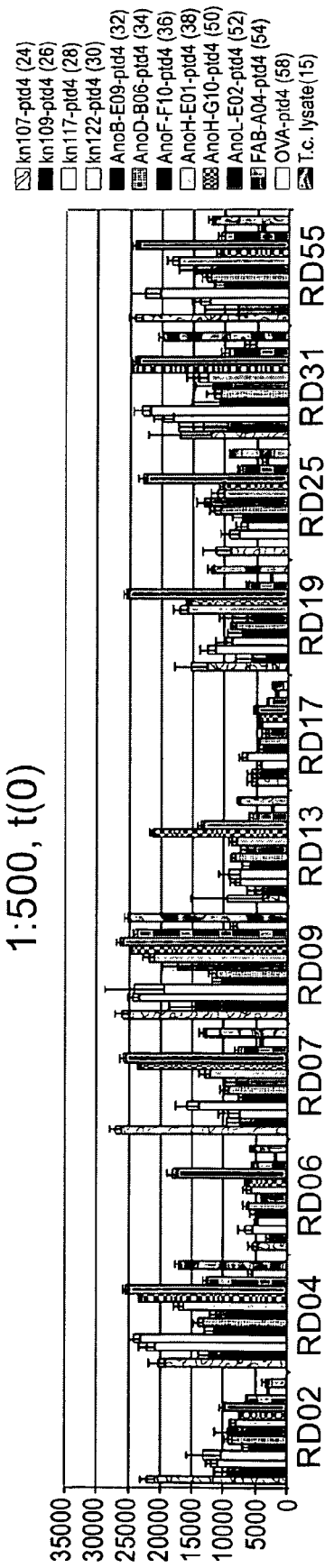
Figure 12B:
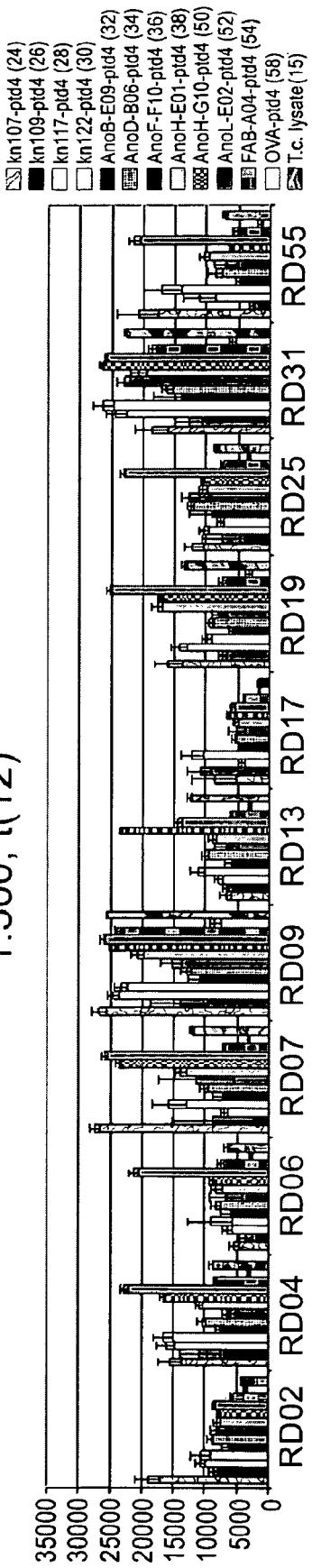

FIG. 12 shows the pattern of responses of 11 subjects to 11 antigens and 2 controls (ovalbumin as the negative control, and *T. cruzi* lysate as a positive control) at the time of the first bleed (FIG. 12A) and 12 months later (FIG. 12B). Three aspects are worthy of mention. First, the pattern of responses is unique in each individual; no one appears to respond similarly. Second, the pattern of responses is stable over the 12 month period. This is a strong indicator that the assay is indeed reproducibly detecting a persistent response. This is also important with respect to using the test to monitor changes after therapy. Third, no single recombinant protein (or even combination of 3 or 4 proteins) detects all responders. This result validates the need for a multicomponent test for *T. cruzi* infection.

Example 11

Monitoring Treatment for Chagas Disease

Figure 13B:
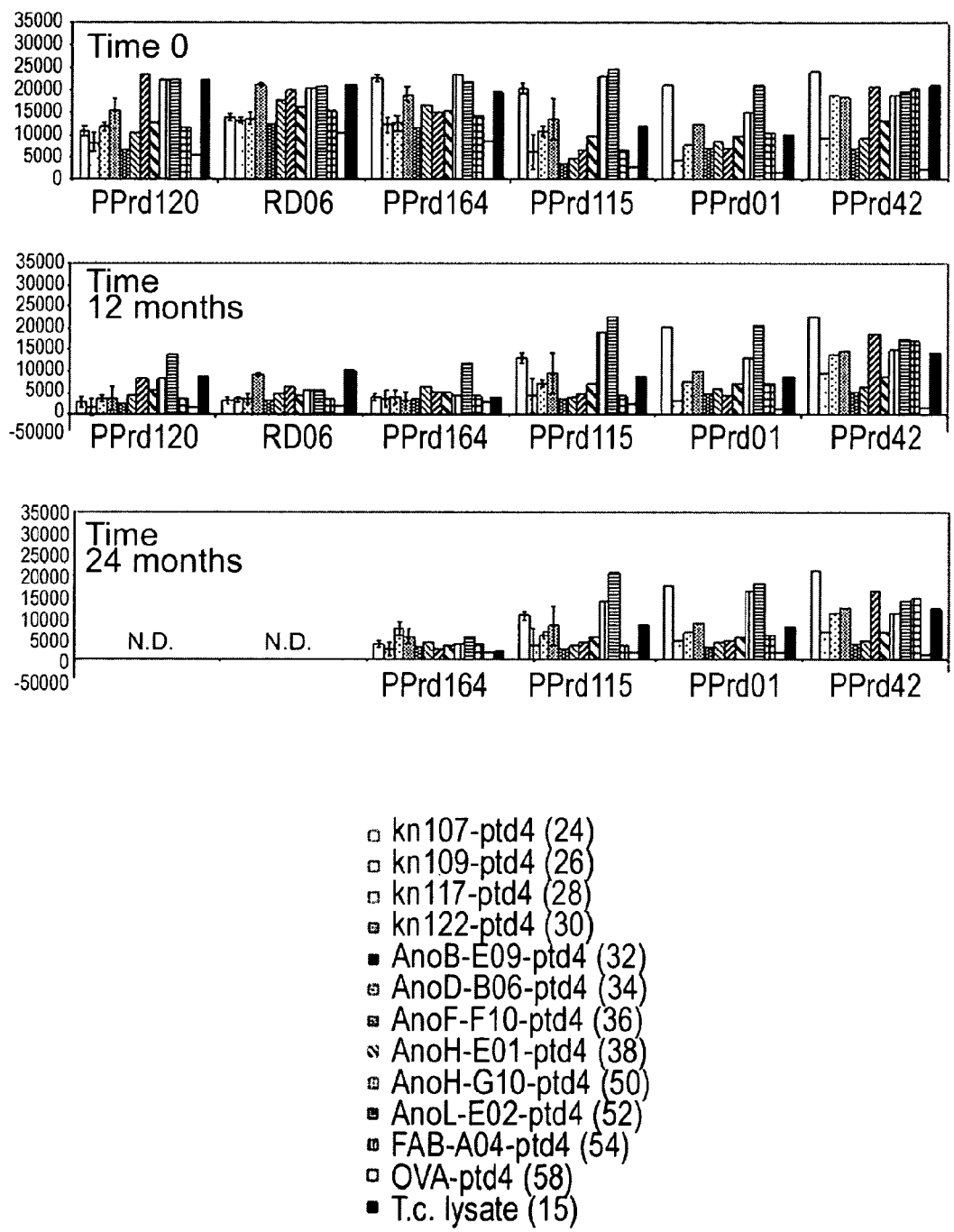
Figure 14:
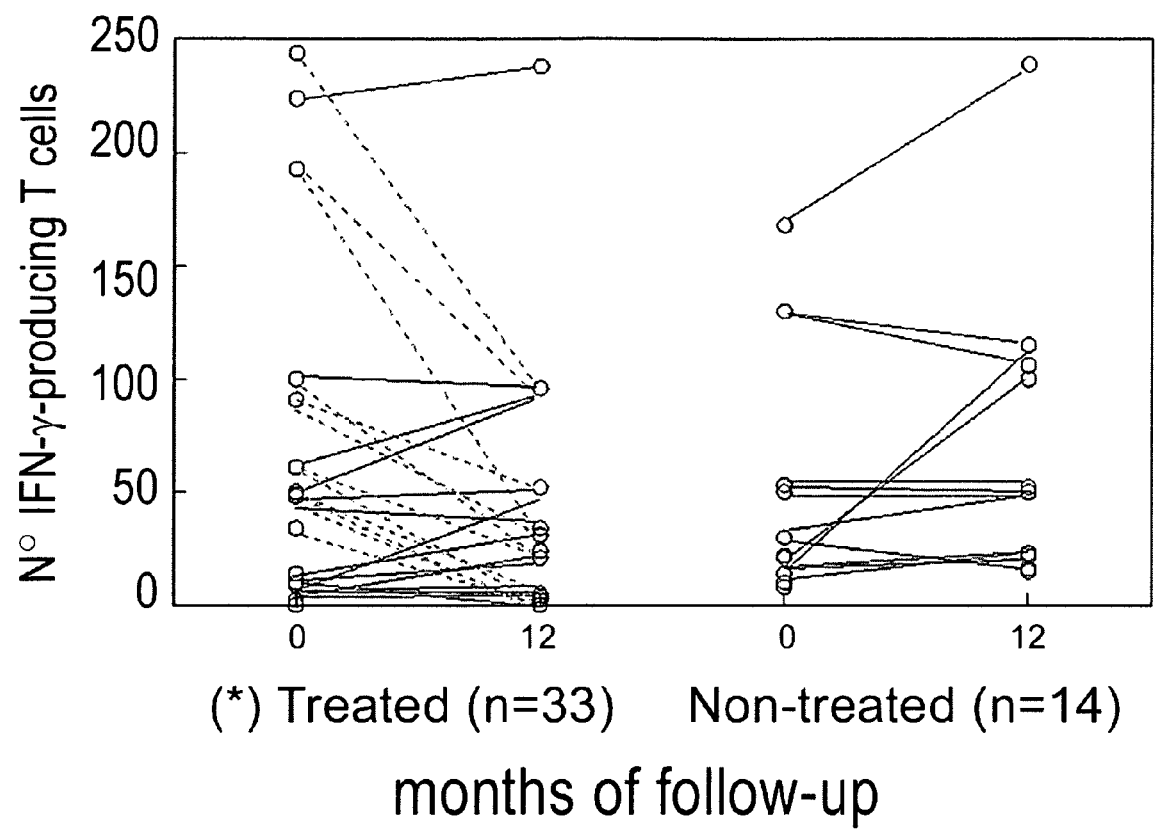
Figure 15A:
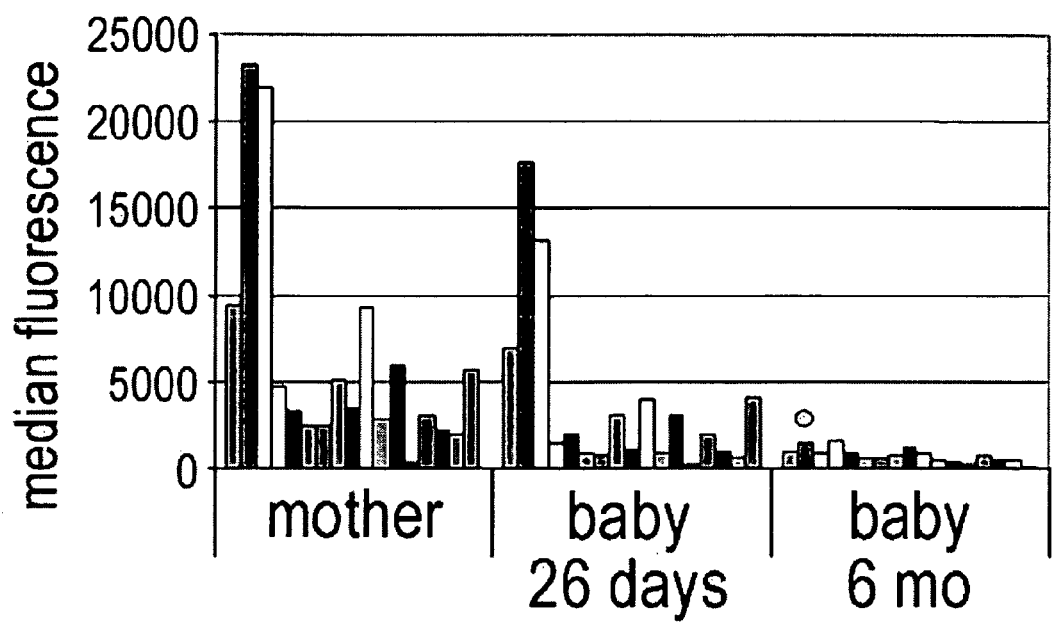
FIG. 15 shows the antibody profiles of four mothers (A, B, C, D) with chronic Chagas disease and their infants at a time point relatively soon after birth, and again later when the infant is 6-7 months old.
Figure 15B:
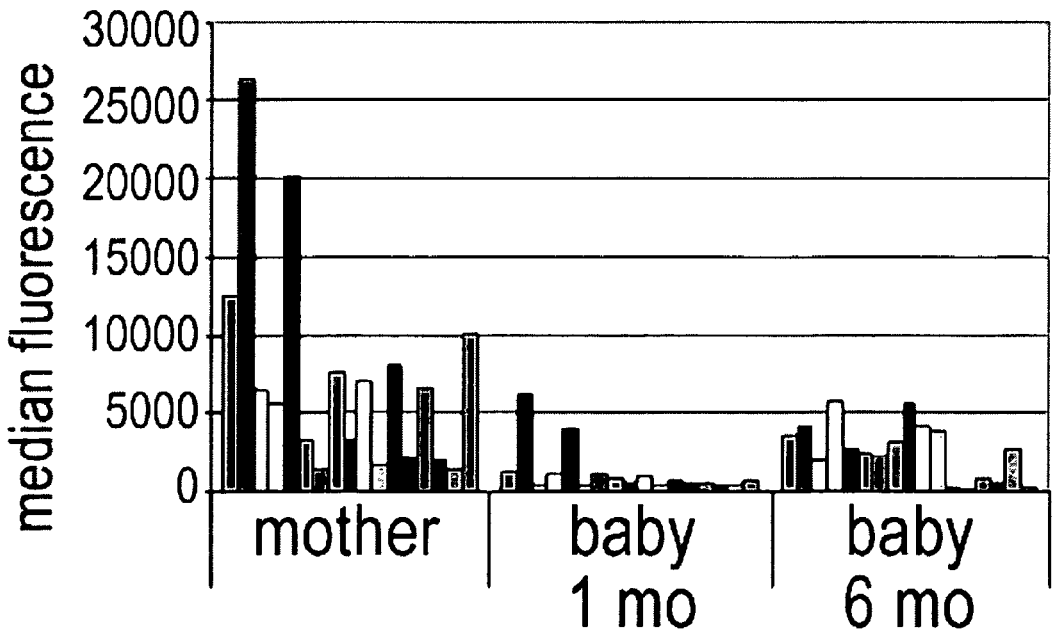
Figure 15C:
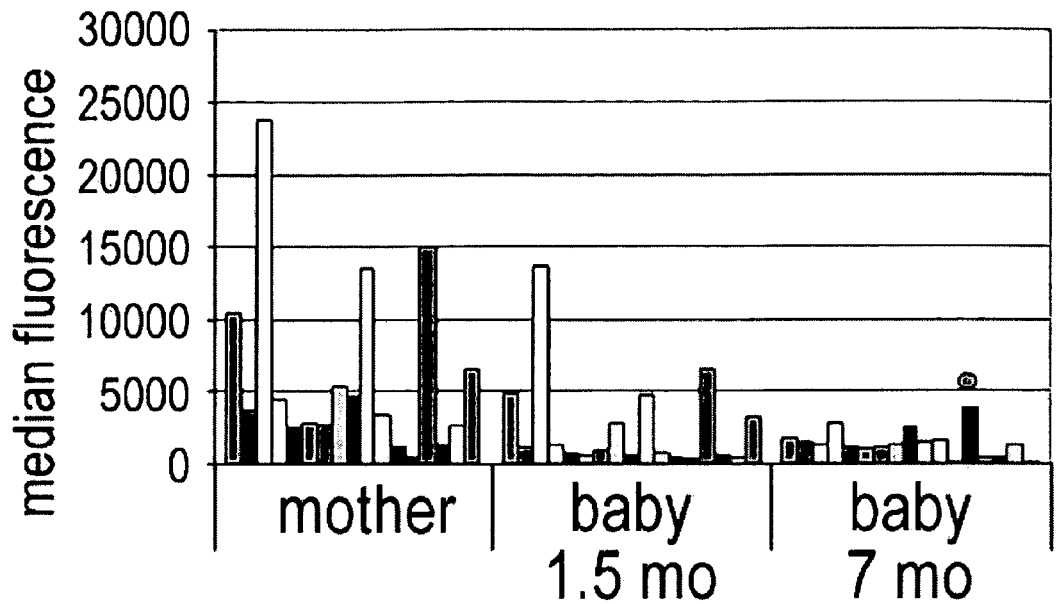
Figure 15D:
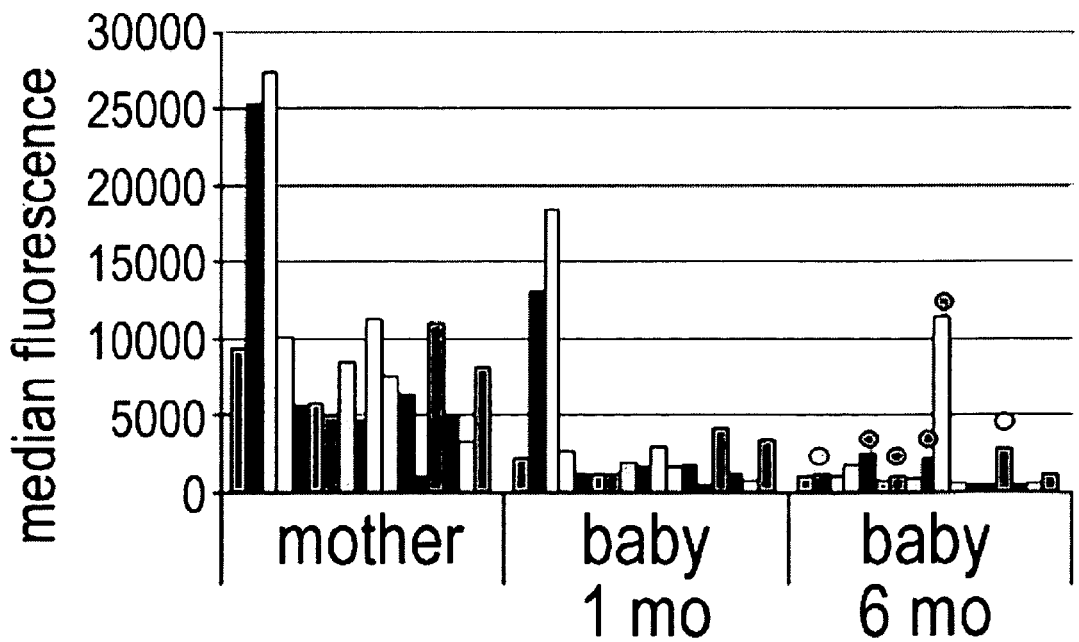

Benzindazole is the primary compound used for treatment of Chagas disease, although there is controversy about its efficacy in treating chronically infected subjects, such as those who have been infected >20 years). The left side of FIG. 13 below shows consistent serologic responses at 0 and 12 months in the absence of treatment in 4 subjects. The right side shows 6 treated subjects, treated at time 0 and reassayed at 12 and 24 months post-treatment. Changes in serology are obvious in 3 of the treated subjects at 12 months. The other 3 subjects have little to no change, even at 24 months. It is worth noting that conventional serology conducted on these same sera showed inconsistent or no changes. Furthermore, the percentage of individuals showing serological changes consistent with cure is similar to that reported in other like studies but using much longer follow-ups. E.g., a recent study by Fabbro et al. (Rev Soc Bras Med. Trop. 2007 January-February; 40(1):1-10), reported a treatment efficacy rate of 35-63% based upon conventional serology but required an average 16 year follow-up to see this change. Moreover, nearly 100% of those showing changes in serology also showed changes in T cell responses (FIG. 14; note decreasing to undetectable responses within 12-25 months). Similar changes were not seen in untreated subjects or in treated subjects who failed to exhibit serological changes. Overall we conclude that this multiplex assay has the capability to relatively rapidly detect treatment success or failure—especially when coupled with assays of T cell reactivity.

Example 12

Maternal/Neonate Diagnostics

The unique pattern of responses in each individual may have utility with respect to monitoring congenital infection, which is currently very difficult. If the pattern of the serologic response in mother and newborn is similar, then we would suspect that the infant's serologic response is a result of maternally derived antibodies rather than to antibodies produced by the infant. However if the patterns are different, then we would suspect that the child is infected and therefore should be treated.

Four separate pairs of mother and newborn were evaluated. Serum antibody titers against individual recombinant *T. cruzi* proteins were determined for both the mother and the infant at a time point relatively soon after birth (within weeks), and again approximately 6 months later. For all pairs, the infant's pattern of response shortly after birth resembles the mother's pattern of response, indicating the presence of maternal antibodies (FIG. 15). At the later time point, two of the infants (FIGS. 15B, and D) show a pattern of response differs from the mother's, indicating that these infants may be infected and producing their own antibodies. Another infant (FIG. 15A) shows a response that is near background levels, suggesting that the infant is likely not infected. Circles over the individual measurements indicate statistically significant responses.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. An article comprising:
a substrate comprising a surface; and
a plurality of different individually addressable antigenic *T. cruzi* polypeptides immobilized onto a surface on said substrate surface;
wherein at least one polypeptide comprises the amino acid sequence of at least one of SEQ ID NO:24-26, 28-34, or 68-70.

2. The article of claim 1 wherein the polypeptides are immobilized on the substrate surface to form a microarray.

3. The article of claim 1 wherein the substrate comprises at least one nanoparticle, and wherein the polypeptides are immobilized on the surface of the nanoparticle.

4. A kit for diagnosis of *T. cruzi* infection comprising:
an article according to claim 1; and
packaging material and instructions for use.

5. A method for obtaining information about a known or suspected *T. cruzi* infection in a mammal, or for determining whether a mammal is or has been infected by *T. cruzi*, said method comprising:
obtaining a biological sample from the mammal;
contacting the biological sample with the article of claim 1; and
evaluating the presence, absence, intensity or pattern of interaction of components of the biological sample with the antigenic *T. cruzi* polypeptides to determine the presence or absence of *T. cruzi* infection, the identity of the infective strain, the length of the infection, the stage of the infection, whether the infection is still present or the mammal has been cured, the vaccination status of the mammal, the success of treatment, or any combination thereof.

6. The method of claim 5 wherein the mammal is a human or a dog.

7. The method of claim 5 wherein the biological sample comprises a body fluid comprising an antibody.

8. The method of claim 7 wherein the body fluid comprises blood, plasma or serum.

9. The method of claim 5 wherein the biological sample comprises a mononuclear blood cell.

10. The method of claim 5 wherein the biological sample comprises a peripheral blood mononuclear cell (PBMC) fraction of blood from the mammal.

11. The method of claim 5 wherein the method is a serodiagnostic method, and wherein the biological sample component that interacts with the antigenic *T. cruzi* polypeptide is an antibody from the mammal.

12. The method of claim 5 wherein the method is a cellular assay method, and wherein the biological sample component that interacts with the antigenic *T. cruzi* polypeptide is T cell from the mammal.

13. The method of claim 5 wherein the method comprises a multiplexed assay wherein the biological sample is contacted simultaneously with the plurality of antigenic *T. cruzi* polypeptides.

14. The method of claim 5 wherein the biological sample is obtained from a blood donor, a potential blood donor, or a transplant donor.

15. The method of claim 5 wherein the biological sample is obtained from a pooled blood product supply intended for use in transfusions or research.

16. A method for detecting contamination of a blood product supply with *T. cruzi*, the method comprising:
selecting a sample from the blood supply;
contacting the sample with the article of claim 1; and
evaluating the presence, absence, intensity or pattern of interaction of components of the sample with the antigenic *T. cruzi* polypeptides to determine whether the blood supply is contaminated with *T. cruzi*.

17. The method of claim 16 wherein the blood product supply comprises whole blood, a blood product, or a blood fraction.

18. The method of claim 16 wherein the blood product supply comprises a cellular blood component, a liquid blood component, a blood protein, or mixtures thereof.

19. The method of claim 16 wherein the blood product supply comprises a red blood cell concentrate, a leukocyte concentrate, a platelet concentrate, plasma, serum, a clotting factor, an enzymes, albumin, plasminogen, or a immunoglobulin, or mixtures of thereof.

20. The method of claim 16 wherein the method is a serodiagnostic method, and wherein the sample component that interacts with the antigenic *T. cruzi* polypeptide is an antibody.

* * * * *

SEQUENCE LISTING

<160> NUMBER OF SEQ ID NOS: 83

<210> SEQ ID NO 1
<211> LENGTH: 442
<212> TYPE: PRT
<213> ORGANISM: Trypanosoma cruzi

<400> SEQUENCE: 1

```
Met Arg Glu Ile Val Cys Val Gln Ala Gly Gln Cys Gly Asn Gln Ile
1               5                   10                  15

Gly Ser Lys Phe Trp Glu Val Ile Ser Asp Glu His Gly Val Asp Pro
            20                  25                  30

Thr Gly Thr Tyr Gln Gly Asp Ser Asp Leu Gln Leu Glu Arg Ile Asn
        35                  40                  45

Val Tyr Phe Asp Glu Ala Thr Gly Gly Arg Tyr Val Pro Arg Ala Val
    50                  55                  60

Leu Ile Asp Leu Glu Pro Gly Thr Met Asp Ser Val Arg Ala Gly Pro
65                  70                  75                  80

Tyr Gly Gln Ile Phe Arg Pro Asp Asn Phe Ile Phe Gly Gln Ser Gly
                85                  90                  95

Ala Gly Asn Asn Trp Ala Gln Gly His Tyr Thr Glu Gly Ala Glu Leu
            100                 105                 110

Ile Asp Ser Val Leu Asp Val Cys Arg Lys Glu Ala Glu Ser Cys Asp
        115                 120                 125

Cys Leu Gln Gly Phe Gln Ile Cys His Ser Leu Gly Gly Gly Thr Gly
    130                 135                 140

Ser Gly Met Gly Thr Leu Leu Ile Ser Lys Leu Arg Glu Glu Tyr Pro
145                 150                 155                 160

Asp Arg Ile Met Met Thr Phe Ser Ile Ile Pro Ser Pro Lys Val Ser
                165                 170                 175

Asp Thr Val Val Glu Pro Tyr Asn Thr Thr Leu Ser Val His Gln Leu
            180                 185                 190

Val Glu Asn Ser Asp Glu Ser Met Cys Ile Asp Asn Glu Ala Leu Tyr
        195                 200                 205

Asp Ile Cys Phe Arg Thr Leu Lys Leu Thr Thr Pro Thr Phe Gly Asp
    210                 215                 220

Leu Asn His Leu Val Ser Ala Val Val Ser Gly Val Thr Cys Cys Leu
225                 230                 235                 240

Arg Phe Pro Gly Gln Leu Asn Ser Asp Leu Arg Lys Leu Ala Val Asn
                245                 250                 255

Leu Val Pro Phe Pro Arg Leu His Phe Met Met Gly Phe Ala Pro
            260                 265                 270

Leu Thr Ser Arg Gly Ser Gln Gln Tyr Arg Gly Leu Ser Val Pro Glu
        275                 280                 285

Leu Thr Gln Gln Met Phe Asp Ala Lys Asn Met Met Gln Ala Ala Asp
    290                 295                 300

Pro Arg His Gly Arg Tyr Leu Thr Ala Ser Ala Leu Phe Arg Gly Arg
305                 310                 315                 320

Met Ser Thr Lys Glu Val Asp Glu Gln Met Leu Asn Val Gln Asn Lys
                325                 330                 335
```

```
Asn Ser Ser Tyr Phe Ile Glu Trp Ile Pro Asn Asn Ile Lys Ser Ser
            340                 345                 350

Ile Cys Asp Ile Pro Pro Lys Gly Leu Lys Met Ala Val Thr Phe Val
            355                 360                 365

Gly Asn Asn Thr Cys Ile Gln Glu Met Phe Arg Arg Val Gly Glu Gln
            370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ile Glu Glu
            420                 425                 430

Glu Gly Glu Phe Asp Glu Glu Glu Gln Tyr
            435                 440

<210> SEQ ID NO 2
<211> LENGTH: 451
<212> TYPE: PRT
<213> ORGANISM: Trypanosoma cruzi

<400> SEQUENCE: 2

Met Arg Glu Ala Ile Cys Ile His Ile Gly Gln Ala Gly Cys Gln Val
1               5                   10                  15

Gly Asn Ala Cys Trp Glu Leu Phe Cys Leu Glu His Gly Ile Gln Pro
            20                  25                  30

Asp Gly Ala Met Pro Ser Asp Lys Thr Ile Gly Val Glu Asp Asp Ala
            35                  40                  45

Phe Asn Thr Phe Phe Ser Glu Thr Gly Ala Gly Lys His Val Pro Arg
        50                  55                  60

Ala Val Phe Leu Asp Leu Glu Pro Thr Val Val Asp Glu Ile Arg Thr
65                  70                  75                  80

Gly Thr Tyr Arg Gln Leu Phe His Pro Glu Gln Leu Ile Ser Gly Lys
                85                  90                  95

Glu Asp Ala Ala Asn Asn Tyr Ala Arg Gly His Tyr Thr Ile Gly Lys
            100                 105                 110

Glu Ile Val Asp Leu Cys Leu Asp Arg Ile Arg Lys Leu Ala Asp Asn
            115                 120                 125

Cys Thr Gly Leu Gln Gly Phe Leu Val Tyr His Ala Val Gly Gly Gly
130                 135                 140

Thr Gly Ser Gly Leu Gly Ala Leu Leu Leu Glu Arg Leu Ser Val Asp
145                 150                 155                 160

Tyr Gly Lys Lys Ser Lys Leu Gly Tyr Thr Val Tyr Pro Ser Pro Gln
                165                 170                 175

Val Ser Thr Ala Val Val Glu Pro Tyr Asn Ser Val Leu Ser Thr His
            180                 185                 190

Ser Leu Leu Glu His Thr Asp Val Ala Ala Met Leu Asp Asn Glu Ala
        195                 200                 205

Ile Tyr Asp Leu Thr Arg Arg Asn Leu Asp Ile Glu Arg Pro Thr Tyr
    210                 215                 220

Thr Asn Leu Asn Arg Leu Ile Gly Gln Val Val Ser Ala Leu Thr Ala
225                 230                 235                 240

Ser Leu Arg Phe Asp Gly Ala Leu Asn Val Asp Leu Thr Glu Phe Gln
                245                 250                 255

Thr Asn Leu Val Pro Tyr Pro Arg Ile His Phe Val Leu Thr Ser Tyr
            260                 265                 270
```

```
Ala Pro Val Ile Ser Ala Glu Lys Ala Tyr His Glu Gln Leu Ser Val
            275                 280                 285

Ser Glu Ile Ser Asn Ala Val Phe Glu Pro Ala Ser Met Met Thr Lys
            290                 295                 300

Cys Asp Pro Arg His Gly Lys Tyr Met Ala Cys Cys Leu Met Tyr Arg
305                 310                 315                 320

Gly Asp Val Val Pro Lys Asp Val Asn Ala Ala Val Ala Thr Ile Lys
                325                 330                 335

Thr Lys Arg Thr Ile Gln Phe Val Asp Trp Ser Pro Thr Gly Phe Lys
            340                 345                 350

Cys Gly Ile Asn Tyr Gln Pro Pro Thr Val Val Pro Gly Gly Asp Leu
            355                 360                 365

Ala Lys Val Gln Arg Ala Val Cys Met Ile Ala Asn Ser Thr Ala Ile
            370                 375                 380

Ala Glu Val Phe Ala Arg Ile Asp His Lys Phe Asp Leu Met Tyr Ser
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Leu Ala Ala Leu Glu Lys Asp Tyr
            420                 425                 430

Glu Glu Val Gly Ala Glu Ser Ala Asp Met Glu Gly Glu Glu Asp Val
            435                 440                 445

Glu Glu Tyr
    450

<210> SEQ ID NO 3
<211> LENGTH: 260
<212> TYPE: PRT
<213> ORGANISM: Trypanosoma cruzi

<400> SEQUENCE: 3

Met Gly Lys Thr Val Leu Thr Cys Arg Lys Gly Asn Gly Ser Val Tyr
1               5                   10                  15

Gln Leu His Gly His Lys Arg Leu Gly Pro Ala Lys Leu Arg Ile Leu
            20                  25                  30

Asp Tyr Ala Glu Arg His Gly Phe Met Arg Gly Val Val Lys Thr Ile
            35                  40                  45

Glu His Glu Pro Gly Arg Gly Ala Pro Leu Ala Arg Val Glu Phe Arg
        50                  55                  60

His Pro Tyr Lys Tyr Arg Arg Val Lys Glu Leu Met Val Ala Pro Glu
65                  70                  75                  80

Gly Met Phe Thr Gly Gln Ser Val Leu Cys Gly Val Lys Ala Pro Leu
                85                  90                  95

Ala Ile Gly Asn Val Leu Pro Leu Gly Gln Ile Thr Glu Gly Cys Ile
            100                 105                 110

Val Cys Asn Val Glu Ala Lys Val Gly Asp Arg Gly Thr Ile Ala Arg
            115                 120                 125

Ala Ser Gly Asp Tyr Cys Ile Ile Ile Ser His Asn His Glu Thr Gly
            130                 135                 140

Arg Thr Arg Leu Lys Leu Pro Ser Gly Gln Lys Lys Thr Val Pro Ser
145                 150                 155                 160

Asn Cys Arg Ala Met Ile Gly Ile Ile Ala Gly Gly Gly Arg Ile Glu
                165                 170                 175

Lys Pro Val Leu Lys Ala Gly Asn Ser Phe Tyr Arg Phe Arg Gly Lys
            180                 185                 190
```

```
Arg Asn Cys Trp Pro Lys Val Arg Gly Val Ala Arg Asn Pro Val Glu
            195                 200                 205

His Pro His Gly Gly Asn His Gln His Ile Gly His Pro Ser Thr
        210                 215                 220

Val Ser Arg His Ala Pro Pro Gly Gln Lys Val Gly Leu Ile Ala Ala
225                 230                 235                 240

Arg Arg Thr Gly Arg Ile Arg Gly Ser Arg Ala Val Lys Gly Ala Trp
            245                 250                 255

His Pro Glu Glu
        260

<210> SEQ ID NO 4
<211> LENGTH: 821
<212> TYPE: PRT
<213> ORGANISM: Trypanosoma cruzi

<400> SEQUENCE: 4

Met His Arg Gln Glu Ser Val Ser Ser Gly Gly Asn Ala Thr Gly
1               5                   10                  15

Arg Gly Ser Leu Thr Thr Ala Glu Val Leu Asp Arg Ala Met Asn Gln
            20                  25                  30

Cys Met Gln Arg Gly Leu Phe Asp Thr Ala Ser Trp Leu Gly Gln Leu
        35                  40                  45

Ala Leu Asn Ala Thr Asp Ser Val Leu Arg Asp Ser Ile Ser Ala Thr
    50                  55                  60

Ser Pro Ala Val Ala Ala Leu Gln Asp Pro Pro Leu Thr Gly Arg Ala
65                  70                  75                  80

His Arg Tyr Leu Val Val Ala Leu Ser Leu Met Gln Lys Ser Glu Tyr
                85                  90                  95

Ile Arg Cys His His Glu Leu Asn Ile Ala Leu Lys Glu Phe Ser Ala
            100                 105                 110

Glu Ser Thr Pro Val Glu Ser Glu Lys Cys Ala Arg Asp His Pro Pro
        115                 120                 125

Met Pro Arg Gly Ser Gly Arg Ser Thr Pro Leu Pro Ala Ala Ser Ser
    130                 135                 140

Ser Pro Met Leu Pro Pro Gln Leu Gln Phe Leu Cys Leu Tyr Ser
145                 150                 155                 160

Leu Tyr Met Ala Gly Glu Cys Ile Lys Ser Thr Ser Ser Asn Pro Arg
                165                 170                 175

Lys Ser Ser Asn Pro His Leu Arg Thr Leu Arg Gly Arg Leu Leu Thr
            180                 185                 190

Leu Leu Glu Gln Gln Arg Arg Ser Leu Ser Ser Ser Pro Ala Ser Ile
        195                 200                 205

Lys Ser Ser Met Lys Pro Thr Pro Leu Ser Ser Ala Ser Met Ala Val
    210                 215                 220

Gly Ala Pro Ala Tyr Gly Asp Pro Phe Leu Cys Trp Leu His Gly Val
225                 230                 235                 240

Val Leu Arg Glu Leu Gly Met Lys Gln Glu Ser Ala Thr Tyr Phe Leu
                245                 250                 255

Ala Ala Leu Cys Asn His Pro Met Leu Trp Cys Ala Trp Glu Asp Leu
            260                 265                 270

Cys Thr Leu Val Ser Arg Glu Asn Gln Ile Glu Glu Ile Glu Ala Ile
        275                 280                 285

Ile Ala Ser Leu Glu Pro Arg Phe Met Ser Glu Ile Phe Leu Ala Ser
    290                 295                 300
```

-continued

```
Ala Lys Ala Ala Leu Asn Val Ala Pro Met Ser Leu Val Pro Pro Ser
305                 310                 315                 320

Leu Ser Thr Ala Ala Ala Ala Met Ala Gln Arg Ser Thr Ser Pro
            325                 330                 335

His Cys Gly Ser Leu Pro Arg Gln Thr Thr Ser Thr Leu Glu Thr Gln
            340                 345                 350

Glu Gln His Tyr Arg Pro Gln His His Gln Arg Arg Gly Glu Ser Gly
                355                 360                 365

Val Ser Pro Arg Leu Val Asn Ser Trp Glu Ala Leu Leu Glu Arg Phe
370                 375                 380

Pro Asn Asn Leu Phe Leu Leu Ala Asn Leu Ala Gly Tyr Tyr Tyr Asn
385                 390                 395                 400

Val Lys Lys Asp Leu Glu Lys Ala Gln Ser Leu Tyr Lys Arg Leu His
                405                 410                 415

Glu Met Asn Pro Tyr Arg Leu Glu Ser Met Asp Asp Tyr Ser Ile Val
                420                 425                 430

Leu Phe Leu Arg Gly Asp Arg Ile Gly Leu Ser Ser Leu Ala Gln Gln
            435                 440                 445

Val Tyr Gln Ile Asp Pro Phe Arg Ala Glu Ser Asn Tyr Val Val Gly
450                 455                 460

Asn Tyr Tyr Val Leu Met Gly Ala His Asp Arg Gly Val Leu His Phe
465                 470                 475                 480

Arg Arg Ala Val Ala Ala Asp Pro Thr Phe Leu Ala Ala Trp Thr Leu
                485                 490                 495

Leu Gly His Ala Tyr Leu Glu Thr Lys Asn Ser Ala Ala Ala Val Glu
            500                 505                 510

Ala Tyr Arg Ala Ala Val Asp Leu Asp Pro Arg Asp Tyr Arg Gly Trp
            515                 520                 525

Tyr Asn Leu Gly Gln Ile Tyr Glu Leu Leu Gln Phe Tyr His His Ala
530                 535                 540

Leu Tyr Tyr Tyr Trp His Thr Thr Thr Leu Arg Pro Thr Asp Pro Arg
545                 550                 555                 560

Met Trp Ser Ala Val Ala Asn Cys Leu Asp Arg Glu Gly Arg Thr Gly
                565                 570                 575

Glu Ala Val Leu Cys Leu Glu Arg Ala Glu Ala His Glu Ser Ser Ser
            580                 585                 590

Ser Asp Tyr Tyr Pro Pro Leu Val His Arg Leu Gly Leu His Tyr Leu
        595                 600                 605

Gly Ile Arg Arg Leu Asp Arg Ala Val Ile Tyr Leu Glu Lys Leu Ala
610                 615                 620

Leu Ser Glu Ala Arg Arg Arg Glu Asp Val Leu Phe Ala Ile Pro His
625                 630                 635                 640

Val Val Pro Tyr Tyr Leu Gln Gln Ala Arg Gln Leu Leu Asp Ile Pro
                645                 650                 655

Ser Arg Ser Pro Ser Tyr Glu Pro Gln Pro His His Ser Thr Thr Ala
            660                 665                 670

Gly Gly Gly Asp Gly Gln Leu Pro Gln Thr Met Ala Ser Ala Met Gly
        675                 680                 685

Ala Thr Asn Ala Ser Thr Gly Gly Asn Val Tyr Arg Ser Ser Leu Ala
        690                 695                 700

Asp Gln Trp Leu Thr Ala Asp Ala Ala Arg Arg Asn Ile Glu Thr
705                 710                 715                 720

Arg Trp Glu Gln Ala Ala Leu Cys Leu Thr Ser Ser Glu Arg His Leu
```

```
                    725                 730                 735
Glu Asn Phe Ala Ser Val Leu Gly Ile Pro Val Ala Ser Ala Ala Asp
                740                 745                 750

Asn Gly Ala Arg Lys Ser Thr Glu Tyr Gly Asp Thr Gly Val Ser Gly
            755                 760                 765

Ser Gly Gly Val Ala Gly Val Thr Met Asp Glu Gly Arg Ser Gln His
        770                 775                 780

Thr Leu Gln Leu Ala Cys Leu Tyr Arg Glu Leu Asn Lys Ile Arg Gln
785                 790                 795                 800

Tyr Leu Thr Ser Gln Gln Glu Gln Val Glu Thr Ala Met Arg Met Arg
                805                 810                 815

Gly Gly Gly Asn Ala
            820

<210> SEQ ID NO 5
<211> LENGTH: 334
<212> TYPE: PRT
<213> ORGANISM: Trypanosoma cruzi

<400> SEQUENCE: 5

Met Leu Ser Arg Arg Ser Leu Thr Thr Ala Phe Ala Ala Met Thr Lys
1               5                   10                  15

Gln Pro Leu Met Gln Gln Arg Arg His Asp His Asp Arg Trp Tyr Gly
            20                  25                  30

His Ala Leu Glu Leu Asp Ser His Asn Tyr Lys Phe Thr Gly Glu Pro
        35                  40                  45

Pro Ser Trp Met Arg Gln Arg Glu Arg Thr Glu Glu Thr Ala Phe
    50                  55                  60

Ala Lys Ser Val Leu Pro His Val Asp Phe Ala Ser Ser Tyr Glu Cys
65                  70                  75                  80

Leu Leu Phe Asp Ala Asp Arg Leu Asn Gly His Leu Asn Arg Lys Glu
                85                  90                  95

Phe Gly Asn Glu Val Thr Phe Arg Leu Glu Lys Gln Ser Asn Thr Val
            100                 105                 110

Ala Arg Ala Gln Gln Met Leu Lys Glu Lys Lys Ser Ser Ser Asp Glu
        115                 120                 125

Arg Leu Glu Asn Thr Met Ile Ala Arg Ile Phe Asp Glu Glu His Val
130                 135                 140

Gln Ala Glu Met Lys Tyr Val Lys Cys Ile Arg Ala Asn Glu Leu Ala
145                 150                 155                 160

Glu Asp Asn Arg Leu Asp Ile Leu Pro Gly Gly Ser Pro Asn Ser Leu
                165                 170                 175

Arg Glu Lys Thr Arg Trp Asn Val Asn Thr Glu Leu His Pro Ala Asp
            180                 185                 190

Arg Ala Glu Ile Gly Ala Arg Leu Thr Ala Trp Leu Pro Glu Lys Tyr
        195                 200                 205

His Ile Val Tyr Phe Asp Asp Phe Gln Thr Val Ala Ala Asn Asp Pro
    210                 215                 220

Ser Ala Arg Arg Glu Met Leu Asn Ile Val Gln Asn Val Glu Arg Glu
225                 230                 235                 240

Tyr Ala Asp Glu Ala Lys Ser Ser Gly Tyr Glu Lys Asp Leu Lys Glu
                245                 250                 255

Val Val Asn Glu Leu Leu Asp Asp Val Asp Pro Ser Arg His Ile Thr
            260                 265                 270

Pro Glu Ala Ile Lys Ala Cys Thr Asp Leu Asn Gln Leu Glu Glu Trp
```

```
                275                 280                 285
Ser Arg Val Val His Glu Tyr Asn Gly Asp Asp Arg Ile Leu Asp Ile
290                 295                 300
Tyr Ala Arg Ala Ala Glu Leu Thr Lys Asn Ala Asp His Gln Ala Leu
305                 310                 315                 320
Val Lys Asn Met Lys Glu Trp Arg Lys Leu Ala Asn Lys Ile
                325                 330

<210> SEQ ID NO 6
<211> LENGTH: 404
<212> TYPE: PRT
<213> ORGANISM: Trypanosoma cruzi

<400> SEQUENCE: 6

Met Met Gly Asp Val Asn Asn Val Glu Ala Lys Glu Lys Met Gly
1               5                   10                  15

Tyr Glu Ala Lys Lys Val Pro Val Ser Pro Val Lys Ser Ser Arg Pro
                20                  25                  30

Thr Ala Tyr Val Arg Lys Pro Ala Ser Ala Arg Asn Val Gly Ser Pro
            35                  40                  45

Ser Ala Lys His Asp Ala Leu Ala Ser Phe Thr Ser Pro Arg Asp Ser
50                  55                  60

Lys Arg His Val Pro Asp Cys Gly Phe Ala Ser Pro His Ser Ser Arg
65                  70                  75                  80

Arg Pro Tyr Arg Thr Asp Pro Lys His Phe Glu Leu His Val Arg Ser
                85                  90                  95

Ser Val Glu Thr Ser Gly Ala Leu Lys Thr Pro Glu Ala Ala Lys Val
            100                 105                 110

Ser Ala Ser Gly Asn Gly Thr Asp Gly Pro Leu Phe Ser Ser Asp Val
        115                 120                 125

Glu Ser Ala Arg Leu Phe Pro Ser Ile Thr Ala Ala Glu Thr Arg Leu
130                 135                 140

Pro Phe Leu Asp Gly Cys Phe Arg Pro Asn Thr Asp Gly Gly Ser Val
145                 150                 155                 160

Val Val Trp Ala Gly Arg Arg Gln Gln Leu Gln Gln
                165                 170                 175

Ser Leu Cys Ser Arg Gln Pro Ala Glu Arg Glu Glu Glu Ala Gly
            180                 185                 190

Ala Val Pro Gln Ala Glu Lys Ser Ala Val Phe Leu Pro Glu Ala Leu
        195                 200                 205

His Gln Glu Ala Lys Gly Phe Cys Leu Pro Leu Thr Ala Ser Leu Glu
210                 215                 220

Asn Phe Thr Ala Ser Gly His Glu Arg Ser Leu His Pro Ser His Val
225                 230                 235                 240

Gly Ser Val Leu Pro Asn Asp Thr Thr Asp Leu Asn Glu Glu Arg Ser
                245                 250                 255

Phe Ala Gln Cys Met Pro Gly Met Asp Leu Ser Ala Ser Pro Leu Arg
            260                 265                 270

Met Asp Ala Arg Val Lys Glu Glu Leu Leu Leu His Phe Leu Asn Leu
        275                 280                 285

Ile Ser Ser Ser Pro Ser Ser Ser Ser Glu Val Gly Ala Ser Phe
290                 295                 300

Gln Ser Asp Arg Asp Ala Ala Thr Glu Thr Glu Leu Val Thr Val Phe
305                 310                 315                 320

Val Arg Gly Glu Asp Ala Gly Val Asp Ala Asp Thr Asn Thr Arg Arg
```

```
                      325                 330                 335
Arg Arg Arg Arg Glu Ala Ser Cys Lys Lys Pro Asp Ala Ile Gln His
            340                 345                 350

Glu Glu Ser Met Ala Met Thr Thr Gln Thr Ser Gly Asn Thr Asp Arg
            355                 360                 365

Ala Gln Leu Gly Arg Tyr Arg Gln Leu Pro Gly Tyr Thr Glu Ala Arg
            370                 375                 380

Arg Met Ala Gln Arg Met Ala Leu Glu Lys Val Arg Gln Gln Phe Cys
385                 390                 395                 400

Cys Ser Ala Glu

<210> SEQ ID NO 7
<211> LENGTH: 442
<212> TYPE: PRT
<213> ORGANISM: Trypanosoma cruzi

<400> SEQUENCE: 7

Met Met Arg Val Cys Arg Pro Gln Leu Leu Arg Val Ser Pro Leu Leu
1               5                   10                  15

Arg Val Trp Ala Ala Glu Glu Asp Asp Ala Asn Ala Pro Pro Thr Thr
            20                  25                  30

Phe Lys Asn Val Lys Pro Gly Arg Leu Leu Arg Leu Trp Arg Gln Ile
            35                  40                  45

Arg His Arg Ser Trp Ile Val Tyr Thr Trp Asp Glu Glu Trp Thr Ser
        50                  55                  60

Pro Gly Ser Glu Gly Tyr Leu His Gln Gln Arg Leu Glu Gln Val Cys
65                  70                  75                  80

Phe Ala Pro Leu Ser Ala Tyr Gly Met Val Pro Gly Ser Tyr Cys Asp
                85                  90                  95

Pro Leu Leu Tyr Asn Thr Lys His Thr Ser Pro Phe Arg Trp His Val
            100                 105                 110

Ala Asn Thr Ser Ser Asp Ile Val Gly His Trp Tyr Met Glu Ala Asp
            115                 120                 125

Glu Ile Phe Arg Ile Lys Asp Trp Gln Pro Lys Asn Pro Asp Asp Pro
        130                 135                 140

Thr Glu Met Phe Pro Arg Pro Pro Gln Ile Leu Lys Trp Asp Glu
145                 150                 155                 160

Thr Val Asp Glu His Gly Asn Arg Thr Phe Arg Tyr Lys Tyr Arg Tyr
                165                 170                 175

Asp Phe Met Gly Pro Thr Gly Met Trp Glu Ala Tyr Pro Arg Tyr Pro
            180                 185                 190

Phe Ser His Ile Tyr Leu Asn Gly Gln Asp His His Gly Arg Ala Glu
            195                 200                 205

Gly Tyr Gly Phe Lys Gln Gly His Leu Leu Arg Cys Ser Glu Glu Glu
        210                 215                 220

Glu Glu Val Leu Arg Arg Ile Met Glu Glu Asp Lys Glu Trp Glu
225                 230                 235                 240

Met Val Lys Arg Thr Glu Val Val Gln Glu Pro Trp Ser Tyr Pro Gly
                245                 250                 255

Lys Ile Arg Pro Gln Asp Phe Lys Gly Ala Val Glu Arg Ala Lys Ala
            260                 265                 270

Arg Phe Arg Glu Gln Ile Lys His Gly Lys Glu Thr Asp Pro Ser Glu
            275                 280                 285

Asp Pro Asp Tyr Asp Leu Val Gln Ala Gly Glu Phe Val Glu Pro Arg
        290                 295                 300
```

Asp Gly Pro Arg Ala Glu Trp Arg His Leu Trp Thr Ser Asn Arg Pro
305                 310                 315                 320

Lys Gly Glu Pro Leu Pro Tyr Gln Val Thr Phe Asn Asp Gly Ile Thr
            325                 330                 335

Phe Glu Asp Asn Glu Gly Arg Pro Pro Val His Pro Glu Ser His Tyr
            340                 345                 350

Glu Gln Thr Pro Lys Glu Ala Pro Tyr Lys Lys Tyr Glu Glu Gln Asp
        355                 360                 365

Thr Lys Glu Glu Glu Glu Gln Lys Arg Arg Lys Ser Ala Trp Asp
370                 375                 380

Gln Ser Phe Lys Glu Ser Ile Ala Lys Tyr Glu Arg Tyr Gly Val
385                 390                 395                 400

Glu Ala Lys Lys Gly Asp Ser Asp Lys Ser Ser Ser Asp Thr Gly
                405                 410                 415

Lys Ser Ser Gly Gly Gly Asp Gly Ser Thr Pro Pro Ser Ser Ser
            420                 425                 430

Ser Ser His Glu Gly Gln Asp Gly Lys Lys
        435                 440

<210> SEQ ID NO 8
<211> LENGTH: 233
<212> TYPE: PRT
<213> ORGANISM: Trypanosoma cruzi

<400> SEQUENCE: 8

Met Leu Arg Arg Ala Val Asn Ile Ser Ile Ala Arg Gly Arg Met Ala
1               5                   10                  15

Leu Met Ser Tyr Ala Thr Leu Pro Asp Leu Leu Lys Pro Ser Gly Ala
            20                  25                  30

Pro Ala Glu Leu Pro Lys Leu Gly Phe Asn Trp Lys Asp Gly Cys Ala
        35                  40                  45

Pro Val Phe Ser Pro Arg Gln Met Glu Leu His Tyr Thr Lys His His
    50                  55                  60

Lys Ala Tyr Val Asp Lys Leu Asn Ala Leu Ala Gly Thr Thr Tyr Asp
65                  70                  75                  80

Gly Lys Ser Ile Glu Glu Ile Ile Leu Ala Val Ala Asn Asp Ala Glu
                85                  90                  95

Lys Lys Gly Leu Phe Asn Gln Ala Ala Gln His Phe Asn His Thr Phe
            100                 105                 110

Tyr Phe Arg Cys Ile Thr Pro Asn Gly Lys Ala Met Pro Lys Ser Leu
        115                 120                 125

Glu Ser Ala Val Thr Ala Gln Phe Gly Ser Val Glu Gln Phe Lys Asp
    130                 135                 140

Ala Phe Val Gln Ala Gly Val Asn Asn Phe Gly Ser Gly Trp Thr Trp
145                 150                 155                 160

Leu Cys Val Asp Pro Ser Asn Lys Asn Gln Leu Val Ile Asp Asn Thr
                165                 170                 175

Ser Asn Ala Gly Cys Pro Leu Thr Lys Gly Leu Arg Pro Val Leu Ala
            180                 185                 190

Val Asp Val Trp Glu His Ala Tyr Tyr Lys Asp Phe Glu Asn Arg Arg
        195                 200                 205

Pro Asp Tyr Leu Lys Glu Ile Trp Ser Val Ile Asp Trp Glu Phe Val
    210                 215                 220

Ala Lys Met His Ala Gln Ala Ile Lys
225                 230

```
<210> SEQ ID NO 9
<211> LENGTH: 354
<212> TYPE: PRT
<213> ORGANISM: Trypanosoma cruzi

<400> SEQUENCE: 9

Met Asp Glu Asn Glu Gly Gly Trp Glu Glu Phe Ala Glu Glu Pro Gln
1               5                   10                  15

Gln Tyr Gly Glu Ala Glu Asp Ala Ala Asp Ile Tyr Ala Glu Glu Thr
            20                  25                  30

Leu Ala Thr Ala Gln Lys Ile Ala Ser Asp Asp Ala Leu Arg Phe
        35                  40                  45

Asp Ser Val Lys Glu Val Thr Leu Leu Leu Arg Ser Ala Tyr Met Ser
50                  55                  60

Arg Met Leu Gln Lys Leu Gly Asp Tyr Ser Glu Gln Glu Val Val Lys
65                  70                  75                  80

Lys Thr Ile Leu Pro Glu Asp Pro Glu Tyr Gln Phe Val Ile Asp Ser
                85                  90                  95

Ser Thr Leu Val Leu Arg Ile Glu Val Glu Lys Ser Lys Ala Val Val
            100                 105                 110

Tyr Leu Arg Ala His Tyr Gly Gln Arg Phe Pro Glu Leu Ala Met Phe
        115                 120                 125

Phe Ser Asp Ser Val Leu Tyr Ala Arg Ile Val Arg Leu Ile Gln Asn
130                 135                 140

Asn Met Asp Leu Ser Val Val Ile Asp Gln Leu Asp Glu Leu Ile Pro
145                 150                 155                 160

Ser Gln Leu Thr Ala Val Val Ile Ala Cys Ala Ser Thr Thr Ala Gly
                165                 170                 175

Arg Glu Leu Ser Glu Glu Glu Leu His Arg Val Val Glu Ala Cys Gln
            180                 185                 190

Glu Ile Asp Ile Leu Glu Ala Ala Lys Gln Thr Phe Leu Glu Tyr Ile
        195                 200                 205

Gln Arg Ser Met Pro Leu Ile Cys Pro Asn Leu Cys Ala Phe Leu Gly
210                 215                 220

Thr Gly Ile Thr Ser Gln Leu Phe Ala Ile Ala Gly Val Ser Ala
225                 230                 235                 240

Leu Ser Thr Met Asp Ser Thr Glu Leu Ala Arg Leu Gly Ser Lys Arg
                245                 250                 255

Ala Asp Ser Ser Gly Val Leu Ile Arg Thr Thr Gly Phe Leu Ser Asn
            260                 265                 270

Ser Asp Leu Val Val Asn His Pro Pro Gln Met Arg Pro Lys Ala Leu
        275                 280                 285

Arg Leu Val Ala Ser Thr Thr Ser Met Leu Ala Arg Ile Asp Ala Asn
290                 295                 300

Arg Arg Ala Ser Ser Gln His Glu Gly Tyr Arg Gln Arg Glu Met Val
305                 310                 315                 320

Arg Leu Lys Met Leu Ser Trp Leu Asp Pro Pro Val Leu Arg Gly Ala
                325                 330                 335

Ala Asn Asn Thr Tyr Ala Arg Arg Gly Arg Lys Arg Pro Arg Arg Gln
            340                 345                 350

Thr Arg

<210> SEQ ID NO 10
<211> LENGTH: 146
```

```
<212> TYPE: PRT
<213> ORGANISM: Trypanosoma cruzi

<400> SEQUENCE: 10

Met Thr His Ser Thr Asp Leu Gln Trp Leu Val Arg Gln Asn Ser
1               5                   10                  15

Lys Phe Leu Gln Lys Arg Asn Gly Ile Arg Leu Ser Ser Asp Pro Phe
                20                  25                  30

Asn Asn Asn Ala Asn Trp Thr Lys Arg His Ala Gly Phe Leu Asn Thr
            35                  40                  45

Lys Ala Ala Val Val Lys Thr Lys Gly Asp Arg Ile Leu Val Thr Thr
        50                  55                  60

Lys Asp Gly Lys Ala Gly Asn Lys Pro Lys Ser Met Tyr Lys Lys Ala
65                  70                  75                  80

Val Met Asp Ala Gly Val Glu Ala Ser Val Ser Lys Ala Val Ala
                85                  90                  95

Ala Val Arg Pro Asp Leu Ala Ser Ile Ala Ser Arg Arg Ala Arg Lys
                100                 105                 110

Met Ala Ser Thr Leu Glu His Met Lys Lys Val Arg Ala Ala Arg Lys
            115                 120                 125

Glu Arg Ser Ser Lys Ile Thr Phe Gln Arg Lys Ala Val Arg Pro Lys
        130                 135                 140

Arg His
145

<210> SEQ ID NO 11
<211> LENGTH: 525
<212> TYPE: PRT
<213> ORGANISM: Trypanosoma cruzi

<400> SEQUENCE: 11

Met Pro Pro Thr Ile His Arg Asn Leu Leu Ser Pro Glu Leu Val Gln
1               5                   10                  15

Trp Ala Leu Lys Ile Glu Lys Asp Ser Arg Leu Thr Ala Arg Gly Ala
                20                  25                  30

Leu Ala Val Met Ser Tyr Ala Lys Thr Gly Arg Ser Pro Leu Asp Lys
            35                  40                  45

Arg Ile Val Asp Thr Asp Val Arg Glu Asn Val Asp Trp Gly Lys
        50                  55                  60

Val Asn Met Lys Leu Ser Glu Glu Ser Phe Ala Arg Val Lys Lys Ile
65                  70                  75                  80

Ala Lys Glu Phe Leu Asp Thr Arg Glu His Leu Phe Val Val Asp Cys
                85                  90                  95

Phe Ala Gly His Asp Glu Arg Tyr Arg Leu Lys Val Arg Val Phe Thr
                100                 105                 110

Thr Arg Pro Tyr His Ala Leu Phe Met Arg Asp Met Leu Ile Val Pro
            115                 120                 125

Thr Pro Glu Glu Leu Ala Thr Phe Gly Glu Pro Asp Tyr Val Ile Tyr
        130                 135                 140

Asn Ala Gly Glu Cys Lys Ala Asp Pro Ser Ile Pro Gly Leu Thr Ser
145                 150                 155                 160

Thr Thr Cys Val Ala Leu Asn Phe Lys Thr Arg Glu Gln Val Ile Leu
                165                 170                 175

Gly Thr Glu Tyr Ala Gly Glu Met Lys Lys Gly Ile Leu Thr Val Met
                180                 185                 190

Phe Glu Leu Met Pro Arg Met Asn His Leu Cys Met His Ala Ser Ala
```

```
                195                 200                 205
Asn Val Gly Lys Gln Gly Asp Val Thr Val Phe Phe Gly Leu Ser Gly
210                 215                 220

Thr Gly Lys Thr Thr Leu Ser Ala Asp Pro His Arg Asn Leu Ile Gly
225                 230                 235                 240

Asp Asp Glu His Val Trp Thr Asp Arg Gly Val Phe Asn Ile Glu Gly
                245                 250                 255

Gly Cys Tyr Ala Lys Ala Ile Gly Leu Asn Pro Lys Thr Glu Lys Asp
            260                 265                 270

Ile Tyr Asp Ala Val Arg Phe Gly Ala Val Ala Glu Asn Cys Val Leu
        275                 280                 285

Asp Lys Arg Thr Gly Glu Ile Asp Phe Tyr Asp Glu Ser Ile Cys Lys
    290                 295                 300

Asn Thr Arg Val Ala Tyr Pro Leu Ser His Ile Glu Gly Ala Leu Ser
305                 310                 315                 320

Lys Ala Ile Ala Gly His Pro Lys Asn Val Ile Phe Leu Thr Asn Asp
                325                 330                 335

Ala Phe Gly Val Met Pro Pro Val Ala Arg Leu Thr Ser Ala Gln Ala
            340                 345                 350

Met Phe Trp Phe Val Met Gly Tyr Thr Ala Asn Val Pro Gly Val Glu
        355                 360                 365

Ala Gly Gly Thr Arg Thr Ala Arg Pro Ile Phe Ser Ser Cys Phe Gly
    370                 375                 380

Gly Pro Phe Leu Val Arg His Ala Thr Phe Tyr Gly Glu Gln Leu Ala
385                 390                 395                 400

Glu Lys Met Gln Lys His Asn Ser Arg Val Trp Leu Leu Asn Thr Gly
                405                 410                 415

Tyr Ala Gly Gly Arg Ala Asp Arg Gly Ala Lys Arg Met Pro Leu Arg
            420                 425                 430

Val Thr Arg Ala Ile Ile Asp Ala Ile His Asp Gly Thr Leu Asp Arg
        435                 440                 445

Thr Glu Tyr Glu Glu Tyr Pro Gly Trp Gly Leu His Ile Pro Lys Tyr
    450                 455                 460

Val Ala Lys Val Pro Glu His Leu Leu Asn Pro Arg Lys Ala Trp Lys
465                 470                 475                 480

Asp Val Arg Gln Phe Asn Glu Thr Ser Lys Glu Leu Val Ala Met Phe
                485                 490                 495

Gln Glu Ser Phe Ser Ala Arg Phe Ala Ala Lys Ala Ser Gln Glu Met
            500                 505                 510

Lys Ser Ala Val Pro Arg Tyr Val Glu Phe Ala Arg Leu
        515                 520                 525

<210> SEQ ID NO 12
<211> LENGTH: 128
<212> TYPE: PRT
<213> ORGANISM: Trypanosoma cruzi

<400> SEQUENCE: 12

Met Gln Ile Phe Val Lys Thr Leu Thr Gly Lys Thr Ile Ala Leu Glu
1               5                   10                  15

Val Glu Ser Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
```

```
                       50                  55                  60
Ser Thr Leu His Leu Val Leu Arg Leu Arg Gly Gly Val Met Glu Pro
 65                  70                  75                  80

Thr Leu Glu Ala Leu Ala Lys Lys Tyr Asn Trp Glu Lys Lys Val Cys
                 85                  90                  95

Arg Arg Cys Tyr Ala Arg Leu Pro Val Arg Ala Ser Asn Cys Arg Lys
                100                 105                 110

Lys Ala Cys Gly His Cys Ser Asn Leu Arg Met Lys Lys Lys Leu Arg
            115                 120                 125

<210> SEQ ID NO 13
<211> LENGTH: 323
<212> TYPE: PRT
<213> ORGANISM: Trypanosoma cruzi

<400> SEQUENCE: 13

Met Pro Ser Val Ser Glu Ala Lys Arg Glu Tyr Glu Glu Arg Phe Asn
  1               5                  10                  15

Gly Cys Leu Thr Lys Tyr Gly Arg Val Leu Phe Cys Leu Met Asp Asn
                 20                  25                  30

Val Arg Ser Gln Gln Val His Asp Val Arg Arg Asp Leu Arg Gly Leu
             35                  40                  45

Gly Glu Leu Val Met Gly Lys Lys Thr Leu Gln Lys Lys Ile Val Glu
 50                  55                  60

Arg Arg Ala Glu Asp Lys Lys Ala Ser Ala Tyr Asp Lys Leu Leu Tyr
 65                  70                  75                  80

Asn Thr Cys Ile Glu Lys Lys Leu Leu Cys Gly Asn Thr Ala Leu Ile
                 85                  90                  95

Phe Thr Asn Glu Glu Ile Pro Val Ile Thr Ala Val Leu Asp Lys His
                100                 105                 110

Arg Val Gln Ala Pro Ala Arg Val Gly Ala Ile Ala Pro Cys Asp Val
            115                 120                 125

Ile Val Pro Ala Gly Asn Thr Gly Met Glu Pro Lys Ala Thr Ser Phe
130                 135                 140

Phe Gln Ala Leu Asn Ile Ala Thr Lys Ile Ala Lys Gly Thr Val Glu
145                 150                 155                 160

Ile Val Ser Asp Lys Lys Val Leu Ser Val Gly Asp Arg Val Asp Asn
                165                 170                 175

Ser Thr Ala Thr Leu Leu Gln Lys Leu Asp Ile Ser Pro Phe Tyr Tyr
            180                 185                 190

Gln Val Glu Val Gln Ser Val Trp Asp Arg Gly Met Leu Phe Leu Arg
        195                 200                 205

Glu Asp Leu Ser Ile Thr Asp Asp Val Val Glu Lys Tyr Leu Leu Glu
    210                 215                 220

Gly Ile Ser Asn Val Ala Ala Leu Ser Leu Gly Ala Gly Ile Pro Thr
225                 230                 235                 240

Ala Ala Thr Leu Pro His Met Ile Met Asp Ala Phe Lys Thr Leu Leu
                245                 250                 255

Gly Ala Ser Val Ala Thr Glu Tyr Glu Phe Asp Glu Phe Asp Gly Lys
            260                 265                 270

Asn Leu Arg Lys Ala Ala Leu Glu Gly Asn Leu Gly Gly Gly Val Ala
        275                 280                 285

Asp Ala Ala Ala Ala Ala Asp Thr Gly Ala Ala Ala Pro Ala Ala
    290                 295                 300

Ala Ala Glu Pro Glu Glu Glu Asp Asp Asp Asp Asp Phe Gly Met Gly
```

-continued

```
                305                 310                 315                 320
Ala Leu Phe

<210> SEQ ID NO 14
<211> LENGTH: 208
<212> TYPE: PRT
<213> ORGANISM: Trypanosoma cruzi

<400> SEQUENCE: 14

Met Gln Ala Arg Gly Thr Val Lys Val Gln Gly Asp Ala Asn Val Asp
  1               5                  10                  15

Gly Lys Met Ser Thr Gly Gln His Pro His Gln His Leu Asn Ser
             20                  25                  30

Thr Gln Ala Asn Ala Thr Thr Thr Ala Leu Glu Tyr Arg Ala Met Asn
         35                  40                  45

Arg Pro Leu Tyr Arg Gly Pro Ile Ser His Asn Ile Ile Ser Glu Met
     50                  55                  60

Ala Glu Gly Phe Tyr Val Leu Ser Gly Gly Tyr Lys Lys Leu Phe Ile
 65                  70                  75                  80

Pro Ser Lys Asp Val Tyr Ala Leu Met Gln Asn Val Gly Met His Leu
                 85                  90                  95

Thr Glu Glu Phe His Asp Ala Leu Arg Val Ile Gly Gln Ser Glu
            100                 105                 110

Pro Gln Asn Ala Asp Glu Leu Ser Phe Ser Asp Phe Leu Leu Leu Met
        115                 120                 125

Thr Arg Glu Val Asp Asp Thr Met Ala Asp Glu Leu Arg Ser Ala Phe
    130                 135                 140

Phe His Tyr Asp Lys His Lys Thr Gly Tyr Val Thr Arg Lys Gln Phe
145                 150                 155                 160

Thr Glu Leu Phe Ala Thr Leu Gly Glu Arg Ser Thr Pro Glu Glu Leu
                165                 170                 175

Glu Glu Leu Leu Ala Val Ala Glu Val Asp Glu Thr Asp Asp Lys Ile
            180                 185                 190

Asp Tyr Asn Arg Phe Val Asn Glu Leu Thr Ser Arg Val Asn Cys Met
        195                 200                 205

<210> SEQ ID NO 15
<211> LENGTH: 589
<212> TYPE: PRT
<213> ORGANISM: Trypanosoma cruzi

<400> SEQUENCE: 15

Met Ser Ala Glu Glu Ala Thr Gly Leu Glu Ala Ala Arg Lys Gln Lys
  1               5                  10                  15

Ile His Asn Leu Lys Leu Lys Thr Ala Cys Leu Glu Asn Glu Glu Leu
             20                  25                  30

Ile Gln Glu Leu His Val Ser Asp Trp Ser Thr Gln Arg Gln Lys
         35                  40                  45

Leu Arg Gly Ala His Leu Lys Ala Glu Leu Val Ala Ser Val Asp
     50                  55                  60

Val Gly Thr Lys Trp Asn Leu Thr Glu Ala Tyr Asp Leu Ala Lys Leu
 65                  70                  75                  80

Met Arg Val Cys Gly Leu Glu Met Ser Gln Arg Glu Leu Tyr Arg Pro
                 85                  90                  95

Glu Asp Lys Ala Gln Phe Met Asp Ile Ile Gly Val Lys Val Leu
            100                 105                 110
```

-continued

```
Gln Asp Leu Lys Gln Asn Arg Asn Lys Thr Arg Val Val Ser Phe Thr
            115                 120                 125

Gln Met Ile Asp Asn Ala Ile Ala Lys Met Glu Lys Val Glu Glu Glu
        130                 135                 140

Leu Arg Arg Ser Gln Leu Asp Ala Thr Gln Leu Ala Gln Val Pro Thr
145                 150                 155                 160

Arg Thr Leu Lys Gln Ile Glu Asp Ile Met Asn Ala Thr Gln Ile Gln
                165                 170                 175

Asn Ala Leu Ala Ser Thr Asp Gln Ile Lys Thr Gln Leu Ala Gln
            180                 185                 190

Leu Glu Lys Thr Asn Glu Ile Gln Asn Val Ala Met His Asp Gly Glu
            195                 200                 205

Met Gln Val Ala Glu Gln Met Trp Thr Lys Val Gln Leu Gln Glu
210                 215                 220

Arg Leu Ile Asp Leu Ile Gln Asp Lys Phe Arg Leu Ile Thr Lys Cys
225                 230                 235                 240

Glu Glu Glu Asn Gln Pro Phe Lys Lys Ile Tyr Glu Val Gln Lys Gln
                245                 250                 255

Ala Asn Gln Glu Thr Ser Gln Met Lys Asp Ala Lys Arg Arg Leu Lys
            260                 265                 270

Gln Arg Cys Glu Thr Asp Leu Lys His Ile His Asp Ala Ile Gln Lys
        275                 280                 285

Ala Asp Leu Glu Asp Ala Glu Ala Met Lys Arg His Ala Ala Asn Arg
290                 295                 300

Glu Lys Ser Asp Gly Phe Val Arg Glu Asn Glu Arg Gln Glu Glu
305                 310                 315                 320

Ala Trp Asn Lys Ile Gln Asp Leu Glu Arg Gln Leu Gln Lys Leu Gly
                325                 330                 335

Thr Glu Arg Phe Glu Glu Val Lys Arg Arg Ile Glu Glu Val Asp Arg
            340                 345                 350

Glu Glu Lys Arg Arg Val Glu Tyr Ser Gln Phe Leu Glu Val Ala Ser
        355                 360                 365

Gln His Lys Lys Leu Leu Glu Leu Thr Val Tyr Asn Cys Asp Leu Ala
    370                 375                 380

Ile Arg Cys Thr Gly Leu Val Glu Glu Leu Val Ser Glu Gly Cys Ala
385                 390                 395                 400

Ala Val Lys Ala Arg His Asp Lys Thr Ser Gln Asp Leu Ala Ala Leu
                405                 410                 415

Arg Leu Glu Val His Lys Glu His Leu Glu Tyr Phe Arg Met Leu Tyr
            420                 425                 430

Leu Thr Leu Gly Ser Leu Ile Tyr Lys Lys Lys Arg Met Glu Glu
        435                 440                 445

Ile Asp Arg Asn Ile Arg Thr Thr His Ile Gln Leu Glu Phe Cys Val
450                 455                 460

Glu Thr Phe Asp Pro Asn Ala Lys Arg His Ala Asp Met Lys Lys Glu
465                 470                 475                 480

Leu Tyr Lys Leu Arg Gln Gly Val Glu Glu Leu Ala Met Leu Lys
                485                 490                 495

Glu Lys Gln Ala Lys Ala Leu Glu Asp Phe Lys Glu Ser Glu Glu Ala
            500                 505                 510

Leu Asp Ala Ala Gly Ile Glu Phe Asn His Pro Val Asp Glu Asn Asn
        515                 520                 525

Glu Glu Val Leu Thr Arg Arg Ser Lys Met Val Glu Tyr Arg Ser His
    530                 535                 540
```

```
Leu Ser Lys Gln Glu Glu Val Lys Ile Ala Ala Glu Arg Glu Glu Ile
545                 550                 555                 560

Lys Arg Ala Arg Leu Leu Arg Thr Gly Gly Gly Ser Gly Glu Gln
                565                 570                 575

Pro Arg Ile Gly Asn Asn Thr Ala Pro Ala Arg Leu Glu
            580                 585
```

<210> SEQ ID NO 16
<211> LENGTH: 513
<212> TYPE: PRT
<213> ORGANISM: Trypanosoma cruzi

<400> SEQUENCE: 16

```
Met Pro Asn Arg Gln Ile Ile Gln Val Phe Glu Glu Tyr Gln Arg Ala
1               5                   10                  15

Arg Val Lys Phe Val Gln Thr Ile Ala Asp Leu Ala Ser Lys Pro Gln
                20                  25                  30

His Ile Glu Ala Leu Gln Gln Ala Gly Val Met Gln Leu Leu Arg Pro
            35                  40                  45

Leu Leu Leu Asp Ser Val Pro Ser Ile Gln Ser Ala Ala Leu Ala
50                  55                  60

Leu Gly Arg Leu Ala Asn Tyr Ser Glu Glu Leu Ala Glu Asn Val Val
65                  70                  75                  80

Ser Gly Asp Ile Leu Ala Gln Leu Val Tyr Ser Leu Ser Asp Gln Ser
                85                  90                  95

Arg Phe Tyr Lys Lys Ser Ala Ala Phe Val Leu Arg Ser Val Ala Arg
            100                 105                 110

His Ser Pro Gln Leu Ala Gln Ala Val Val Asp Ser Gln Ala Val Glu
        115                 120                 125

Ala Leu Val Gly Cys Leu Glu Glu Phe Asp Pro Thr Val Lys Glu Ser
130                 135                 140

Ala Ala Trp Ala Leu Gly Tyr Val Ala Arg His Asn Ala Pro Leu Ala
145                 150                 155                 160

Gln Glu Val Val Asp Lys Gly Ala Ile Pro Pro Leu Val Leu Cys Val
                165                 170                 175

Gln Glu Pro Glu Leu Ser Leu Lys Arg Thr Ala Ala Ser Thr Leu Ser
            180                 185                 190

Asp Ile Ala Lys His Leu Pro Glu Leu Ala Gln Ala Val Val Asp Gln
        195                 200                 205

Asp Ala Val Thr His Leu Ala Pro Leu Ile Met Ser Asn Asp Ser Lys
210                 215                 220

Leu Arg Arg Gln Val Cys Gln Cys Leu Ala Gln Ile Ser Lys His Ser
225                 230                 235                 240

Val Glu Leu Ala Glu Leu Val Val Glu Gly Glu Ile Phe Pro Lys Ile
                245                 250                 255

Phe Thr Leu Leu Lys Asp Ser Asp Glu Val Val Arg Lys Asn Ala Ala
            260                 265                 270

Thr Cys Ile Arg Glu Ile Ala Lys His Thr Pro Glu Leu Ala Gln Leu
        275                 280                 285

Val Val Asn Ala Gly Gly Val Gly Ala Leu Val Asp Tyr Thr Ser Glu
290                 295                 300

Ser Arg Asp Ser Ala Arg Leu Pro Gly Ile Met Thr Leu Gly Phe Ile
305                 310                 315                 320

Ser Ala Phe Ser Glu Thr Leu Ala Leu Ala Val Ile Val Ser His Gly
                325                 330                 335
```

```
Ile Val Pro Leu Ala Asp Ala Leu Glu Lys Glu Pro Glu Asp His Ile
                340                 345                 350

Lys Ala Ala Ala Ala Trp Ser Leu Gly Gln Ile Gly Arg His Ser Ala
                355                 360                 365

Asp His Ala Lys Ala Val Ala Asp Cys Asn Val Leu Pro Arg Leu Leu
            370                 375                 380

Asp Val Tyr Leu Asn Pro Lys Ser Ser Glu Asp Leu Arg Met Lys Ser
385                 390                 395                 400

Lys Arg Ala Leu Lys Asn Ile Ile Gln Arg Cys Leu Gln Leu Pro Ala
                405                 410                 415

Leu Glu Pro Leu Leu His Pro Asp Ala Pro Gln Lys Val Leu Lys Tyr
                420                 425                 430

Val Cys Gly Gln Phe Ala Lys Val Leu Pro Thr Asp Ile Ala Ala Lys
                435                 440                 445

Arg Glu Phe Val Ala Asn Arg Gly Leu Ala Thr Val Gln Arg Ile His
                450                 455                 460

Pro Glu Pro Gly Ser Lys Leu Ala Glu Tyr Ile Gln Ser Ile Asn Asn
465                 470                 475                 480

Cys Tyr Pro Pro Glu Ile Val Gln Tyr Tyr Ser Pro Gln Tyr Ala Gln
                485                 490                 495

Thr Phe Leu Glu Lys Ile Glu Asn Tyr His Val Gln Gln Val Gln Gln
                500                 505                 510

Ser

<210> SEQ ID NO 17
<211> LENGTH: 466
<212> TYPE: PRT
<213> ORGANISM: Trypanosoma cruzi

<400> SEQUENCE: 17

Met Ala Arg Pro Leu Ile Tyr Pro Ile Leu Ser Leu Val Ala Ala Ala
1               5                   10                  15

Thr Leu Val Thr Thr Ala Val Glu Ala Leu Tyr Val Val Pro Gln Gly
                20                  25                  30

Arg Leu Arg Glu Thr Gly Ser Gly Trp His Pro Cys Asp Pro Asp Val
            35                  40                  45

Pro Gln Trp Ser Gly Tyr Phe Asp Ile Pro Gly Arg Glu Gly Asp Lys
    50                  55                  60

His Tyr Phe Tyr Trp Ala Phe Gly Pro Arg Asn Gly Asn Pro Glu Ala
65              70                  75                  80

Pro Val Leu Leu Trp Met Thr Gly Gly Pro Gly Cys Ser Ser Met Phe
                85                  90                  95

Ala Leu Leu Ala Glu Asn Gly Pro Cys Leu Val Asn Glu Thr Thr Gly
                100                 105                 110

Asp Ile Tyr Lys Asn Asn Tyr Ser Trp Asn Asn Glu Ala Tyr Val Ile
            115                 120                 125

Tyr Val Asp Gln Pro Ala Gly Val Gly Phe Ser Tyr Ala Glu Val Glu
130                 135                 140

Asp Tyr Asp Ser Asn Glu Glu Val Ser Glu Asp Met Tyr His Phe
145                 150                 155                 160

Leu Gln Ala Phe Phe Gly Ala His Gln Lys Leu Arg Lys Asn Lys Leu
                165                 170                 175

Phe Val Val Gly Glu Ser Tyr Gly Gly His Tyr Ala Pro Ala Thr Ala
                180                 185                 190
```

```
His Tyr Ile Asn Lys Ala Asn Arg Glu His Val Gly Leu Pro Ile Arg
        195                 200                 205

Leu Ala Gly Leu Ala Val Gly Asn Gly Leu Thr Asp Pro His Thr Gln
        210                 215                 220

Tyr Ala Ala Tyr Pro Ser Leu Ala Trp Gly Trp Cys Arg Glu Lys Leu
225                 230                 235                 240

Gly Glu Pro Cys Val Ser Glu Glu Gly Tyr Gln Gln Met Ser Ser Met
                245                 250                 255

Val Thr Pro Cys Gln Lys Ala Ile Glu Ile Cys Asn Ser Asp Asn Asn
                260                 265                 270

Phe Ile Ala Lys Ala Ala Cys Val Thr Ala Arg Val Leu Cys Asn Pro
            275                 280                 285

Ile Ile Gly Val Tyr Ser Ala Thr Gly Leu Asn Asn Tyr Asp Ile Arg
        290                 295                 300

Lys Pro Cys Ile Gly Thr Leu Cys Tyr Asn Phe Asp Ala Leu Asn Ala
305                 310                 315                 320

Phe Met Asn Arg Glu Asp Val Gln Ser Ser Leu Gly Ala Lys Arg Gln
                325                 330                 335

Val Trp Gln Ser Cys Asn Met Glu Val Asn Leu Met Phe Leu Met Asp
            340                 345                 350

Trp Phe Lys Asn Phe Asn Tyr Thr Val Pro Thr Leu Leu Glu Asp Gly
        355                 360                 365

Val Ser Val Met Ile Tyr Ala Gly Glu Met Asp Phe Ile Cys Asn Trp
370                 375                 380

Ile Gly Asn Lys Gln Trp Thr Thr Ala Leu Asn Trp Pro Gly Lys Ala
385                 390                 395                 400

Val Phe Asn Ala Ala Pro Asp Glu Pro Phe Arg Ala Pro Asp Gly Thr
                405                 410                 415

Val Ala Gly Leu Val Arg Thr Ala Ala Ala Ser Thr Ser Asn Leu
            420                 425                 430

Thr Phe Val Gln Val Tyr Asn Ala Gly His Met Val Pro Met Asp Gln
        435                 440                 445

Pro Ala Ser Ala Phe Val Met Ile Ser Asn Phe Leu Gln Gly Arg Pro
        450                 455                 460

Phe Asn
465

<210> SEQ ID NO 18
<211> LENGTH: 381
<212> TYPE: PRT
<213> ORGANISM: Trypanosoma cruzi

<400> SEQUENCE: 18

Met Ser Arg Asn Val Ala Ala Glu Glu Glu Trp Glu Asp Val Asp Ala
1               5                   10                  15

Pro Asn Glu Glu Asp Glu Glu Glu Asp Thr Thr Ile Asn Asn Ser
            20                  25                  30

Asp Val Met Met Arg Tyr Lys Lys Ala Ala Leu Trp Cys Asn Glu Thr
            35                  40                  45

Leu Gln Leu Leu Leu Asp Ala Thr Lys Pro Gly Ala Lys Val His Glu
        50                  55                  60

Leu Cys Lys Leu Gly Asp Glu Thr Val Ala Lys Lys Leu Lys Thr Met
65                  70                  75                  80

Phe Lys Gly Thr Glu Lys Gly Leu Ala Phe Pro Thr Cys Ile Ser Val
                85                  90                  95
```

Asn Ser Cys Val Ala His Asn Ser Pro Ser Ala Asp Asp Glu Val Ala
                100                 105                 110

Ser Gln Glu Ile Gln Leu Gly Asp Val Val His Ile Asp Leu Gly Ile
            115                 120                 125

His Val Asp Gly Tyr Cys Ala Gln Val Ala His Thr Val Gln Val Thr
        130                 135                 140

Glu Asn Asn Glu Leu Ala Ala Asp Asp Ala Ser Lys Val Ile Ser
145                 150                 155                 160

Ala Thr Tyr Gly Ile Leu Asn Thr Ala Met Arg Lys Met Arg Pro Gly
                165                 170                 175

Val Ser Val Tyr Glu Val Thr Glu Val Ile Glu Lys Ala Ala His
            180                 185                 190

Tyr Gly Val Thr Pro Val Asp Gly Val Leu Ser His Met Leu Lys Arg
        195                 200                 205

Tyr Ile Val Asp Ser Phe Arg Cys Val Pro Gln Arg Lys Val Ala Glu
    210                 215                 220

His Leu Val His Asp Tyr Thr Leu Glu Ala Gly Gln Val Trp Thr Leu
225                 230                 235                 240

Asp Ile Val Met Ser Ser Gly Lys Gly Lys Leu Lys Glu Arg Asp Val
                245                 250                 255

Arg Pro Thr Val Tyr Lys Val Ala Leu Asp Ser Asn Tyr Thr Met Lys
            260                 265                 270

Met Glu Ser Ala Arg Glu Leu Gln Arg Glu Ile Glu Ala Lys Tyr Gln
        275                 280                 285

Thr Phe Pro Phe Ala Leu Arg Asn Leu Glu Thr Lys Arg Ala Arg Leu
    290                 295                 300

Gly Leu Ser Glu Met Leu Lys His Gly Ala Val Val Pro Tyr Pro Val
305                 310                 315                 320

Leu Tyr Glu Arg Asp Gly Glu Val Val Gly His Phe Lys Ile Thr Leu
                325                 330                 335

Leu Ile Thr Ala Lys Lys Ile Glu Pro Val Thr Gly Leu Lys Pro Gln
            340                 345                 350

Lys Ala Pro Thr Leu Pro Ala Tyr Thr Asp Glu Leu Leu Leu Glu Ala
        355                 360                 365

Ser Lys Leu Pro Leu Thr Leu Glu Lys Lys Arg Lys Asn
370                 375                 380

<210> SEQ ID NO 19
<211> LENGTH: 411
<212> TYPE: PRT
<213> ORGANISM: Trypanosoma cruzi

<400> SEQUENCE: 19

Met Ser Leu Thr Leu Trp Ser Gly Val Asn Pro Glu Asn Ala Arg Thr
1               5                   10                  15

His Lys Leu Leu Ala Ala Ala Leu Ala Asn Val Ala Val Thr Leu
            20                  25                  30

Lys Ala Cys Glu Tyr Gly Arg Glu Asn Glu Thr Ala Glu Tyr Cys Arg
        35                  40                  45

Asn Cys Ser Pro Cys Gly Arg Tyr Pro Val Leu Gln Thr Glu Glu Gly
    50                  55                  60

Cys Val Phe Glu Ser Asn Ala Ile Leu Arg His Ile Ala Arg Leu Asp
65                  70                  75                  80

Arg Ser Gly Gly Phe Leu Tyr Arg Thr Pro Leu Glu Gly Ser Gln
            85                  90                  95

Val Asp Met Trp Leu Asp Phe Ser Ala Thr Glu Leu Asp Ala Ala Ser
            100                 105                 110

Glu Pro Phe Val His His Ala Phe Arg Gly Glu Pro Leu Pro Ala Asn
        115                 120                 125

Ala Met Asp Arg Val His Glu Val Leu Arg Ala Leu Glu Ala Trp Leu
130                 135                 140

Glu Thr Arg Thr Phe Leu Val Gly Glu Arg Met Thr Val Ala Asp Val
145                 150                 155                 160

Ala Val Ala Phe Ala Leu Gln Trp His Tyr Arg Leu Asn Gly Ala Glu
                165                 170                 175

Gly Glu Ala Leu Thr Lys Lys Tyr Arg Asn Ala Tyr Arg Leu Tyr Asn
            180                 185                 190

Thr Val Met Gln Gln Pro Lys Thr Val Glu Val Leu Arg Ser Gln Gly
        195                 200                 205

Ala Thr Phe Gly Pro Val Lys Ala Glu Arg Lys Gly Lys Asp Ala Ala
210                 215                 220

Ala Pro Ala Arg Ala Glu Lys Lys Pro Lys Ala Ala Ala Ala Ala Ala
225                 230                 235                 240

Asp Gly Ala Glu Glu Asp Glu Ala Pro Arg Glu Lys Lys Lys Pro
                245                 250                 255

Asn Pro Leu Asp Glu Leu Pro Pro Ser Pro Phe Val Leu Asp Ala Phe
            260                 265                 270

Lys Arg Glu Tyr Ser Asn Thr Asp Thr Arg Thr Val Ala Ala Pro Tyr
        275                 280                 285

Phe Phe Gln His Tyr Asp Ala Ala Gly Tyr Thr Thr Phe Trp Cys Arg
290                 295                 300

Tyr Lys Tyr Asn Glu Asp Asn Lys Met Gln Phe Met Thr Ala Asn Leu
305                 310                 315                 320

Ile Arg Gly Trp Phe Gln Arg Met Glu His Val Arg Lys Tyr Ala Phe
                325                 330                 335

Gly Val Ala Leu Ile Ile Gly Glu Glu Arg Arg His Asp Ile Val Ala
            340                 345                 350

Leu Trp Val Phe Arg Gly Arg Gly Met Pro Ala Ile Val Glu Asp Val
        355                 360                 365

Glu Asp Thr Glu Leu Phe Asp Trp Glu Val Ala Asp Val Ala Ala
370                 375                 380

Gln Arg Glu Arg Ile Thr Asp Tyr Leu Cys Trp Gly Pro Thr Ile
385                 390                 395                 400

Pro Arg Pro Val Leu Glu Gly Arg Val Phe Lys
                405                 410

<210> SEQ ID NO 20
<211> LENGTH: 982
<212> TYPE: PRT
<213> ORGANISM: Trypanosoma cruzi

<400> SEQUENCE: 20

Met Ser Gly Asp Gly Asp Ser Ser Leu Asp Pro Ser Ile Leu Val Val
1               5                   10                  15

Glu Ala Arg Phe Asn Glu Ser Leu Gly Asn Gln Ser Val Ser Gly Gly
            20                  25                  30

Gly Gly Ser Glu Arg Trp Gln His Glu Glu Lys Gln Gln Gln Gln
        35                  40                  45

Gln Gln Pro Leu Ser Leu Pro Pro Arg Ser Arg Gly Asp Val Asn Trp
50                  55                  60

```
Asn Ala Ser Ser Ser Ser Pro Ser Thr Ile Glu Glu Ala Glu Gly
 65                  70                  75                  80

Gly Asp Gly Asp Arg Arg Thr Ala Asp Arg Trp Ser Asp Asp Gly
             85                   90                  95

Ser Asn Ala Gly Asn Asp Arg Asp Gly Gly Ile Glu Thr Asn Glu Glu
            100                 105                 110

Asn Glu Asp Glu Ile Ala Glu Arg Val Leu Arg Ala Leu Arg Cys Lys
            115                 120                 125

Asp Met Leu Met Asp Glu Gln Ala Arg Lys Leu Gln Arg Arg Glu Met
        130                 135                 140

Glu Ala Arg Gln Leu Arg Arg Glu Leu Asp Leu Arg Gly Glu Lys
145                 150                 155                 160

Gln Leu Leu Met Gln Gln Leu Arg Gly Phe Leu Asp Gly Ser Thr Pro
                165                 170                 175

Met Thr Thr Ala Ser Glu Thr Gly Pro Leu Lys Asp Ser Gly Gln Leu
            180                 185                 190

Tyr Pro Ser Met Leu Leu Gln Arg Ala Asp Ser Gln Leu Gln Asp Glu
            195                 200                 205

Arg Ala Glu Arg Gln Gln Asp Ala Arg His Phe Met Ala His Ile Glu
210                 215                 220

Gln Leu Thr Ala Gln Leu Ala Glu Ala Gln His Glu Ala Arg Thr Arg
225                 230                 235                 240

Glu Ala Arg His Ala Gln Asp Leu Asp Thr Ile Gln Gln Glu Met Gln
                245                 250                 255

Glu Leu Ser Thr Val Val Asp Asp Met His Ala Thr Lys Ala Ala Leu
            260                 265                 270

Cys Arg Thr Gln Glu Gln Leu Ala Lys Ala Asn Glu Glu Lys Ala Gln
            275                 280                 285

Cys Gln Leu Glu Arg Asp Arg Leu Val Arg Ser Leu Gln Glu Ala Leu
            290                 295                 300

Arg Arg Glu Gly Ser Glu His Gln Arg Thr Leu Glu Arg Met Arg Ala
305                 310                 315                 320

Glu Ala Gly Ala Tyr Glu Arg Ala Lys Ala Ala Glu Ala Lys Cys
                325                 330                 335

Arg Arg Ala Glu Ala Glu Gln Leu Lys Leu Ala Glu Glu Leu Arg Ala
            340                 345                 350

Leu Arg Ile Glu Met Gln Gln Leu Val Asp Glu Asn Ala Ala Leu Thr
            355                 360                 365

Leu Arg Met Glu Ser Ser Glu Gln Gln Leu Arg Arg Ala Gln Lys Gln
        370                 375                 380

His Val Glu Glu Arg Ala Ala Glu Ala Glu Ala Arg Arg Arg Leu Gln
385                 390                 395                 400

Glu Glu Leu Asp Ala Lys Val Arg Glu Met Ala Gln Leu Arg Ser Thr
                405                 410                 415

Arg Asp Ala Gln Ser Gln Leu Leu Val Glu Glu Gly Arg His Ala
            420                 425                 430

Leu Phe Gln Ala Glu Val Glu Cys Val Gln Ser Thr Arg Gln Leu
            435                 440                 445

Glu Glu Ala Leu Met Arg Cys Glu Arg Arg Cys Glu Ala Glu Glu
450                 455                 460

Arg Glu Thr Arg Val Ala Ala Glu Arg Asp Ala Leu Arg Val Gln Leu
465                 470                 475                 480

Gln Arg Val Thr Ala Ala Ser Arg Gln Glu Leu Leu Glu Gln Gln Gln
                485                 490                 495
```

```
Leu Thr Glu Glu Met Arg Ser Phe His Gln Ala Lys Leu Gln Gln Met
            500                 505                 510
Gln Gln Ala Ala Glu His Gln Arg Gln Arg Ala Glu Arg Leu Glu Glu
            515                 520                 525
Lys Ser Glu Glu Ala Val Arg Glu Tyr Arg Thr Leu Gln Ala Leu Leu
            530                 535                 540
Asp Ser Thr Gln Arg Gln Met Glu Glu Val Ala Gly Lys Leu His Glu
545                 550                 555                 560
Leu Arg Gln Gln Arg Met Ser Leu Glu Ser Met Leu Ala Glu Thr Gln
                565                 570                 575
Gln Glu Asn Asn Glu Cys Ala Ala Arg Glu Lys Asn Ala Ala Ala Gln
            580                 585                 590
Leu Asp Ala Ile Arg Ser Arg Leu Lys Gln Arg Glu Cys Ala Trp Arg
            595                 600                 605
Glu Leu Arg Ala Lys Met Gln Arg Leu Glu Glu Arg Glu Gln Arg Arg
            610                 615                 620
Arg Leu Ala Glu Ala Ala Asp Ser Leu Leu Arg Met Arg Gln Asn His
625                 630                 635                 640
His Ser Gln Gly Lys Cys Lys Thr Lys Leu Gln Thr Cys Ile Arg Asp
                645                 650                 655
Lys Ile Ser Arg Ala Arg Leu Glu Glu Asn Leu Leu Asp Asn Ile Ala
            660                 665                 670
Gly Val Asp Val Asn Thr Thr Leu Ser Thr Lys Glu Pro Ser Ser Met
            675                 680                 685
Thr Ala Pro Pro Pro Pro Glu Thr Lys Arg Thr Pro Leu Arg Gly
            690                 695                 700
Pro Gln Leu Asp Ala Trp Gln Ala Lys Leu Gln Ala Leu Glu Ala Arg
705                 710                 715                 720
Asn Ala Asn Leu Glu Arg Gln Leu Ala Ser Arg Gln Ile Gly His Arg
                725                 730                 735
Ala Leu Val Glu Asp Arg Lys Ala Leu His Gln Gln Met His Thr Leu
            740                 745                 750
Gln Glu Thr Ala Gln Gly Leu Met Ser Ala Leu Glu Arg Gln His Arg
            755                 760                 765
Asp Ala Ile Lys His Leu Glu Glu Ala His Arg His Thr Leu Val
            770                 775                 780
Ala Cys Arg Glu Ala Ser Asp Ala Leu Ala Ser His Glu Ser Cys Val
785                 790                 795                 800
Arg Ser Gly Val Val Arg Val Ser Glu Leu Met Ala Phe Ile Arg
                805                 810                 815
Ala Leu Glu Ala Asn Ala Thr Leu Val Ala Arg His His Glu Arg Leu
            820                 825                 830
Gln Glu Ala Pro Val Gln Met Ala Asp Asp Asp Lys Glu Asn Met
            835                 840                 845
Leu Arg Ala Ala Cys Asp Asp Ile Thr Arg Asn Phe Leu Gly Val Glu
            850                 855                 860
Gly Gly Trp Glu Ala Leu Leu Gln His Ser Leu Arg Thr Thr Ser Gly
865                 870                 875                 880
Arg Lys Ser Ser Arg Ala Asp Gly Gly Ser Leu Thr Ala Ala Met Arg
                885                 890                 895
Arg Arg Ile Arg Cys Phe Leu Met Asp Tyr Leu Gln Ala Gln Leu Leu
            900                 905                 910
Gly Lys Pro Ala Ala Ala Val Leu Pro Ala Leu Arg Arg Gln Ser Gly
```

```
                    915                 920                 925
Asn Lys Lys Lys Ala Leu Asn Val Ser Phe Ala Ala Ser Ser Asp Gly
            930                 935                 940

Ser Thr Glu Ser His Asp Asp Trp Asp Glu Glu Gln Glu Asn Cys Gly
945                 950                 955                 960

Glu Arg Pro Leu Val Glu Leu Met Glu Arg Val Arg Cys Val Tyr
                965                 970                 975

Gly Asp Asp Thr Pro Tyr
            980

<210> SEQ ID NO 21
<211> LENGTH: 221
<212> TYPE: PRT
<213> ORGANISM: Trypanosoma cruzi

<400> SEQUENCE: 21

Met Pro Asn Leu Arg Glu Arg Leu Arg Gly Gln Gln Ser Ser Pro Pro
1               5                   10                  15

Gln Leu Ser Phe Leu Leu Phe Leu Leu Ser Thr Ala Leu Leu Ser Leu
            20                  25                  30

Thr Val Cys Leu Ile Gly Val Glu Ala Ala Thr Thr Val Gly Ser
        35                  40                  45

Gly Glu Lys Leu Cys Leu Arg Glu Val Pro Pro Gln Ser Arg Val
    50                  55                  60

Thr Phe Gln Phe Gln Val Val Gly Gly Asn His Asp Ile Arg Ala
65                  70                  75                  80

Ser Val Ala Asp Gln Glu Gly His Ile Leu Lys Glu Trp Gly Glu Thr
                85                  90                  95

Ser Asp Gly Leu Tyr Glu Val Leu Ala Gln Ser Gly Thr Lys Ala Ile
            100                 105                 110

Val Ala Cys Leu Asp Asn Thr Tyr Ala His Tyr Thr Pro Lys Leu Ile
        115                 120                 125

Val Phe His Phe Arg Tyr His Val Asp Tyr Thr Ser Val Ala Lys Gln
    130                 135                 140

Ser Glu Leu Asp Pro Val Glu Arg Lys Val Glu His Ile Ser Ser Leu
145                 150                 155                 160

Met Arg Gln Val Glu Ser Leu Gln Met Leu Leu Arg Thr Gln Gln Lys
                165                 170                 175

Glu His Arg Ala Thr Val Glu Glu Ser Ser Glu Arg Leu Leu Ile Trp
            180                 185                 190

Ser Val Phe Gln Val Leu Thr Leu Val Ile Met Ser Cys Phe Gln Leu
        195                 200                 205

Tyr Phe Leu Lys Arg Phe Leu Glu Arg Lys Ser Phe Val
    210                 215                 220

<210> SEQ ID NO 22
<211> LENGTH: 149
<212> TYPE: PRT
<213> ORGANISM: Trypanosoma cruzi

<400> SEQUENCE: 22

Met Ala Asp Gln Leu Ser Asn Glu Gln Ile Ser Glu Phe Lys Glu Ala
1               5                   10                  15

Phe Ser Leu Phe Asp Lys Asp Gly Asp Gly Thr Ile Thr Thr Lys Glu
            20                  25                  30

Leu Gly Thr Val Met Arg Ser Leu Gly Gln Asn Pro Thr Glu Ala Glu
        35                  40                  45
```

```
Leu Gln Asp Met Ile Asn Glu Val Asp Gln Asp Gly Ser Gly Thr Ile
    50                  55                  60

Asp Phe Pro Glu Phe Leu Thr Leu Met Ala Arg Lys Met Gln Asp Ser
65                  70                  75                  80

Asp Ser Glu Glu Glu Ile Lys Glu Ala Phe Arg Val Phe Asp Lys Asp
                85                  90                  95

Gly Asn Gly Phe Ile Ser Ala Ala Glu Leu Arg His Val Met Thr Asn
                100                 105                 110

Leu Gly Glu Lys Leu Thr Asp Glu Glu Val Asp Glu Met Ile Arg Glu
            115                 120                 125

Ala Asp Val Asp Gly Asp Gly Gln Ile Asn Tyr Glu Glu Phe Val Lys
            130                 135                 140

Met Met Met Ser Lys
145

<210> SEQ ID NO 23
<211> LENGTH: 518
<212> TYPE: PRT
<213> ORGANISM: Trypanosoma cruzi

<400> SEQUENCE: 23

Met Leu Thr Arg Leu Arg Ser Ala Ala Leu Arg Gly Ala Ala Gly Thr
1               5                   10                  15

Arg Ala Ala Ser Gly Met Pro Thr Ala Asp His Lys Gly Arg Val Gly
                20                  25                  30

Tyr Val Ser Gln Val Ile Gly Ala Val Val Asp Val His Phe Ala Glu
            35                  40                  45

Gly Val Pro Pro Val Leu Thr Ala Leu Asp Val Val Glu Lys Leu Gly
        50                  55                  60

Arg Asp Glu Pro Leu Thr Leu Glu Ile Val Gln His Leu Asp Ala His
65                  70                  75                  80

Thr Gly Arg Cys Ile Ala Met Gln Thr Thr Asp Leu Leu Lys Leu Lys
                85                  90                  95

Ser Lys Val Val Ser Ser Gly Asn Ile Ser Val Pro Val Gly Arg
                100                 105                 110

Glu Thr Leu Gly Arg Ile Phe Asn Val Leu Gly Asp Ala Ile Asp Gln
            115                 120                 125

Arg Gly Pro Val Gly Glu Lys Gln Arg Met Pro Ile His Ala Val Ala
        130                 135                 140

Pro Lys Leu Ala Asp Gln Ala Ala Glu Asp Thr Ile Leu Thr Thr Gly
145                 150                 155                 160

Ile Lys Val Ile Asp Leu Ile Leu Pro Tyr Cys Lys Gly Gly Lys Ile
                165                 170                 175

Gly Leu Phe Gly Gly Ala Gly Val Gly Lys Thr Val Ile Ile Met Glu
                180                 185                 190

Leu Ile Asn Asn Val Ala Lys Gly His Gly Gly Phe Ser Val Phe Ala
            195                 200                 205

Gly Val Gly Glu Arg Thr Arg Glu Gly Thr Asp Leu Tyr Leu Glu Met
        210                 215                 220

Met Gln Ser Lys Val Ile Asp Leu Lys Gly Asp Ser Lys Cys Val Leu
225                 230                 235                 240

Val Tyr Gly Gln Met Asn Glu Pro Pro Gly Ala Arg Ala Arg Val Ala
                245                 250                 255

Gln Ser Ala Leu Thr Met Ala Glu Tyr Phe Arg Asp Val Glu Gly Gln
            260                 265                 270
```

```
Asp Val Leu Leu Phe Ile Asp Asn Ile Phe Arg Phe Thr Gln Ala Asn
            275                 280                 285

Ser Glu Val Ser Ala Leu Leu Gly Arg Ile Pro Ala Val Gly Tyr
        290                 295                 300

Gln Pro Thr Leu Ala Glu Asp Leu Gly Gln Leu Gln Glu Arg Ile Thr
305                 310                 315                 320

Ser Thr Thr Lys Gly Ser Ile Thr Ser Val Gln Ala Val Tyr Val Pro
                325                 330                 335

Ala Asp Asp Ile Thr Asp Pro Ala Pro Ala Thr Thr Phe Ser His Leu
                340                 345                 350

Asp Ala Thr Thr Val Leu Asp Arg Ala Val Ala Glu Ser Gly Ile Tyr
            355                 360                 365

Pro Ala Val Asn Pro Leu Glu Cys Ala Ser Arg Ile Met Asp Pro Asp
        370                 375                 380

Val Ile Ser Val Asp His Tyr Asn Val Ala Gln Asp Val Val Gln Met
385                 390                 395                 400

Leu Thr Lys Tyr Lys Glu Leu Gln Asp Ile Ile Ala Val Leu Gly Ile
                405                 410                 415

Asp Glu Leu Ser Glu Glu Asp Lys Leu Ile Val Asp Arg Ala Arg Lys
                420                 425                 430

Val Thr Lys Phe Leu Ser Gln Pro Phe Gln Val Ala Glu Val Phe Thr
            435                 440                 445

Gly Met Thr Gly His Tyr Val Gln Leu Glu Glu Thr Ile Glu Ser Phe
        450                 455                 460

Ser Gly Leu Leu Met Gly Thr Tyr Asp Gln Val Pro Glu Met Ala Phe
465                 470                 475                 480

Tyr Met Val Gly Gly Ile Thr Ser Val Leu Glu Lys Gly Lys Lys Met
                485                 490                 495

Ala Glu Glu Ala Ala Glu Leu Glu Lys Leu Arg Arg Ala Arg Ala Ala
                500                 505                 510

Gln Ala Gly Gln Lys Glu
            515

<210> SEQ ID NO 24
<211> LENGTH: 655
<212> TYPE: PRT
<213> ORGANISM: Trypanosoma cruzi

<400> SEQUENCE: 24

Met Phe Ala Arg Arg Leu Cys Gly Ala Gly Ser Leu Ala Ala Ala Ser
1               5                   10                  15

Leu Ala Arg Trp Gln Ser Ser Lys Val Thr Gly Asp Val Ile Gly Ile
            20                  25                  30

Asp Leu Gly Thr Thr Tyr Ser Cys Val Ala Val Met Glu Gly Asp Lys
        35                  40                  45

Pro Arg Val Leu Glu Asn Thr Glu Gly Phe Arg Thr Thr Pro Ser Val
    50                  55                  60

Val Ala Phe Lys Gly Gln Glu Lys Leu Val Gly Leu Ala Ala Lys Arg
65                  70                  75                  80

Gln Ala Ile Thr Asn Pro Gln Ser Thr Phe Phe Ala Val Lys Arg Leu
                85                  90                  95

Ile Gly Arg Arg Phe Glu Asp Ser Asn Ile Gln His Asp Ile Lys Asn
                100                 105                 110

Val Pro Tyr Lys Ile Val Arg Ser Ser Asn Gly Asp Ala Trp Val Gln
            115                 120                 125
```

```
Asp Ala Asn Gly Lys Gln Tyr Ser Pro Ser Gln Val Gly Ala Phe Val
    130                 135                 140
Leu Glu Lys Met Lys Glu Thr Ala Glu Asn Phe Leu Gly Arg Lys Val
145                 150                 155                 160
Ser Asn Ala Val Val Thr Cys Pro Ala Tyr Phe Asn Asp Ala Gln Arg
                165                 170                 175
Gln Ala Thr Lys Asp Ala Gly Thr Ile Ala Gly Leu Asn Val Ile Arg
            180                 185                 190
Val Val Asn Glu Pro Thr Ala Ala Leu Ala Tyr Gly Leu Asp Lys
        195                 200                 205
Thr Lys Asp Ser Met Ile Ala Val Tyr Asp Leu Gly Gly Gly Thr Phe
    210                 215                 220
Asp Ile Ser Val Leu Glu Ile Ala Gly Gly Val Phe Glu Val Lys Ala
225                 230                 235                 240
Thr Asn Gly Asp Thr His Leu Gly Gly Glu Asp Phe Asp Leu Cys Leu
                245                 250                 255
Ser Asp Tyr Ile Leu Thr Glu Phe Lys Lys Ser Thr Gly Ile Asp Leu
            260                 265                 270
Ser Asn Glu Arg Met Ala Leu Gln Arg Ile Arg Glu Ala Ala Glu Lys
        275                 280                 285
Ala Lys Cys Glu Leu Ser Thr Thr Met Glu Thr Glu Val Asn Leu Pro
    290                 295                 300
Phe Ile Thr Ala Asn Gln Asp Gly Ala Gln His Val Gln Met Thr Val
305                 310                 315                 320
Ser Arg Ser Lys Phe Glu Ser Leu Ala Glu Lys Leu Val Gln Arg Ser
                325                 330                 335
Leu Gly Pro Cys Lys Gln Cys Ile Lys Asp Ala Ala Val Asp Leu Lys
            340                 345                 350
Glu Ile Ser Glu Val Val Leu Val Gly Gly Met Thr Arg Met Pro Lys
        355                 360                 365
Val Ile Glu Ala Val Lys Gln Phe Phe Gly Arg Asp Pro Phe Arg Gly
    370                 375                 380
Val Asn Pro Asp Glu Ala Val Ala Leu Gly Ala Ala Thr Leu Gly Gly
385                 390                 395                 400
Val Leu Arg Gly Asp Val Lys Gly Leu Val Leu Asp Val Thr Pro
                405                 410                 415
Leu Ser Leu Gly Ile Glu Thr Leu Gly Gly Val Phe Thr Arg Met Ile
            420                 425                 430
Pro Lys Asn Thr Thr Ile Pro Thr Lys Lys Ser Gln Thr Phe Ser Thr
        435                 440                 445
Ala Ala Asp Asn Gln Thr Gln Val Gly Ile Lys Val Phe Gln Gly Glu
    450                 455                 460
Arg Glu Met Ala Ala Asp Asn Gln Met Met Gly Gln Phe Asp Leu Val
465                 470                 475                 480
Gly Ile Pro Pro Ala Pro Arg Gly Val Pro Gln Ile Glu Val Thr Phe
                485                 490                 495
Asp Ile Asp Ala Asn Gly Ile Cys His Val Thr Ala Lys Asp Lys Ala
            500                 505                 510
Thr Gly Lys Thr Gln Asn Ile Thr Ile Thr Ala Ser Gly Gly Leu Ser
        515                 520                 525
Lys Glu Gln Ile Glu Arg Met Ile Arg Asp Ser Glu Ser His Ala Glu
    530                 535                 540
Ser Asp Arg Leu Lys Arg Glu Leu Val Glu Val Arg Asn Asn Ala Glu
```

```
545                 550                 555                 560
Thr Gln Ala Asn Thr Ala Glu Arg Gln Leu Thr Glu Trp Lys Tyr Val
                565                 570                 575

Ser Asp Ala Glu Lys Glu Asn Val Arg Thr Leu Leu Ala Glu Leu Arg
            580                 585                 590

Lys Ser Met Glu Asn Pro Asn Val Thr Lys Asp Glu Leu Ser Ala Ala
        595                 600                 605

Thr Asp Lys Leu Gln Lys Ala Val Met Glu Cys Gly Arg Thr Glu Tyr
    610                 615                 620

Gln Gln Ala Ala Ala Ala Asn Ser Ser Ser Ser Gly Asn Thr Asp
625                 630                 635                 640

Ser Ser Gln Gly Glu Gln Gln Gln Gly Asp Gln Gln Lys Gln
                645                 650                 655

<210> SEQ ID NO 25
<211> LENGTH: 600
<212> TYPE: PRT
<213> ORGANISM: Trypanosoma cruzi

<400> SEQUENCE: 25

Met Ser Tyr Lys Glu Ala Ser Gly Ala Val Gly Pro Ala Asp Gln Gln
1               5                   10                  15

Gln Pro Ala Val Pro Glu Val Thr Asp Val Thr Leu Glu Ala Ala Arg
            20                  25                  30

Lys Gln Lys Ile His Asn Leu Lys Leu Lys Thr Ser Cys Leu Ser Asn
        35                  40                  45

Glu Glu Phe Ile Gln Asp Leu His Val Ser Asp Trp Ser Glu Thr Gln
    50                  55                  60

Lys Gln Lys Leu Leu Ala Ala His Glu Lys Ala Gln Glu Leu Leu Ser
65                  70                  75                  80

Ser Val Glu Gly Gly Thr Lys Trp Asn Leu Thr Glu Ala Tyr Asp Ile
                85                  90                  95

Lys Lys Leu Met Arg Val Cys Gly Leu Gln Leu Ser Val Arg Glu Leu
            100                 105                 110

Tyr Lys Pro Glu Asp Lys Pro His Phe Met Glu Val Val Ala Leu Lys
        115                 120                 125

Lys Thr Leu Asn Glu Leu Lys Gln His His Asn Lys Thr Arg Thr Val
    130                 135                 140

Ser Phe Thr Gly Thr Ile Asp Asn Ala Ile Ala Lys Leu Glu Lys Ile
145                 150                 155                 160

Glu Asp Glu Leu Arg Arg Ser Gln Leu Asp Ala Ser Glu Met Ala Gln
                165                 170                 175

Val Pro Val Ala Val Leu Lys Asn Leu Glu Glu Cys Met Asn Val Thr
            180                 185                 190

Val Val Gln Thr Ala Leu Leu Gly Asn Glu Glu Gln Ile Lys Ala Gln
        195                 200                 205

Leu Ala Ala Ile Glu Lys Ala Lys Glu Ile Arg Asn Val Ala Ile Ala
    210                 215                 220

Asp Gly Glu Met Ala Ile Ala Glu Glu Gln Tyr Tyr Ile Lys Ala Gln
225                 230                 235                 240

Leu Leu Glu His Leu Val Glu Leu Val Ala Asp Lys Phe Arg Ile Ile
                245                 250                 255

Gly Gln Thr Glu Asp Glu Asn Lys Pro Phe Gly Arg Ile Gln Asp Val
            260                 265                 270

Gln Lys Lys Ser Phe Gln Glu Thr Ser Ala Ile Lys Asp Ala Lys Arg
```

```
                275                 280                 285
Arg Leu Lys Gln Arg Cys Glu Asp Asp Leu Lys Asn Leu His Asp Ala
        290                 295                 300
Ile Gln Lys Ala Asp Met Glu Asp Ala Glu Ala Met Lys Arg Phe Ala
305                 310                 315                 320
Thr Gln Lys Glu Lys Ser Glu Lys Phe Ile Gln Glu Asn Leu Asp Arg
                325                 330                 335
Gln Asp Glu Ala Trp Arg Arg Ile Gln Glu Leu Glu Arg Val Leu Gln
        340                 345                 350
Arg Leu Gly Thr Glu Arg Phe Glu Val Lys Arg Arg Ile Glu Glu
        355                 360                 365
Asn Asp Arg Glu Glu Lys Arg Lys Val Glu Tyr Gln Gln Phe Leu Asp
        370                 375                 380
Val Cys Gly Gln His Lys Lys Leu Leu Glu Leu Ser Val Tyr Asn Cys
385                 390                 395                 400
Asp Leu Ala Met Arg Cys Ile Gly Met Met Glu Glu Leu Val Ala Glu
                405                 410                 415
Gly Cys Ser Ala Ile Lys Ser Arg His Asp Lys Thr Asn Glu Glu Leu
        420                 425                 430
Ala Asp Leu Arg Leu Gln Val His Gln Glu Tyr Leu Glu Ala Phe Arg
        435                 440                 445
Arg Leu Tyr Lys Thr Leu Gly Gln Leu Val Tyr Lys Lys Glu Lys Arg
        450                 455                 460
Leu Glu Glu Ile Asp Arg Asn Ile Arg Thr Thr His Ile Gln Leu Glu
465                 470                 475                 480
Phe Ala Ile Glu Thr Phe Asp Pro Asn Ala Lys Lys His Ser Asp Ala
                485                 490                 495
Lys Lys Glu Leu Tyr Lys Leu Arg Ala Gln Val Glu Glu Glu Leu Glu
        500                 505                 510
Met Leu Lys Asp Lys Met Ala Gln Ala Leu Glu Met Phe Gly Pro Thr
        515                 520                 525
Glu Asp Ala Leu Asn Gln Ala Gly Ile Glu Phe Val His Pro Ala Glu
        530                 535                 540
Glu Val Glu Asp Gly Asn Leu Thr Arg Arg Ser Lys Met Val Glu Tyr
545                 550                 555                 560
Arg Ala His Leu Ala Lys Gln Glu Glu Val Lys Ile Ala Ala Glu Arg
                565                 570                 575
Glu Glu Leu Lys Arg Ser Lys Thr Leu Gln Ser Gln Tyr Arg Gly
        580                 585                 590
Lys Thr Val Gln Gln Ile Thr Gln
        595                 600

<210> SEQ ID NO 26
<211> LENGTH: 2655
<212> TYPE: PRT
<213> ORGANISM: Trypanosoma cruzi
<220> FEATURE:
<221> NAME/KEY: misc_feature
<222> LOCATION: (2625)..(2625)
<223> OTHER INFORMATION: Xaa can be any naturally occurring amino acid

<400> SEQUENCE: 26

Cys Phe Ala Ala Arg Thr Ser Ser Ile Ser Gly Cys Glu Cys Val Cys
1               5                   10                  15
Ala Ala Gly Gly Tyr Gly Asp Thr Cys Val Pro Ala Ala Val Pro Asp
            20                  25                  30
```

```
Gly Leu Gly Pro Leu Pro Leu Pro Asp Ala Asp Asp Thr Glu Val Arg
         35                  40                  45

Cys Val His Gly Gly Ser Ile Ser Pro Val Asp Tyr Pro Asp Pro Gly
 50                      55                  60

Val Arg Gly Leu Cys Phe Val Asn Val Thr Phe Thr Ala Ala Ile Val
 65                  70                  75                  80

Leu Asp Leu Ser Arg Phe Asp Ala Gln Gln Lys Thr Leu Ser Ile Thr
                 85                  90                  95

Leu Leu Gln Cys Val Leu Met Gly Leu Ser Val Arg Gly Ser Gly Ala
                100                 105                 110

Arg Val His Val Asn Val Thr Ser Ser Met Met Asp Ser Gly Ala Leu
            115                 120                 125

Lys Phe Arg Gly Asp Phe Gly Ala Ser Ser Gln Ile Leu Val Ala Gly
        130                 135                 140

Ser Thr Leu Val Thr Lys Ser Arg His Ala Thr Ala Phe Trp Glu Phe
145                 150                 155                 160

Thr Leu Gly Thr Asn Ser Thr Leu Leu Leu Asp Asn Tyr Ile Glu
                165                 170                 175

Ala Asn Ile Tyr Ala Leu Ser Phe Ser Asp Ser Val Val Asp Gly Gly
                180                 185                 190

Gly Ile Ile Met Lys Gly Asn Thr Leu Arg Ala Thr Gly Asn Asp Asp
            195                 200                 205

Gly Val Glu Ser Ala Val Tyr Ile Glu Thr Phe Asp Val Gly Asn Gly
        210                 215                 220

Gly Tyr Phe Asp Val Glu Asn Asn Thr Met Ser Gly Ala Asn Gly Ile
225                 230                 235                 240

Tyr Leu Leu Gly Gly Thr Thr Val Asn Ser Ala Gly Leu Leu Arg Val
                245                 250                 255

Ala Asp Cys Ser Phe Ala Gly Ser Thr Phe Pro Phe Asp Ser Thr Leu
            260                 265                 270

Ile Tyr Leu Asp Ser Ser Val Thr Leu Glu Gly Gly Ala Gln Trp Arg
        275                 280                 285

Val Glu Gly Asn Glu Val Ser Ala Ala Ser Val Leu Ile Met Pro Lys
    290                 295                 300

Ser Ala Tyr Ile Ile Gln Val Ser Gly Ser Gly Thr Thr Val Ala Leu
305                 310                 315                 320

Ala His Asn Arg Gln Val Asp Asn Ser Tyr Pro Phe Ala Asp Leu Pro
                325                 330                 335

Leu Ser Lys Thr Val Val Glu Ser Pro Ala Arg Phe Val Val Gly Cys
            340                 345                 350

Asn Leu Gln Gly Gly Glu Glu Val Ser Cys Asp Gly Val Phe Pro Glu
        355                 360                 365

Asp Val Val Leu Phe Ile Cys Gly Thr Cys Asn Asp Asp Ala Ala Cys
    370                 375                 380

Tyr Val Pro Gly Thr Glu Ser Val Asp Arg Ser Ser Cys Ser Cys Ser
385                 390                 395                 400

Cys Lys Glu Gly Trp His Gly Ala Ser Cys Leu Pro Phe Glu Val Pro
                405                 410                 415

Asn Ala Val Val Pro Pro Val Ala Glu Arg Ala Val Asp Gly Asp Thr
            420                 425                 430

Ser Cys Val Val Asn Gln Thr Leu Lys Asn Leu Thr Leu Asn Met Trp
        435                 440                 445

Lys Thr His His Cys Tyr Val Gly Val Thr Phe Ser Gly Val Gly Ala
    450                 455                 460
```

```
Val Leu Thr Phe Phe Leu Asp Arg Met Pro Leu His Leu Leu Ile Asn
465                 470                 475                 480

Ile Thr Leu Thr Gly Cys Thr Phe Ser Gly Ala Ala Leu Gln Phe
            485                 490                 495

Val Gly Gly Ala Gly Ala Ala Glu Ser Ser Gly Val Leu Ile Arg Val
                500                 505                 510

Ser Gln Thr Val Met Arg Ser Ser Val Val Ala Phe Ser Leu Ala Leu
            515                 520                 525

Pro Gln His Cys Asp Ile Ala Val Thr Glu Val Asp Ala Leu Gln Ser
        530                 535                 540

Ser Lys Leu Lys Leu Gln Glu Ser Ala Asn Asn Met Trp Ser Val Val
545                 550                 555                 560

Val Leu His Asp Val Leu Ser Ala Ser Ser Leu Leu Val Ser Asn
                565                 570                 575

Val Lys Ala His Ser Lys Arg Tyr Gly Ala Phe Gly Leu Tyr Ser Thr
                580                 585                 590

Gly Thr Leu Thr Leu Val Arg Gly Ser Ser Leu Tyr Thr Arg Tyr Cys
            595                 600                 605

Ser Phe Glu Gly Tyr Thr His Leu Phe Tyr Val Tyr Arg Leu Ser Val
610                 615                 620

Arg Asp His Ser Val Phe Ala Leu Leu Asn Asn Thr Met Ser Ser Gly
625                 630                 635                 640

Arg Thr Leu Leu Phe Gln His Ser Arg Phe Ser Val Ser Asp Tyr Ser
            645                 650                 655

Val Leu Arg Val Val Gly Asn Ser Gly Phe Val Ser Cys Ala Ile Ser
                660                 665                 670

Ala His Ile Pro Trp Val Leu Gln Asn Ser Ser Trp Leu Asp Trp Arg
        675                 680                 685

Asp Asn Asp Val Glu Val Gly Ala Met Leu Cys Cys Phe Ser Ser Ala
690                 695                 700

Thr Val Ser Ile Asp Ser Ser Val Val Thr Leu Lys Gly Cys Lys
705                 710                 715                 720

Met Gly Ser Thr Gly Leu Ser Val Pro Leu Leu Ser Gln Ser Asp Ala
            725                 730                 735

Gly Tyr Arg Phe Val Ala Gly Cys Leu Thr Val Ala Gly Arg Leu Val
                740                 745                 750

Thr Thr Ala Ala Glu Leu Glu Leu Asn Gly Ile Thr Asn Val Thr Lys
            755                 760                 765

Val Val Ala Cys Gly Gln Cys Thr Lys Asp Gly Asp Cys Phe Ala Pro
770                 775                 780

Leu Thr Thr Ala Val Ile Asp Cys Lys Cys Gln Cys Ala Ala Gly Gly
785                 790                 795                 800

His Gly Asp Val Cys Val Pro Ala Pro Met Pro Ala Gly Pro Pro
            805                 810                 815

Pro Leu Thr Pro Pro Thr Leu Pro Thr Pro Pro Val Gly Glu Cys
        820                 825                 830

Ile Ser Asp Met Val Tyr Pro Glu Val Ala Gln Ala Val Gly Ser Gly
            835                 840                 845

Leu Ser Trp Leu Cys Tyr Arg Asn Val Thr Phe Ser Gly Gly Met
        850                 855                 860

Ser Leu Thr Val Leu Ile Glu Ala Met Thr Gly Asp Val Ala Asn Val
865                 870                 875                 880

Thr Phe Asp Gly Cys Thr Trp Arg Asp Gly Ala Val Leu Leu Leu Leu
```

-continued

```
                    885                 890                 895
Gly Asn Ala Tyr Ala Ala Val Gly Ser Leu Asn Ile Val Thr Gly
                900                 905                 910

Asn Thr Phe Asp Asp Ala Leu Leu Ser Pro Glu Gly Val Phe Pro Pro
            915                 920                 925

His Thr Asn Ile Thr Ile Ser Gly Asn Arg Phe Thr Val Thr Gly Leu
        930                 935                 940

Ile Pro Arg Ser Gly Leu Asp Ile Arg Arg Pro Ser Cys Val Ala Met
945                 950                 955                 960

Asn Ala Leu Ala Ile Ser Asn Gly Ser Ala Val Val Leu Ser Gly Asn
                965                 970                 975

Val Phe Gln Ser Val Arg Ala Ser Ser Ile Ala Ile His Val Val Arg
            980                 985                 990

Ser Ala Leu Arg Val Ser Trp His Ser Val Phe Ala Val Val Gly Asn
        995                 1000                1005

Thr Phe His Met Ala Gly Ser Asp Gly Thr Leu Ile His Leu Glu
    1010                1015                1020

Gly Thr Ser Gln Ser Phe Ser Leu Ser Val Leu Asn Asn Ser Ala
    1025                1030                1035

Met Val Ile Arg Gly Asn Ala Val Ser Arg Pro Val Arg Tyr Val
    1040                1045                1050

Ile Ile Phe Val Trp Val Phe Cys Val Glu Ser Phe Ser Ala Val
    1055                1060                1065

Val Phe Gln Gly Asn Asp Met Arg Gly Ser Val Ala Ala Phe Phe
    1070                1075                1080

Ser Gly Phe Tyr Ser Tyr Ile Tyr Tyr Asn Ser Trp Leu Gln Leu
    1085                1090                1095

Ser Gly Asn Phe Cys Arg Glu Ser Pro Ser Glu Ala Phe Ala Val
    1100                1105                1110

Phe Asn Pro Thr Val Asn Leu Arg Asp Ser Thr Met Ser Val Ser
    1115                1120                1125

Gly Asn Gln Phe Met Phe Gly Thr Gly Thr Pro Thr Leu Ile Lys
    1130                1135                1140

Ile Pro Lys Arg Ser Ser Asp Leu Thr Asn Gly Thr Ile Val Ala
    1145                1150                1155

Ala Cys Asn Thr Gly Ser Asp Glu Glu Glu Ala Asn Tyr Val Ile
    1160                1165                1170

Pro Ser Val Tyr Asn Ala Thr Ile Leu Thr Cys Ser Asp Pro Cys
    1175                1180                1185

Thr Leu Ala Ala Ser Cys Phe Pro Ala Tyr Thr Thr Thr Ala Ser
    1190                1195                1200

Ser Asp Gly Cys Ala Cys Ala Cys Ala Glu Gly Gly His Gly Asp
    1205                1210                1215

Ala Cys Leu Pro Val Ala Val Pro Glu Ala Pro Ser Thr Asp Gly
    1220                1225                1230

Ala Asp Leu Cys Val Arg Asp Val Arg Val Asp Val Glu Val Asn
    1235                1240                1245

Ala Val Leu Gly Thr Ser Val Val Cys Tyr Val Gly Val Thr Phe
    1250                1255                1260

Ala Ala Asp Val Val Val Asp Val Glu Ser Met Ser Gly Ser Val
    1265                1270                1275

Arg Asn Val Thr Leu Ala Asn Cys Thr Phe Val Gly Gly Ala Ser
    1280                1285                1290
```

-continued

```
Leu Tyr Val Val Gly Trp Arg Ser Asp Pro Ala Gly Glu Arg
    1295                1300                1305

Ala Asp Ala Leu Ile Ser Gly Leu Glu Ser Arg Ser Gly Gly Gly
1310                1315                1320

Val Leu Val Ala Asn Arg Phe Pro Pro Gly Ser Arg Val Thr Val
1325                1330                1335

Val Asp Ser Val Leu Ile Ala Glu Lys Arg Val Ala Tyr Arg Gly
1340                1345                1350

Ala Tyr Gly Leu Gly Asp Ala Ser Ala Cys Leu Val Val His Asn
1355                1360                1365

Val Asn Leu Thr Gly Ser Val Leu Thr Ile Ala Arg Thr His Val
1370                1375                1380

Ala Ala Val Phe Arg Asp Ala Val Gly Val Leu Val Phe Gly Asp
1385                1390                1395

Val Ala Leu Ser Ser Arg Gly Ala Leu Tyr Leu Asp Gly Leu Leu
1400                1405                1410

Val Gln Thr Ala Leu Gly Leu Cys Val Ser Val Glu Gly Gly Val
1415                1420                1425

Ala Ala Ser Gly Gly Ser Val Val Ala Phe Val Asp Ser Asp Phe
1430                1435                1440

Leu Leu Cys Lys His Ala Val Ser Val Arg Glu Ala Val Ser Val
1445                1450                1455

Ser Gly Ala Ala Val Ala Leu Val Arg Ser Asp Phe Ser Ser Thr
1460                1465                1470

Glu Asp Tyr Ala Val Ala Phe Tyr Ser Thr Val Ser Leu Ala Asp
1475                1480                1485

Gly Ser Met Leu Leu Ala Lys Gly Asn Val His Asp Gly Val Ser
1490                1495                1500

Arg Glu Met Leu Tyr Ala Ala Gly Ala Val Thr Ala Ala Gly Ser
1505                1510                1515

Thr Leu Ser Phe Val Arg Asn Arg Ala Leu Leu Pro Arg Met Leu
1520                1525                1530

Ser Val Ser Leu Ser Leu Ser Ala Gly Ala His Leu Arg Val Ala
1535                1540                1545

Cys Asn Asp Ala Gly Gly Arg Phe Leu Ser Thr Ala Glu Glu Tyr
1550                1555                1560

Ala Ala Ala Gly Phe Gly Asp Ala Gly Ser Ile Asp Phe Ala Gly
1565                1570                1575

Cys Asp Ala Cys Asp Arg Asp Thr His Cys Tyr Ala Pro Gly Thr
1580                1585                1590

Ala Ser Ala Ser Met Arg Asn Gly Val Cys Val Cys Val Cys Gly
1595                1600                1605

Ser Gly Gly Tyr Gly Glu Ala Cys Val Pro Val Gly Ala Pro Ala
1610                1615                1620

Leu Pro Pro Ala Val Gly Thr Ala Pro Ser Val Phe Val Arg Glu
1625                1630                1635

Gly Val Thr Val Arg Ser Val Phe Val Pro Ala Gly Ala Ser
1640                1645                1650

Glu Val Thr Leu Arg His Val Val Leu Asp Gly Val Ser Pro Val
1655                1660                1665

Leu Tyr Val Pro Trp Met Ala Arg Asp Gly Met Arg Ile Val Val
1670                1675                1680

Gln Asn Val Ser Leu Leu Asn Gly Ala Val Leu Tyr Val Met Gly
1685                1690                1695
```

-continued

```
Gly Gly Gly Val Leu Arg Gly Ala Gly Ala Ala Gly Ser Asp Glu
    1700                1705            1710

Ser Gly Pro Val Glu Leu Ser Val Cys Asp Val Glu Ala Leu Asn
    1715                1720            1725

Gly Ala Leu Val Leu Ser Gly Thr Phe Pro Pro Gly Ser Val Leu
    1730                1735            1740

Thr Val Thr Asp Ser Leu Leu Val Ala Ala Arg Pro Thr Pro Leu
    1745                1750            1755

Val Cys Leu Pro Asp Ser Gln Ser Ser Pro Tyr Ala Pro Val Leu
    1760                1765            1770

Val Leu Ser Gly Leu Arg Leu Val Arg Ser Val Leu Val Val Ser
    1775                1780            1785

Gly Val Ala Leu Val Thr Val Met Thr Gly Gly Arg Thr Val Val
    1790                1795            1800

Val Asp Gly Ala Val Leu Glu Leu Val Gly Gly Val Ala Leu
    1805                1810            1815

Asp Ala Ala Val Leu Gly Gly Glu Tyr Ala Leu Tyr Ala Ser Ala
    1820                1825            1830

Arg Val Val Ala Ser Glu Gly Ala Val Leu Arg Val Ser Gly Ser
    1835                1840            1845

Gln Val Tyr Ala Ala His Gly Leu Val Phe Gly Ser Gly Val Val
    1850                1855            1860

Ala Asn Ala Ser Thr Val Val Val Asn Asp Asn Ala Gly Val Leu
    1865                1870            1875

Thr Asp Gly Ala Leu Leu Val Leu Arg Gly Ser Ala Ser Phe Val
    1880                1885            1890

Ser Gly Ser Trp Leu Ser Val Arg Gly Asn Ser Ile Ser Gly Arg
    1895                1900            1905

Leu Leu Ser Val Pro Ser Tyr Pro Arg Ser Ala Asp Leu Val Gln
    1910                1915            1920

Ser Thr Leu Thr Phe His Gly Asn Ala Gly Ser Gly Thr Val Val
    1925                1930            1935

Met Asp Gly Thr Val Ala Leu Gly Gly Ala Gly Arg Arg Phe Val
    1940                1945            1950

Val Gly Cys Leu Thr Leu Asn Gly Leu Thr Leu Arg Pro Ile Asp
    1955                1960            1965

Tyr Arg Ser Ala Gly Ile Ile Gly Glu Phe Arg Pro Val Ala Cys
    1970                1975            1980

Gly Val Cys Asp Ala Glu Val Arg Cys Phe Ala Ala Ala Thr Arg
    1985                1990            1995

Ala Met Thr Val Ser Cys Arg Cys Arg Cys Ala Glu Gly Gly Tyr
    2000                2005            2010

Gly Arg Asp Cys Leu Pro Val Tyr Leu Pro His Val Asp Gly Cys
    2015                2020            2025

Asn Arg Thr Pro Gly Met Pro Leu Leu Ser His Thr Ala Thr Leu
    2030                2035            2040

Thr Glu Thr Arg Ser Pro Thr Pro Thr Trp Thr Pro Ser Pro Thr
    2045                2050            2055

Pro Ser Met Ser Ala Thr His Tyr Ser Pro Thr Arg Tyr Gly Pro
    2060                2065            2070

Thr Glu Thr Leu Gln Val Thr Glu Thr Val Ala Leu Ser Pro Thr
    2075                2080            2085

Arg Thr Pro Thr Ala Ser Val Ser Ser Thr Leu Trp Trp Ser Asp
```

```
                2090                    2095                    2100

Val Ala Cys Pro Thr Leu Thr Val Thr Thr Thr Ala Ala Gly Gly
    2105                    2110                    2115

Ser Leu Thr Gln Asn Asp Ile Arg Gly Gly Gly Ser Ala Val Pro
    2120                    2125                    2130

Thr Arg Leu Met Val Ala Leu Pro Pro Pro Phe Arg Trp Ala Arg
    2135                    2140                    2145

Asp Pro Gln Leu Gly Thr His Leu Ser Phe Val Pro Val Ser Thr
    2150                    2155                    2160

Ala Gln Pro Ser Gly Phe Gly Gly Pro Trp Gly Ala Met Leu Arg
    2165                    2170                    2175

Asn Ala Thr Trp Val Arg Asn Ala Thr Asn Pro Ser Thr Val Leu
    2180                    2185                    2190

Glu Leu Ala Val Pro Val His Arg Gly Tyr Phe Ile Val Ala Asp
    2195                    2200                    2205

Glu Thr Ile Val Ile Arg Cys Gly Ala Ala Val Ser Gly Gly
    2210                    2215                    2220

Cys Lys Gly Val Leu Leu Gly Ser Phe Thr Ile Arg Ser Asn Thr
    2225                    2230                    2235

Leu Pro Ala Ala Ala Ser Ala Leu Ser Ala Ile Thr Gly Val Val
    2240                    2245                    2250

Ala Gly Ala Ala Ala Val Ala Val Val Val Thr Gly Gly Leu Gly
    2255                    2260                    2265

Ser Val Leu Glu Met Gln Ala Leu Gly Val Phe Ala Arg Met Ser
    2270                    2275                    2280

Cys Ala Ser Ala Gln Glu Arg Ala Ser Thr Ala Ala Leu Pro Tyr
    2285                    2290                    2295

Phe Leu Ser Val Phe Ala Ala Leu Asp Pro Leu Trp Met Val Val
    2300                    2305                    2310

Gly Asn Ala Leu Leu Ala Ala Val Phe Gly Cys Val His Cys Gly
    2315                    2320                    2325

Val Thr Ala Ala Phe Gln Arg Trp Arg Gly Val Asp Ala Ala Ser
    2330                    2335                    2340

Ala Trp Ala Ala Met Arg Phe Pro Ser Leu Thr Tyr Val Val Ala
    2345                    2350                    2355

His Ala Met His Leu Gly Ile Phe Phe Gly Ser Val Leu Ala Leu
    2360                    2365                    2370

Ala Met Pro Gly Ala Arg Val Gln His Arg Val Ile Gly Ala Val
    2375                    2380                    2385

Gly Val Leu Tyr Gly Val Ala Phe Pro Ala Gly Val Cys Tyr Leu
    2390                    2395                    2400

Ile Ala Arg His Val Gly Ala Ser Phe Thr Arg Tyr Trp Gln Phe
    2405                    2410                    2415

Ser Arg Lys Pro Leu His Glu Arg Leu Leu Tyr Pro Val Gly Cys
    2420                    2425                    2430

Trp His Pro Ala Ala Gln Gln Arg Met Tyr Gly Gly Met Leu Thr
    2435                    2440                    2445

Asn Met Arg Gly Ser Arg Val Tyr Trp Cys Val Phe Gln Leu Ser
    2450                    2455                    2460

Val Leu Cys Val Val Gly Leu Ile Ala Ala Val His Pro Pro Val
    2465                    2470                    2475

Gly Gly Cys His Val Gln Tyr Phe Cys Met Ala Ala Val Leu Leu
    2480                    2485                    2490
```

-continued

```
Ala Gly Ala Gly Val Val Ala Phe Thr Asn Met Met Arg Ser Ala
    2495                2500                2505

Phe Leu Thr Val Met His Ala Ala Gly Phe Val Leu Leu Ala Ala
    2510                2515                2520

Leu Cys Leu Val Ser Ala Ala Asn His Leu Ala Pro Ser Asp Gly
    2525                2530                2535

Val Ala Arg Ala Tyr Ala Ala Met Val Leu Leu Leu Thr Thr Val
    2540                2545                2550

Leu Leu Ala Ile Thr Val Tyr Ser Val Val Val Trp Tyr Ala Glu
    2555                2560                2565

Asp Arg His Trp Gln Asp Leu Arg Glu Pro Gln Arg Cys Gly Leu
    2570                2575                2580

Glu Ala Leu Leu Arg Asp Asp Glu Glu Ser Asp Glu Glu Thr Gln
    2585                2590                2595

Lys Leu His Asp Met Thr Ser Leu Ser Tyr Ala Ser Glu Thr Thr
    2600                2605                2610

Gly Ala Ser Ser Tyr Arg Pro Pro Ala Pro Pro Xaa Gln Ser Val
    2615                2620                2625

Thr Gly Asp Thr Arg Ser Asp Val Leu Ser Pro Leu Asp Arg Ala
    2630                2635                2640

Ser Ser Ala Ser Gly Lys Ile Asp His Ala Leu Leu
    2645                2650                2655

<210> SEQ ID NO 27
<211> LENGTH: 152
<212> TYPE: PRT
<213> ORGANISM: Trypanosoma cruzi

<400> SEQUENCE: 27

Met Ser Ile Glu Ser Ala Phe Tyr Ala Phe Ala Ser Phe Gly Gly Ala
1               5                   10                  15

Pro Thr Lys Glu Met Asp Asn Ala His Phe Ser Lys Met Leu Lys Glu
            20                  25                  30

Thr Lys Val Ile Gly Lys Gln Phe Thr Ser Thr Asp Ala Asp Leu Leu
        35                  40                  45

Phe Asn Lys Val Lys Ala Lys Gly Ala Arg Lys Ile Thr Leu Ser Asp
    50                  55                  60

Phe Val Asp Lys Ala Val Pro Glu Ile Ala Ser Lys Leu Lys Lys Ser
65                  70                  75                  80

Val Glu Glu Leu Ile Ala Asp Ile Ser Ser Cys Ser Pro Glu Ala Arg
                85                  90                  95

Ala Thr Lys Ala Asp Ala Val Lys Phe His Asp Asp Lys Asn Met Tyr
            100                 105                 110

Thr Gly Val Tyr Lys Ala Gly Gly Pro Thr Asn Val Asp Arg Asn Ser
        115                 120                 125

Gly Ser Leu Ser Gly Val Val Asp Arg Arg Val Ala Gln Thr Asp Val
    130                 135                 140

Cys Gly Thr Thr Ala Ser Gln Lys
145                 150

<210> SEQ ID NO 28
<211> LENGTH: 2106
<212> TYPE: PRT
<213> ORGANISM: Trypanosoma cruzi
<220> FEATURE:
<221> NAME/KEY: misc_feature
<222> LOCATION: (2076)..(2076)
<223> OTHER INFORMATION: Xaa can be any naturally occurring amino acid
```

<400> SEQUENCE: 28

```
Glu Ser Ala Asn Asn Met Trp Ser Val Val Leu His Asp Val Val
1               5                   10                  15

Leu Ser Ala Ser Ser Leu Leu Val Ser Asn Val Lys Ala His Ser Lys
            20                  25                  30

Arg Tyr Gly Ala Phe Gly Leu Tyr Ser Thr Gly Thr Leu Thr Leu Val
        35                  40                  45

Arg Gly Ser Ser Leu Tyr Thr Arg Tyr Cys Ser Phe Glu Gly Tyr Thr
    50                  55                  60

His Leu Phe Tyr Val Tyr Arg Leu Ser Val Arg Asp His Ser Val Phe
65                  70                  75                  80

Ala Leu Leu Asn Asn Thr Met Ser Ser Gly Arg Thr Leu Leu Phe Gln
                85                  90                  95

His Ser Arg Phe Ser Val Ser Asp Tyr Ser Val Leu Arg Val Val Gly
            100                 105                 110

Asn Ser Gly Phe Val Ser Cys Ala Ile Ser Ala His Ile Pro Trp Val
        115                 120                 125

Leu Gln Asn Ser Ser Trp Leu Asp Trp Arg Asp Asn Asp Val Glu Val
    130                 135                 140

Gly Ala Met Leu Cys Cys Phe Ser Ser Ala Thr Val Ser Ile Asp Ser
145                 150                 155                 160

Ser Ser Val Val Thr Leu Lys Gly Cys Lys Met Gly Ser Thr Gly Leu
                165                 170                 175

Ser Val Pro Leu Leu Ser Gln Ser Asp Ala Gly Tyr Gln Phe Val Ala
            180                 185                 190

Gly Cys Leu Thr Val Ala Gly Arg Leu Val Thr Thr Ala Ala Glu Leu
        195                 200                 205

Glu Leu Asn Gly Ile Thr Asn Val Thr Thr Val Ala Ala Cys Gly Gln
    210                 215                 220

Cys Thr Lys Asp Gly Asp Cys Phe Ala Pro Leu Thr Thr Ala Val Ile
225                 230                 235                 240

Asp Cys Lys Cys Gln Cys Ala Ala Gly His Gly Asp Val Cys Val
                245                 250                 255

Pro Ala Pro Met Pro Ala Gly Pro Pro Pro Leu Thr Pro Thr
            260                 265                 270

Leu Pro Thr Pro Pro Pro Pro Val Gly Glu Cys Ile Ser Asp Met
    275                 280                 285

Val Tyr Pro Glu Val Ala Gln Ala Val Gly Ser Gly Leu Ser Trp Leu
                290                 295                 300

Cys Tyr Arg Asn Val Thr Phe Ser Gly Gly Gly Met Ser Leu Thr Val
305                 310                 315                 320

Leu Ile Glu Ala Met Thr Gly Asp Val Ala Asn Val Val Phe Asp Gly
                325                 330                 335

Cys Thr Trp Arg Asp Gly Ala Leu Leu Leu Leu Gly Asn Ala Tyr
            340                 345                 350

Ala Ala Val Gly Ser Leu Asn Ile Val Val Thr Gly Asn Thr Phe Asp
        355                 360                 365

Asp Ala Leu Leu Ser Pro Glu Gly Val Phe Pro Pro His Thr Asn Ile
    370                 375                 380

Thr Ile Ser Gly Asn Arg Phe Thr Val Thr Arg Leu Ile Pro Arg Ser
385                 390                 395                 400

Gly Leu Asp Ile Met Arg Pro Ser Cys Val Ala Met Asn Ala Leu Ala
                405                 410                 415
```

-continued

```
Ile Ser Asn Gly Ser Ala Val Val Leu Ser Gly Asn Val Phe Gln Ser
            420                 425                 430

Val Arg Ala Ser Ser Ile Ala Ile His Val Val Arg Ser Ala Leu Arg
            435                 440                 445

Val Ser Trp His Ser Val Phe Ala Val Val Gly Asn Thr Phe His Met
450                 455                 460

Ala Gly Ser Asp Gly Thr Pro Ile Asn Leu Glu Gly Thr Ser Gln Ser
465                 470                 475                 480

Phe Ser Leu Ser Val Leu Asn Asn Ser Ala Met Val Ile Arg Gly Asn
                485                 490                 495

Ala Val Ser Arg Pro Val Arg Tyr Phe Leu Leu Ile Leu Ala Leu
                500                 505                 510

His Val Glu Ser Phe Ser Ala Val Phe Gln Gly Asn Asp Met Arg
            515                 520                 525

Gly Ser Val Ala Ala Phe Leu Ser Gly Phe Tyr Ser Tyr Ile Tyr Tyr
530                 535                 540

Asn Ser Trp Leu Gln Leu Ser Gly Asn Phe Cys Arg Glu Ser Pro Ser
545                 550                 555                 560

Glu Ala Phe Ala Val Phe Asn Pro Thr Val Asn Leu Arg Asp Ser Thr
                565                 570                 575

Val Ser Val Ser Gly Asn Gln Phe Met Phe Gly Thr Gly Thr Pro Thr
                580                 585                 590

Leu Ile Lys Ile Pro Lys Arg Ser Ser Asp Leu Thr Asn Gly Thr Ile
                595                 600                 605

Val Ala Ala Cys Asn Thr Gly Ser Asp Glu Glu Ala Asn Tyr Val
610                 615                 620

Ile Pro Ser Val Tyr Asn Ala Thr Ile Leu Thr Cys Ser Asp Pro Cys
625                 630                 635                 640

Thr Leu Ala Ala Ser Cys Phe Pro Ala Tyr Thr Thr Ala Ser Ser
                645                 650                 655

Asp Gly Cys Ala Cys Ala Cys Ala Glu Gly Gly His Gly Asp Ala Cys
            660                 665                 670

Leu Pro Val Ala Val Pro Glu Pro Pro Ser Thr Asp Gly Ala Asp Leu
            675                 680                 685

Cys Val Arg Glu Val Arg Val Gly Val Glu Val Ile Ala Gly Leu Gly
            690                 695                 700

Thr Ser Val Val Cys Tyr Val Gly Val Thr Phe Ala Ala Asp Val Val
705                 710                 715                 720

Val Asp Val Glu Ser Met Ser Gly Ser Val Arg Asn Val Thr Leu Val
                725                 730                 735

Asn Cys Thr Phe Val Gly Gly Ala Ser Leu Tyr Val Val Gly Trp Arg
            740                 745                 750

Ser Asp Pro Thr Ala Gly Glu Arg Ala Asp Ala Leu Ile Ser Gly Leu
            755                 760                 765

Glu Ser Arg Ser Gly Gly Val Leu Val Ala Asn Arg Phe Pro Pro
            770                 775                 780

Gly Ser Arg Val Thr Leu Val Asp Ser Val Leu Ile Ala Glu Ala Arg
785                 790                 795                 800

Val Ala Tyr Arg Gly Ala Tyr Asp Leu Gly Asp Leu Ser Ala Cys Leu
                805                 810                 815

Val Val His Ser Val Asn Leu Thr Gly Ser Val Leu Thr Ile Ala Arg
                820                 825                 830

Thr His Val Ala Ala Val Phe Arg Asp Ala Val Gly Val Leu Phe Phe
```

-continued

```
                835                 840                 845
Gly Gly Val Ala Leu Ser Ser Arg Gly Ala Leu Tyr Val Asp Gly Leu
            850                 855                 860
Leu Val Gln Thr Val Leu Gly Leu Cys Val Ser Val Glu Asp Gly Val
865                 870                 875                 880
Ala Val Ser Gly Gly Ser Val Ala Phe Val Asp Ser Asp Phe Leu
                885                 890                 895
Leu Cys Lys His Ala Val Ser Val Arg Gly Ala Val Gly Val Ser Gly
                900                 905                 910
Ser Ala Val Ala Phe Met Arg Ser Glu Phe Leu Ser Thr Glu Asp Tyr
                915                 920                 925
Ala Val Ala Phe Tyr Ser Thr Leu Ser Leu Ala Asp Gly Ser Met Leu
                930                 935                 940
Leu Ala Lys Gly Asn Val His Asp Gly Val Ser Arg Glu Met Ile Tyr
945                 950                 955                 960
Ala Ala Gly Ala Val Thr Ala Ala Gly Ser Thr Leu Ser Phe Val Arg
                965                 970                 975
Asn Arg Ala Leu Leu Pro Arg Met Leu Ser Leu Ser Leu Ser Leu Ala
                980                 985                 990
Ala Gly Ala His Leu Arg Val Ala Cys Asn Asp Ala Gly Gly Arg Val
                995                1000                1005
Leu Ser Thr Ala Glu Glu Tyr Ala Ala Ala Gly Phe Gly Asp Ala
            1010                1015                1020
Gly Arg Ile Asp Val Ala Gly Cys Asp Asp Cys Asp Arg Asp Thr
            1025                1030                1035
His Cys Tyr Ala Pro Gly Thr Ala Ser Ala Thr Met Arg Asn Gly
            1040                1045                1050
Val Cys Val Cys Ala Cys Gly Ser Gly Gly Tyr Gly Glu Ala Cys
            1055                1060                1065
Val Pro Val Gly Ala Pro Ala Leu Pro Pro Ala Val Gly Thr Ala
            1070                1075                1080
Ser Ser Leu Phe Phe Arg Glu Gly Val Thr Val Arg Ser Val Phe
            1085                1090                1095
Val Val Pro Ala Gly Ala Ser Glu Val Thr Leu Arg His Val Val
            1100                1105                1110
Leu Asp Gly Val Ser Pro Val Leu Tyr Val Pro Trp Met Ala Arg
            1115                1120                1125
Asp Gly Val Arg Ile Val Val Gln Ser Val Ser Leu Arg Asn Gly
            1130                1135                1140
Ala Val Leu Tyr Val Met Gly Gly Gly Ala Leu Arg Gly Ala Val
            1145                1150                1155
Ala Ala Val Ser Asp Glu Ser Gly Pro Val Glu Leu Ser Val Cys
            1160                1165                1170
Asp Val Glu Ala Leu Asn Gly Ala Leu Val Leu Ser Gly Thr Phe
            1175                1180                1185
Pro Pro Gly Ser Val Leu Thr Val Thr Asp Thr Leu Leu Val Ala
            1190                1195                1200
Ala Arg Pro Thr Pro Leu Val Cys Leu Pro Asp Ser Gln Phe Ser
            1205                1210                1215
Pro Tyr Ala Pro Val Leu Val Leu Ser Gly Leu Arg Leu Val Arg
            1220                1225                1230
Ser Val Leu Val Val Ser Gly Val Ala Leu Val Thr Val Met Thr
            1235                1240                1245
```

```
Gly Gly Arg Thr Val Val Asp Gly Ala Val Leu Glu Leu Val
    1250                1255                1260

Gly Gly Gly Val Ala Leu Asp Ala Ala Val Leu Gly Gly Glu Tyr
    1265                1270                1275

Ala Leu Tyr Ala Ser Ala Arg Val Val Ala Leu Glu Gly Ala Val
    1280                1285                1290

Leu Arg Val Ser Gly Ser Gln Val Tyr Ala Ala His Gly Leu Val
    1295                1300                1305

Phe Asp Ser Gly Val Met Ala Asn Ala Ser Thr Val Val Val Asn
    1310                1315                1320

Asp Asn Ala Gly Val Leu Thr Asp Gly Ala Leu Leu Glu Leu Arg
    1325                1330                1335

Gly Ser Ala Ser Phe Val Ser Gly Ser Trp Leu Ser Val Arg Gly
    1340                1345                1350

Asn Ser Ile Ser Gly Arg Leu Leu Ser Val Pro Ser Tyr Pro Arg
    1355                1360                1365

Ser Ala Asp Leu Val Gln Ser Thr Leu Thr Phe His Gly Asn Ala
    1370                1375                1380

Gly Ser Gly Thr Val Val Met Asp Gly Thr Val Ala Leu Gly Gly
    1385                1390                1395

Ala Gly Arg Arg Phe Val Val Gly Cys Leu Thr Leu Asn Gly Gln
    1400                1405                1410

Ala Leu Arg Pro Ile Asp Tyr Arg Ser Ala Gly Ile Ile Gly Glu
    1415                1420                1425

Phe Arg Pro Val Ala Cys Gly Val Cys Asp Ala Glu Val Arg Cys
    1430                1435                1440

Phe Ala Ala Ala Thr Arg Ala Met Thr Val Ser Cys Arg Cys Arg
    1445                1450                1455

Cys Ala Glu Gly Gly Tyr Gly Arg Asp Cys Leu Pro Val Tyr Leu
    1460                1465                1470

Pro His Val Asp Gly Cys Asn Cys Thr Pro Gly Met Pro Leu Leu
    1475                1480                1485

Ser His Thr Ala Thr Leu Thr Glu Thr Arg Ser Pro Thr Pro Thr
    1490                1495                1500

Trp Thr Pro Asn Pro Thr Pro Ser Met Ser Ala Thr His Tyr Ser
    1505                1510                1515

Pro Thr Gln Tyr Gly Pro Thr Lys Thr Leu Gln Met Thr Glu Thr
    1520                1525                1530

Val Ala Leu Ser Pro Thr Arg Thr Pro Thr Ala Ser Val Ser Ser
    1535                1540                1545

Thr Leu Trp Trp Ser Asp Val Ala Cys Pro Thr Leu Thr Val Thr
    1550                1555                1560

Thr Thr Ala Ala Gly Gly Ser Leu Thr Gln Asn Asp Ile Arg Gly
    1565                1570                1575

Gly Gly Ser Ala Val Pro Thr Arg Leu Met Val Ala Leu Pro Pro
    1580                1585                1590

Pro Phe Arg Trp Ala Ser Asp Pro Gln Leu Gly Thr His Leu Ser
    1595                1600                1605

Phe Val Pro Val Ser Thr Ala Gln Pro Ser Gly Phe Gly Gly Pro
    1610                1615                1620

Trp Gly Ala Met Leu Arg Asn Ala Thr Trp Val Arg Asn Ala Thr
    1625                1630                1635

Asn Pro Phe Thr Val Val Glu Leu Ala Val Pro Val His Arg Gly
    1640                1645                1650
```

```
Tyr Phe Ile Val Ala Asp Glu Thr Ile Val Ile Arg Cys Gly Ala
    1655            1660            1665

Ala Ala Val Ser Gly Gly Cys Lys Gly Ala Leu Leu Gly Ser Phe
    1670            1675            1680

Thr Ile Arg Ser Asn Thr Pro Pro Ala Val Ala Ser Ala Leu Ser
    1685            1690            1695

Ala Ile Thr Gly Val Val Ala Gly Ala Ala Val Ala Val Val
    1700            1705            1710

Val Thr Gly Gly Leu Gly Ser Ile Leu Glu Met Gln Ala Leu Gly
    1715            1720            1725

Val Phe Ala Arg Met Ser Cys Ala Ser Ala Gln Glu Arg Ala Ser
    1730            1735            1740

Thr Ala Ala Leu Pro Tyr Phe Leu Ser Val Phe Ala Ala Leu Asp
    1745            1750            1755

Pro Leu Trp Met Val Gly Asn Ala Leu Leu Ala Ala Val Phe
    1760            1765            1770

Gly Cys Val His Cys Gly Val Thr Ala Ala Phe Gln Arg Trp Arg
    1775            1780            1785

Gly Val Asp Ala Ala Ser Ala Trp Ala Ala Met Arg Phe Pro Ser
    1790            1795            1800

Leu Thr Tyr Val Val Ala His Ala Met His Leu Gly Val Phe Phe
    1805            1810            1815

Gly Ser Val Leu Ala Leu Ala Val Pro Gly Ala Arg Val Gln His
    1820            1825            1830

Arg Val Ile Gly Val Val Gly Val Leu Tyr Gly Val Ala Phe Pro
    1835            1840            1845

Ala Gly Val Cys Tyr Leu Ile Ala Arg His Met Gly Ala Ser Phe
    1850            1855            1860

Glu Arg Tyr Trp Gln Phe Ser Arg Lys Pro Leu His Glu Arg Leu
    1865            1870            1875

Leu Tyr Pro Val Gly Cys Trp His Pro Ala Ala Gln Gln Arg Met
    1880            1885            1890

Tyr Gly Gly Met Leu Thr Thr Met Arg Gly Ser Arg Val Tyr Trp
    1895            1900            1905

Cys Val Phe Gln Leu Ser Val Leu Cys Val Val Gly Leu Ile Ala
    1910            1915            1920

Ala Val His Pro Pro Val Gly Gly Cys His Val Gln Tyr Phe Cys
    1925            1930            1935

Met Ala Thr Leu Leu Leu Ala Gly Ala Gly Val Val Ala Phe Thr
    1940            1945            1950

Asn Met Met Arg Ser Ala Phe Leu Thr Val Met His Ala Ala Gly
    1955            1960            1965

Phe Val Leu Leu Ala Ala Leu Cys Leu Val Ser Ala Ala Asn His
    1970            1975            1980

Leu Ala Pro Ser Asp Gly Val Ala Arg Ala Tyr Ala Ala Ile Val
    1985            1990            1995

Leu Leu Leu Thr Thr Val Leu Leu Ala Ile Thr Val Tyr Ser Val
    2000            2005            2010

Val Val Trp Tyr Ala Glu Asp Arg His Trp Gln Glu Leu Arg Glu
    2015            2020            2025

Pro Arg Arg Gly Gly Leu Glu Ala Leu Leu Arg Asp Asp Glu Asp
    2030            2035            2040

Ser Asp Glu Glu Thr Gln Lys Leu His Asp Met Thr Ser Leu Ser
```

```
                2045                2050                2055
Tyr Ala Ser Glu Thr Thr Gly Ala Ser Tyr Arg Pro Pro Ala
        2060                2065                2070

Pro Pro Xaa Gln Ser Val Thr Gly Asp Thr Arg Ser Asp Val Leu
    2075                2080                2085

Ser Pro Leu Asp Arg Ala Ser Ser Ala Arg Gly Lys Ile Asp His
    2090                2095                2100

Ala Leu Leu
    2105

<210> SEQ ID NO 29
<211> LENGTH: 318
<212> TYPE: PRT
<213> ORGANISM: Trypanosoma cruzi

<400> SEQUENCE: 29

Met Met His Asn Ser Ala Ala Cys Leu Ser Lys Val Ala Val Leu Gly
1               5                   10                  15

Ala Ala Gly Gly Ile Gly Gln Pro Leu Ser Leu Leu Leu Lys Asn Asn
            20                  25                  30

Pro Leu Val Ser Ala Leu Ser Cys Tyr Asp Leu Arg Gly Ala Pro Gly
        35                  40                  45

Val Ala Ala Asp Leu Ser His Ile Cys Ser Pro Ala Lys Val Thr Gly
    50                  55                  60

Tyr Thr Lys Glu Glu Ile Asn Lys Ala Leu Asp Gly Ala Glu Leu Val
65                  70                  75                  80

Leu Ile Pro Ala Gly Val Pro Arg Lys Pro Gly Met Thr Arg Asp Asp
                85                  90                  95

Leu Phe Asn Thr Asn Ala Ser Ile Val Arg Asp Leu Val Ile Ala Cys
            100                 105                 110

Ala Lys Val Cys Pro Lys Ala Phe Ile Gly Val Val Ser Asn Pro Val
        115                 120                 125

Asn Ser Thr Val Pro Ile Ala Ala Glu Thr Leu Lys Lys Ala Gly Val
    130                 135                 140

Phe Asp Pro Ala Arg Leu Phe Gly Val Thr Thr Leu Asp Leu Val Arg
145                 150                 155                 160

Ala Arg Thr Phe Val Ala Glu Ala Gly Gly Lys Ser Pro Tyr Asp Val
                165                 170                 175

His Val Pro Val Val Gly Gly His Ser Gly Pro Thr Ile Val Pro Leu
            180                 185                 190

Leu Ser Gln Ser Gly Val Glu Leu Ser Asp Ser Gln Val Lys Ala Ile
        195                 200                 205

Thr His Arg Val Gln Tyr Gly Gly Asp Glu Val Val Gln Ala Lys Asp
    210                 215                 220

Gly Ala Gly Ser Ala Thr Leu Ser Met Ala Tyr Ala Gly Ala Glu Trp
225                 230                 235                 240

Ser Asn Ser Ile Leu Lys Ala Leu Arg Gly Asp Ser Gly Val Val Glu
                245                 250                 255

Tyr Thr Phe Ile Gln Thr Asp Val Trp Pro Asn Leu Pro Tyr Phe Ser
            260                 265                 270

Cys Ala Val Glu Ile Gly Lys Asn Gly Val Val Lys Ala His Lys Pro
        275                 280                 285

Gln Leu Asn Lys Phe Glu Glu Ser Leu Met Glu Lys Ala Ile Val Asp
    290                 295                 300

Leu Gln Lys Asn Ile Ala Arg Gly Lys Ser Phe Val Thr Asn
```

<210> SEQ ID NO 30
<211> LENGTH: 550
<212> TYPE: PRT
<213> ORGANISM: Trypanosoma cruzi

<400> SEQUENCE: 30

Met Ser Asn Phe Pro Ala Ala Ser Pro Ser Ile Trp Val Gly Gly Leu
1               5                   10                  15

Asp Pro Asn Leu Asn Glu Gln Lys Leu Tyr Asp His Phe Val Arg Leu
            20                  25                  30

Gly Pro Val Ala Ser Val Arg Val Cys Val Asp Ser Val Thr Gln Lys
        35                  40                  45

Ser Leu Gly Tyr Gly Tyr Val Asn Phe Gln Asn Pro Ala Asp Ala Glu
    50                  55                  60

Lys Ala Leu Asp Gln Ala Gly Val Lys Leu Gly Ser Lys His Ile Arg
65                  70                  75                  80

Ile Ala Lys Ile Gln Arg Asp Pro Ser Lys Arg Arg Ser Gly Val Thr
                85                  90                  95

Asn Ile Val Val Lys Lys Leu Pro Pro Ser Val Asp Thr Tyr Ala Leu
            100                 105                 110

Lys Glu Met Phe Ser Lys Tyr Gly Arg Leu Thr Ala Ile Gly Leu Ala
        115                 120                 125

Thr Asn Glu Asn Gly Glu Ser Arg Gly Tyr Ala Arg Ile Ser Tyr Glu
    130                 135                 140

Lys Glu Glu Ser Ala Ile Gln Ala Val Gln Glu Val Asn Gly Met Val
145                 150                 155                 160

Ile Asp Asp Cys Ala Ile Thr Val Glu Arg Tyr Gln Pro His His Arg
                165                 170                 175

Glu Glu Gln Leu Lys Gln Phe Thr Asn Leu Tyr Val Lys Asn Leu Asp
            180                 185                 190

Pro Ser Val Asn Asp Glu Lys Leu Lys Glu Val Phe Ser Ala Phe Gly
        195                 200                 205

Glu Val Thr Ser Ala Lys Val Arg Asp Leu Gly Ala Asn Gln Thr Val
    210                 215                 220

Gly Phe Ala Tyr Val Ala Tyr Ala Thr His Glu Ala Ala Ala Lys Ala
225                 230                 235                 240

Val Glu Glu Leu Asp Glu Lys Glu Ser Pro Leu Ala Lys Glu Gly Met
                245                 250                 255

Lys Leu Ser Val Cys Arg Phe Arg Ser Arg Asp Glu Arg Gln Arg Glu
            260                 265                 270

Arg Glu Arg Leu Arg Arg Glu Arg Gln Gln Gln His Ser Lys Tyr Pro
        275                 280                 285

Asn Leu Tyr Val Lys Asn Phe Asp Asp Thr Val Thr Ser Glu Arg Leu
    290                 295                 300

Lys Glu Leu Phe Glu Arg Cys Gly Glu Thr Val Ser Val Ser Val Met
305                 310                 315                 320

Met Asp Arg Ala Thr Arg Val Ser Arg Cys Phe Gly Phe Val Ser Phe
                325                 330                 335

Lys Glu Gln Ser Ala Ala Ser Arg Ala Ile Gln Glu Leu His Gly Ser
            340                 345                 350

Thr Ala Leu Gly Pro Arg Pro Leu Phe Val Thr Tyr Ala Leu Arg Lys
        355                 360                 365

Asp Ala Arg Arg Gln Thr Leu Glu Asp Met Arg Asn Lys Gln Pro Arg

-continued

```
              370                 375                 380
Met Arg Gln Pro Pro Met Gly Ser Leu Met Gly Gly Met Met Gly Pro
385                 390                 395                 400

Gln Leu Gly Phe Met Gly Pro Gln Ala Met Phe Asn Gly Val Pro Phe
                405                 410                 415

Val Asn Pro Arg Met Ser Met Met Pro Thr Pro Met Gly Met Gly Gly
                420                 425                 430

Gln Leu Arg Pro Met Gly Pro Thr Pro Met Asn Gln Val Arg Ala Arg
                435                 440                 445

Pro Met Pro Gln Arg Pro Pro Met Gln Pro Ile Met Ala Pro Pro Pro
450                 455                 460

Gln Pro Gln Ser Leu Ala Ser Gln Gly Gln Asn Leu Ser Thr Val Leu
465                 470                 475                 480

Ala Asn Leu Thr Pro Glu Gln Gln Lys Asn Val Leu Gly Glu Arg Leu
                485                 490                 495

Tyr Asn His Ile Val Ala Ile Asn Pro Ala Ala Ala Lys Val Thr
                500                 505                 510

Gly Met Leu Leu Glu Met Asp Asn Gly Glu Ile Leu Asn Leu Leu Asp
                515                 520                 525

Thr Pro Gly Leu Leu Asp Ala Lys Val Gln Glu Ala Leu Glu Val Leu
530                 535                 540

Asn Arg His Met Asn Val
545                 550

<210> SEQ ID NO 31
<211> LENGTH: 1091
<212> TYPE: PRT
<213> ORGANISM: Trypanosoma cruzi

<400> SEQUENCE: 31

Ser Val Pro Cys Arg Trp Lys Ser Lys Arg Met Trp Gly Arg Ala Thr
1               5                   10                  15

Leu Ile Pro Thr Thr Ser Ala Arg Arg Leu Arg Thr Arg Thr Gly Pro
                20                  25                  30

Leu Ile Pro Arg Arg Thr Ser Ala Pro Cys Arg Arg Lys Ser Lys Arg
                35                  40                  45

Met Trp Gly Arg Ala Thr Leu Ile Pro Thr Thr Ser Ala Arg Arg Leu
                55                  60
50

Arg Thr Arg Thr Gly Pro Leu Ile Pro Arg Arg Thr Ser Val Pro Cys
65                  70                  75                  80

Arg Trp Lys Ser Lys Arg Met Trp Gly Pro Arg His Val Asp Pro Asp
                85                  90                  95

His Phe Arg Ser Thr Thr Gln Asp Ala Tyr Arg Pro Val Asp Pro Ser
                100                 105                 110

Ala Tyr Lys Arg Ala Leu Pro Leu Glu Glu Glu Asp Val Gly Pro
                115                 120                 125

Arg His Val Asp Pro Asp His Phe Arg Ser Thr Thr Gln Asp Ala Tyr
                130                 135                 140

Arg Pro Val Asp Pro Ser Ala Tyr Lys Arg Ala Leu Pro Leu Glu Glu
145                 150                 155                 160

Glu Glu Asp Val Gly Pro Arg His Val Asp Pro Asp His Phe Arg Ser
                165                 170                 175

Thr Thr Gln Asp Ala Tyr Arg Pro Val Asp Pro Ser Ala Tyr Lys Arg
                180                 185                 190

Ala Leu Pro Gln Glu Glu Glu Asp Val Gly Pro Arg His Val Asp
```

-continued

```
                195                 200                 205
Pro Asp His Phe Arg Ser Thr Thr Gln Asp Ala Tyr Arg Pro Val Asp
210                     215                     220

Pro Ser Ala Tyr Lys Arg Ala Leu Pro Leu Glu Glu Gln Glu Asp Val
225                 230                     235                 240

Gly Pro Arg His Val Asp Pro His Phe Arg Ser Thr Thr Gln Asp
                        245                 250                 255

Ala Tyr Arg Pro Val Asp Pro Ser Ala Tyr Lys Arg Ala Leu Pro Gln
            260                     265                     270

Glu Glu Glu Glu Asp Val Gly Pro Arg His Val Asp Pro Asp His Phe
            275                     280                     285

Arg Ser Thr Thr Gln Asp Ala Tyr Arg Pro Val Asp Pro Ser Ala Tyr
            290                     295                     300

Lys Arg Ala Leu Pro Gln Glu Glu Glu Glu Asp Val Gly Pro Arg His
305                     310                     315                 320

Val Asp Pro Asp His Phe Arg Ser Thr Thr Gln Asp Ala Tyr Arg Pro
                        325                     330                 335

Val Asp Pro Ser Ala Tyr Lys Arg Ala Leu Pro Gln Glu Glu Glu Glu
                340                     345                     350

Asp Val Gly Pro Arg His Val Asp Pro Asp His Phe Arg Ser Thr Thr
                    355                     360                 365

Gln Asp Ala Tyr Arg Pro Val Asp Pro Ser Ala Tyr Lys Arg Ala Leu
370                     375                         380

Pro Gln Glu Glu Glu Glu Asp Val Gly Pro Arg His Val Asp Pro Asp
385                     390                     395                 400

His Phe Arg Ser Thr Thr Gln Asp Ala Tyr Arg Pro Val Asp Pro Ser
                    405                     410                     415

Ala Tyr Lys Arg Ala Leu Pro Gln Glu Glu Glu Glu Asp Val Gly Pro
                420                     425                     430

Arg His Val Asp Pro Asp His Phe Arg Ser Thr Thr Gln Asp Ala Tyr
                    435                     440                 445

Arg Pro Val Asp Pro Ser Ala Tyr Lys Arg Ala Leu Pro Gln Glu Glu
450                     455                     460

Glu Glu Asp Val Gly Pro Arg His Val Asp Pro Asp His Phe Arg Ser
465                     470                     475                 480

Thr Thr Gln Asp Ala Tyr Arg Pro Val Asp Pro Ser Ala Tyr Lys Arg
                    485                     490                     495

Ala Leu Pro Gln Glu Glu Glu Glu Asp Val Gly Pro Arg His Val Asp
                500                     505                     510

Pro Asp His Phe Arg Ser Thr Thr Gln Asp Ala Tyr Arg Pro Val Asp
                515                     520                     525

Pro Ser Ala Tyr Lys Arg Ala Leu Pro Gln Glu Glu Glu Glu Asp Val
530                     535                     540

Gly Pro Arg His Val Asp Pro Asp His Phe Arg Ser Thr Thr Gln Asp
545                     550                     555                 560

Ala Tyr Arg Pro Val Asp Pro Ser Ala Tyr Lys Arg Ala Leu Pro Gln
                    565                     570                     575

Glu Glu Glu Glu Asp Val Gly Pro Arg His Val Asp Pro Asp His Phe
                580                     585                     590

Arg Ser Thr Thr Gln Asp Ala Tyr Arg Pro Val Asp Pro Ser Ala Tyr
                595                     600                     605

Lys Arg Ala Leu Pro Gln Glu Glu Glu Glu Asp Val Gly Pro Arg His
    610                     615                     620
```

-continued

```
Val Asp Pro Asp His Phe Arg Ser Thr Thr Gln Asp Ala Tyr Arg Pro
625                 630                 635                 640

Val Asp Pro Ser Ala Tyr Lys Arg Ala Leu Pro Gln Glu Glu Glu Glu
                645                 650                 655

Asp Val Gly Pro Arg His Val Asp Pro Asp His Phe Arg Ser Thr Thr
            660                 665                 670

Gln Asp Ala Tyr Arg Pro Val Asp Pro Ser Ala Tyr Lys Arg Ala Leu
        675                 680                 685

Pro Gln Glu Glu Glu Asp Val Gly Pro Arg His Val Asp Pro Asp
690                 695                 700

His Phe Arg Ser Thr Thr Gln Asp Ala Tyr Arg Pro Val Asp Pro Ser
705                 710                 715                 720

Ala Tyr Lys Arg Ala Leu Pro Gln Glu Glu Glu Asp Val Gly Pro
            725                 730                 735

Arg His Val Asp Pro Asp His Phe Arg Ser Thr Thr Gln Asp Ala Tyr
            740                 745                 750

Arg Pro Val Asp Pro Ser Ala Tyr Lys Arg Ala Leu Pro Gln Glu Glu
        755                 760                 765

Glu Glu Asp Val Gly Pro Arg His Val Asp Pro Asp His Phe Arg Ser
770                 775                 780

Thr Thr Gln Asp Ala Tyr Arg Pro Val Asp Pro Ser Ala Tyr Lys Arg
785                 790                 795                 800

Ala Leu Pro Gln Glu Glu Glu Glu Asp Val Gly Pro Arg His Val Asp
            805                 810                 815

Pro Asp His Phe Arg Ser Thr Thr Gln Asp Ala Tyr Arg Pro Val Asp
        820                 825                 830

Pro Ser Ala Tyr Lys Arg Glu Ser Pro Val Val Lys Asp Val Arg Ala
        835                 840                 845

Val Asn Val Arg His Ala Tyr Pro Asp Thr Leu Arg Ser Val Ser His
850                 855                 860

Glu Ser Tyr Lys Ser Val Asp Ser Ser Ala Tyr Lys Arg Glu Ser Pro
865                 870                 875                 880

Val Val Lys Asp Leu Arg Ala Val Asn Val Arg His Ala Tyr Pro Asp
            885                 890                 895

Thr Leu Arg Ser Val Ser His Glu Ser Tyr Lys Leu Leu Asn Val Ala
        900                 905                 910

Ser Thr Arg Asp Gly Leu Ser Arg Ala Val Cys His Arg Ile Ser Asp
        915                 920                 925

Gly Lys Ala Ala Gln Tyr Gly Glu Ser Ser Phe Ser Ser Phe Val Ser
930                 935                 940

Asn Gly Asp Arg Asn Gly Thr Asp Gly Ala Ser Ser Ser Cys Arg Gly
945                 950                 955                 960

Ser Ala Arg Ala Cys Phe Gly Lys Ser Ser Glu Val Phe Glu Ser
            965                 970                 975

Asn Phe Gln Thr Pro Leu Lys Gly Thr Asp Gly His Phe Ser Ser
        980                 985                 990

Lys Gly Tyr Phe Cys Pro Cys His Thr Asp Pro Glu Met Tyr Arg Ser
        995                 1000                1005

Thr Ser His Ala Asp Tyr Lys Ala His His Lys Asp Ala Tyr Ser
    1010                1015                1020

Arg Pro Tyr Leu Lys Pro Leu Asp Arg Lys Phe Pro Leu Glu Arg
    1025                1030                1035

Arg Asp Phe Leu Ser Glu Tyr Arg Lys Asn Phe Leu Arg Pro Glu
    1040                1045                1050
```

```
Pro Gln Ser Leu Ser Arg Pro Val Ala Ala Ser Thr Val Thr Val
    1055                1060                1065

Arg His Val Asp Pro Ser Val Tyr Thr Thr Thr Asn Gln Ala Val
    1070                1075                1080

Phe Lys Asp His Trp Lys Lys Phe
    1085                1090

<210> SEQ ID NO 32
<211> LENGTH: 305
<212> TYPE: PRT
<213> ORGANISM: Trypanosoma cruzi

<400> SEQUENCE: 32

Met Met Met His Pro Phe Leu Cys Ala Leu Leu Phe Phe Ala Leu Cys
1               5                   10                  15

Cys Cys Phe Pro Asn Ser Val Cys Ala Ala Asp Asp Thr Ala Thr Asn
            20                  25                  30

Thr Thr Glu Asn Ala Ser Ala Met Ala Pro Pro Ala Asp Met Arg Gly
        35                  40                  45

Ala Leu Arg Glu Val Leu Gly Ala Met Gln Lys Ala Gln Glu Tyr Ala
    50                  55                  60

Asp Glu Ala Asn Arg His Cys Val Gln Ala Arg Met Ser Ala Glu Asn
65                  70                  75                  80

Ala Arg Glu His Glu Glu Gly Ala Lys Asn Ala Leu Arg Lys Leu Gly
                85                  90                  95

Ser Glu Ala Thr Arg Met Ser Arg Ala Leu Gln Gln Ala Asp Glu Ala
            100                 105                 110

Val Lys Leu Ala Asp Ala Ala Val Ala Glu Cys Lys Ala Ala Glu Glu
        115                 120                 125

Ala Ala Gln Ala Ala Gly Ile Met Thr Leu Asp Ala Val Gly Glu Val
    130                 135                 140

Leu Lys His Val Lys Asp Glu Lys Thr Lys Val Gly Ser Gly Pro Glu
145                 150                 155                 160

Leu Leu Lys Arg Ala Ala Glu Gln Thr Val Leu Ser Leu Glu Lys Ala
                165                 170                 175

Lys Glu Ala Glu Ala Glu Ala Glu Lys Ala Ala Ala Ala Gln Lys
            180                 185                 190

Thr Arg Glu Ala Ala Glu Lys Ala Ala Ala Ala Arg Thr Leu Ala Gln
    195                 200                 205

Asp Val Ala Ala Thr Ala Ser Ala Leu Leu Arg Gln Arg Glu Lys Glu
    210                 215                 220

Glu Glu Arg Arg Arg Ala Ser Asp Arg Glu Val Ala Glu Ala Ala Lys
225                 230                 235                 240

Lys Ala Ala Val Ala Glu Val Met Asn Lys Phe Ala Ala Lys Lys Gly
                245                 250                 255

Asn Asp Ala Ala Pro Gly Arg Asn Ser Thr Ser Thr Arg Phe Gln Arg
            260                 265                 270

Thr Arg Pro Arg Val Asp Gly Gly Ile Pro Leu Leu Leu Arg Ala
    275                 280                 285

Pro Leu Leu Met Leu Ala Ala Val Ala Ser Val Ser Gly Phe Leu Ser
    290                 295                 300

Cys
305

<210> SEQ ID NO 33
```

```
<211> LENGTH: 204
<212> TYPE: PRT
<213> ORGANISM: Trypanosoma cruzi

<400> SEQUENCE: 33

Met Ser Arg Ala Leu Gln Gln Ala Glu Val Lys Leu Ala Asp
1               5                   10                  15

Ala Ala Val Ala Glu Cys Lys Ala Ala Glu Ala Ala Gln Ala Ala
            20                  25                  30

Gly Ile Met Thr Leu Asp Ala Val Gly Glu Val Leu Lys His Val Lys
            35                  40                  45

Asp Glu Lys Thr Lys Val Gly Ser Gly Pro Glu Leu Leu Lys Arg Ala
50                  55                  60

Ala Glu Gln Thr Val Leu Ser Leu Glu Lys Ala Lys Glu Ala Glu Ala
65                  70                  75                  80

Glu Thr Glu Lys Ala Ala Ala Ala Gln Lys Thr Arg Glu Ala Ala
                85                  90                  95

Glu Lys Ala Ala Ala Ala Gln Thr Leu Ala Gln Asp Val Ala Ala Thr
            100                 105                 110

Ala Ile Ala Leu Leu Arg Gln Arg Glu Lys Glu Glu Arg Arg Arg
            115                 120                 125

Ala Arg Asp Arg Glu Glu Ala Glu Ala Ala Lys Lys Ala Ala Val Ala
130                 135                 140

Glu Val Met Asn Lys Phe Ala Ala Lys Lys Gly Asn Asp Ala Ala Pro
145                 150                 155                 160

Gly Arg Asn Ser Thr Ala Thr Arg Ile Gln Arg Thr Arg Pro Arg Val
                165                 170                 175

Asp Gly Gly Ile Pro Leu Leu Leu Arg Ala Pro Leu Leu Met Leu
            180                 185                 190

Ala Ala Val Ala Ser Val Phe Gly Phe Leu Ser Cys
            195                 200

<210> SEQ ID NO 34
<211> LENGTH: 310
<212> TYPE: PRT
<213> ORGANISM: Trypanosoma cruzi

<400> SEQUENCE: 34

Met Leu Ala Val Met Val Met Arg Pro Phe Leu Cys Ala Leu Leu Phe
1               5                   10                  15

Phe Ala Leu Cys Cys Cys Phe Pro Asn Ser Val Cys Ala Ala Asp Asp
            20                  25                  30

Thr Ala Thr Asn Thr Thr Glu Asp Val Asn Ala Ser Ala Ile Pro Thr
            35                  40                  45

Asn Met Lys Glu Ala Phe Asp Trp Ala Phe Lys Ala Met Phe Lys Ala
50                  55                  60

Arg Glu Glu Val Asp Glu Ala Asn Gln His Cys Val Gln Ala Lys Leu
65                  70                  75                  80

Ser Ala Thr Lys Ala Ala Gly Leu Glu Lys Glu Ala Glu Met Ala Leu
                85                  90                  95

Lys Lys Leu Gly Ala Glu Ala Val Thr Leu Ser Lys Ala Leu Gln Asp
            100                 105                 110

Ala Arg Glu Ala Asn Arg Glu Ala Ala Val Thr Glu Cys Glu
            115                 120                 125

Ala Ala Glu Ala Ala Ala Gln Gln Ala Glu Ile Ala Thr Leu Asp Ala
130                 135                 140
```

Ala Tyr Glu Val Leu Asn His Val Lys Thr Asp Arg Lys Asp Lys Asn
145                 150                 155                 160

Ser Lys Thr Arg Asp Leu Leu Asp Lys Ala Asn His Thr Ala Ile
        165                 170                 175

Ala Val Lys Lys Ala Lys Glu Ala Glu Ala Glu Ser Glu Lys Ala Ala
            180                 185                 190

Ala Ala Ala Gln Lys Thr Leu Glu Ala Ala Glu Lys Ala Ala Ala Ala
        195                 200                 205

Arg Thr Leu Ala Gln Asp Val Ala Ala Thr Ala Ser Ala Leu Leu Arg
    210                 215                 220

Gln Arg Glu Arg Glu Glu Ile Arg Arg Ala Arg Asp Arg Glu Val
225                 230                 235                 240

Ala Glu Ala Ala Lys Lys Ala Ala Val Ala Glu Val Met Lys Lys Phe
            245                 250                 255

Ala Ala Arg Lys Gly Asn Asp Ala Ala Leu Gly Arg Asn Ser Thr Ser
        260                 265                 270

Thr Arg Leu Gln Arg Thr Arg Pro Arg Val Asp Gly Gly Ile Pro
    275                 280                 285

Leu Leu Leu Arg Ala Pro Leu Leu Met Leu Ala Ala Val Ala Ser Phe
            290                 295                 300

Phe Gly Phe Leu Leu Cys
305                 310

<210> SEQ ID NO 35
<211> LENGTH: 230
<212> TYPE: PRT
<213> ORGANISM: Trypanosoma cruzi

<400> SEQUENCE: 35

Met Pro Ala Tyr Pro Ser Arg Glu Glu Tyr Arg Arg Val Arg Lys Thr
1               5                   10                  15

Asp Gly Glu Lys Glu Lys Gly Gln Gly Pro Glu Asn Glu Ile Arg Val
            20                  25                  30

Thr Ala Lys His Gly Gln Arg Ser Tyr Ile Thr Tyr Ala Ile Ala Leu
        35                  40                  45

Leu Arg Gly Glu Asp Gly Lys Val Gln Asn Asp Thr Ile Lys Ile Ser
    50                  55                  60

Ala Met Gly Ala Ala Ile His Asn Ala Val Asn Ile Ala Glu Ile Val
65                  70                  75                  80

Lys Arg Arg Val Val Gly Leu His Gln Thr Thr Asp Val Ser Ser Glu
            85                  90                  95

Ile Ile His Asp Glu Tyr Glu Ala Ile Asp Gly Lys Lys Glu Asn Met
        100                 105                 110

Lys Val Glu Arg Lys Val Ser Thr Ile Leu Ile Thr Leu Ser Leu Lys
    115                 120                 125

Pro Leu Asp Arg Asn His Val Gly Tyr Gln Pro Leu Pro Glu Ser
130                 135                 140

Glu Val Lys Glu Gln Asp Asp Pro Glu Pro Gly Glu Ser Ala Gly Glu
145                 150                 155                 160

Asn Arg Asn Arg Gly Glu Arg Gly Glu Arg Thr Asp Arg Gly Gly Arg
        165                 170                 175

Gly Gly Gly Arg Gly Asn Asn Ser Gly Arg Gly Arg Gly Tyr Ser
    180                 185                 190

Arg Gly Gly Gln Arg Gly Gly Ser Asn Ile Gly Ala Ser Arg Ser Gly
        195                 200                 205

```
Arg Gly Gly Asn Gly Arg Gly Ser Arg Gly Gly Pro Asp Arg Arg
    210                 215                 220

Asn Asp Arg Arg Val Asp
225                 230

<210> SEQ ID NO 36
<211> LENGTH: 272
<212> TYPE: PRT
<213> ORGANISM: Trypanosoma cruzi

<400> SEQUENCE: 36

Met Pro Pro Met Leu Ala Ala Lys Ser Leu Thr Leu Tyr Lys Asp
  1               5                  10                  15

Phe Asn Lys Asp Val Lys Asp Met Leu Thr Lys Ser Tyr Ser Asp Ala
                 20                  25                  30

Gln Lys Trp Lys Leu Glu Ser Lys Phe Lys Gly Pro Glu Asp Lys Leu
             35                  40                  45

Phe Val Asn Pro Met Ala Thr Ser Asp Gly Lys Phe Ser Val Asp Val
             50                  55                  60

Glu Tyr Ala Pro Arg Cys Gly Ala Ala Leu Lys Ala Thr Leu Glu Pro
 65                  70                  75                  80

Ser Asn Cys Asn Ala Asn Leu Thr Ala Ser Tyr Leu Cys Gln Gly His
                 85                  90                  95

Lys Val Glu Ala Val Gly Lys Lys Asn Gly Tyr Glu Leu Ser His
                100                 105                 110

Glu Phe Val Met Pro Ser Arg Met Ser Ser His Ala Lys Leu Val Asn
            115                 120                 125

Lys Thr Val Glu Val Gly Val Ala Thr Ala Val Ala Pro His Cys Gln
130                 135                 140

Val Gly Cys Gly Ala Leu Tyr Thr Leu Asp Gly Lys Lys Asp Tyr Asp
145                 150                 155                 160

Leu Thr Leu Gly Cys Arg Tyr Ala His Ala Gly Tyr Ala Leu Ala Val
                165                 170                 175

Arg Thr Asn Lys Leu Arg Ser Tyr Thr Thr Ser Phe Val Thr Pro Ile
            180                 185                 190

Pro Lys Cys Pro His His Val Leu Val Gly Ala Glu Val Val Cys Gly
            195                 200                 205

Arg Gly Gln Gly Trp Thr Gly Thr Leu Gly Phe Glu Thr Ala Cys Val
        210                 215                 220

Leu Phe Lys Gly Asn Thr Leu Lys Ala Arg Val Asn Lys Asn Lys Glu
225                 230                 235                 240

Trp Ala Val Val Tyr Ile Ala Lys Leu Val Asp Asn Trp Thr Ala Ala
                245                 250                 255

Val Thr Leu Asp Lys Asn Leu Lys Pro Gly Val Leu Leu Thr His Ser
                260                 265                 270

<210> SEQ ID NO 37
<211> LENGTH: 534
<212> TYPE: PRT
<213> ORGANISM: Trypanosoma cruzi

<400> SEQUENCE: 37

Met Arg Val Ile Leu Asp Gly Cys Ser Leu Thr Pro Asp Val Leu Tyr
  1               5                  10                  15

Ala Leu Gly Tyr Glu Lys Gly Ala Thr Ile Glu Ile Ser Asp Glu Ala
                 20                  25                  30

Val Ala Arg Ile Thr Ala Ala Arg Ala Val Ile Asp Lys Ile Val Asn
```

-continued

```
                35                  40                  45
Asp Arg Gln Thr Val Tyr Gly Ile Asn Thr Gly Phe Gly Lys Phe Glu
 50                  55                  60
Ser Thr Ile Ile Pro Pro His Gln Leu Glu Glu Leu Gln Leu Asn Leu
 65                  70                  75                  80
Ile Arg Ser His Ser Ala Cys Val Gly Glu Pro Leu Thr Pro Glu Arg
                 85                  90                  95
Ala Arg Met Met Leu Ala Leu Arg Val Asn Val Leu Cys Lys Gly His
                100                 105                 110
Ser Gly Ile Arg Leu Glu Thr Val Gln Lys Tyr Val Lys Ala Phe Asn
                115                 120                 125
Ala Gly Val Val Pro Tyr Ile Pro Glu Gln Gly Thr Val Gly Ala Ser
            130                 135                 140
Gly Asp Leu Gly Pro Leu Ser His Leu Ala Leu Gly Met Leu Gly Glu
145                 150                 155                 160
Gly Leu Leu Ala Thr Leu Asn Asn Lys Lys Phe Arg Asp Ala Gly Ser
                165                 170                 175
Val Leu Arg Glu Leu Gly Val Glu Pro Ile Thr Leu Ala Ala Lys Glu
            180                 185                 190
Gly Leu Ala Leu Ile Asn Gly Thr Gln Phe Ile Ser Ala Leu Gly Ala
            195                 200                 205
Glu Ala Val Val Arg Ala Arg Lys Ile Ala Arg Leu Ala Asp Val Ala
210                 215                 220
Leu Ala Met Ser His Glu Ala Leu Arg Ala Thr Asn Ser Thr Leu Asn
225                 230                 235                 240
Pro Asp Ile His Arg Val Arg Pro His Lys Gly Gln Gln Leu Val Ala
                245                 250                 255
Gln Arg Leu Arg Ala Leu Leu His Ser Glu Glu Tyr Pro Ser Met Ile
            260                 265                 270
Asn Glu Ser His Val Asn Cys Gly Arg Val Gln Asp Ala Tyr Ser Ile
            275                 280                 285
Arg Cys Ala Pro Gln Val His Gly Ile Ser Asn Glu Val Ile Glu Trp
290                 295                 300
Val Tyr Gly Ile Leu Thr Thr Glu Leu Asn Cys Ala Thr Asp Asn Pro
305                 310                 315                 320
Leu Val Phe Pro Asp Gly Val Lys Lys Val Ser Gly Gly Asn Phe
                325                 330                 335
His Gly Glu Tyr Pro Ala Lys Ala Leu Asp Met Leu Ala Ile Gly Val
                340                 345                 350
His Glu Leu Gly Asn Ile Ser Glu Arg Arg Ile Glu Arg Leu Asn Asn
            355                 360                 365
Pro Thr Leu Ser Arg Leu Pro Ala Phe Leu Val Lys Asn Gly Gly Leu
370                 375                 380
Asn Ser Gly Phe Met Ile Ala His Cys Thr Ala Ala Leu Val Ser
385                 390                 395                 400
Glu Asn Lys Val Tyr Cys His Pro Ala Ser Ala Asp Ser Ile Ser Thr
                405                 410                 415
Ser Ala Ala Gln Glu Asp His Val Ser Met Gly Gly Phe Ser Ala Arg
                420                 425                 430
Lys Ala Ile Lys Val Val Glu Asn Val Glu Arg Ile Ala Ile Glu
            435                 440                 445
Leu Leu Gly Ala Cys Gln Gly Ile Asp Leu Leu Arg Pro Leu Arg Thr
            450                 455                 460
```

Thr Glu Pro Met Glu Lys Val Trp Ser Leu Val Arg Ser Val Ser Pro
465                 470                 475                 480

Pro Trp Glu Glu Asp Arg Val Ile Asn Thr Asp Ile Asp Asn Val Thr
            485                 490                 495

Lys Leu Leu Arg Ser Gly Ala Val Trp Lys Thr Val Lys Pro Tyr Val
        500                 505                 510

Pro Glu Glu Ala Arg Phe Leu Gly Val Leu Thr Val Lys Lys Pro Phe
            515                 520                 525

Glu Leu Lys Ser Lys Met
        530

<210> SEQ ID NO 38
<211> LENGTH: 185
<212> TYPE: PRT
<213> ORGANISM: Trypanosoma cruzi

<400> SEQUENCE: 38

Ala Gly Arg Gly Lys Met Arg Asn Arg Arg Tyr Val Ala Arg Arg Gly
1               5                   10                  15

Pro Met Leu Val Met Pro Asp Asn Lys Gly Thr Arg Ala Phe Arg Asn
            20                  25                  30

Ile Phe Gly Leu Asp Leu Ala Asn Val Asn Ala Leu Asn Leu Leu His
        35                  40                  45

Leu Ala Pro Gly Gly His Val Gly Arg Phe Val Val Trp Thr Lys Gly
    50                  55                  60

Ala Phe Glu Lys Leu Asp Ser Ile Phe Gly Thr Phe Thr Lys Ala Ser
65                  70                  75                  80

Met Val Lys Lys Gly Phe Met Leu Pro Ala Pro Met Leu Thr Asn Thr
                85                  90                  95

Asp Val Thr Arg Ile Met Gln Ser Glu Glu Val Arg Arg Val Leu Lys
            100                 105                 110

Pro Lys Lys Leu Gln Pro Lys Lys Ala Ser Arg Leu Thr Gln Pro Thr
        115                 120                 125

Asn Gly Phe Arg Asn Arg Arg Leu Arg Leu Arg Leu Asn Pro Phe Gln
    130                 135                 140

Lys Lys Glu Ser Ser Met Leu Arg Gly Leu Arg Asn Arg Lys Asn Arg
145                 150                 155                 160

Glu Val Arg His Lys Ser Lys Ala Val Arg Ile Ala Lys Ala Lys Lys
                165                 170                 175

Ala Ile Ala Gly Gly Ala Lys Lys Lys
            180                 185

<210> SEQ ID NO 39
<211> LENGTH: 372
<212> TYPE: PRT
<213> ORGANISM: Trypanosoma cruzi

<400> SEQUENCE: 39

Met Ala Gln Arg Val Glu Val Leu Gln Thr Gln Leu Pro Ala Tyr Asn
1               5                   10                  15

Arg Leu Lys Thr Pro Tyr Glu Ala Glu Leu Ile Ala Thr Ala Lys Lys
            20                  25                  30

Met Thr Ala Pro Gly Lys Gly Leu Leu Ala Ala Asp Glu Ser Ile Gly
        35                  40                  45

Ser Cys Ala Lys Arg Phe Ala Pro Leu Gly Leu Ser Asn Thr Glu Glu
    50                  55                  60

His Arg Arg Gln Tyr Arg Ala Leu Met Leu Glu Cys Glu Gly Met Glu

```
                65                  70                  75                  80
Gln Tyr Ile Ser Gly Val Ile Leu His Asp Glu Thr Val Tyr Gln Lys
                    85                  90                  95
Ala Ser Thr Gly Glu Thr Phe Val Gln Leu Leu Gln Arg Lys Gly Val
                100                 105                 110
Val Pro Gly Ile Lys Thr Asp Met Gly Leu Asn Pro Leu Val Glu Gly
            115                 120                 125
Ala Glu Gly Gln Met Thr Gly Gly Leu Asp Gly Tyr Val Glu Arg
130                 135                 140
Ala Arg Lys Tyr Tyr Ser Leu Gly Cys Arg Phe Cys Lys Trp Arg Asn
145                 150                 155                 160
Val Tyr Lys Ile Gln Asn Gly Thr Val Ser Glu Ala Ala Val Arg Phe
                165                 170                 175
Asn Ala Glu Thr Leu Ala Arg Tyr Ala Val Leu Ser Gln Leu Ser Gly
                180                 185                 190
Leu Val Pro Ile Val Glu Pro Glu Val Met Ile Asp Gly Thr His Ser
            195                 200                 205
Ile Glu Thr Cys Gln Arg Val Ser Gln His Val Trp Ala Glu Val Val
210                 215                 220
Thr Ala Leu His Arg His Gly Val Met Trp Glu Gly Cys Leu Leu Lys
225                 230                 235                 240
Pro Asn Met Val Val Pro Gly Ala Glu Ser Gly Val Lys Ala Thr Pro
                245                 250                 255
Gly Gln Val Ala Gln Tyr Thr Val Ser Thr Leu Ala Arg Val Leu Pro
            260                 265                 270
Pro Ala Leu Pro Gly Val Thr Phe Leu Ser Gly Gly Leu Ser Glu Val
            275                 280                 285
Gln Ala Ser Glu Tyr Leu Asn Ala Met Asn Ile Cys Asn Leu Pro Arg
290                 295                 300
Pro Trp Lys Leu Thr Phe Ser Tyr Ala Arg Ala Leu Gln Ser Ser Ala
305                 310                 315                 320
Leu Lys Ala Trp Gly Gly Lys Asp Ser Gly Ile Ala Ala Gly Arg Arg
                325                 330                 335
Ala Phe Met His Arg Ala Lys Met Asn Ser Leu Ala Gln Leu Gly Arg
                340                 345                 350
Tyr Asn Arg Ala Glu Asp Asp Lys Glu Ser His Ser Leu Tyr Val Ala
                355                 360                 365
Gly Asn Ser Tyr
            370

<210> SEQ ID NO 40
<211> LENGTH: 477
<212> TYPE: PRT
<213> ORGANISM: Trypanosoma cruzi

<400> SEQUENCE: 40

Met Phe Arg Arg Cys Ala Val Lys Leu Asn Pro Tyr Asp Val Val
1               5                   10                  15
Ile Gly Gly Gly Pro Gly Gly Tyr Val Ala Ser Ile Lys Ala Ala Gln
                20                  25                  30
Leu Gly Met Lys Thr Ala Cys Val Glu Lys Arg Gly Thr Leu Gly Gly
            35                  40                  45
Thr Cys Leu Asn Val Gly Cys Ile Pro Ser Lys Ala Leu Leu His Ala
        50                  55                  60
Thr His Leu Tyr His Asp Ala His Ala Ser Phe Ala Arg Tyr Gly Leu
```

```
               65                  70                  75                  80
Met Gly Gly Glu Gly Val Thr Met Asp Ser Ala Lys Met Gln Gln Gln
                    85                  90                  95

Lys Glu Arg Ala Val Lys Gly Leu Thr Gly Val Glu Tyr Leu Phe
                100                 105                 110

Lys Lys Asn Lys Val Thr Tyr Tyr Lys Gly Glu Gly Ser Phe Glu Thr
                115                 120                 125

Ala His Ser Ile Arg Val Asn Gly Leu Asp Gly Lys Gln Glu Met Leu
            130                 135                 140

Glu Thr Lys Lys Thr Ile Ile Ala Thr Gly Ser Glu Pro Thr Glu Leu
145                 150                 155                 160

Pro Phe Leu Pro Phe Asp Glu Lys Val Val Leu Ser Ser Thr Gly Ala
                165                 170                 175

Leu Ala Leu Pro Arg Val Pro Lys Thr Met Val Val Ile Gly Gly Gly
                180                 185                 190

Val Ile Gly Leu Glu Leu Gly Ser Val Trp Ala Arg Leu Gly Ala Glu
                195                 200                 205

Val Thr Val Val Glu Phe Ala Pro Arg Cys Ala Pro Thr Leu Asp Glu
            210                 215                 220

Asp Val Thr Asn Ala Leu Val Gly Ala Leu Ala Lys Asn Glu Lys Met
225                 230                 235                 240

Lys Phe Met Thr Ser Thr Lys Val Val Gly Gly Lys Asn Asn Gly Asp
                245                 250                 255

Ser Val Ser Leu Glu Val Glu Gly Lys Asn Gly Lys Arg Glu Thr Leu
                260                 265                 270

Thr Cys Glu Ala Leu Leu Val Ser Val Gly Arg Arg Pro Phe Thr Gly
            275                 280                 285

Gly Leu Gly Leu Asp Lys Ile Asn Ala Ala Lys Asn Glu Arg Gly Phe
                290                 295                 300

Val Lys Ile Gly Asp His Phe Glu Thr Ser Ile Pro Asp Val Tyr Ala
305                 310                 315                 320

Ile Gly Asp Val Val Asp Lys Gly Pro Met Leu Ala His Lys Ala Glu
                325                 330                 335

Asp Glu Gly Val Ala Cys Ala Glu Ile Leu Ala Gly Lys Pro Gly His
                340                 345                 350

Val Asn Tyr Gly Val Ile Pro Ala Val Ile Tyr Thr Met Pro Glu Val
            355                 360                 365

Ala Ser Val Gly Lys Ser Glu Asp Glu Leu Lys Lys Glu Gly Val Ala
370                 375                 380

Tyr Lys Val Gly Lys Phe Pro Phe Asn Ala Asn Ser Arg Ala Lys Ala
385                 390                 395                 400

Val Ser Thr Glu Asp Gly Phe Val Lys Val Leu Val Asp Lys Ala Thr
                405                 410                 415

Asp Arg Ile Leu Gly Val His Ile Val Cys Thr Thr Ala Gly Glu Leu
            420                 425                 430

Ile Gly Glu Ala Cys Leu Ala Met Glu Tyr Gly Ala Ser Ser Glu Asp
                435                 440                 445

Val Gly Arg Thr Cys His Ala His Pro Thr Met Ser Glu Ala Leu Lys
            450                 455                 460

Glu Ala Cys Met Ala Cys Phe Ala Lys Thr Ile Asn Phe
465                 470                 475

<210> SEQ ID NO 41
<211> LENGTH: 195
```

```
<212> TYPE: PRT
<213> ORGANISM: Trypanosoma cruzi

<400> SEQUENCE: 41

Met Val Phe Ser Ile Pro Pro Leu Pro Trp Gly Tyr Asp Gly Leu Ala
1               5                   10                  15

Ala Lys Gly Leu Ser Lys Gln Gln Val Thr Leu His Tyr Asp Lys His
            20                  25                  30

His Gln Gly Tyr Val Thr Lys Leu Asn Ala Ala Gln Thr Asn Ser
        35                  40                  45

Ala Leu Ala Thr Lys Ser Ile Glu Glu Ile Ile Arg Thr Glu Lys Gly
    50                  55                  60

Pro Ile Phe Asn Leu Ala Ala Gln Ile Phe Asn His Thr Phe Tyr Trp
65              70                  75                  80

Glu Ser Met Cys Pro Asn Gly Gly Gly Glu Pro Thr Gly Lys Val Ala
                85                  90                  95

Asp Glu Ile Asn Ala Ser Phe Gly Ser Phe Ala Lys Phe Lys Glu Glu
            100                 105                 110

Phe Thr Asn Val Ala Val Gly His Phe Gly Ser Gly Trp Ala Trp Leu
        115                 120                 125

Val Lys Asp Thr Asn Ser Gly Lys Leu Lys Val Tyr Gln Thr His Asp
    130                 135                 140

Ala Gly Cys Pro Leu Thr Glu Pro Asn Leu Lys Pro Leu Leu Thr Cys
145                 150                 155                 160

Asp Val Trp Glu His Ala Tyr Tyr Val Asp Tyr Lys Asn Asp Arg Ala
                165                 170                 175

Ala Tyr Val Gln Thr Phe Trp Asn Val Val Asn Trp Lys Asn Val Glu
            180                 185                 190

Arg Gln Leu
        195

<210> SEQ ID NO 42
<211> LENGTH: 464
<212> TYPE: PRT
<213> ORGANISM: Trypanosoma cruzi

<400> SEQUENCE: 42

Met Glu Asn Glu Met Pro Arg Leu Pro Val Trp Phe Gly Gly Ala Ala
1               5                   10                  15

Leu Leu Gly Gly Gly Tyr Tyr Ala Phe Tyr Tyr His Phe Tyr Thr Pro
            20                  25                  30

Arg His Thr Thr Arg Ser Glu Ile Glu Thr Ala Ile Glu Ala Glu Lys
        35                  40                  45

Leu Lys Trp Gln Ser Val Met Gln Arg Tyr Ala Ile Leu His His Met
    50                  55                  60

Val Gln Lys Leu Arg Asp Gly Thr Asp Ala Thr Asn Arg Glu Arg
65              70                  75                  80

Leu Tyr Ile Tyr Cys Glu Leu Gln Lys Leu Arg Glu Ala Phe Tyr Asn
                85                  90                  95

Leu Ser Ile Arg Ala Gln Ser Ala Ser Glu Lys Gln Thr Val Leu Arg
            100                 105                 110

Asp Leu Asp Glu Val Thr Ala Asn Cys Thr Val Leu Asn Phe Arg
        115                 120                 125

Glu Glu Ala Leu Thr Val Gly Gln Ile Ile Thr Cys Gln Leu Cys Phe
    130                 135                 140

Ser Leu Tyr Val Leu Cys Phe Cys Leu Ile Asp Pro Val Leu Arg Arg
```

```
                    145                 150                 155                 160
Val His Cys Glu Ala Val Glu Arg Val Arg Arg Gly Leu His Ile
                165                 170                 175

Val Ser Trp Trp Met Met Arg Leu Leu Arg Ile Pro Val Thr Met Thr
                180                 185                 190

Leu Glu Asn Thr Leu Pro Pro Asp Gly Asp Val Asn Glu Val Thr
                195                 200                 205

Arg Glu Asp Glu Glu Tyr Ile Val Phe Ser Pro Gln His Trp Ile Glu
    210                 215                 220

Val Val Gly Phe Trp Ala Cys Pro Thr Asn Pro Leu Leu Thr Asn Ile
225                 230                 235                 240

Arg Val Arg Trp Leu Leu Pro Cys Asp Ala Val Pro Phe Glu Ile His
                245                 250                 255

Trp Arg Gly Arg Trp Gln Gln Met Gln Gln Glu Leu Arg Asp Pro Ile
                260                 265                 270

Leu Val Val Lys Lys Glu Glu Asn Arg Arg Pro Val Val Gln Ser
                275                 280                 285

Ser Phe Gly Tyr Pro Leu Ala Ser Arg Leu Thr Cys Gly Gly Gly Met
290                 295                 300

Gln Asp Asp Ser Asn Ser Asp His Val Leu Ala Thr Thr Asp Val Tyr
305                 310                 315                 320

Thr Pro Arg Phe Phe Pro Val Val Ser Thr Gly Met Pro Arg Val Leu
                325                 330                 335

Phe Val Ser Asp Ala Val Ala Arg Arg Asp Val Arg Thr Arg Arg Thr
                340                 345                 350

Leu His Glu Val Tyr Thr Asn Val Lys His Arg Gln Phe Pro Val Thr
                355                 360                 365

His Asn Val Val Lys Asn Asn Lys Ala Asp Asp Cys Val Lys Gly Tyr
                370                 375                 380

Asp Val Thr Tyr Glu Gln Leu His Ala Trp Arg Lys His Gly Gly Val
385                 390                 395                 400

Pro Val Trp His Arg Val Glu Trp Gly Ser Val Tyr Gly Asp Val Gly
                405                 410                 415

Ser Gly Gly Asn Arg Asn Arg Arg Glu Leu Thr Phe Arg Met Gly Arg
                420                 425                 430

Pro Cys Ser Ala Asn Glu Leu Met Val Arg Gln Leu Glu Leu Leu Gln
                435                 440                 445

Asn Leu Leu Leu Gln Thr Glu Ser Asn Gly Glu Glu Val Ser Leu Leu
                450                 455                 460

<210> SEQ ID NO 43
<211> LENGTH: 416
<212> TYPE: PRT
<213> ORGANISM: Trypanosoma cruzi

<400> SEQUENCE: 43

Met Ser Ser Trp Asp Val Ser Met Ser Asn His Ala Gly Leu Val Phe
1               5                   10                  15

Asn Pro Ile Arg Thr Val Ser Asp Asn Ala Lys Pro Ser Pro Ser Pro
                20                  25                  30

Lys Pro Ile Ile Lys Leu Ser Val Gly Asp Pro Thr Leu Asp Lys Asn
                35                  40                  45

Leu Leu Thr Ser Ala Ala Gln Ile Lys Lys Leu Lys Glu Ala Ile Asp
        50                  55                  60

Ser Gln Glu Cys Asn Gly Tyr Phe Pro Thr Val Gly Ser Pro Glu Ala
```

```
                65                  70                  75                  80
Arg Glu Ala Val Ala Thr Trp Trp Arg Asn Ser Phe Val His Lys Glu
                    85                  90                  95

Glu Leu Lys Ser Thr Ile Val Lys Asp Asn Val Val Leu Cys Ser Gly
                100                 105                 110

Gly Ser His Gly Ile Leu Met Ala Ile Thr Ala Ile Cys Asp Ala Gly
                115                 120                 125

Asp Tyr Ala Leu Val Pro Gln Pro Gly Phe Pro His Tyr Glu Thr Val
                130                 135                 140

Cys Lys Ala Tyr Gly Ile Gly Met His Phe Tyr Asn Cys Arg Pro Glu
145                 150                 155                 160

Asn Asp Trp Glu Ala Asp Leu Asp Glu Ile Arg Arg Leu Lys Asp Asp
                165                 170                 175

Lys Thr Lys Leu Leu Ile Val Thr Asn Pro Ser Asn Pro Cys Gly Ser
                180                 185                 190

Asn Phe Ser Arg Lys His Val Glu Asp Ile Val Arg Leu Ala Glu Glu
                195                 200                 205

Leu Arg Leu Pro Leu Phe Ser Asp Glu Ile Tyr Ala Gly Met Val Phe
                210                 215                 220

Lys Gly Lys Asp Pro Asn Ala Thr Phe Thr Ser Val Ala Asp Phe Glu
225                 230                 235                 240

Thr Thr Val Pro Arg Val Ile Leu Gly Gly Thr Ala Lys Asn Leu Val
                245                 250                 255

Val Pro Gly Trp Arg Leu Gly Trp Leu Leu Tyr Val Asp Pro His Gly
                260                 265                 270

Asn Gly Pro Ser Phe Leu Asp Gly Leu Lys Arg Val Gly Met Leu Val
                275                 280                 285

Cys Gly Pro Cys Thr Val Val Gln Ala Ala Leu Gly Glu Ala Leu Leu
290                 295                 300

Asn Thr Pro Gln Glu His Leu Asp Gln Ile Val Ala Lys Ile Glu Glu
305                 310                 315                 320

Ser Ala Met Tyr Leu Tyr Asn His Ile Gly Glu Cys Ile Gly Leu Ala
                325                 330                 335

Pro Thr Met Pro Arg Gly Ala Met Tyr Leu Met Ser Arg Ile Asp Leu
                340                 345                 350

Glu Lys Tyr Arg Asp Ile Lys Thr Asp Val Glu Phe Phe Glu Lys Leu
                355                 360                 365

Leu Glu Glu Asn Val Gln Val Leu Pro Gly Thr Ile Phe His Ala
                370                 375                 380

Pro Gly Phe Thr Arg Leu Thr Thr Thr Arg Pro Val Glu Val Tyr Arg
385                 390                 395                 400

Glu Ala Val Glu Arg Ile Lys Ala Phe Cys Gln Arg His Ala Ala Val
                405                 410                 415

<210> SEQ ID NO 44
<211> LENGTH: 254
<212> TYPE: PRT
<213> ORGANISM: Trypanosoma cruzi

<400> SEQUENCE: 44

Leu Leu Lys Lys Leu Asp Lys Thr Val Lys Ser Glu Glu Pro Ser Gly
1               5                   10                  15

Leu Glu Leu Val Asp Leu Arg Asp Phe Glu Ser His Asp Leu Cys Leu
                20                  25                  30

Glu Gly Met Gly Ala Met Asn Phe Ser Tyr Asn Gly Glu Phe Val Tyr
```

```
                35                  40                  45
Met Ala Leu Ser Asp Arg Ser Ser Glu Lys Leu Leu Asp Val Val Cys
 50                  55                  60

Ser Pro Glu Asn Leu Asn Ile Pro Lys Glu Lys Arg Phe Val Phe Thr
 65                  70                  75                  80

Ala Val Leu Pro Arg Phe Ser Gly Glu Asn Lys Arg Cys Val Gly Glu
                 85                  90                  95

Asp Val Val His His Thr Asn Leu Ile Gly Trp Cys Gly Lys Gly Ile
                100                 105                 110

Cys Ala Trp Gly Leu Asn Phe Leu Arg Phe Ser Ser Glu Glu Lys Lys
            115                 120                 125

Gln Ala Phe Phe Glu His Leu Glu Ala Thr Tyr Lys Lys Ile Ile Asn
130                 135                 140

Leu Ser Ala Glu Glu Ile Arg Ala Phe Ala Gly Asn Ala Cys Glu Ile
145                 150                 155                 160

Ala Leu Ser Ser Glu Glu Glu Arg His Val Leu Cys Ile Ser Asn
                165                 170                 175

Glu Ala Leu Asn Ser Leu His His Arg Asn Tyr Gln Ile Leu Glu Glu
            180                 185                 190

Trp Tyr Gly Arg Glu Asn Ile Phe Val Phe Tyr Ala Glu Thr Leu Glu
        195                 200                 205

Arg Arg Ser Gly Thr Ser Ile Ser Ser Leu Ile Ser Cys Pro Val Thr
210                 215                 220

His Gly Glu Val Leu Pro Ala Pro Gly Glu Val Thr Ala Leu Glu Val
225                 230                 235                 240

Ala His Val Asp Glu Lys Val Ile Ala Asn Leu Leu Asn Arg
                245                 250

<210> SEQ ID NO 45
<211> LENGTH: 376
<212> TYPE: PRT
<213> ORGANISM: Trypanosoma cruzi

<400> SEQUENCE: 45

Met Phe Gln Leu Ser Ser Gly Thr Thr Ser Phe Leu Val Leu Leu Leu
 1               5                  10                  15

Ala Val Ala Thr Leu Ala Ser Val Ala Arg Ala Gly Asp Pro Ser Val
                20                  25                  30

Ser Leu Glu Gly Ile Val Asp Leu Thr Ala Ser Asn Phe Asp Glu His
            35                  40                  45

Val Gly Lys Gly Val Pro Ala Leu Val Glu Phe Tyr Ala Pro Trp Cys
 50                  55                  60

Gly His Cys Lys Lys Met Val Pro Glu Phe Lys Val Gly Gln Ala
 65                  70                  75                  80

Val Lys Thr Ala Arg Asp Lys Val Leu Val Gly Lys Val Asp Ala Thr
                 85                  90                  95

Gln Asn Arg Asp Leu Ala Glu Arg Phe Gly Val Asn Gly Tyr Pro Thr
            100                 105                 110

Ile Leu Phe Phe Pro Ala Asp Ser Gln Thr Lys Gln Gln Tyr Ser Glu
        115                 120                 125

Ala Arg Glu Ala Ala Ala Phe Leu Ser Phe Leu Asn Arg Gln Val Pro
130                 135                 140

Gly Leu Asn Ile Gly Val Pro His Glu His Thr Tyr Ala Val Glu Leu
145                 150                 155                 160

Thr Lys Arg Asn Phe Asp Ala Val Val Met Asp Glu Ala Lys Asp Ala
```

```
                        165                 170                 175
Leu Val Met Phe Tyr Ala Pro Trp Cys Gly His Cys Lys Lys Leu His
            180                 185                 190

Pro Val Phe Glu Arg Leu Ala Thr Ala Phe Lys Glu Glu Ala Asp Ile
            195                 200                 205

Val Ile Gly Lys Leu Asn Ala Asp Asp Ala Ser Asn Gly Ala Val Arg
            210                 215                 220

Asn Arg Tyr Lys Val Asp Gly Tyr Pro Thr Leu Ala Phe Phe Gln Lys
225                 230                 235                 240

Arg Ser Lys Ser Glu Pro Gln Tyr Tyr Ser Gly Gly Arg Ser Leu Glu
            245                 250                 255

Glu Leu Val Glu Tyr Val Asn Glu Arg Thr Gly Lys Asn Arg Leu Pro
            260                 265                 270

Ser Gly Asp Leu Ser Glu Lys Val Gly Val Asn Asp Glu Leu Ser Lys
            275                 280                 285

Val Leu Arg Asp Met Met Leu Lys Glu Lys Ser Val Asp Glu Lys Lys
            290                 295                 300

Gln Tyr Leu Glu Lys Val Lys Lys Ala Ala Asp Leu Thr Gly Val
305                 310                 315                 320

Glu Ala Val His Tyr Pro Arg Ile Ala Glu Lys Ile Leu Gln Leu Gly
            325                 330                 335

Ala Glu Tyr Val Glu Met Glu Leu Gly Arg Ile Ala Arg Leu Lys Gln
            340                 345                 350

Gly Asp Val Lys Gly Glu Lys Arg Asp Met Leu Thr Ile Arg Asn Asn
            355                 360                 365

Ile Leu Ala Ser Leu Lys Asp Glu
            370                 375

<210> SEQ ID NO 46
<211> LENGTH: 410
<212> TYPE: PRT
<213> ORGANISM: Trypanosoma cruzi

<400> SEQUENCE: 46

Met Leu Gly Asp Pro Val Asn Arg Leu Glu Glu Leu Gln Ala Glu Leu
1               5                   10                  15

Leu Ser Arg Gln Asn Ala Leu Ser Ser Arg Ile Gln Ser Ile Leu Ser
            20                  25                  30

Glu Thr Gly Glu Lys Glu Leu Pro Glu Leu Gln Val Leu Ser Glu Asp
        35                  40                  45

Arg Ala Gln Leu Ile Lys Glu Ile Gln His Thr Lys Asp Glu Gly Asp
    50                  55                  60

Ala Leu Leu Leu Gln Val Glu Gly Asn Gly Ala Ala Ser Met Tyr
65                  70                  75                  80

Arg Val Ala Ala Arg Val Gln Arg Phe Glu Glu Phe Ala Asn Arg Ala
                85                  90                  95

Asn Glu Tyr Val Lys Asn Val Leu Pro Glu Glu Ile Glu Arg Val Ala
            100                 105                 110

Asp Ala Asp Arg His His Ser Asp Asp Glu Val Ala Ala Tyr Ile Lys
        115                 120                 125

Glu Leu Gln Ala Lys Arg Glu Glu Leu Arg Lys Ile Gly Ile Leu
    130                 135                 140

Lys Glu Arg Thr Thr Lys Arg Ala Asn Asp Leu Arg Asn Gly Pro Arg
145                 150                 155                 160

Val Glu Asn Gly Glu Leu Asn Ala Leu Cys Arg Val Ser Arg Ala Lys
```

```
                165                 170                 175
Glu Glu Glu Leu Asp Lys Glu Thr Lys Glu Thr Gln Glu Tyr Val Asp
            180                 185                 190

Glu Ala Arg Leu Lys Lys Ala Asp Leu Ile Ala Lys Ile Arg Glu Leu
            195                 200                 205

Arg Gln Ala Lys Ser Lys Leu Gln Val Glu Leu Leu Asp Thr Lys His
            210                 215                 220

Lys Asn Glu Lys Val Asn Glu Met Lys Ala Arg Ile Arg His Ala
225                 230                 235                 240

Glu Leu Ala Asn Lys Arg Asp Ile Arg Val Cys Gln Gln Leu Asn Thr
            245                 250                 255

Thr Asn Ala Ala Leu Thr Thr Asn Ala Gln Thr Leu Leu Gly Gln Leu
            260                 265                 270

Asn Val Glu His Tyr Gly Ile Glu Gly Ala Pro Ser Glu Lys Ala Leu
            275                 280                 285

Ile Thr Met Arg Lys Glu Glu Arg Ala Ala Ala Val Leu Ala
            290                 295                 300

Asn Gly Arg Gly Asn Asn Asn Asn Asn Gly Ser His Pro Ala Gly
305                 310                 315                 320

Asn Glu Thr Glu Gly Leu Cys Pro Arg Arg Asp Thr Gly Asn Phe Asn
            325                 330                 335

Gly Asp Ala Ser Ala Ser Ser Arg Gln Ser Asn Gln Gln Asn
            340                 345                 350

Thr Gly Leu Ala Ala Met Gln Arg Thr Ala Ser Gln Arg Ser Arg Asp
            355                 360                 365

Ala Ser Gln Lys Ala Asp Leu Asp Gln Arg Arg Gln Ser Gly Gln Ser
            370                 375                 380

Ser Gln Ala Ser Arg His Ser Ala Thr Ser Lys Asp Arg Gln Ala Gly
385                 390                 395                 400

Arg Thr Asn Ser Arg Gly Ser Ser Ala Pro
            405                 410

<210> SEQ ID NO 47
<211> LENGTH: 518
<212> TYPE: PRT
<213> ORGANISM: Trypanosoma cruzi

<400> SEQUENCE: 47

Met Leu Thr Arg Leu Arg Ser Ala Ala Leu Arg Gly Ala Ala Gly Thr
1               5                   10                  15

Arg Ala Ala Ser Gly Met Pro Thr Ala Asp His Lys Gly Arg Val Gly
            20                  25                  30

Tyr Val Ser Gln Val Ile Gly Ala Val Val Asp Val His Phe Ala Glu
        35                  40                  45

Gly Val Pro Pro Val Leu Thr Ala Leu Asp Val Glu Lys Leu Gly
    50                  55                  60

Arg Asp Glu Pro Leu Thr Leu Glu Ile Val Gln His Leu Asp Ala His
65              70                  75                  80

Thr Gly Arg Cys Ile Ala Met Gln Thr Thr Asp Leu Leu Lys Leu Lys
            85                  90                  95

Ser Lys Val Val Ser Ser Gly Asn Ile Ser Val Pro Val Gly Arg
        100                 105                 110

Glu Thr Leu Gly Arg Ile Phe Asn Val Leu Gly Asp Ala Ile Asp Gln
        115                 120                 125

Arg Gly Pro Val Gly Glu Lys Gln Arg Met Pro Ile His Ala Val Ala
```

```
                130                 135                 140
Pro Lys Leu Ala Asp Gln Ala Ala Glu Asp Thr Ile Leu Thr Thr Gly
145                 150                 155                 160
Ile Lys Val Ile Asp Leu Ile Leu Pro Tyr Cys Lys Gly Gly Lys Ile
                165                 170                 175
Gly Leu Phe Gly Gly Ala Gly Val Gly Lys Thr Val Ile Ile Met Glu
                180                 185                 190
Leu Ile Asn Asn Val Ala Lys Gly His Gly Gly Phe Ser Val Phe Ala
                195                 200                 205
Gly Val Gly Glu Arg Thr Arg Glu Gly Thr Asp Leu Tyr Leu Glu Met
210                 215                 220
Met Gln Ser Lys Val Ile Asp Leu Lys Gly Asp Ser Lys Cys Val Leu
225                 230                 235                 240
Val Tyr Gly Gln Met Asn Glu Pro Pro Gly Ala Arg Ala Arg Val Ala
                245                 250                 255
Gln Ser Ala Leu Thr Met Ala Glu Tyr Phe Arg Asp Val Glu Gly Gln
                260                 265                 270
Asp Val Leu Leu Phe Ile Asp Asn Ile Phe Arg Phe Thr Gln Ala Asn
                275                 280                 285
Ser Glu Val Ser Ala Leu Leu Gly Arg Ile Pro Ala Ala Val Gly Tyr
                290                 295                 300
Gln Pro Thr Leu Ala Glu Asp Leu Gly Gln Leu Gln Glu Arg Ile Thr
305                 310                 315                 320
Ser Thr Thr Lys Gly Ser Ile Thr Ser Val Gln Ala Val Tyr Val Pro
                325                 330                 335
Ala Asp Asp Ile Thr Asp Pro Ala Pro Ala Thr Thr Phe Ser His Leu
                340                 345                 350
Asp Ala Thr Thr Val Leu Asp Arg Ala Val Ala Glu Ser Gly Ile Tyr
                355                 360                 365
Pro Ala Val Asn Pro Leu Glu Cys Ala Ser Arg Ile Met Asp Pro Asp
                370                 375                 380
Val Ile Ser Val Asp His Tyr Asn Val Ala Gln Asp Val Val Gln Met
385                 390                 395                 400
Leu Thr Lys Tyr Lys Glu Leu Gln Asp Ile Ile Ala Val Leu Gly Ile
                405                 410                 415
Asp Glu Leu Ser Glu Glu Asp Lys Leu Ile Val Asp Arg Ala Arg Lys
                420                 425                 430
Val Thr Lys Phe Leu Ser Gln Pro Phe Gln Val Ala Glu Val Phe Thr
                435                 440                 445
Gly Met Thr Gly His Tyr Val Gln Leu Glu Glu Thr Ile Glu Ser Phe
                450                 455                 460
Ser Gly Leu Leu Met Gly Thr Tyr Asp Gln Val Pro Glu Met Ala Phe
465                 470                 475                 480
Tyr Met Val Gly Gly Ile Thr Ser Val Leu Glu Lys Gly Lys Lys Met
                485                 490                 495
Ala Glu Glu Ala Ala Glu Leu Glu Lys Leu Arg Arg Ala Arg Ala Ala
                500                 505                 510
Gln Ala Gly Gln Lys Glu
        515

<210> SEQ ID NO 48
<211> LENGTH: 415
<212> TYPE: PRT
<213> ORGANISM: Trypanosoma cruzi
```

-continued

```
<400> SEQUENCE: 48

His Thr Tyr Ala Leu Ser Leu Thr Leu Trp Ser Gly Val Asn Pro Glu
1               5                   10                  15

Asn Ala Arg Thr His Lys Leu Leu Ala Ala Ala Leu Ala Asn Val
            20                  25                  30

Ala Val Thr Leu Lys Ala Cys Glu Tyr Gly Arg Glu Asn Glu Thr Ala
        35                  40                  45

Glu Tyr Cys Arg Asn Cys Ser Pro Cys Gly Arg Tyr Pro Val Leu Gln
    50                  55                  60

Thr Glu Glu Gly Cys Val Phe Glu Ser Asn Ala Ile Leu Arg His Ile
65                  70                  75                  80

Ala Arg Leu Asp Arg Ser Gly Gly Phe Leu Tyr Gly Arg Thr Pro Leu
                85                  90                  95

Glu Gly Ser Gln Val Asp Met Trp Leu Asp Phe Ser Ala Thr Glu Leu
            100                 105                 110

Asp Ala Ala Ser Ala Pro Phe Val His His Ala Phe Arg Gly Glu Pro
        115                 120                 125

Leu Pro Ala Asn Ala Met Asp Arg Val His Glu Val Leu Arg Ala Leu
130                 135                 140

Glu Ala Trp Leu Glu Thr Arg Thr Phe Leu Val Gly Glu Arg Met Thr
145                 150                 155                 160

Val Ala Asp Val Ala Val Ala Phe Ala Leu Gln Trp His Tyr Arg Leu
                165                 170                 175

Asn Gly Ala Glu Gly Glu Ala Leu Thr Lys Lys Tyr Arg Asn Ala Tyr
            180                 185                 190

Arg Leu Tyr Asn Thr Val Met Gln Gln Pro Lys Thr Val Glu Val Leu
        195                 200                 205

Arg Ser Gln Gly Ala Thr Phe Gly Pro Val Lys Ala Glu Arg Lys Gly
    210                 215                 220

Lys Asp Ala Ala Ala Pro Ala Arg Ala Glu Lys Lys Pro Lys Ala Ala
225                 230                 235                 240

Ala Ala Ala Ala Asp Gly Ala Glu Glu Glu Asp Glu Ala Pro Arg Glu
                245                 250                 255

Lys Lys Lys Pro Asn Pro Leu Asp Glu Leu Pro Pro Ser Pro Phe Val
            260                 265                 270

Leu Asp Ala Phe Lys Arg Glu Tyr Ser Asn Thr Asp Thr Arg Thr Val
        275                 280                 285

Ala Ala Pro Tyr Phe Gln His Tyr Asp Ala Ala Gly Tyr Thr Thr
    290                 295                 300

Phe Trp Cys Arg Tyr Lys Tyr Asn Glu Asp Asn Lys Met Gln Phe Met
305                 310                 315                 320

Thr Ala Asn Leu Ile Arg Gly Trp Phe Gln Arg Met Glu His Val Arg
                325                 330                 335

Lys Tyr Ala Phe Gly Val Ala Leu Ile Ile Gly Glu Glu Arg Arg His
            340                 345                 350

Asp Ile Val Ala Leu Trp Val Phe Arg Gly Arg Gly Met Pro Ala Ile
        355                 360                 365

Val Glu Asp Val Glu Asp Thr Glu Leu Phe Asp Trp Glu Glu Val Ala
    370                 375                 380

Asp Val Ala Ala Gln Arg Glu Arg Ile Thr Asp Tyr Leu Cys Trp Glu
385                 390                 395                 400

Gly Pro Thr Ile Pro Arg Pro Val Leu Glu Gly Arg Val Phe Lys
                405                 410                 415
```

```
<210> SEQ ID NO 49
<211> LENGTH: 153
<212> TYPE: PRT
<213> ORGANISM: Trypanosoma cruzi

<400> SEQUENCE: 49

Met Thr Ser Glu Arg Thr Phe Ile Ala Val Lys Pro Asp Gly Val Gln
1               5                   10                  15

Arg Cys Leu Val Gly Glu Ile Ile Gln Arg Phe Glu Lys Lys Gly Tyr
            20                  25                  30

Lys Leu Val Ala Leu Lys Met Leu Gln Pro Ser Ala Glu Gln Ala Gln
        35                  40                  45

Gln His Tyr Ile Asp Leu Ala Ser Lys Pro Phe Tyr Lys Asp Leu Val
    50                  55                  60

Ala Tyr Phe Ser Ser Gly Pro Ile Val Gly Met Val Trp Glu Gly Lys
65                  70                  75                  80

Gly Val Val Lys Gly Arg Val Leu Leu Gly Ala Thr Asn Pro Ala
                85                  90                  95

Asp Ser Leu Pro Gly Thr Ile Arg Gly Asp Phe Ala Val Asp Val Gly
            100                 105                 110

Arg Asn Val Cys His Gly Ser Asp Ser Val Asp Ser Ala Lys Arg Glu
        115                 120                 125

Ile Ala Phe Trp Phe Lys Pro Glu Glu Leu Val Asn Trp Thr Ser His
    130                 135                 140

Ser Val Lys Gln Val Tyr Glu Ser Ala
145                 150

<210> SEQ ID NO 50
<211> LENGTH: 260
<212> TYPE: PRT
<213> ORGANISM: Trypanosoma cruzi

<400> SEQUENCE: 50

Met Gly Lys Thr Val Leu Thr Cys Arg Lys Gly Asn Gly Ser Val Tyr
1               5                   10                  15

Gln Leu His Gly His Lys Arg Leu Gly Pro Ala Lys Leu Arg Ile Leu
            20                  25                  30

Asp Tyr Ala Glu Arg His Gly Phe Met Arg Gly Val Val Lys Thr Ile
        35                  40                  45

Glu His Glu Pro Gly Arg Gly Ala Pro Leu Ala Arg Val Glu Phe Arg
    50                  55                  60

His Pro Tyr Lys Tyr Arg Arg Val Lys Glu Leu Met Val Ala Pro Glu
65                  70                  75                  80

Gly Met Phe Thr Gly Gln Ser Val Leu Cys Gly Val Lys Ala Pro Leu
                85                  90                  95

Ala Ile Gly Asn Val Leu Pro Leu Gly Gln Ile Thr Glu Gly Cys Ile
            100                 105                 110

Val Cys Asn Val Glu Ala Lys Val Gly Asp Arg Gly Thr Ile Ala Arg
        115                 120                 125

Ala Ser Gly Asp Tyr Cys Ile Ile Ile Ser His Asn His Glu Thr Gly
    130                 135                 140

Arg Thr Arg Leu Lys Leu Pro Ser Gly Gln Lys Lys Thr Val Pro Ser
145                 150                 155                 160

Asn Cys Arg Ala Met Ile Gly Ile Ile Ala Gly Gly Gly Arg Ile Glu
                165                 170                 175

Lys Pro Val Leu Lys Ala Gly Asn Ser Phe Tyr Arg Phe Arg Gly Lys
```

```
                    180                 185                 190
Arg Asn Cys Trp Pro Lys Val Arg Gly Val Ala Arg Asn Pro Val Glu
            195                 200                 205

His Pro His Gly Gly Gly Asn His Gln His Ile Gly His Pro Ser Thr
        210                 215                 220

Val Ser Arg His Ala Pro Pro Gly Gln Lys Val Gly Leu Ile Ala Ala
225                 230                 235                 240

Arg Arg Thr Gly Arg Ile Arg Gly Ser Arg Ala Val Lys Gly Ala Trp
            245                 250                 255

His Pro Glu Glu
            260

<210> SEQ ID NO 51
<211> LENGTH: 852
<212> TYPE: PRT
<213> ORGANISM: Trypanosoma cruzi
<220> FEATURE:
<221> NAME/KEY: misc_feature
<222> LOCATION: (129)..(129)
<223> OTHER INFORMATION: Xaa can be any naturally occurring amino acid
<220> FEATURE:
<221> NAME/KEY: misc_feature
<222> LOCATION: (211)..(211)
<223> OTHER INFORMATION: Xaa can be any naturally occurring amino acid
<220> FEATURE:
<221> NAME/KEY: misc_feature
<222> LOCATION: (218)..(218)
<223> OTHER INFORMATION: Xaa can be any naturally occurring amino acid

<400> SEQUENCE: 51

Met Gln Ile Phe Val Lys Thr Leu Thr Gly Lys Thr Ile Ala Leu Glu
1               5                   10                  15

Val Glu Ser Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Val Met Glu Pro
65                  70                  75                  80

Thr Leu Glu Ala Leu Ala Lys Lys Tyr Asn Trp Glu Lys Lys Val Cys
                85                  90                  95

Arg Arg Cys Tyr Ala Arg Leu Pro Val Arg Ala Ser Asn Cys Arg Lys
            100                 105                 110

Lys Ala Cys Gly His Cys Ser Asn Leu Arg Met Lys Lys Lys Leu Arg
        115                 120                 125

Xaa Ser Ala Met Leu Trp Thr Asp Ala Leu Lys Tyr Thr Pro Ser Leu
    130                 135                 140

Ala Phe Leu Phe Phe Phe Phe Asp Leu Phe Phe Leu Leu Arg Cys Phe
145                 150                 155                 160

Val Leu Phe Phe Ser Val Phe Met Ile Ser Ala Val Cys Pro Pro Ala
                165                 170                 175

Phe Met Gln Cys Leu Val Ile Leu Ser Ile Phe Trp Asn Tyr Gly Asp
            180                 185                 190

Asn Ile Leu Val Phe Lys Leu Leu Ile Thr Asn Cys Ala Leu Glu Phe
        195                 200                 205

Pro Ala Xaa Leu Leu Leu Thr His Cys Xaa Glu Arg Glu Thr Met Gln
    210                 215                 220

Ile Phe Val Lys Thr Leu Thr Gly Lys Thr Ile Ala Leu Glu Val Glu
```

```
                225                 230                 235                 240
        Ser Ser Asp Thr Ile Glu Asn Val Lys Ala Lys Ile Gln Asp Lys Glu
                        245                 250                 255
        Gly Ile Pro Pro Asp Gln Gln Arg Leu Ile Phe Ala Gly Lys Gln Leu
                        260                 265                 270
        Glu Asp Gly Arg Thr Leu Ala Asp Tyr Asn Ile Gln Lys Glu Ser Thr
                        275                 280                 285
        Leu His Leu Val Leu Arg Leu Arg Gly Met Gln Ile Phe Val Lys
                290                 295                 300
        Thr Leu Thr Gly Lys Thr Ile Ala Leu Glu Val Glu Ser Ser Asp Thr
        305                 310                 315                 320
        Ile Glu Asn Val Lys Ala Lys Ile Gln Asp Lys Glu Gly Ile Pro Pro
                        325                 330                 335
        Asp Gln Gln Arg Leu Ile Phe Ala Gly Lys Gln Leu Glu Asp Gly Arg
                        340                 345                 350
        Thr Leu Ala Asp Tyr Asn Ile Gln Lys Glu Ser Thr Leu His Leu Val
                        355                 360                 365
        Leu Arg Leu Arg Gly Met Gln Ile Phe Val Lys Thr Leu Thr Gly
                370                 375                 380
        Lys Thr Ile Ala Leu Glu Val Glu Ser Ser Asp Thr Ile Glu Asn Val
        385                 390                 395                 400
        Lys Ala Lys Ile Gln Asp Lys Glu Gly Ile Pro Pro Asp Gln Gln Arg
                        405                 410                 415
        Leu Ile Phe Ala Gly Lys Gln Leu Glu Asp Gly Arg Thr Leu Ala Asp
                        420                 425                 430
        Tyr Asn Ile Gln Lys Glu Ser Thr Leu His Leu Val Leu Arg Leu Arg
                        435                 440                 445
        Gly Gly Met Gln Ile Phe Val Lys Thr Leu Thr Gly Lys Thr Ile Ala
                450                 455                 460
        Leu Glu Val Glu Ser Ser Asp Thr Ile Glu Asn Val Lys Ala Lys Ile
        465                 470                 475                 480
        Gln Asp Lys Glu Gly Ile Pro Pro Asp Gln Gln Arg Leu Ile Phe Ala
                        485                 490                 495
        Gly Lys Gln Leu Glu Asp Gly Arg Thr Leu Ala Asp Tyr Asn Ile Gln
                        500                 505                 510
        Lys Glu Ser Thr Leu His Leu Val Leu Arg Leu Arg Gly Gly Met Gln
                        515                 520                 525
        Ile Phe Val Lys Thr Leu Thr Gly Lys Thr Ile Ala Leu Glu Val Glu
                        530                 535                 540
        Ser Ser Asp Thr Ile Glu Asn Val Lys Ala Lys Ile Gln Asp Lys Glu
        545                 550                 555                 560
        Gly Ile Pro Pro Asp Gln Gln Arg Leu Ile Phe Ala Gly Lys Gln Leu
                        565                 570                 575
        Glu Asp Gly Arg Thr Leu Ala Asp Tyr Asn Ile Gln Lys Glu Ser Thr
                        580                 585                 590
        Leu His Leu Val Leu Arg Leu Arg Gly Gly Met Gln Ile Phe Val Lys
                        595                 600                 605
        Thr Leu Thr Gly Lys Thr Ile Ala Leu Glu Val Glu Ser Ser Asp Thr
                        610                 615                 620
        Ile Glu Asn Val Lys Ala Lys Ile Gln Asp Lys Glu Gly Ile Pro Pro
        625                 630                 635                 640
        Asp Gln Gln Arg Leu Ile Phe Ala Gly Lys Gln Leu Glu Asp Gly Arg
                        645                 650                 655
```

```
Thr Leu Ala Asp Tyr Asn Ile Gln Lys Glu Ser Thr Leu His Leu Val
            660                 665                 670

Leu Arg Leu Arg Gly Gly Met Gln Ile Phe Val Lys Thr Leu Thr Gly
        675                 680                 685

Lys Thr Ile Ala Leu Glu Val Glu Ser Ser Asp Thr Ile Glu Asn Val
690                 695                 700

Lys Ala Lys Ile Gln Asp Lys Glu Gly Ile Pro Pro Asp Gln Gln Arg
705                 710                 715                 720

Leu Ile Phe Ala Gly Lys Gln Leu Glu Asp Gly Arg Thr Leu Ala Asp
                725                 730                 735

Tyr Asn Ile Gln Lys Glu Ser Thr Leu His Leu Val Leu Arg Leu Arg
            740                 745                 750

Gly Gly Met Gln Ile Phe Val Lys Thr Leu Thr Gly Lys Thr Ile Ala
        755                 760                 765

Leu Glu Val Glu Ser Ser Asp Thr Ile Glu Asn Val Lys Ala Lys Ile
770                 775                 780

Gln Asp Lys Glu Gly Ile Pro Pro Asp Gln Gln Arg Leu Ile Phe Ala
785                 790                 795                 800

Gly Lys Gln Leu Glu Asp Gly Arg Thr Leu Ala Asp Tyr Asn Ile Gln
                805                 810                 815

Lys Glu Ser Thr Leu His Leu Val Leu Arg Leu Arg Gly Gly Met Gln
            820                 825                 830

Ile Phe Val Lys Thr Leu Thr Gly Lys Thr Ile Ala Leu Glu Val Glu
        835                 840                 845

Ser Ser Asp Thr
    850

<210> SEQ ID NO 52
<211> LENGTH: 225
<212> TYPE: PRT
<213> ORGANISM: Trypanosoma cruzi

<400> SEQUENCE: 52

Met Arg Arg Val Leu Phe Ser Ala Ala Leu Ser Leu Val Pro Lys Ala
1               5                   10                  15

Pro Leu Phe Arg Arg Cys Val Pro Ser Val Ala Lys Ala Ala Ser Met
            20                  25                  30

Gly Pro Leu Val Ala Met Glu Gln Arg Arg Leu Ala Ser His Ala Ala
        35                  40                  45

Leu Ser Ser Ala Leu Arg His Glu Leu Glu Glu Gln Gln Arg Ser
    50                  55                  60

Glu Lys Pro Ala Lys Pro Glu Leu Pro Ala Gly Trp Thr Leu Glu Arg
65                  70                  75                  80

Lys Pro Gly Gln Met Leu Phe Thr Met Arg Lys Lys His Glu Asp Glu
                85                  90                  95

Glu Ile Ile Ile Arg Cys Leu Gly Glu Glu Ser Gly Asp Asp Val
            100                 105                 110

Val Ser Leu Asp Phe Asp Ala Tyr Ile Thr Cys Asn Asn Lys Ala Leu
        115                 120                 125

Val Cys Arg Met Ser Phe Glu Ser Glu Val Ile Met Gly Gln Val
130                 135                 140

Ser Phe Leu Asp Asp Ala Lys Leu Ala Leu Asp Asp Ser Val Glu Gly
145                 150                 155                 160

Asn Arg Lys Arg Gln Trp Leu Tyr Lys Gly Pro Lys Leu Asp Glu Leu
                165                 170                 175
```

Asp Glu Arg Leu Val Asp Ser Leu Thr Ser Tyr Leu Lys Asp Arg Gly
            180                 185                 190

Val Asn Glu Asp Leu Cys Arg Phe Met Glu Glu Tyr Phe Phe Trp Ala
            195                 200                 205

Glu Gln Ala Glu Tyr Glu Glu Trp Leu Ser Ala Ile Asn Arg Phe Val
            210                 215                 220

Ser
225

<210> SEQ ID NO 53
<211> LENGTH: 651
<212> TYPE: PRT
<213> ORGANISM: Trypanosoma cruzi

<400> SEQUENCE: 53

Met Leu Leu Gln Ala Leu Leu Val Leu Ser Ala Val Val Ala Val
1               5                   10                  15

Ala Ala Pro Asp Gly Thr Gly Lys Val Glu Ala Pro Cys Val Gly Ile
            20                  25                  30

Asp Leu Gly Thr Thr Tyr Ser Val Val Gly Val Trp Gln Lys Gly Asp
            35                  40                  45

Val His Ile Ile Pro Asn Asp Met Gly Asn Arg Ile Thr Pro Ser Val
    50                  55                  60

Val Ala Phe Thr Glu Thr Glu Arg Leu Ile Gly Asp Gly Ala Lys Asn
65                  70                  75                  80

Gln Leu Pro Gln Asn Pro His Asn Thr Ile Tyr Ala Ile Lys Arg Leu
                85                  90                  95

Ile Gly Arg Lys Tyr Ser Asp Ala Thr Val Gln Thr Asp Lys Lys Leu
            100                 105                 110

Leu Ser Tyr Glu Val Val Ala Asp Lys Asp Gly Lys Pro Lys Val Gln
        115                 120                 125

Val Glu Val Gly Gly Lys Lys Gln Phe Thr Pro Glu Glu Val Ser
        130                 135                 140

Ala Met Val Leu Gln Lys Met Lys Glu Ile Ala Glu Thr Tyr Leu Gly
145                 150                 155                 160

Glu Lys Val Lys Asn Ala Val Val Thr Val Pro Ala Tyr Phe Asn Asp
                165                 170                 175

Ala Gln Arg Gln Ser Thr Lys Asp Ala Gly Thr Ile Ala Gly Leu Asn
            180                 185                 190

Val Val Arg Ile Ile Asn Glu Pro Thr Ala Ala Ile Ala Tyr Gly
        195                 200                 205

Leu Asn Lys Ala Gly Glu Lys Asn Ile Leu Val Phe Asp Leu Gly Gly
    210                 215                 220

Gly Thr Phe Asp Val Ser Leu Leu Thr Ile Asp Glu Gly Phe Phe Glu
225                 230                 235                 240

Val Val Ala Thr Asn Gly Asp Thr His Leu Gly Gly Glu Asp Phe Asp
                245                 250                 255

Asn Asn Met Met Arg Tyr Phe Val Asp Met Leu Lys Lys Lys Lys Asn
            260                 265                 270

Val Asp Val Ser Lys Asp Gln Lys Ala Leu Ala Arg Leu Arg Lys Ala
        275                 280                 285

Cys Glu Ala Ala Lys Arg Gln Leu Ser Ser His Pro Glu Ala Arg Val
    290                 295                 300

Glu Val Asp Ser Leu Thr Glu Gly Phe Asp Phe Ser Glu Lys Ile Thr
305                 310                 315                 320

```
Arg Ala Lys Phe Glu Glu Leu Asn Met Glu Leu Phe Lys Gly Thr Leu
            325                 330                 335

Val Pro Val Gln Arg Val Leu Glu Asp Ala Lys Leu Lys Lys Ser Asp
            340                 345                 350

Ile His Glu Ile Val Leu Val Gly Gly Ser Thr Arg Val Pro Lys Val
            355                 360                 365

Gln Gln Leu Ile Arg Asp Phe Phe Gly Gly Lys Glu Pro Asn Arg Gly
            370                 375                 380

Ile Asn Pro Asp Glu Ala Val Ala Tyr Gly Ala Ala Val Gln Ala Ala
385                 390                 395                 400

Val Leu Thr Gly Glu Ser Glu Val Gly Gly Arg Val Leu Val Val Asp
            405                 410                 415

Val Ile Pro Leu Ser Leu Gly Ile Glu Thr Val Gly Gly Val Met Thr
            420                 425                 430

Lys Leu Ile Glu Arg Asn Thr Gln Ile Pro Thr Lys Lys Ser Gln Val
            435                 440                 445

Phe Ser Thr Tyr Gln Asp Asn Gln Pro Gly Val Leu Ile Gln Val Tyr
            450                 455                 460

Glu Gly Glu Arg Gln Met Thr Lys Asp Asn Arg Leu Leu Gly Lys Phe
465                 470                 475                 480

Glu Leu Ser Gly Ile Pro Pro Ala Pro Arg Gly Val Pro Gln Ile Glu
            485                 490                 495

Val Thr Phe Asp Val Asp Glu Asn Ser Ile Leu Gln Val Ser Ala Val
            500                 505                 510

Asp Lys Ser Ser Gly Lys Lys Glu Ile Thr Ile Thr Asn Asp Lys
            515                 520                 525

Gly Arg Leu Ser Glu Glu Ile Glu Arg Met Val Arg Glu Ala Ala
530                 535                 540

Glu Phe Glu Asp Glu Asp Arg Lys Val Arg Glu Arg Val Asp Ala Arg
545                 550                 555                 560

Asn Ser Leu Glu Ser Val Ala Tyr Ser Leu Arg Asn Gln Val Asn Asp
            565                 570                 575

Lys Glu Lys Leu Gly Gly Lys Leu Ser Ala Asp Asp Lys Ser Ala Val
            580                 585                 590

Glu Ala Ala Val Lys Glu Ala Met Gln Phe Leu Asp Asp Asn Pro Asn
            595                 600                 605

Ala Asp Lys Glu Glu Tyr Asp Glu Ala Arg Asp Lys Leu Gln Ser Val
            610                 615                 620

Thr Asn Pro Ile Ile Gln Lys Val Tyr Gln Ser Gly Gly Gly Ala Asp
625                 630                 635                 640

Gly Asp Glu Arg Pro Glu Pro Met Asp Asp Leu
            645                 650

<210> SEQ ID NO 54
<211> LENGTH: 3481
<212> TYPE: PRT
<213> ORGANISM: Trypanosoma cruzi

<400> SEQUENCE: 54

Met Val Asp Gly Ala Ser Ala Thr Arg His Asp Ser Pro Val Asp Thr
1               5                   10                  15

Cys Leu Gly Trp Trp Met Arg Ser Ala Val Gly Ala Cys Pro Arg Ser
            20                  25                  30

Arg His Arg Val Gln Arg Arg Ala Ile Ala Ala Val Arg Val Ala Leu
            35                  40                  45
```

```
Leu Val Val Leu Ala Leu Val Ala Ala Ala Trp Met Pro Ala Val
 50                  55                  60

His Ala Val Val Leu Arg Leu Arg Gly Gly Thr Val Asp Arg Ala Ile
 65                  70                  75                  80

Thr Val Gly Arg Ala Val Asp Thr Val Leu Met Asp Gly Val His Ile
                 85                  90                  95

Thr Asn Gly Val Ala Val Val Leu Asp Val Pro Ala Met Leu Pro Gly
            100                 105                 110

Ala Leu Arg Ile Glu Leu Arg Asn Cys Val Cys Asp Gly Gly Ala Gln
        115                 120                 125

Ile Tyr Val Arg Gly Tyr Ser Gly Glu Pro Ala Ser Asp Arg Ser Leu
    130                 135                 140

Glu Val Ser Val Ser Gly Leu Ser Gly Ser Tyr Cys Ser Leu Val Phe
145                 150                 155                 160

Val His Asn Leu Pro Ala His Thr Asn Val Thr Val Arg Asp Ser Thr
                165                 170                 175

Ile Val Thr Ala Gly Pro Met Arg Tyr Ser Gln Leu Ser Gly Leu Thr
            180                 185                 190

Asp Ala Val Ala Ser Pro Leu Val Leu His Ala Thr Ser Leu Leu Gln
        195                 200                 205

Thr Gln Leu Arg Val Ser Lys Thr Val Leu Arg Ser Leu Gln Ala Gly
    210                 215                 220

Gly Ser Ala Val Tyr Val Gly Gly Val Asp Leu Leu Ser Ser Ala
225                 230                 235                 240

Val Val Leu Asp Gly Val Ser Leu Glu Ala Ser Gly Gly Pro Thr Ala
                245                 250                 255

Ser Ala Met His Val Ala Ser Ser Arg Leu Ser Leu Trp Ser His
            260                 265                 270

Ser Val Phe Ser Val Thr Asn Val Ser Val Val Ser Ser Gly Gly Gly
        275                 280                 285

Ile Val Leu Gly Glu Arg Leu Ala Val Phe Tyr Ser Val Leu Arg Phe
    290                 295                 300

Val Gly Val Glu Gly Pro Val Ala Ser Ser Leu Val Arg Cys Asp Gly
305                 310                 315                 320

Gly Thr Val Gly Ala Gly Gly Trp Leu Glu Leu Arg Asp Val Trp Ala
                325                 330                 335

Val Gly Glu Ala Ser Ser Val Ala Ser Leu Leu Gly Val Thr Leu Ser
            340                 345                 350

Gly Gly Thr Val Ser Ile Val Arg Cys Ala Ala Thr Gly Ala Thr Leu
        355                 360                 365

Val Ser Gly Leu Ala Ile Thr Ser Gly Thr Val Thr Val Gln Cys Asn
    370                 375                 380

Arg Ala Gly Gly Arg Val Leu Gln Ser Gly Gly Asp Tyr Arg Met Ala
385                 390                 395                 400

Gly Leu Pro Ser Val Ser Val Pro Cys Asp Gly Cys Ala Ser Ala
                405                 410                 415

Leu Ala Cys Phe Asp Ala Leu Thr Ala Ser Phe Val Asp Cys Val Cys
            420                 425                 430

Gly Cys Arg Asp Gly Val Gly Glu Ala Cys Leu Pro Phe Asp Val
        435                 440                 445

Pro Pro Ala Arg Ser Gly Gly Gly Gly Ala Gln Asp Cys Val
    450                 455                 460

Ser Gly Val Thr Leu Thr Glu Ser Val Thr Val Gly Gly Gly Arg Ala
465                 470                 475                 480
```

```
Arg Ala Cys Phe Asp Ser Val Met Phe Ser Gly Pro Ile Ile Val Ala
                485                 490                 495

Val Asp Leu Arg Ser Met Asp Ala Phe Ala Asp Ala Leu Asn Val Thr
            500                 505                 510

Leu Arg His Cys Val Leu Glu Gly Gly Ala Gln Leu Arg Ile Gly Gly
        515                 520                 525

Leu Ser Glu Ser Thr Ala Arg Leu Met Pro His Ala Leu Val Asn Met
    530                 535                 540

Thr Asn Val Thr Ser Leu Glu Gly Thr Ile Val Leu His Gly Ala Met
545                 550                 555                 560

Pro Leu His Ser Thr Val Leu Leu Ala Asn Ser Thr Leu Arg Ala Thr
                565                 570                 575

Val Gly Gly Ser Gln Tyr Val Pro Thr Thr Arg Gly His Glu Gly Phe
            580                 585                 590

Arg Tyr Asp Pro Ala Leu Val Leu Asp Gly Val Arg Leu Leu Ser Thr
        595                 600                 605

Arg Phe Val Met Thr Arg Ser Thr Leu Val Cys Gly Gly Ser Cys
    610                 615                 620

Ala Ala Ile Leu Val Glu Arg Ala Phe Val Val Asn Leu Ser Ser Ala
625                 630                 635                 640

Phe Tyr Met Asp Asn Cys Ala Val Arg Ser Gln Met His Val Met Tyr
                645                 650                 655

Ala Leu Ala Ser Asp Leu Arg Val Gly Gly Ser Val Phe Ser Ile
            660                 665                 670

Gln Asn Ser Ser Trp Ser Ala Pro Ser Thr Glu Tyr Gly Lys Ala Ala
        675                 680                 685

Cys Val Phe Glu Asp Ile Val Ala Gly Gly Ser Val Leu Gln Ile
    690                 695                 700

Val Ser Ser Thr Phe Arg Leu Gly Phe Ala Met Leu Met Ala Asn Thr
705                 710                 715                 720

Leu Thr Val Thr Gly Gly Ser Trp Leu Val His Arg Asp Ser Glu Phe
                725                 730                 735

His Thr Ala Tyr Val Val Tyr Ile Val Lys Glu Asn Gly Val Lys Phe
            740                 745                 750

Arg Asp Arg Ser Val Trp Ser Ile Ile Asp Asn Asn Phe Thr Tyr Gly
        755                 760                 765

Ser Phe Ser Pro Phe Thr Tyr Met Thr Ser Asn Trp Ser Pro Pro Ser
    770                 775                 780

Asp Thr His Pro Ile Ile Tyr Gly Val Cys Asn Glu Leu Arg Gly Ser
785                 790                 795                 800

Pro Val Thr Asp Tyr Gln Tyr Asp Leu Asn Ile Gly Ala Ser Val Met
                805                 810                 815

Val Leu Asp Cys Gly Ala Cys Thr Met Glu Ala Val Cys Phe Ala Ala
            820                 825                 830

Arg Thr Ser Ser Ile Ser Gly Cys Glu Cys Val Cys Ala Ala Gly Gly
        835                 840                 845

Tyr Gly Asp Thr Cys Leu Pro Ala Ala Val Pro Asp Gly Leu Gly Pro
    850                 855                 860

Leu Pro Pro Pro Asp Ala Lys Asp Thr Glu Val Arg Cys Val His Gly
865                 870                 875                 880

Gly Ser Ile Asp Ser Leu Asp Val Pro Asp Pro Gly Val Arg Gly Leu
                885                 890                 895

Cys Phe Val Asn Val Thr Phe Thr Ala Ala Ile Val Leu Asp Leu Ser
```

-continued

```
                900                 905                 910
Tyr Phe Asp Ala Pro Gln Gln Thr Leu Asn Ile Thr Leu Leu His Cys
            915                 920                 925

Val Leu Ile Gly Leu Ser Ile Lys Gly Ser Gly Ala Arg Val His Val
            930                 935                 940

Asn Val Val Ser Ser Met Leu Asp Ser Gly Glu Leu Glu Phe Arg Gly
945                 950                 955                 960

Val Phe Gly Val Ser Ser Gln Ile Leu Leu Val Gly Ser Thr Leu Val
                965                 970                 975

Thr Thr Ser Gly His Ala Ile Leu Phe Val Lys Phe Ala Leu Ser Ala
            980                 985                 990

Asn Met Thr Leu Leu Leu Leu Asp Asn Tyr Ile Glu Gly Asn Trp Tyr
            995                 1000                1005

Ala Val Tyr Phe Ser Ser Gly Val Val Asp Gly Gly Ile
            1010                1015                1020

Ile Val Lys Gly Asn Thr Leu Ser Thr Thr Lys Asp Asp Gly
            1025                1030                1035

Val Glu Ser Ser Val Cys Val Tyr Ala Val Asp Val Arg Asn Gly
            1040                1045                1050

Gly His Phe Asp Val Glu Asn Asn Thr Met Ser Ala Val Asn Gly
            1055                1060                1065

Val Ile Leu Phe Gly Asp Thr Thr Val Ser Ser Ala Gly Leu Leu
            1070                1075                1080

Arg Val Ala Asp Cys Val Phe Val Gly Gly Thr Glu Ile Phe Asp
            1085                1090                1095

Ser Ala Leu Val Tyr Leu Ser Gly Ser Ala Thr Leu Glu Gly Gly
            1100                1105                1110

Ala Gln Trp Arg Val Glu Gly Asn Ser Val Gly Ala Ala Ser Val
            1115                1120                1125

Leu Ser Ile Pro Tyr Ser Gln Tyr Lys Ile Gln Leu Ser Gly Ser
            1130                1135                1140

Gly Thr Thr Val Ala Leu Ala His Asn Arg Gln Val Glu Gly Ser
            1145                1150                1155

Ala Val Phe Val Lys Leu Phe Arg Pro Asn Thr Ile Val Glu Leu
            1160                1165                1170

Pro Ala Arg Phe Val Val Gly Cys Asn Leu Gln Gly Asp Gly Glu
            1175                1180                1185

Leu Ser Tyr Asp Gly Leu Phe Pro Glu Glu Leu Val Leu Phe Arg
            1190                1195                1200

Cys Gly Thr Cys Asn Asp Asp Ala Ala Cys Tyr Met Pro Gly Thr
            1205                1210                1215

Glu Ser Val Asp Arg Gly Ser Cys Ser Cys Ser Cys Lys Asp Gly
            1220                1225                1230

Trp His Gly Ala Ser Cys Leu Pro Phe Glu Val Pro Asp Thr Val
            1235                1240                1245

Val Pro Pro Val Ala Glu Arg Ala Val Asp Gly Asp Thr Ser Cys
            1250                1255                1260

Val Val Asn Gln Thr Leu Thr Ser Leu Ala Leu Asn Leu Trp Lys
            1265                1270                1275

Thr His His Cys Tyr Val Gly Val Thr Phe Ser Gly Val Gly Ala
            1280                1285                1290

Val Leu Thr Phe Phe Leu Asn Ser Met Pro Leu His Leu Pro Ile
            1295                1300                1305
```

-continued

```
Asn Ile Thr Leu Thr Gly Cys Thr Phe Arg Asp Gly Ala Ala Leu
1310                1315                1320

Gln Phe Val Gly Gly Val Gly Ala Ala Glu Ser Ser Gly Val Leu
1325                1330                1335

Ile Arg Val Ser Gln Thr Val Met Arg Ser Ser Thr Val Ala Phe
1340                1345                1350

Ile His Ala Leu Pro Gln His Cys Asp Ile Ala Ile Thr Glu Val
1355                1360                1365

Asp Ala Val Leu Ser Phe Asp Phe Glu Leu Ser Gly Thr Val Asn
1370                1375                1380

Asn Met Trp Ser Val Phe Leu Leu Gly Asn Val Val Leu Ser Ala
1385                1390                1395

Ser Thr Leu Leu Val Ser Asn Val Lys Ala His Ala Thr Asn Arg
1400                1405                1410

Asp Ala Leu Gly Leu Tyr Ser Thr Gly Thr Leu Thr Leu Val Gly
1415                1420                1425

Gly Ser Ser Leu Tyr Leu Arg Tyr Cys Ser Phe Glu Gly Tyr Lys
1430                1435                1440

Tyr Leu Phe Tyr Val His Ser Leu Ser Val Ser Asp His Ser Val
1445                1450                1455

Phe Ala Leu Leu Asn Asn Thr Met Leu Phe Gly Ala Ser Leu Leu
1460                1465                1470

Tyr Gln His Gln Gly Phe Ser Val Ser Asp His Ser Val Leu Arg
1475                1480                1485

Val Val Gly Asn Ser Gly Ser Ala Arg Tyr Ala Ile Cys Asn Asp
1490                1495                1500

Asp Leu Trp Thr Val Gln Arg Ser Ser Trp Leu Asp Trp Arg Asp
1505                1510                1515

Asn Asp Val Glu Val Gly Ala Met Leu Tyr Asp Ser Gly Phe Ala
1520                1525                1530

Phe Val Thr Ile Asp Ser Ser Ser Ala Val Thr Leu Thr Gly Cys
1535                1540                1545

Arg Met Gly Ser Thr Gly Leu Ser Val Ser Leu Leu Lys Arg Ile
1550                1555                1560

Glu Ala Gly Tyr Arg Phe Val Ala Gly Cys Leu Thr Val Ala Gly
1565                1570                1575

Arg Glu Val Thr Thr Ala Ala Glu Leu Glu Leu Asn Gly Ile Thr
1580                1585                1590

Gly Val Thr Thr Ala Ala Val Cys Gly Gln Cys Thr Lys Glu Gly
1595                1600                1605

Asp Cys Phe Ala Pro Leu Thr Thr Ala Val Ile Asp Cys Lys Cys
1610                1615                1620

Gln Cys Ala Ala Gly Gly His Gly Asp Val Cys Val Pro Ala Pro
1625                1630                1635

Val Pro Ala Gly Pro Pro Pro Pro Leu Pro Pro Ala Pro Pro
1640                1645                1650

Thr Pro Leu Pro Pro Val Gly Glu Cys Ile Ser Asp Met Val
1655                1660                1665

Tyr Pro Glu Val Ala Gln Ala Val Gly Gly Leu Ser Trp Leu
1670                1675                1680

Cys Tyr Arg Asn Val Thr Phe Ser Gly Gly Met Ser Leu Thr
1685                1690                1695

Val Leu Ile Gly Ala Met Thr Gly Asp Val Ala Asn Val Thr Phe
1700                1705                1710
```

```
Asp Gly Cys Thr Trp Arg Asp Gly Ala Val Leu Leu Leu Leu Gly
    1715                1720                1725

Asn Ala Tyr Ala Ala Val Gly Ser Leu Asn Ile Leu Val Ala Gly
    1730                1735                1740

Asn Thr Phe Ser Asp Ala Leu Leu Ser Pro Glu Gly Val Phe Pro
    1745                1750                1755

Pro Gln Thr Asn Ile Thr Ile Ser Gly Asn Arg Phe Thr Val Thr
    1760                1765                1770

Arg Leu Ile Pro Arg Ser Gly Leu Asp Ile Trp Ser Pro Ser Cys
    1775                1780                1785

Val Met Met Asn Gly Leu Ala Ile Ser Asn Asp Ser Val Val Val
    1790                1795                1800

Leu Ser Gly Asn Val Phe Gln Ser Val Thr Ala Ser Ser Ile Ala
    1805                1810                1815

Ile Tyr Val Val Arg Ser Ala Leu Arg Val Ser Trp His Ser Val
    1820                1825                1830

Phe Ala Val Val Gly Asn Thr Phe His Met Ala Gly Gly Asp Gly
    1835                1840                1845

Thr Leu Ile His Leu Glu Gly Ser Ser Gln Ser Ser Ser Leu Ser
    1850                1855                1860

Val Leu Asn Asn Ser Ala Val Val Ile Arg Gly Asn Leu Val Thr
    1865                1870                1875

Arg Pro Val Arg Tyr Phe Leu Leu Leu Thr Leu Ala Leu Arg Val
    1880                1885                1890

Glu Ser Arg Ser Ala Val Val Phe Gln Gly Asn Asp Met Gln Arg
    1895                1900                1905

Ser Ser Val Val Phe Phe Pro Gly Phe Ser Ser Tyr Ile Tyr Tyr
    1910                1915                1920

Asn Ser Trp Leu Gln Leu Ser Gly Asn Leu Cys His Met Ser Pro
    1925                1930                1935

Ser Glu Ala Phe Ala Phe Leu Tyr Pro Lys Val Asn Leu Arg Asp
    1940                1945                1950

Ser Thr Val Ser Val Ser Gly Asn Arg Phe Met Cys Ser Thr Asp
    1955                1960                1965

Lys Pro Thr Asp Leu Arg Val Ser Thr Ala Ser Arg Asp Ile Thr
    1970                1975                1980

Asn Gly Ala Ile Val Ala Ala Cys Asn Thr Val Asn Gly Glu Glu
    1985                1990                1995

Gly Val Glu Tyr Ile Ile Pro Ser Val Tyr Asn Val Thr Ile Leu
    2000                2005                2010

Thr Cys Ser Asp Pro Cys Ala Leu Ala Ala Ser Cys Phe Pro Ala
    2015                2020                2025

Tyr Thr Thr Thr Ala Ser Ser Asp Gly Cys Ala Cys Thr Cys Ala
    2030                2035                2040

Glu Gly Gly Arg Gly Asp Ala Cys Leu Pro Ile Ala Val Pro Glu
    2045                2050                2055

Pro Pro Ser Thr Asp Gly Ala Asp Leu Cys Val Arg Glu Val Arg
    2060                2065                2070

Val Asp Val Glu Val Asn Ala Gly Leu Gly Thr Ser Val Ala Cys
    2075                2080                2085

Tyr Val Gly Val Thr Phe Ala Ala Asp Val Val Val Asp Val Glu
    2090                2095                2100

Leu Met Ser Gly Ser Val Arg Asn Val Thr Leu Ala Asn Cys Thr
```

```
            2105                2110                2115

Phe Val Gly Gly Ala Ser Leu Tyr Val Val Gly Trp Arg Ser Asp
    2120                2125                2130

Pro Pro Ala Gly Glu Arg Ala Asp Val Leu Ile Ser Gly Leu Glu
    2135                2140                2145

Ser Arg Ser Gly Gly Gly Val Leu Val Ala Asn Arg Phe Ser Pro
    2150                2155                2160

Gly Ser Arg Val Thr Leu Val Asp Ser Val Leu Ile Ala Glu Lys
    2165                2170                2175

Arg Val Val Tyr Arg Gly Ala Tyr Gly Leu Gly Asp Val Ser Ala
    2180                2185                2190

Cys Leu Val Leu His Asn Val Asn Leu Thr Gly Ser Val Leu Thr
    2195                2200                2205

Ile Ala Arg Thr His Val Ala Ala Val Phe Arg Gly Ala Val Gly
    2210                2215                2220

Val Leu Phe Phe Gly Gly Val Ala Leu Ser Ser Arg Gly Ala Leu
    2225                2230                2235

Tyr Val Asp Gly Leu Ser Val Gln Thr Ala Leu Gly Leu Cys Val
    2240                2245                2250

Ser Val Glu Gly Gly Val Ser Ala Ser Gly Gly Ser Val Val Ala
    2255                2260                2265

Phe Val Asp Ser Asp Phe Leu Leu Cys Lys His Ala Val Ser Val
    2270                2275                2280

Arg Gly Ile Val Ser Val Ser Gly Ser Ala Val Ala Leu Val Arg
    2285                2290                2295

Asn Glu Phe Ser Ser Thr Glu Asp Asn Ala Val Lys Phe Tyr Ser
    2300                2305                2310

Thr Val Ser Leu Ala Gly Gly Ser Met Leu Leu Ala Lys Gly Asn
    2315                2320                2325

Val His Asp Gly Val Ser Arg Glu Met Leu Tyr Ala Ala Gly Ala
    2330                2335                2340

Val Thr Ala Ala Gly Ser Thr Leu Ser Phe Val Arg Asn Arg Ala
    2345                2350                2355

Leu Leu Pro Arg Met Val Ser Leu Ser Leu Ser Leu Ala Ala Gly
    2360                2365                2370

Ala His Leu Arg Val Ala Cys Asn Tyr Ala Gly Gly Arg Val Leu
    2375                2380                2385

Ser Thr Ala Glu Glu Tyr Ala Ala Ala Gly Phe Gly Asp Ala Gly
    2390                2395                2400

Ser Ile Asp Val Val Gly Cys Asp Ala Cys Asp Arg Asp Thr His
    2405                2410                2415

Cys Tyr Ala Pro Gly Thr Ala Ser Ala Ser Met Thr Asn Gly Val
    2420                2425                2430

Cys Val Cys Asp Cys Asp Ser Gly Gly Tyr Gly Glu Ala Cys Val
    2435                2440                2445

Pro Val Gly Ala Pro Ala Leu Pro Pro Ala Val Gly Thr Ala Pro
    2450                2455                2460

Ser Val Phe Phe Arg Glu Ser Val Thr Val Arg Ser Val Phe Val
    2465                2470                2475

Val Pro Ala Gly Ala Ser Glu Val Thr Leu Arg His Val Val Leu
    2480                2485                2490

Asp Gly Val Ser Pro Val Leu Tyr Val Pro Trp Met Ala Arg Asp
    2495                2500                2505
```

```
Gly Val Arg Ile Val Val Gln Asn Val Ser Leu Arg Asn Gly Ala
            2510                2515                2520

Val Leu Tyr Val Met Gly Gly Gly Leu Arg Gly Ala Val Ala
            2525                2530                2535

Ala Gly Ser Asp Glu Ser Gly Pro Val Glu Leu Ser Met Cys Glu
            2540                2545                2550

Val Glu Ala Leu Asn Gly Ala Leu Val Leu Thr Gly Thr Phe Pro
            2555                2560                2565

Ala Gly Ser Val Leu Thr Val Thr Asp Ser Leu Leu Val Ala Ala
            2570                2575                2580

Arg Pro Thr Pro Leu Val Tyr Leu Pro Gly Ser Arg Ser Ser Pro
            2585                2590                2595

Tyr Ala Pro Val Leu Val Leu Ser Gly Leu Arg Leu Val Arg Ser
            2600                2605                2610

Val Leu Val Val Ser Gly Val Ala Leu Val Thr Val Val Thr Gly
            2615                2620                2625

Gly Arg Thr Val Ala Val Asp Gly Ala Val Leu Glu Leu Val Gly
            2630                2635                2640

Gly Gly Val Ala Leu Asp Ala Ala Val Leu Gly Gly Asp Phe Ala
            2645                2650                2655

Leu Tyr Ala Ser Ala Arg Val Val Ala Ser Gly Gly Ala Val Leu
            2660                2665                2670

Arg Val Ser Gly Ser Gln Val Tyr Ala Ala His Gly Leu Val Phe
            2675                2680                2685

Asp Ser Gly Val Glu Ala Asn Ala Ser Ala Val Val Val Asn Asp
            2690                2695                2700

Asn Ala Gly Ala Leu Thr Asp Gly Ala Leu Leu Glu Leu Arg Gly
            2705                2710                2715

Ser Ala Ser Phe Gly Ser Gly Ser Trp Leu Ser Val Arg Gly Asn
            2720                2725                2730

Ser Ile Ser Gly Arg Leu Leu Ser Val Pro Ser His Pro Arg Ser
            2735                2740                2745

Ala Lys Leu Val Gln Ser Thr Leu Thr Leu His Gly Asn Thr Gly
            2750                2755                2760

Ser Gly Pro Val Val Met Asp Gly Thr Val Ala Leu Val Gly Ala
            2765                2770                2775

Gly Arg Arg Phe Val Val Gly Cys Leu Thr Leu Asn Gly Gln Val
            2780                2785                2790

Leu Arg Pro Met Asp Tyr Arg Ser Ala Gly Ile Ile Gly Glu Phe
            2795                2800                2805

Arg Pro Val Ala Cys Gly Val Cys Asp Ala Asp Val Arg Cys Phe
            2810                2815                2820

Ala Ala Ala Thr Arg Ala Met Ser Gly Ser Cys Gly Cys Arg Cys
            2825                2830                2835

Ala Glu Gly Gly Tyr Gly Arg Asp Cys Leu Pro Val Tyr Leu Pro
            2840                2845                2850

His Val Asp Gly Cys Asn Arg Thr Pro Ala Met Pro Pro Leu Ser
            2855                2860                2865

His Thr Ala Thr Leu Thr Glu Thr Arg Ser Pro Thr Pro Thr Trp
            2870                2875                2880

Thr Pro Ser Leu Ser Thr Pro His Tyr Ser Pro Thr His Tyr Gly
            2885                2890                2895

Pro Thr Lys Thr Leu Gln Val Thr Gly Thr Val Ala Leu Ser Pro
            2900                2905                2910
```

```
Thr Arg Thr Pro Thr Ala Ser Val Ser Ser Thr Leu Trp Trp Ser
    2915            2920                2925

Asp Val Ala Cys Pro Thr Leu Thr Val Thr Thr Thr Ala Ala Gly
    2930            2935                2940

Gly Ser Leu Thr Gln Asn Asp Ile Arg Gly Gly Gly Ser Ala Val
    2945            2950                2955

Pro Thr Trp Leu Met Val Ala Leu Pro Pro Phe Arg Trp Ala
    2960            2965                2970

Arg Asp Pro Gln Ile Gly Thr His Leu Ser Phe Val Pro Val Ser
    2975            2980                2985

Thr Ala Gln Pro Ser Gly Phe Gly Gly Pro Trp Gly Ala Met Leu
    2990            2995                3000

Ser Asn Ala Thr Trp Val His Asn Ala Thr Asn Pro Ser Thr Val
    3005            3010                3015

Leu Glu Leu Ala Val Pro Val His Arg Gly Tyr Phe Ile Ala Ala
    3020            3025                3030

Asp Glu Thr Ile Val Ile Arg Cys Asp Ala Val Ala Val Ser Gly
    3035            3040                3045

Gly Cys Lys Gly Val Leu Leu Gly Ser Phe Thr Ile Arg Ser Ala
    3050            3055                3060

Thr Leu Pro Ala Ala Ala Ser Val Leu Ser Ala Ile Thr Gly Val
    3065            3070                3075

Val Ala Gly Ala Thr Ala Val Ala Val Val Thr Gly Gly Leu
    3080            3085                3090

Gly Ser Ile Leu Glu Met Gln Ala Leu Gly Val Phe Ala Arg Met
    3095            3100                3105

Pro Cys Ala Ser Ala Gln Glu Arg Ala Ser Thr Val Ala Leu Pro
    3110            3115                3120

Tyr Phe Leu Ser Val Phe Ala Ala Leu Asp Pro Leu Trp Met Val
    3125            3130                3135

Val Gly Asn Ala Leu Leu Ala Ala Val Phe Gly Cys Val His Cys
    3140            3145                3150

Gly Val Thr Ala Ala Phe Gln Arg Trp Arg Gly Val Asp Ala Ala
    3155            3160                3165

Ser Ala Trp Ala Ala Met Arg Phe Pro Ser Leu Thr Tyr Val Val
    3170            3175                3180

Gly His Ala Met His Leu Gly Ile Phe Phe Gly Ser Val Leu Ser
    3185            3190                3195

Leu Ala Thr Pro Gly Ala Arg Val Gln His Arg Val Ile Gly Val
    3200            3205                3210

Val Gly Val Leu Tyr Gly Val Ala Phe Pro Ala Gly Val Cys Tyr
    3215            3220                3225

Phe Ile Ala Arg His Thr Gly Ala Ser Phe Thr Lys Tyr Trp Gln
    3230            3235                3240

Phe Ser Arg Lys Pro Leu His Glu Arg Leu Leu Tyr Pro Val Gly
    3245            3250                3255

Tyr Trp His Pro Ala Ala Gln Gln Arg Met Tyr Gly Gly Met Leu
    3260            3265                3270

Thr Asn Met Arg Gly Ser His Val Tyr Trp Cys Val Phe Gln Leu
    3275            3280                3285

Ser Val Leu Cys Val Cys Leu Ile Ala Ala Val His Ser Pro
    3290            3295                3300

Val Gly Gly Cys His Val Gln Tyr Phe Cys Met Ala Ala Val Leu
```

```
                3305                3310                3315

Leu Ala Gly Ala Gly Val Val Ala Phe Thr Asn Met Met Arg Ser
    3320                3325                3330

Ala Phe Leu Thr Val Met Cys Thr Ala Ser Phe Val Leu Leu Ala
    3335                3340                3345

Val Leu Cys Val Val Ser Ala Ala Asn His Leu Ala Pro Ser Asp
    3350                3355                3360

Gly Gly Ala Arg Ala Tyr Ala Ala Ile Val Leu Leu Leu Thr Thr
    3365                3370                3375

Val Leu Leu Ala Val Thr Val Tyr Ser Val Val Val Trp His Val
    3380                3385                3390

Glu Asp Arg His Trp Gln Glu Leu Arg Glu Pro Leu Arg Gly Gly
    3395                3400                3405

Leu Glu Ala Leu Leu Arg Asp Asp Glu Ser Gly Asp Glu Thr
    3410                3415                3420

Gln Lys Pro His Glu Met Ala Ser Ser Ser Tyr Ala Ser Gly Thr
    3425                3430                3435

Thr Ala Ala Ser Ser Tyr Gln Pro Pro Ala Pro Pro Leu Gln Pro
    3440                3445                3450

Met Ala Gly Gly Thr Arg Ser Asp Ala Leu Ser Leu Phe Asp Arg
    3455                3460                3465

Ala Ser Ser Ala Ser Arg Met Phe Asp Tyr Ala Ala Met
    3470                3475                3480

<210> SEQ ID NO 55
<211> LENGTH: 262
<212> TYPE: PRT
<213> ORGANISM: Trypanosoma cruzi

<400> SEQUENCE: 55

Met Ala Glu Gly Ile Lys Trp His Asn Ala Ala Ile Gln Asp Glu Leu
1               5                   10                  15

Val Pro Lys Lys Ser Pro Leu Glu Phe Lys Leu Pro Asp Ser Ala Lys
                20                  25                  30

Glu Leu Val Phe Met Ala Lys Leu Thr Glu Glu Ala Glu Arg Tyr Asp
            35                  40                  45

Glu Met Val Leu Cys Met Arg Lys Leu Val Lys Leu Asn Ser Glu Leu
        50                  55                  60

Asp Thr Glu Glu Arg Asn Leu Leu Ser Met Ala Tyr Lys Asn Val Ile
65                  70                  75                  80

Gly Ser Arg Arg Asn Ala Trp Arg Ile Ile Thr Ser Ile Glu Ser Arg
                85                  90                  95

Glu Ser Ala Arg Glu Lys Ser Glu Asn Leu Gln Leu Ile Ala Ser Leu
            100                 105                 110

Arg Lys Glu Phe Glu Ala Glu Leu Ala Ala Ile Cys Asp Asp Leu Leu
        115                 120                 125

Ala Leu Leu Asp Thr Tyr Leu Ile Pro Ala Ser Gln Gly Gly Glu Val
    130                 135                 140

Lys Val Phe Tyr Leu Lys Met Lys Gly Asp Tyr His Arg Tyr Tyr Ala
145                 150                 155                 160

Glu Ile Ala Pro Glu Ala Gly Gln Arg Gln Ala Ala Leu Asp Ala Tyr
                165                 170                 175

Ala Lys Ala Thr Glu Val Ala Asn Ser Ser Leu Ala Ser Thr His Pro
            180                 185                 190

Ile Arg Leu Gly Leu Ala Leu Asn Phe Ser Val Phe Tyr Tyr Glu Ile
```

```
              195                 200                 205
Met Lys Glu His Glu Lys Gly Phe Gln Leu Ala Arg Gln Ala Tyr Asp
210                 215                 220

Glu Ala Val Thr Glu Leu Glu Thr Leu Asp Asp Glu Ala Tyr Arg Glu
225                 230                 235                 240

Ser Asn Leu Ile Val Arg Leu Leu Arg Asp Asn Leu Asn Leu Trp Thr
                245                 250                 255

Asp Glu Gln Pro Ser Ser
            260

<210> SEQ ID NO 56
<211> LENGTH: 252
<212> TYPE: PRT
<213> ORGANISM: Trypanosoma cruzi

<400> SEQUENCE: 56

Met Ser Ser Phe Thr Val Pro Glu Lys Arg Glu Gln Leu Ile Ile Met
1               5                   10                  15

Ala Lys Leu Ala Glu Gln Cys Glu Arg Tyr Asp Glu Ile Leu Val Cys
            20                  25                  30

Met Lys Arg Val Lys Leu Asn Pro Val Leu Ser Ser Glu Glu Arg
        35                  40                  45

Asn Leu Leu Ser Val Ala Tyr Lys Asn Val Ile Gly Ala Arg Arg Ala
    50                  55                  60

Cys Trp Arg Ser Ile Thr Ala Leu Glu Gln Lys Glu Asp Ile Lys Lys
65                  70                  75                  80

Glu Lys Asn Ile Thr Leu Ile Lys Gly Phe Lys Arg Gln Ile Glu Lys
                85                  90                  95

Glu Leu Ser Asp Val Cys Ser Asp Ile Leu Glu Leu Ile Glu Glu His
            100                 105                 110

Leu Leu Pro Asn Ala Ser Thr Glu Glu Thr Lys Val Tyr Tyr Leu Lys
        115                 120                 125

Met Lys Gly Asp Tyr His Arg Tyr Tyr Ala Glu Ile Glu Thr Asn Thr
    130                 135                 140

Glu Glu Gln Lys Asn Lys Ala Leu Glu Ala Tyr Thr Gln Ala Met Gln
145                 150                 155                 160

Tyr Asn Ser Ser Leu Lys Pro Thr Ser Pro Ile Arg Leu Gly Leu Ala
                165                 170                 175

Leu Asn Phe Ser Val Phe Tyr Tyr Glu Ile Leu Lys Ser Pro Asp Arg
            180                 185                 190

Gly Cys Gln Leu Ala Arg Gln Ala Phe Glu Glu Ala Leu Ser Asp Pro
        195                 200                 205

Ser Val Leu Asp Glu Glu Gln His Lys Glu Ala Ala Leu Ile Met Gln
    210                 215                 220

Leu Leu Arg Asp Asn Leu Ala Leu Trp Thr Glu Asp Ala His Pro Glu
225                 230                 235                 240

Gly His Asp Asp Gly Thr Ala Met Glu Glu Leu Glu
                245                 250

<210> SEQ ID NO 57
<211> LENGTH: 357
<212> TYPE: PRT
<213> ORGANISM: Trypanosoma cruzi

<400> SEQUENCE: 57

Met Ala Ser Ala Glu Val Val Ser Lys Leu Glu Ala Ala Phe Ala Lys
1               5                   10                  15
```

```
Leu Gln Asn Ala Ser Asp Cys His Ser Leu Leu Lys Lys Tyr Leu Thr
                20                  25                  30

Lys Glu Val Phe Asp Gln Leu Lys Gly Lys Gln Thr Lys Met Gly Ala
            35                  40                  45

Thr Leu Met Asp Val Ile Gln Ser Gly Val Glu Asn Leu Asp Ser Gly
 50                  55                  60

Ile Gly Val Tyr Ala Pro Asp Ala Glu Ser Tyr Thr Leu Phe Ala Ala
 65                  70                  75                  80

Leu Phe Asp Pro Ile Ile Glu Asp Tyr His Lys Gly Phe Lys Pro Ser
                 85                  90                  95

Asp Lys Gln Pro Pro Lys Asp Phe Gly Asp Leu Asn Thr Phe Ile Asp
               100                 105                 110

Val Asp Pro Asp Lys Lys Tyr Val Ile Ser Thr Arg Val Arg Cys Gly
               115                 120                 125

Arg Ser Leu Glu Gly Tyr Pro Phe Asn Pro Cys Leu Lys Lys Gln Gln
           130                 135                 140

Tyr Glu Glu Met Glu Ser Arg Val Lys Gly Gln Leu Glu Ser Met Ser
145                 150                 155                 160

Gly Glu Leu Arg Gly Lys Tyr Tyr Pro Leu Thr Gly Met Thr Lys Glu
                165                 170                 175

Thr Gln Lys Gln Leu Ile Asp Asp His Phe Leu Phe Lys Glu Gly Asp
            180                 185                 190

Arg Phe Leu Gln Ala Ala His Ala Cys Glu Phe Trp Pro Thr Gly Arg
        195                 200                 205

Gly Ile Tyr His Asn Asp Ala Lys Thr Phe Leu Val Trp Val Asn Glu
210                 215                 220

Glu Asp His Leu Arg Ile Ile Ser Met Gln Lys Gly Gly Asn Leu Lys
225                 230                 235                 240

Glu Val Phe Gly Arg Leu Val Thr Ala Val Gly Val Ile Glu Glu Lys
                245                 250                 255

Val Lys Phe Ser Arg Asp Asp Arg Leu Gly Phe Leu Thr Phe Cys Pro
            260                 265                 270

Thr Asn Leu Gly Thr Thr Ile Arg Ala Ser Val His Ile Lys Leu Pro
        275                 280                 285

Lys Leu Gly Ala Asp Arg Lys Lys Leu Glu Glu Val Ala Ala Lys Tyr
290                 295                 300

Asn Leu Gln Val Arg Gly Thr Ala Gly Glu His Ser Asp Ser Pro Asp
305                 310                 315                 320

Gly Val Tyr Asp Ile Ser Asn Lys Arg Arg Leu Gly Leu Ser Glu Tyr
                325                 330                 335

Glu Ala Val Lys Glu Met Gln Asp Gly Ile Leu Glu Leu Ile Lys Ala
            340                 345                 350

Glu Glu Ser Ala Arg
        355

<210> SEQ ID NO 58
<211> LENGTH: 181
<212> TYPE: PRT
<213> ORGANISM: Trypanosoma cruzi

<400> SEQUENCE: 58

Met Ser Thr Pro Gln Val Gln Asn Pro Val Glu Asp Asp Glu Val
1               5                   10                  15

Pro Thr Leu Glu Ala Ala Glu Val Pro Gln Val Ala Lys Gln Thr Lys
            20                  25                  30
```

```
Arg Tyr Ala Lys Ala Met Ala Lys Met Gly Leu Lys Pro Glu Pro Asn
             35                  40                  45

Val Val Lys Val His Ile Arg Lys His Gly Ser Leu Ser Phe Leu Val
 50                  55                  60

Asn Gln Pro Glu Leu Tyr Arg Phe Pro Gly Thr Asn Thr Phe Leu Val
 65                  70                  75                  80

Phe Gly Glu Ala Gln Leu Gly Asp Thr Ala Met Glu Ala Gln Glu Ala
                 85                  90                  95

Ala Ala Arg Ala Val Ser Gly Val Val Pro Glu Thr Glu Ser Arg Val
            100                 105                 110

Glu Glu Val Pro Thr Thr Ala Glu Thr Pro Glu Thr Pro Val Pro Ala
            115                 120                 125

Glu Lys Thr Asp Asp Ala Asp Ala Glu Asp Gly Gly Glu Leu Asp Glu
            130                 135                 140

Arg Glu Ile Lys Val Val Met Ser Gln Gly Asn Thr Asp Arg Ala Gly
145                 150                 155                 160

Ala Ile Arg Ala Leu Lys Asn Asn Lys Gly Asp Ile Val Asn Ala Ile
                165                 170                 175

Leu Glu Leu Thr Met
            180

<210> SEQ ID NO 59
<211> LENGTH: 177
<212> TYPE: PRT
<213> ORGANISM: Trypanosoma cruzi

<400> SEQUENCE: 59

Met Ser Tyr Lys Pro His His Ala Thr Val Pro Thr Asn Pro Lys Val
  1               5                  10                  15

Phe Phe Asp Val Ser Ile Gly Gly Gln Ser Ala Gly Arg Val Val Phe
             20                  25                  30

Glu Leu Phe Ala Asp Ala Val Pro Lys Thr Ala Glu Asn Phe Arg Ala
             35                  40                  45

Leu Cys Thr Gly Glu Lys Asn Phe Gly Tyr Ala Gly Ser Gly Phe His
 50                  55                  60

Arg Ile Ile Pro Gln Phe Met Cys Gln Gly Gly Asp Phe Thr Asn His
 65                  70                  75                  80

Asn Gly Thr Gly Gly Arg Ser Ile Tyr Gly Glu Lys Phe Ala Asp Glu
                 85                  90                  95

Ser Phe Ala Gly Lys Ala Gly Lys His Phe Gly Leu Gly Thr Leu Ser
            100                 105                 110

Met Ala Asn Ala Gly Pro Asn Thr Asn Gly Ser Gln Phe Phe Ile Cys
            115                 120                 125

Thr Ala Pro Thr Gln Trp Leu Asp Gly Lys His Val Val Phe Gly Gln
            130                 135                 140

Val Leu Glu Gly Ile Glu Val Val Lys Ala Met Glu Ala Val Gly Ser
145                 150                 155                 160

Gln Thr Gly Lys Thr Ser Lys Pro Val Lys Ile Glu Ala Ser Gly Gln
                165                 170                 175

Leu

<210> SEQ ID NO 60
<211> LENGTH: 340
<212> TYPE: PRT
<213> ORGANISM: Trypanosoma cruzi
```

<400> SEQUENCE: 60

Met Ser Leu Arg Leu Cys Val Cys Thr Ala Thr Ala Asn Gly Glu Tyr
1               5                   10                  15

Tyr Met Ser Met Phe Asn Lys His Leu Ser Ser Phe Lys Thr Ile
            20                  25                  30

Thr Leu Gly Ser Thr Val Asp Asp Phe Lys Gln Asp Lys Asp Ser Lys
        35                  40                  45

Asp Ser Ile Ile Leu Tyr Val Glu Gly Pro Val Gly His Asp Ala Ile
50                  55                  60

Lys Tyr Leu Cys Asp Asp Tyr His Leu Pro Lys Glu Gln Arg Arg Val
65                  70                  75                  80

Leu Trp Ile Tyr Ser Leu Thr Ala Gly Val Asp Val Tyr Arg Leu Gly
                85                  90                  95

Glu Leu Val Lys Glu Leu Gln Asp Ile Pro Phe Ala Asn Ala Arg Gly
            100                 105                 110

Cys Tyr Ser Ser Val Leu Ala Glu His Val Met Tyr Ser Met Leu Tyr
        115                 120                 125

Phe Tyr Arg Gln Thr Trp Arg Ser Leu Ala Ser Arg Ala Glu His Lys
130                 135                 140

Trp Asp Pro Phe Leu Met Val Glu Leu Arg Gly Lys Lys Val Gly Ile
145                 150                 155                 160

Ile Gly Tyr Gly Asp Ile Gly Gln Ala Ser Ala Lys Leu Leu Ser Ala
                165                 170                 175

Phe Gly Met Glu Val Thr Gly Val Lys Arg Ser Ala Ser Thr Lys Glu
            180                 185                 190

Val Asp Glu Tyr Gly Val Arg Leu Val His Gly Asp Ala Glu Arg Glu
        195                 200                 205

Arg Val Leu Arg Glu Ser Asp Phe Val Val Asn Ile Leu Pro Gly Thr
210                 215                 220

Glu Glu Thr Lys Arg Phe Phe Asn Lys Glu Leu Phe Ser Met Met Lys
225                 230                 235                 240

Pro Ser Ala Val Tyr Ile Ser Ile Gly Arg Gly Ile Thr Gln Asn Glu
                245                 250                 255

Asp Asp Leu Ala Cys Ala Leu Arg Asp Gly Val Ile Arg Gly Ala Ser
            260                 265                 270

Val Asp Val Phe Glu Arg Glu Pro Leu Pro Ala Glu Ser Pro Leu Trp
        275                 280                 285

Asp Ile Ser Asp Asp Lys Leu Leu Leu Thr Ala His Ser Ala Asp Arg
290                 295                 300

Thr Ala Asn Leu Val Pro Asp Ser Val Arg Arg Phe Ile Gly Leu Val
305                 310                 315                 320

Asn Glu Tyr Ala Lys Thr Lys Arg Leu Asp Thr Tyr Leu Val Asp Pro
                325                 330                 335

Val Arg Gly Tyr
            340

<210> SEQ ID NO 61
<211> LENGTH: 273
<212> TYPE: PRT
<213> ORGANISM: Trypanosoma cruzi

<400> SEQUENCE: 61

Met Ser Ala Glu Arg Ala Ile Gly Ser Thr Ile Thr Leu Ile Thr Asn
1               5                   10                  15

Ser Leu Ile Arg Tyr Glu Gly Thr Leu Gly Gln Ile Asp Gly Pro Asn

```
                  20                  25                  30
Asn Thr Val Ser Leu Thr Asn Val Arg Val Phe Gly Thr Glu Gly Arg
            35                  40                  45
Gly Gln Glu Ala Gly Leu Ala Gln Ile Pro Ala Asp Gln Leu Phe
        50                  55                  60
Asp Gln Ile Val Phe Arg Gly Ser Asp Ile Lys Glu Leu Thr Val Phe
65                  70                  75                  80
Glu Glu Pro His Asn Ala Met Met Asp Pro Ala Val Val Thr Ala Leu
                85                  90                  95
Pro Ala Arg Asn Asn Ser Ala Lys Thr Val Ser Ile Asn Gln Arg Asn
            100                 105                 110
Gly Pro Ser Ser Gly Asn Thr Ser Ala Gln Tyr His Gln Thr His His
        115                 120                 125
Gln His Gln His Gln His Gln Gln Gln Gln Arg Tyr Gly Gly
    130                 135                 140
Gly Gly Tyr Arg Arg Gly Gly Gly Ser Gly Tyr Arg Gly Ser Arg Arg
145                 150                 155                 160
Val Asp Gly His Thr Gly Gln Asp Phe Arg Pro Ala Thr Gly Ala Ala
                165                 170                 175
Lys Glu Glu Phe Lys Asp Asp Phe Asp Phe Ser Lys Ser Arg Glu Glu
            180                 185                 190
Phe Glu Lys Lys Lys Ser Glu Phe Glu Lys Ala Lys Glu Asp Ala Lys
        195                 200                 205
Val His Ser Lys Ala Tyr Asp Lys Ser Ser Phe Phe Asp Lys Ile Ser
    210                 215                 220
Cys Asp Gln Gln Asp Arg Ala Leu Arg Met Asp Arg Glu Gly Val Lys
225                 230                 235                 240
Arg Ala Asp Ala Glu Thr Phe Gly Ser Glu Met Val Gly Asn Met Arg
                245                 250                 255
Gly Pro Arg Arg Gly Arg Gly Gly Arg Gly Arg Gly Tyr Asn Gly Arg Tyr
            260                 265                 270
Asn

<210> SEQ ID NO 62
<211> LENGTH: 304
<212> TYPE: PRT
<213> ORGANISM: Trypanosoma cruzi
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (126)..(126)
<223> OTHER INFORMATION: Xaa can be any naturally occurring amino acid
<220> FEATURE:
<221> NAME/KEY: misc_feature
<222> LOCATION: (195)..(195)
<223> OTHER INFORMATION: Xaa can be any naturally occurring amino acid
<220> FEATURE:
<221> NAME/KEY: misc_feature
```

<222> LOCATION: (245)..(245)
<223> OTHER INFORMATION: Xaa can be any naturally occurring amino acid
<220> FEATURE:
<221> NAME/KEY: misc_feature
<222> LOCATION: (274)..(274)
<223> OTHER INFORMATION: Xaa can be any naturally occurring amino acid
<220> FEATURE:
<221> NAME/KEY: misc_feature
<222> LOCATION: (291)..(291)
<223> OTHER INFORMATION: Xaa can be any naturally occurring amino acid

<400> SEQUENCE: 62

```
Cys Phe Phe Ala Leu Leu Ser Ala Ala Gly Leu Ile Ile Thr Arg Arg
1               5                   10                  15

Ser Ser Ala Lys Val Leu Leu Val Ser Met Ala Pro Thr Thr His Ser
            20                  25                  30

Arg Leu Leu Ser Met Glu Gln Lys Xaa Leu Val Val Ser Ile Pro Lys
        35                  40                  45

Arg Pro Glu Xaa Thr Thr Leu Asp Tyr Leu Ser Leu Val Pro Ser Arg
    50                  55                  60

Arg Leu Leu Arg Gln Gln Ala Leu Thr Pro Leu Xaa Ser Thr Ser Leu
65                  70                  75                  80

His Leu Thr Val Arg Pro Leu Leu Arg Arg Pro Leu Met Pro Lys Phe
                85                  90                  95

Pro Leu Leu Leu Ser Leu Leu Arg Glu Phe Arg Ser Gly Ile Cys Phe
            100                 105                 110

Ala Xaa Ser Pro Cys Phe Phe Leu Arg Thr Arg Arg Val Xaa Leu Asp
        115                 120                 125

Pro Thr Val Leu Val Leu Ser Val Arg Lys Ser Ala Lys Leu Val Ser
130                 135                 140

Cys Leu Val Ile Ser Thr Arg Lys Ala Ala Leu Val Trp Tyr Pro Gly
145                 150                 155                 160

Ala Ala His Ser His Met Arg Arg Leu Leu Arg Pro Gln Arg Arg Val
                165                 170                 175

Ser Ala Asn Arg Cys Ala Leu Val Leu Val Ala Ile Arg Ser Met Val
            180                 185                 190

Arg Thr Xaa Leu Thr Val Ser Asn Phe Ile Leu Arg Ile Leu Arg Arg
        195                 200                 205

Arg Val Leu Phe Leu Leu Val Arg Leu Val Glu Leu Gln Arg Arg Lys
    210                 215                 220

Pro Gln Ser Leu Ser Arg Thr Thr Pro Ser Arg Ser Arg Trp Tyr His
225                 230                 235                 240

Ser Leu Ala Ala Xaa Leu Leu Arg Gln Ala Val Val Trp Ala Met Gln
                245                 250                 255

Val Pro Trp Phe Leu Val Asp Arg Val Gln Arg Ala Lys Trp Lys
            260                 265                 270

Arg Xaa Lys Leu Arg Ala Ser Leu Phe Leu Ser Pro Leu Pro Ser Leu
        275                 280                 285

Val Ser Xaa Trp Pro Arg Leu Ser Val Arg Ser Ala Glu Gln Arg Asn
    290                 295                 300
```

<210> SEQ ID NO 63
<211> LENGTH: 3032
<212> TYPE: PRT
<213> ORGANISM: Trypanosoma cruzi
<220> FEATURE:
<221> NAME/KEY: misc_feature
<222> LOCATION: (1571)..(1571)
<223> OTHER INFORMATION: Xaa can be any naturally occurring amino acid

<400> SEQUENCE: 63

```
Met Pro Phe Asp Val Pro Ser Ala Arg Thr Gly Gly Gly Gly Gly
1               5                   10                  15

Ala Gln Asp Cys Val Ser Gly Val Thr Leu Thr Glu Ser Val Thr Ile
            20                  25                  30

Gly Gly Gly Arg Ala Thr Ala Cys Leu Asp Ser Val Phe Ser Gly
                35                  40                  45

Pro Ile Ile Val Ala Val Asp Leu Arg Ser Met Asp Ala Phe Ala Asp
    50                  55                  60

Ala Leu Asn Val Thr Leu Arg His Cys Val Leu Ala Gly Gly Ala Gln
65                  70                  75                  80

Leu Arg Ile Gly Gly Leu Ser Glu Ser Thr Ala Arg Leu Met Pro His
                85                  90                  95

Ala Leu Val Asn Met Thr Asn Val Thr Ser Leu Glu Gly Thr Ile Val
                100                 105                 110

Leu His Gly Ala Met Pro Pro Asn Ser Ser Val Leu Leu Ala Asn Ser
            115                 120                 125

Thr Leu Arg Ala Thr Val Gly Gly Ser Gln Tyr Val Pro Thr Thr Leu
        130                 135                 140

Asp Tyr Glu Gly Phe Arg Tyr Gly Pro Ala Leu Val Leu Asp Gly Val
145                 150                 155                 160

Arg Leu Leu Ser Thr Arg Phe Val Met Thr Arg Ser Thr Leu Leu Cys
                165                 170                 175

Gly Gly Gly Ser Cys Ala Ala Ile Leu Val Glu Arg Gly Leu Gly Ala
            180                 185                 190

Asn Leu Ser Ser Val Phe Tyr Met Asp Asn Cys Ala Val Ser Ser Arg
            195                 200                 205

Thr His Val Met Tyr Ala Leu Ala Ser Asp Leu Arg Val Gly Gly Gly
        210                 215                 220

Ser Val Phe Ser Ile Gln Asn Ser Ser Trp Ser Ala Pro Ser Asn Glu
225                 230                 235                 240

Phe Tyr Lys Gly Ala Cys Val Phe Glu Asp Val Ala Val Asp Gly Gly
                245                 250                 255

Ser Val Leu Gln Ile Val Ser Ser Thr Phe Arg Leu Gly Phe Ala Met
            260                 265                 270

Leu Ile Ala Asn Thr Leu Thr Val Ala Asp Gly Ser Trp Leu Val His
        275                 280                 285

Arg Asn Ser Glu Phe Arg Thr Ala Tyr Val Val Tyr Val Val Lys Glu
    290                 295                 300

Asn Gly Val Ser Phe Arg Asp Arg Ser Val Trp Ser Ile Leu Asp Asn
305                 310                 315                 320

Asn Phe Thr Tyr Gly Ser Tyr Pro Ser Thr His Ala His Ile Thr Asn
                325                 330                 335

Asp Trp Ser Pro Pro Ser Asp Ser Arg Pro Ile Ile Tyr Gly Met Cys
            340                 345                 350

Asn Glu Ala Arg Gly Ser Pro Val Thr Asp Tyr Arg Asp Asp Leu Asn
        355                 360                 365

Ile Gly Thr Ser Val Thr Val Leu Asp Cys Gly Thr Cys Thr Val Asp
    370                 375                 380

Ala Val Cys Phe Ala Ala Arg Thr Ser Ser Ile Ser Gly Cys Glu Cys
385                 390                 395                 400

Val Cys Ala Ala Gly His Gly Asp Pro Cys Leu Pro Ala Ala Val
                405                 410                 415
```

```
Pro Asp Gly Leu Gly Pro Leu Pro Leu Pro Asp Ala Lys Asp Thr Glu
            420                 425                 430

Val Arg Cys Val His Gly Gly Ser Ile Ser Val Asp Asp Pro Asp
            435                 440                 445

Pro Gly Val Arg Gly Leu Cys Phe Val Asn Val Thr Phe Thr Ala Ala
            450                 455                 460

Ile Val Leu Asn Leu Trp Ser Phe Asp Ala Pro Gln Gln Thr Leu Asn
465                 470                 475                 480

Ile Thr Leu Leu Gln Cys Val Leu Met Gly Leu Leu Ile Arg Gly Ser
                485                 490                 495

Gly Ala Arg Val His Val Ser Val Val Ser Ser Ile Leu Asp Ala Gly
            500                 505                 510

Asp Leu Glu Phe Arg Gly Asp Phe Asp Ser Arg Ser Gln Ile Leu Val
            515                 520                 525

Ala Gly Ser Lys Leu Val Met Thr Ser Gly His Thr Ile Gln Phe Gln
            530                 535                 540

Arg Phe Ser Leu Gly Ala Asn Ser Thr Leu Leu Leu Asp Asn Leu
545                 550                 555                 560

Ile Glu Gly Glu Ser Tyr Ala Val Arg Leu Ser Phe Val Val Leu Asp
                565                 570                 575

Gly Gly Gly Ile Leu Ile Lys Gly Asn Thr Leu Arg Gly Ala Glu Glu
            580                 585                 590

Asn Phe Leu Leu Glu Ser Ala Val Leu Phe Glu Phe Ala Val Leu Lys
    595                 600                 605

Asp Gly Gly His Phe Asp Val Glu Asn Asn Thr Met Ser Ala Val Ser
            610                 615                 620

Gly Ile Tyr Phe Tyr Gly Asp Ile Val Ser Ser Ala Gly Leu Leu
625                 630                 635                 640

Arg Val Ala Asp Cys Thr Phe Val Gly Ile Thr Leu Phe Phe Glu Pro
                645                 650                 655

Ala Leu Val His Leu Asp Gly Thr Val Thr Leu Gln Gly Gly Ala Gln
            660                 665                 670

Trp Arg Val Glu Gly Asn Asp Val Ser Ala Ala Ser Val Met Gly Val
            675                 680                 685

Pro Lys Ser Leu Tyr Lys Met Arg Leu Leu Gly Ser Gly Thr Ala Val
            690                 695                 700

Val Leu Ala Asn Asn Arg Gln Val Asp Asp Ser Cys Pro Phe Ala Asp
705                 710                 715                 720

Leu Ala Leu Pro Asn Met Ile Val Ser Pro Ala Arg Phe Val Val
                725                 730                 735

Gly Cys Asn Leu Gln Gly Asp Glu Glu Val Leu Tyr Asp Gly Leu Phe
            740                 745                 750

Pro Gly Glu Val Val Phe Arg Cys Gly Thr Cys Asn Asp Asn Ala
            755                 760                 765

Ala Cys Tyr Met Pro Gly Thr Glu Ser Val Asp Arg Asp Ser Cys Ser
            770                 775                 780

Cys Ser Cys Lys Asp Gly Trp Arg Gly Ala Ser Cys Leu Pro Phe Glu
785                 790                 795                 800

Val Pro Asp Thr Val Pro Leu Leu Pro Glu Arg Ala Val Asp Gly
            805                 810                 815

Asp Thr Ser Cys Val Val Asn Gln Thr Leu Thr Asn Leu Thr Leu Asn
            820                 825                 830

Met Trp Lys Thr His His Cys Tyr Val Gly Val Thr Phe Asn Gly Val
            835                 840                 845
```

```
Gly Ala Val Leu Lys Phe Phe Asn Gly Met Pro Leu His Leu Pro
    850             855             860
Ile Asn Ile Thr Leu Ser Gly Cys Thr Phe Arg Glu Gly Ala Ala Leu
865             870             875             880
Lys Phe Val Gly Gly Ala Ala Glu Ser Ser Gly Val Leu Ile
            885             890             895
Arg Val Ser Gln Thr Val Met Arg Arg Ser Ser Val Val Phe Ala
            900             905             910
Leu Ala Leu Pro Gln His Cys Asp Ile Ala Val Thr Glu Val Asp Ala
            915             920             925
Val Gln Phe Ser Val Val Gln Leu Leu Glu Ser Val Asn Asn Met Trp
    930             935             940
Ser Val Met Met Leu Arg Asn Val Val Leu Ser Ala Ser Ser Leu Leu
945             950             955             960
Val Ser Asn Val Lys Ala Arg Ala Phe Gly Tyr Gly Gly Phe Gly Leu
            965             970             975
Tyr Ser Thr Gly Thr Leu Thr Leu Val Ser Gly Ser Ser Leu Tyr Val
            980             985             990
Arg Tyr Cys Ser Leu Asp Gly Tyr Glu His Leu Phe Tyr Val His Gly
            995             1000            1005
Leu Ser Val Arg Asp Tyr Ser Val Phe Ala Leu Leu Asn Asn Thr
    1010            1015            1020
Met Val Ser Gly Thr Ser Phe Leu Tyr Gln Lys Gln Asn Phe Ser
    1025            1030            1035
Val Ser Asp His Ser Val Leu Arg Val Val Gly Asn Ser Gly Ser
    1040            1045            1050
Val Ser Asn Ala Ile Cys Ala Tyr Asn Leu Trp Ile Val Glu Gln
    1055            1060            1065
Ser Ser Trp Leu Asp Trp Arg Asp Asn Asp Val Gly Val Gly Ala
    1070            1075            1080
Met Phe Arg Tyr Ser Leu Ile Thr Ala Phe Ile Ile Asp Asp Ser
    1085            1090            1095
Ser Val Thr Thr Leu Thr Gly Cys Lys Met Gly Leu Thr Gly Leu
    1100            1105            1110
Ser Gly Pro Leu Leu Ser Gln Ala Asp Ala Gly Tyr Arg Phe Val
    1115            1120            1125
Ser Gly Cys Leu Thr Val Ala Gly Arg Val Leu Thr Thr Ala Ala
    1130            1135            1140
Glu Leu Glu Leu Asn Gly Ile Thr Asn Val Thr Met Val Ala Ala
    1145            1150            1155
Cys Gly Gly Cys Thr Lys Glu Val Asp Cys Phe Ala Pro Leu Thr
    1160            1165            1170
Thr Ala Val Ile Asp Cys Lys Cys Gln Cys Ala Ala Gly Gly His
    1175            1180            1185
Gly Asp Val Cys Val Pro Ala Pro Val Pro Ala Gly Ser Leu Ser
    1190            1195            1200
Pro Pro Pro Val Pro Pro Pro Pro Pro Pro Pro Arg Thr Pro
    1205            1210            1215
Pro Pro Pro Pro Phe Gly Glu Cys Ile Ser Asp Met Val Tyr Pro
    1220            1225            1230
Glu Val Ala Gln Ala Val Gly Gly Gly Leu Ser Trp Leu Cys Tyr
    1235            1240            1245
Arg Asn Val Thr Phe Ser Gly Gly Gly Met Ser Leu Thr Val Leu
```

-continued

```
            1250                1255                1260
Ile Gly Ala Met Thr Gly Glu Val Ala Asn Ile Thr Phe Asp Gly
    1265                1270                1275
Cys Thr Trp Arg Asp Gly Ala Val Leu Leu Leu Gly Asn Ala
    1280                1285                1290
Tyr Ala Ala Val Gly Ser Leu Asn Ile Val Val Thr Gly Asn Thr
    1295                1300                1305
Phe Ser Asp Ala Leu Leu Ser Pro Glu Gly Gly Phe Pro Pro His
    1310                1315                1320
Thr Asn Ile Thr Ile Ser Gly Asn Arg Phe Thr Val Thr Arg Leu
    1325                1330                1335
Ile Pro Arg Phe Cys Leu Gly Val Arg Arg Pro Ser Cys Val Ala
    1340                1345                1350
Met Asn Gly Leu Ala Val Ser Asn Asp Ser Ala Val Val Leu Ser
    1355                1360                1365
Gly Asn Val Phe Gln Thr Val Thr Ala Ser Ser Ser Ala Ile Tyr
    1370                1375                1380
Val Val Gly Ser Ser Leu Arg Val Ser Trp His Ser Val Phe Ala
    1385                1390                1395
Val Val Gly Asn Thr Phe His Met Ala Gly Ala Asn Gly Thr Leu
    1400                1405                1410
Ile Tyr Ile Gly Gly Ser Arg His Ser Leu Ser Leu Ser Val Leu
    1415                1420                1425
Asn Asn Ser Ala Val Val Ile Arg Gly Asn Val Val Thr Arg Pro
    1430                1435                1440
Val Lys Tyr Phe Ile Val Phe Leu Trp Ser Leu Arg Val Glu Ser
    1445                1450                1455
Gln Cys Ala Val Val Phe Gln Gly Asn Asp Met Gln Gly Ser Leu
    1460                1465                1470
Val Val Phe Tyr Ser Val Phe Ser Ser Tyr Ile Phe Tyr Asn Ser
    1475                1480                1485
Trp Leu Gln Leu Ser Gly Asn Leu Cys Arg Val Ser Pro Ser Glu
    1490                1495                1500
Gly Leu Thr Val Phe Asn Pro Thr Val Asn Leu Arg Asp Ser Thr
    1505                1510                1515
Val Ser Val Ser Gly Asn Arg Phe Met Ser Ser Thr Val Ser Pro
    1520                1525                1530
Thr Val Leu Leu Ile Pro Lys Ser Ser Arg Asp Leu Thr Asn Gly
    1535                1540                1545
Ala Ile Val Ala Ala Cys Asn Thr Val Asn Gly Gly Glu Glu Ala
    1550                1555                1560
Asn Tyr Val Ile Pro Phe Val Xaa Asn Ala Thr Ile Leu Thr Cys
    1565                1570                1575
Ser Gly Pro Cys Ala Leu Ala Ala Ser Cys Phe Pro Pro Tyr Thr
    1580                1585                1590
Ser Thr Ala Ser Ser Asp Gly Cys Ala Cys Thr Cys Ala Glu Gly
    1595                1600                1605
Gly His Gly Asp Ala Cys Leu Pro Val Ala Val Pro Glu Pro Pro
    1610                1615                1620
Ser Thr Asp Gly Ala Asp Leu Cys Val Gln Asp Val Arg Val Gly
    1625                1630                1635
Val Glu Val Ser Ala Gly Leu Gly Thr Ser Val Ala Cys Tyr Val
    1640                1645                1650
```

```
Gly Val Thr Phe Ala Ala Asp Val Val Asp Val Gly Leu Met
    1655             1660             1665

Ser Gly Ser Val Arg Asn Val Thr Leu Ala Asn Cys Thr Phe Val
    1670             1675             1680

Asp Gly Ala Ser Leu Tyr Val Val Gly Trp Leu Ser Asp Pro Thr
    1685             1690             1695

Ala Gly Gln Arg Ala Asp Val Leu Ile Ser Gly Leu Glu Ser Arg
    1700             1705             1710

Ser Gly Gly Gly Val Val Val Ala Asn Arg Phe Pro Pro Gly Ser
    1715             1720             1725

Arg Val Thr Val Val Asp Ser Val Leu Ile Ala Glu Arg Arg Val
    1730             1735             1740

Ala Tyr Arg Gly Val Tyr Asp Leu Gly Asp Ala Ser Ala Cys Leu
    1745             1750             1755

Val Val His Asn Val Asn Leu Thr Gly Ser Val Leu Thr Ile Ala
    1760             1765             1770

Arg Thr Gln Val Val Ala Val Phe Arg Asp Ala Val Gly Val Leu
    1775             1780             1785

Val Val Gly Gly Val Ala Leu Ser Ser Arg Gly Ala Leu Tyr Val
    1790             1795             1800

Asp Gly Leu Ala Val Gln Thr Ala Leu Gly Leu Cys Val Ser Val
    1805             1810             1815

Glu Gly Gly Val Ala Ala Ser Gly Gly Ser Val Val Ala Phe Val
    1820             1825             1830

Asp Ser Asp Phe Leu Leu Cys Lys His Ala Val Thr Val Arg Gly
    1835             1840             1845

Ala Val Ser Val Ser Gly Ser Met Val Ala Phe Val Arg Ser Asp
    1850             1855             1860

Phe Leu Ser Thr Glu Asn His Ala Val Ala Phe Tyr Ser Ala Val
    1865             1870             1875

Ser Leu Ala Gly Gly Ser Met Leu Leu Val Lys Gly Asn Val His
    1880             1885             1890

Asp Gly Val Ser Arg Glu Met Leu Tyr Ala Ala Gly Ala Val Thr
    1895             1900             1905

Ala Ala Gly Ser Thr Leu Ser Phe Val Arg Asn Arg Ala Leu Leu
    1910             1915             1920

Pro Arg Met Leu Thr Val Ser Leu Ser Leu Val Ala Gly Ala His
    1925             1930             1935

Leu Arg Val Ala Cys Asn Asp Ala Gly Gly Arg Val Leu Leu Thr
    1940             1945             1950

Ala Glu Glu Tyr Ala Ala Ala Gly Phe Gly Asp Ala Gly Arg Ile
    1955             1960             1965

Asp Val Ala Gly Cys Asp Ala Cys Asn Met Asp Thr His Cys Tyr
    1970             1975             1980

Ala Pro Gly Thr Ala Ser Ala Ser Val Thr Asp Gly Val Cys Val
    1985             1990             1995

Cys Ala Cys Ser Ser Gly Gly Tyr Gly Glu Ala Cys Val Pro Val
    2000             2005             2010

Gly Val Pro Ala Leu Pro Pro Pro Val Gly Thr Ala Ser Ser Val
    2015             2020             2025

Phe Val Arg Glu Gly Val Thr Val Arg Ser Val Phe Val Val Pro
    2030             2035             2040

Ala Gly Ala Ser Glu Val Thr Leu Arg His Val Val Leu Asp Gly
    2045             2050             2055
```

-continued

Val Ser Pro Val Leu Tyr Val Pro Trp Met Ala Arg Asp Gly Val
    2060            2065            2070

Arg Ile Val Val Gln Asn Val Ser Leu Leu Asn Gly Ala Val Leu
    2075            2080            2085

Tyr Val Met Gly Gly Gly Leu Arg Gly Ala Gly Ala Ala Gly
    2090            2095            2100

Ser Asp Glu Gly Gly Pro Val Glu Leu Ser Val Cys Asp Val Glu
    2105            2110            2115

Ala Leu Asn Gly Ala Leu Val Leu Thr Asp Thr Phe Pro Ala Gly
    2120            2125            2130

Ser Val Leu Thr Val Thr Asp Ser Leu Leu Val Ala Ala Arg Pro
    2135            2140            2145

Thr Pro Leu Val Tyr Leu Pro Gly Ser Gln Ser Ser Pro Tyr Ala
    2150            2155            2160

Pro Val Leu Val Leu Ser Gly Leu Arg Leu Val Arg Ser Val Leu
    2165            2170            2175

Val Val Tyr Gly Val Ala Leu Val Thr Val Met Thr Gly Gly Arg
    2180            2185            2190

Thr Val Leu Val Asp Gly Ala Val Leu Gly Leu Val Gly Gly Gly
    2195            2200            2205

Val Ala Leu Asp Ala Ala Val Leu Gly Gly Asp Val Ala Leu Tyr
    2210            2215            2220

Ala Ser Ala Arg Val Val Ser Glu Gly Ala Val Leu Arg Val
    2225            2230            2235

Ser Gly Ser Arg Val Tyr Ala Ala His Gly Leu Val Phe Asp Ser
    2240            2245            2250

Gly Val Glu Ser Asn Ala Ser Ala Val Val Val Asn Asp Asn Ala
    2255            2260            2265

Gly Ala Leu Thr Asp Gly Ala Leu Leu Val Leu Arg Gly Ser Ala
    2270            2275            2280

Ser Phe Ala Ser Gly Ser Trp Leu Ser Val Arg Gly Asn Ser Ile
    2285            2290            2295

Ser Gly Arg Leu Leu Ser Val Pro Ser Tyr Pro Arg Ser Ala Glu
    2300            2305            2310

Leu Val Gln Ser Thr Leu Thr Leu His Gly Asn Ala Gly Ser Gly
    2315            2320            2325

Pro Val Val Met Asp Gly Thr Val Ala Leu Val Gly Ala Gly Gly
    2330            2335            2340

Lys Phe Val Leu Gly Cys Leu Thr Leu Asn Gly Gln Val Leu Arg
    2345            2350            2355

Pro Met Asp Tyr Arg Ser Ala Gly Ile Ile Gly Glu Phe Arg Pro
    2360            2365            2370

Val Ala Cys Gly Val Cys Asp Ala Asp Val Arg Cys Phe Ala Ala
    2375            2380            2385

Ala Thr Arg Ala Met Ser Gly Ser Cys Gly Cys Arg Cys Ala Glu
    2390            2395            2400

Gly Gly His Gly Arg Asp Cys Leu Pro Val Tyr Leu Pro His Val
    2405            2410            2415

Asp Gly Cys Asn Arg Thr Pro Gly Met Pro Pro Leu Ser His Thr
    2420            2425            2430

Ala Thr Leu Thr Glu Thr Arg Ser Leu Thr Pro Thr Trp Thr Pro
    2435            2440            2445

Ser Leu Ser Ala Ala His Tyr Ser Pro Thr His Tyr Arg Pro Thr

-continued

```
                2450                2455                2460
Glu Thr Gln Arg Val Thr Glu Thr Val Val Leu Pro Leu Thr Arg
2465                2470                2475
Thr Pro Thr Ala Ser Val Ser Ser Thr Leu Trp Trp Ser Asp Val
2480                2485                2490
Ala Cys Pro Thr Leu Ala Val Thr Thr Thr Ala Ala Gly Gly Ser
2495                2500                2505
Leu Thr Gln Asn Asp Ile Arg Gly Gly Gly Ser Ala Val Pro Thr
2510                2515                2520
Arg Leu Met Val Ala Leu Pro Pro Pro Phe Arg Trp Ala Arg Asp
2525                2530                2535
Pro Gln Leu Gly Thr His Leu Ser Phe Val Pro Val Ser Thr Ala
2540                2545                2550
Gln Pro Arg Gly Phe Gly Gly Pro Trp Gly Ala Met Leu Ser Asn
2555                2560                2565
Ala Thr Trp Val Arg Asn Ala Thr Asn Pro Ser Thr Val Leu Glu
2570                2575                2580
Leu Ala Val Pro Val His Arg Gly Tyr Phe Ile Ala Ala Asp Glu
2585                2590                2595
Thr Leu Val Ile Arg Cys Asp Ala Val Ala Val Ser Gly Gly Cys
2600                2605                2610
Lys Gly Val Leu Leu Gly Ser Phe Thr Ile Arg Ser Asn Thr Leu
2615                2620                2625
Pro Ala Ala Ala Ser Ala Leu Ser Ala Ile Thr Gly Val Val Ala
2630                2635                2640
Gly Ala Ala Ala Val Gly Val Val Val Thr Gly Gly Leu Gly Ser
2645                2650                2655
Ile Leu Glu Met Gln Ala Leu Gly Val Phe Ala Arg Met Ser Cys
2660                2665                2670
Ala Ser Ala Gln Glu Arg Ala Ser Thr Val Ala Leu Pro Tyr Phe
2675                2680                2685
Leu Ser Val Phe Ala Ala Leu Asp Pro Leu Trp Met Val Val Gly
2690                2695                2700
Asn Ala Leu Leu Ala Ala Val Phe Gly Cys Val His Cys Gly Val
2705                2710                2715
Thr Ala Ala Phe Gln Arg Trp Arg Gly Val Asp Ala Ala Ser Ala
2720                2725                2730
Trp Ala Ala Met Arg Phe Pro Ser Leu Thr Tyr Val Val Ala His
2735                2740                2745
Ala Met His Leu Gly Ile Phe Phe Gly Ser Val Leu Ala Leu Ala
2750                2755                2760
Met Pro Asp Ala Arg Val His His Arg Val Val Gly Val Val Gly
2765                2770                2775
Val Leu Tyr Gly Val Ala Phe Pro Ala Gly Val Cys Tyr Leu Ile
2780                2785                2790
Ala Arg His Val Gly Ala Ser Phe Thr Arg Tyr Trp Gln Phe Ser
2795                2800                2805
Arg Lys Pro Leu His Glu Arg Leu Leu Tyr Pro Val Gly Tyr Trp
2810                2815                2820
His Pro Ala Val Gln Gln Arg Met Tyr Gly Gly Met Leu Thr Asn
2825                2830                2835
Met Arg Gly Ser His Val Tyr Trp Cys Val Phe Gln Leu Ser Val
2840                2845                2850
```

Leu Cys Val Val Cys Leu Ile Ala Ala Val His Pro Pro Val Gly
2855                2860                2865

Gly Cys His Val Leu Tyr Phe Cys Met Ala Ala Val Leu Leu Ala
2870                2875                2880

Gly Ala Gly Val Val Ala Phe Thr Asn Met Met Arg Ser Ala Phe
2885                2890                2895

Leu Thr Val Met Gln Thr Ala Ser Phe Val Leu Ala Ala Leu
2900                2905                2910

Cys Val Ile Ser Ala Ala Asn His Leu Ala Pro Ser Asp Gly Gly
2915                2920                2925

Ala Arg Ala Tyr Ala Ala Ile Val Leu Leu Leu Thr Thr Val Val
2930                2935                2940

Leu Ala Val Thr Val Tyr Ser Val Val Val Trp Tyr Ala Glu Asp
2945                2950                2955

His His Trp Gln Glu Leu Arg Glu Pro Arg Arg Gly Gly Leu Glu
2960                2965                2970

Ala Leu Leu Arg Asp Asp Glu Glu Ser Asp Glu Thr Gln Lys
2975                2980                2985

Pro His Asp Met Ala Ser Ser Tyr Ala Ser Gly Thr Thr Val
2990                2995                3000

Ala Ser Ser Tyr Arg Pro Pro Ala Pro Ser Leu Gln Leu Met Ala
3005                3010                3015

Val Thr Pro Ala Arg Pro Cys Ile Gln Cys Glu Leu Gln His
3020                3025                3030

<210> SEQ ID NO 64
<211> LENGTH: 257
<212> TYPE: PRT
<213> ORGANISM: Trypanosoma cruzi

<400> SEQUENCE: 64

Met Pro Ala Lys Ser Ala Asn Lys Pro Ala Ser Lys Pro Ala Ser Lys
1               5                   10                  15

Pro Ala Ala Lys Pro Ala Ala Lys Pro Ala Ala Lys Ala Pro Ala Pro
                20                  25                  30

Lys Ala Glu Lys Lys Gly Ala Ala Lys Ala Pro Ala Pro Lys Ala Ala
            35                  40                  45

Ala Pro Ala Pro Lys Ala Ala Ala Ala Ala Pro Lys Pro Ala Val Arg
        50                  55                  60

Asp Ala Lys Gln Arg Ser Asp Ala Ala Asn His Asn Gly Leu Tyr Val
65                  70                  75                  80

Lys Asn Trp Gly Gln Gly Ser Val Asp Asp Ala Arg Ala Leu Phe Gly
                85                  90                  95

Thr Ala Gly Lys Val Val Gly Val Arg Val Arg Arg Arg Tyr Ala
            100                 105                 110

Ile Ile Phe Phe Glu Asn Ala Ala Ala Val Lys Lys Ala Ile Asp Leu
        115                 120                 125

Phe Asn Gly Lys Glu Phe Met Gly Asn Val Leu Ser Val Val Pro Ala
130                 135                 140

Lys Thr Thr Pro Lys Pro Asp Pro His Ala Asn Ser Ser Val Val Phe
145                 150                 155                 160

Val Ser Pro Ile Phe Arg Ala Ser Thr Thr Lys Lys Gln Ile Leu Glu
                165                 170                 175

Leu Phe Ser Gly Met Lys Val Leu Arg Leu Arg Thr Tyr Arg Asn Asn
            180                 185                 190

Tyr Ala Tyr Val Tyr Leu Asp Thr Pro Ala Ala Gln Arg Ala Val
        195                 200                 205

Lys Glu Lys Asn Gly Ala Glu Phe Arg Gly Lys Gln Leu Arg Val Ala
    210                 215                 220

Leu Ser Thr Arg Ser Leu Ala Lys Asp Arg Ala Arg Ala Glu Arg Ala
225                 230                 235                 240

Arg Leu Leu Met Ala Ala Gln Lys Phe Asn Lys Arg Lys Asn His Thr
                245                 250                 255

Lys

<210> SEQ ID NO 65
<211> LENGTH: 134
<212> TYPE: PRT
<213> ORGANISM: Trypanosoma cruzi

<400> SEQUENCE: 65

Met Ala Asp Asn Ala Met Thr Arg Gly Ser Arg Ala Cys Tyr Asn Cys
1               5                   10                  15

Gly Gln Pro Gly His Leu Ser Arg Glu Cys Pro Thr Arg Pro Pro Gly
            20                  25                  30

Val Met Gly Asp Arg Ala Cys Tyr Asn Cys Gly Arg Met Gly His Leu
        35                  40                  45

Ser Arg Glu Cys Pro Thr Arg Pro Pro Gly Val Met Gly Asp Arg Ala
    50                  55                  60

Cys Tyr Asn Cys Gly Arg Met Gly His Leu Ser Arg Glu Cys Pro Asn
65                  70                  75                  80

Arg Pro Ala Gly Gly Phe Arg Gly Val Ala Arg Gly Ala Cys Tyr His
                85                  90                  95

Cys Gln Gln Glu Gly His Leu Ala Arg Asp Cys Pro Asn Ala Pro Pro
            100                 105                 110

Gly Gly Glu Arg Ala Cys Tyr Asn Cys Gly Gln Thr Gly His Thr Ser
        115                 120                 125

Arg Ala Cys Pro Val Lys
    130

<210> SEQ ID NO 66
<211> LENGTH: 222
<212> TYPE: PRT
<213> ORGANISM: Trypanosoma cruzi

<400> SEQUENCE: 66

Met Ser Val Lys Asp Val Asn Lys Arg Ser Gly Glu Leu Glu Gly Lys
1               5                   10                  15

Leu Lys Gly Lys Leu Phe Leu Gly Gly Thr Lys Pro Ser Gln Glu Asp
            20                  25                  30

Val Lys Leu Phe Asn Asp Leu Leu Gly Ala Glu Asn Thr Ser Leu Tyr
        35                  40                  45

Arg Trp Val Lys His Met Ala Ser Phe Thr Glu Ala Glu Arg Lys Ala
    50                  55                  60

Trp Gly Ala Pro Val Lys Val Thr Ala Thr Ser Ala Ser Ala Pro
65                  70                  75                  80

Ala Lys Gln Ala Pro Lys Lys Ala Ala Ser Ala Pro Ala Lys Gln Ala
                85                  90                  95

Asp Glu Asp Glu Asp Ile Asp Leu Phe Gly Glu Ala Thr Glu Glu Glu
            100                 105                 110

Thr Ala Ala Leu Glu Ala Lys Lys Lys Lys Asp Ala Asp Ala Lys Lys
        115                 120                 125

```
Ala Lys Lys Glu Val Ile Ala Lys Ser Ser Ile Leu Phe Asp Val Lys
    130                 135                 140

Pro Trp Asp Asp Thr Val Asp Leu Gln Ala Leu Ala Asp Lys Leu His
145                 150                 155                 160

Ala Val Lys Arg Asp Gly Leu Leu Trp Gly Asp His Lys Leu Val Pro
                165                 170                 175

Val Ala Phe Gly Val Lys Lys Leu Gln Gln Leu Ile Val Ile Glu Asp
            180                 185                 190

Asp Lys Val Ser Ser Asp Asp Leu Glu Glu Leu Ile Met Ser Phe Glu
        195                 200                 205

Asp Glu Val Gln Ser Met Asp Ile Val Ala Trp Asn Lys Ile
    210                 215                 220

<210> SEQ ID NO 67
<211> LENGTH: 675
<212> TYPE: PRT
<213> ORGANISM: Trypanosoma cruzi
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid
<220> FEATURE:
<221> NAME/KEY: misc_feature
<222> LOCATION: (143)..(143)
<223> OTHER INFORMATION: Xaa can be any naturally occurring amino acid
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<222> LOCATION: (166)..(166)
<223> OTHER INFORMATION: Xaa can be any naturally occurring amino acid
<220> FEATURE:
<221> NAME/KEY: misc_feature
<222> LOCATION: (209)..(209)
<223> OTHER INFORMATION: Xaa can be any naturally occurring amino acid
<220> FEATURE:
<221> NAME/KEY: misc_feature
<222> LOCATION: (213)..(214)
<223> OTHER INFORMATION: Xaa can be any naturally occurring amino acid
<220> FEATURE:
<221> NAME/KEY: misc_feature
<222> LOCATION: (275)..(275)
<223> OTHER INFORMATION: Xaa can be any naturally occurring amino acid

<400> SEQUENCE: 67

Met Gln Gly Gly Gly Gly Cys Thr Gly Gly Asp Asn Asp Ala
1               5                   10                  15

Xaa Cys Arg Trp Gly Gly Ala Glu Ala Cys Glu Gly Arg Glu Asp Xaa
                20                  25                  30

Gly Trp Lys Trp Thr Gly Ala Val Glu Glu Gly Gly Gly Ala Asp Cys
            35                  40                  45

Ala Phe Ser Gly Glu Gly Lys Gly Gly Gly Gly Gly Xaa Glu Gly
        50                  55                  60

Gly Ser Gly Gly Ala Glu Asn Pro Gly Ser Ser Arg Glu Gly Ser Ser
```

```
            65                  70                  75                  80
Gly Ala Asp Leu Gly Thr Arg Cys Cys Arg Asn Gly Gln Cys Ala Ala
                    85                  90                  95

Ala Ala Ala Gly Glu Gly Gly Glu Ala Lys Ser Glu Gly Gln Gly
                100                 105                 110

Glu Asp Leu Arg Trp Lys Xaa Thr Arg Glu Cys His Glu Gly Cys
            115                 120                 125

Val Ala Gly Val Gly Gly Val Leu Cys Cys Gly Ser Phe Gln Xaa Arg
        130                 135                 140

Asn Xaa Ser Trp Gln Trp His Phe Phe Phe Leu Tyr Phe Lys Ile Asp
145                 150                 155                 160

Tyr Cys Tyr Gly Asn Xaa Asp Phe Leu Cys Met Asn Gly Asp Val Ile
                165                 170                 175

Tyr Leu Cys Val Cys Gly Trp Val Leu Phe Thr Ser Thr Phe Ile Cys
                180                 185                 190

Thr Ala Phe Cys Cys Arg Phe Phe Leu Ile Leu Leu Lys Phe Leu Lys
                195                 200                 205

Xaa Asn Ser Phe Xaa Xaa Ala Cys Val Ser Val Met Tyr Phe Phe Gly
    210                 215                 220

Phe Phe Phe Phe Leu Leu Leu Phe Leu Phe Val Leu Phe Gly Ser Cys
225                 230                 235                 240

Thr Ala Pro His Leu Asn Phe Gly Gln Leu Pro Leu Arg Leu Leu Thr
                245                 250                 255

Phe Trp Met Pro Leu Phe Ile Val Phe Phe Phe Ser Phe Phe Leu Leu
                260                 265                 270

Leu Leu Xaa Gly Lys Phe Cys Val Ile Phe Phe Glu Leu Tyr Leu Phe
            275                 280                 285

Phe Phe Phe Cys Phe Gln Cys Val Phe Tyr Val Leu Arg Ser Ala Gly
        290                 295                 300

Asp Leu Thr Cys Asp Pro Val Phe Phe Leu Cys Phe Phe Phe Phe
305                 310                 315                 320

Arg Leu Gln Glu Cys Ala Ile Gln Lys Thr Phe Met Thr Arg Asn Arg
                325                 330                 335

Pro Phe Phe Ser Leu Leu Leu Leu Ser Cys Ser Val Ile Val Gly
                340                 345                 350

Ala Asn Ser Leu Glu Lys Lys Ala Ala Thr Pro Gly Lys Ala Glu Gly
            355                 360                 365

Ala Gln Pro Gln Ser Ile Ser Pro Ser Ser Ser Pro Gly Asp Arg
        370                 375                 380

Thr Gly Val Pro Leu Lys Leu Glu Leu Gly Glu Leu Arg Asp Lys Thr
385                 390                 395                 400

Leu Leu Thr Ala Lys Asp Ala Phe Gly Asn Thr Thr Gly Ala Ala Leu
                405                 410                 415

Gln Cys Met Gln Ala Lys Thr Asp Val Glu Glu Thr Lys Lys Tyr Ala
                420                 425                 430

Glu Glu Ala Lys Lys Leu Phe Asp Lys Ile Gly Arg Asp Tyr Val Ser
            435                 440                 445

Lys Ser Ala Ala Leu Ala Asp Ala Val Asn Ala Ser Thr Asp Ala Glu
    450                 455                 460

Glu Ala Leu Lys Ser Cys Val Glu Ala Glu Lys Ala Ala Val Asp Ala
465                 470                 475                 480

Asp Thr Ala Val Leu Ala Ala Leu Leu Glu Val Leu Gln His Ser Lys
                485                 490                 495
```

```
Phe Trp Arg Arg Asp Thr Ala Val Ser Thr Glu Lys Leu Ala Asn Val
                500                 505                 510

Ser Lys His Ser Ala Asn Ala Thr Asn Glu Ala Gln Lys Ala Glu Ile
        515                 520                 525

Gln Ala Ser Lys Ala Ala Glu Ala Ala Lys Arg Ala Ala Glu Ser Lys
    530                 535                 540

Lys Lys Ala Ala Ala Ala Leu Asp Thr Val Lys Glu Val Val Ala Met
545                 550                 555                 560

Ala Glu Met Leu Lys Lys Lys Phe Phe Glu Asn Glu Arg Leu Gln Lys
                565                 570                 575

Glu Lys His Lys Ala Gln Leu Glu Ala Glu Arg Arg Phe Ile Gln Glu
        580                 585                 590

Lys Leu Glu Lys Lys Glu Ala Glu Val Lys Lys Ala Leu Asn Arg Ala
    595                 600                 605

Ala Ala Ala Asp Lys Arg Val Ala Glu Leu Glu Arg Ala Arg Gln Lys
    610                 615                 620

Gln Ser Lys Glu Gln Gly Asn Glu Gly Ser Gly His Arg Arg Val Arg
625                 630                 635                 640

Arg Ser Gly Ser Asp Ser Ser Ser His Tyr Ala Pro Ala Tyr Glu Pro
                645                 650                 655

Arg Leu Leu Leu Pro Leu Leu Ser Phe Thr Leu Phe Cys Phe Val
        660                 665                 670

Ala Trp Cys
        675

<210> SEQ ID NO 68
<211> LENGTH: 235
<212> TYPE: PRT
<213> ORGANISM: Trypanosoma cruzi

<400> SEQUENCE: 68

Cys Val Gln Ala Gly Met Ser Ala Lys Asn Ala Arg Glu His Glu Glu
1               5                   10                  15

Gly Ala Lys Asn Ala Leu Arg Lys Leu Gly Ser Glu Ala Thr Arg Met
                20                  25                  30

Ser Arg Ala Leu Gln Gln Ala Glu Glu Ala Val Lys Leu Ala Asp Ala
        35                  40                  45

Ala Val Ala Glu Cys Lys Ala Ala Glu Glu Ala Gln Ala Ala Gly
    50                  55                  60

Ile Met Thr Leu Asp Ala Val Gly Glu Val Leu Lys His Val Lys Asp
65                  70                  75                  80

Glu Lys Thr Lys Val Gly Ser Gly Pro Glu Leu Leu Lys Arg Ala Ala
                85                  90                  95

Glu Gln Thr Val Leu Ser Leu Glu Lys Ala Lys Glu Ala Glu Ala Glu
            100                 105                 110

Ser Glu Lys Ala Ala Ala Ala Arg Lys Thr Leu Glu Ala Ala Glu
        115                 120                 125

Lys Ala Ala Ala Ala Arg Thr Leu Ala Gln Asp Val Ala Ala Thr Ala
    130                 135                 140

Ser Ala Leu Leu Arg Gln Arg Glu Arg Glu Glu Arg Arg Ala
145                 150                 155                 160

Lys Asp Arg Glu Ala Ala Glu Ala Ala Lys Lys Ala Ala Ile Ala Glu
                165                 170                 175

Val Met Lys Lys Phe Ala Ala Lys Lys Gly Asn Asp Ala Ala Ser Gly
            180                 185                 190
```

```
Arg Asn Ser Thr Ala Thr Arg Ile Gln Arg Thr Arg Pro Arg Val Asp
        195                 200                 205

Gly Gly Gly Ile Pro Leu Leu Leu Arg Ala Pro Leu Leu Met Val Ala
        210                 215                 220

Ala Val Ala Ser Val Phe Gly Phe Leu Leu Cys
225                 230                 235

<210> SEQ ID NO 69
<211> LENGTH: 152
<212> TYPE: PRT
<213> ORGANISM: Trypanosoma cruzi

<400> SEQUENCE: 69

Met Ser Ile Glu Ser Ala Phe Tyr Ala Phe Ala Ser Phe Gly Gly Ala
1               5                   10                  15

Pro Thr Lys Glu Met Asp Asn Ala His Phe Ser Lys Met Leu Lys Glu
            20                  25                  30

Thr Lys Val Ile Gly Lys Gln Phe Thr Ser Thr Asp Ala Asp Leu Leu
        35                  40                  45

Phe Asn Lys Val Lys Ala Lys Gly Ala Arg Lys Ile Thr Leu Ser Asp
50                  55                  60

Phe Val Asp Lys Ala Val Pro Glu Ile Ala Ser Lys Leu Lys Lys Ser
65                  70                  75                  80

Val Glu Glu Leu Ile Ala Asp Ile Ser Ser Cys Ser Pro Glu Ala Arg
                85                  90                  95

Ala Thr Lys Ala Asp Ala Val Lys Phe His Asp Asp Lys Asn Met Tyr
            100                 105                 110

Thr Gly Val Tyr Lys Ala Gly Gly Pro Thr Asn Val Asp Arg Asn Ser
        115                 120                 125

Gly Ser Leu Ser Gly Val Val Asp Arg Arg Val Ala Gln Thr Asp Val
    130                 135                 140

Cys Gly Thr Thr Ala Ser Gln Lys
145                 150

<210> SEQ ID NO 70
<211> LENGTH: 211
<212> TYPE: PRT
<213> ORGANISM: Trypanosoma cruzi

<400> SEQUENCE: 70

Met Gly Ala Cys Gly Ser Lys Gly Ser Thr Ser Asp Lys Gly Leu Ala
1               5                   10                  15

Ser Asp Lys Asp Gly Lys Asn Ala Lys Asp Arg Lys Glu Ala Trp Glu
            20                  25                  30

Arg Ile Arg Gln Ala Ile Pro Arg Glu Lys Thr Ala Gly Ala Lys Gln
        35                  40                  45

Arg Arg Ile Glu Leu Phe Lys Lys Phe Asp Lys Asn Glu Thr Gly Lys
50                  55                  60

Leu Cys Tyr Asp Glu Val His Ser Gly Cys Leu Glu Val Leu Lys Leu
65                  70                  75                  80

Asp Glu Phe Thr Pro Arg Val Arg Asp Ile Thr Lys Arg Ala Phe Asp
                85                  90                  95

Lys Ala Arg Ala Leu Gly Ser Lys Leu Glu Asn Lys Gly Ser Glu Asp
            100                 105                 110

Phe Val Glu Phe Leu Glu Phe Arg Leu Met Leu Cys Tyr Ile Tyr Asp
        115                 120                 125

Phe Phe Glu Leu Thr Val Met Phe Asp Glu Ile Asp Ala Ser Gly Asn
```

-continued

```
            130                 135                 140
Met Leu Val Asp Glu Glu Phe Lys Arg Ala Ala Pro Lys Leu Glu
145                 150                 155                 160

Ala Trp Gly Ala Lys Val Glu Asp Pro Ala Ala Leu Phe Lys Glu Leu
                165                 170                 175

Asp Lys Asn Gly Thr Gly Ser Val Thr Phe Asp Glu Phe Ala Ala Trp
            180                 185                 190

Ala Ser Ala Val Lys Leu Asp Ala Asp Gly Asp Pro Asp Asn Val Pro
                195                 200                 205

Glu Ser Ala
    210

<210> SEQ ID NO 71
<211> LENGTH: 233
<212> TYPE: PRT
<213> ORGANISM: Trypanosoma cruzi

<400> SEQUENCE: 71

Met Leu Arg Arg Ala Val Asn Ile Ser Ile Ala Arg Gly Arg Met Ala
1               5                   10                  15

Leu Met Ser Tyr Ala Thr Leu Pro Asp Leu Leu Lys Pro Ser Gly Ala
            20                  25                  30

Pro Ala Glu Leu Pro Lys Leu Gly Phe Asn Trp Lys Asp Gly Cys Ala
        35                  40                  45

Pro Val Phe Ser Pro Arg Gln Met Glu Leu His Tyr Thr Lys His His
    50                  55                  60

Lys Ala Tyr Val Asp Lys Leu Asn Ala Leu Ala Gly Thr Thr Tyr Asp
65                  70                  75                  80

Gly Lys Ser Ile Glu Glu Ile Ile Leu Ala Val Ala Asn Asp Ala Glu
                85                  90                  95

Lys Lys Gly Leu Phe Asn Gln Ala Ala Gln His Phe Asn His Thr Phe
            100                 105                 110

Tyr Phe Arg Cys Ile Thr Pro Asn Gly Lys Ala Met Pro Lys Ser Leu
        115                 120                 125

Glu Ser Ala Val Thr Ala Gln Phe Gly Ser Val Glu Gln Phe Lys Asp
    130                 135                 140

Ala Phe Val Gln Ala Gly Val Asn Asn Phe Gly Ser Gly Trp Thr Trp
145                 150                 155                 160

Leu Cys Val Asp Pro Ser Asn Lys Asn Gln Leu Val Ile Asp Asn Thr
                165                 170                 175

Ser Asn Ala Gly Cys Pro Leu Thr Lys Gly Leu Arg Pro Val Leu Ala
            180                 185                 190

Val Asp Val Trp Glu His Ala Tyr Tyr Lys Asp Phe Glu Asn Arg Arg
        195                 200                 205

Pro Asp Tyr Leu Lys Glu Ile Trp Ser Val Ile Asp Trp Glu Phe Val
    210                 215                 220

Ala Lys Met His Ala Gln Ala Ile Lys
225                 230

<210> SEQ ID NO 72
<211> LENGTH: 114
<212> TYPE: PRT
<213> ORGANISM: Trypanosoma cruzi

<400> SEQUENCE: 72

Ser Thr Arg Ala Arg Val Phe Thr Val Leu Ala Phe Pro Cys Asn Gln
1               5                   10                  15
```

-continued

```
Phe Ala Gly Gln Glu Pro Gly Thr Ala Leu Glu Val Lys Glu Phe Ala
            20                  25                  30

Cys Thr Arg Phe Lys Ala Asp Phe Pro Ile Met Ala Lys Ile Asp Val
        35                  40                  45

Asn Gly Ser Lys Ala His Pro Leu Tyr Glu Phe Met Lys Ala Thr Ile
 50                  55                  60

Pro Gly Leu Phe Gly Thr Lys Ala Ile Lys Trp Asn Phe Thr Ser Phe
 65                  70                  75                  80

Leu Ile Asp Arg His Gly Val Pro Val Glu Arg Phe Ser Pro Gly Ala
                85                  90                  95

Ser Val Glu Asp Ile Glu Lys Lys Leu Leu Pro Leu Leu Gly Ala
               100                 105                 110

Arg Ile
```

<210> SEQ ID NO 73
<211> LENGTH: 556
<212> TYPE: PRT
<213> ORGANISM: Trypanosoma cruzi

<400> SEQUENCE: 73

```
Met Asp Ala Thr Glu Leu Lys Asn Arg Gly Asn Gln Glu Phe Ser Ser
 1               5                  10                  15

Gly Arg Tyr Lys Glu Ala Ala Glu Phe Phe Ser Gln Ala Ile Asn Leu
            20                  25                  30

Asp Pro Ser Asn His Val Leu Tyr Ser Asn Arg Ser Ala Cys His Ala
        35                  40                  45

Ala Leu His Gln Tyr Pro Asn Ala Leu Gln Asp Ala Glu Lys Cys Val
 50                  55                  60

Ser Ile Lys Pro Asp Trp Val Lys Gly Tyr Val Arg Lys Gly Ala Ala
 65                  70                  75                  80

Leu His Gly Leu Arg Arg Tyr Glu Glu Ala Ala Ala Tyr Asn Lys
                85                  90                  95

Gly Leu Ser Leu Asp Pro Ser Ser Ala Ala Cys Thr Glu Gly Ile Ala
               100                 105                 110

Ala Val Glu Lys Asp Lys Val Ala Ser Arg Met Gln Asn Pro Phe Ala
           115                 120                 125

Asn Val Phe Gly Pro Asp Ala Ile Gly Lys Ile Gln Ala His Pro Lys
       130                 135                 140

Leu Ser Leu Phe Leu Leu Gln Pro Asp Tyr Val Arg Met Ile Asp Glu
145                 150                 155                 160

Val Met Lys Asp Pro Ser Ser Val Gln Lys Tyr Leu Lys Asp Gln Arg
               165                 170                 175

Phe Met Ala Thr Phe Met Val Leu Ser Gly Leu Glu Leu Pro Glu Asp
           180                 185                 190

Glu Asp Glu Glu Glu Lys Val Arg Arg Gln Gln Lys Gln Lys
       195                 200                 205

Glu Lys Glu Met Arg Glu Gln Lys Lys Arg Ala Ala Ala Thr
   210                 215                 220

Glu Leu Ser Ser Glu Ala Lys Glu Ala Leu Arg Lys Lys Glu Glu Gly
225                 230                 235                 240

Asn Ala Leu Tyr Lys Gln Arg Lys Phe Asp Glu Ala Leu Gln Lys Tyr
               245                 250                 255

Gln Glu Ala Leu Ala Lys Asp Ser Thr Asn Thr Val Tyr Leu Leu Asn
           260                 265                 270
```

```
Ile Thr Ala Val Ile Phe Glu Lys Gly Glu Tyr Ala Ala Cys Val Glu
        275                 280                 285

Lys Cys Glu Glu Ala Leu Glu His Gly Arg Glu Asn Arg Cys Asp Tyr
290                 295                 300

Thr Val Leu Ala Lys Leu Met Thr Arg Glu Ala Leu Cys Leu Gln Arg
305                 310                 315                 320

Leu Lys Arg Phe Asp Glu Ala Ile Ala Leu Phe Lys Lys Ala Leu Val
                325                 330                 335

Glu His Arg Asn Ala Asp Thr Leu Ala Lys Leu Thr Ala Cys Glu Lys
            340                 345                 350

Glu Lys Glu Lys Phe Glu Ile Glu Ala Tyr Leu Asp Pro Glu Ile Ala
        355                 360                 365

Leu Gln Lys Lys Glu Gly Asn Thr Phe Phe Lys Ser Asp Lys Phe
370                 375                 380

Pro Glu Ala Val Glu Ala Tyr Thr Glu Ala Ile Lys Arg Asn Pro Asp
385                 390                 395                 400

Glu His Thr Thr Tyr Ser Asn Arg Ala Ala Tyr Leu Lys Leu Gly
            405                 410                 415

Ala Tyr Ser Gln Ala Leu Ala Asp Ala Glu Lys Cys Ile Ser Leu Lys
            420                 425                 430

Pro Glu Phe Val Lys Ala His Ala Arg Arg Gly His Ala Phe Phe Trp
            435                 440                 445

Thr Lys Gln Tyr Asn Lys Ala Leu Gln Ala Tyr Asp Glu Gly Leu Lys
        450                 455                 460

His Asp Lys Glu Asn Ala Glu Cys Lys Glu Gly Arg Met Arg Thr Leu
465                 470                 475                 480

Met Lys Ile Gln Glu Met Ala Thr Gly Asn Ser Ala Asp Gly Asp Glu
                485                 490                 495

Val Ala Lys Arg Ala Met Ala Asp Pro Glu Val Ala Ala Ile Met Gln
            500                 505                 510

Asp Ser Tyr Met Gln Leu Val Leu Gly Glu Met Gln Arg Asp Pro Ser
        515                 520                 525

Arg Val Gln Glu Tyr Met Arg Asp Pro Thr Ile Ala Ala Lys Ile Asn
530                 535                 540

Thr Leu Ile Ser Ala Gly Ile Ile Arg Phe Gly Lys
545                 550                 555

<210> SEQ ID NO 74
<211> LENGTH: 396
<212> TYPE: PRT
<213> ORGANISM: Trypanosoma cruzi

<400> SEQUENCE: 74

Met Ala Ala Arg Ser Met Asp His Thr Gln Trp Leu Ala Lys Leu Val
1               5                   10                  15

Ala Phe Asp Thr Thr Ser Arg Asn Ser Asn Leu Glu Leu Ile His Tyr
                20                  25                  30

Cys Lys Asp Tyr Leu Glu Gly Leu Gly Val Lys Cys Thr Leu Leu His
            35                  40                  45

Asn Ala Glu Arg Asn Lys Ala Asn Leu Trp Ala Thr Leu Pro Gly Asp
        50                  55                  60

Gly Gly Val Thr Lys Gly Gly Ile Ile Leu Ser Gly His Thr Asp Val
65                  70                  75                  80

Val Pro Val Asp Gly Gln Lys Trp Asp Ser Asp Pro Phe Thr Leu Thr
                85                  90                  95
```

```
Glu Arg Asp Gly Lys Leu Tyr Gly Arg Gly Thr Ser Asp Met Lys Gly
                100                 105                 110

Phe Val Ala Val Cys Met Ser Leu Ala Pro Glu Leu Leu Lys Met Lys
            115                 120                 125

Arg Ala Lys Pro Ile His Phe Ala Trp Ser Tyr Asp Glu Glu Val Ser
        130                 135                 140

Cys Leu Gly Gly Met Glu Leu Ala Glu Phe Ala Arg Asp His Asp Val
145                 150                 155                 160

Arg Ala Glu Gly Cys Ile Ile Gly Glu Pro Thr Gly Met Thr Val Val
                165                 170                 175

Ile Ala His Lys Gly Thr Ser His Phe Trp Val Arg Val Arg Gly Lys
            180                 185                 190

Ala Ala His Ser Ser Leu Ala Leu Thr Gly Glu Ser Cys Asn Ala Ile
        195                 200                 205

Asp Tyr Ala Thr Lys Leu Ile Thr Lys Leu Arg Glu Ile Ala Glu Glu
210                 215                 220

Tyr Arg Arg Asn Gly Thr Arg His Asp Phe Gln Val Pro Phe Ser Thr
225                 230                 235                 240

Leu Ser Thr Asn Leu Ile Ser Gly Gly Asn Ala Ser Asn Thr Val Pro
                245                 250                 255

Ala Glu Cys Glu Phe Leu Phe Glu Phe Arg Ala Leu Pro Asn Glu Thr
            260                 265                 270

Val Ser Lys Met Met Gln Gln Val Arg Ser Tyr Val Glu Thr Gln Leu
        275                 280                 285

Leu Pro Ala Met Lys Ala Glu Phe Glu Asp Ala Glu Ile Val Ile Thr
290                 295                 300

Pro Arg Asp Glu Thr Pro Ser Phe Glu Gly Ser Glu Glu Ala Pro Ile
305                 310                 315                 320

Thr Lys Leu Ala Cys Ala Ile Ile Asn Asp Tyr Lys Val Trp Lys Lys
                325                 330                 335

Asn Tyr Cys Thr Glu Ala Gly His Tyr Ser Gly Ile Ala Gly Ala Pro
            340                 345                 350

Thr Val Ile Cys Gly Pro His Gly Gly Ala Ile His Cys Ala Asn Glu
        355                 360                 365

Tyr Val Thr Pro Ala Gln Leu Asp Lys Cys Arg Glu Phe Val Leu Arg
370                 375                 380

Val Ala Glu Ser Leu Lys Ala Ser Pro Ala His Leu
385                 390                 395

<210> SEQ ID NO 75
<211> LENGTH: 1125
<212> TYPE: PRT
<213> ORGANISM: Trypanosoma cruzi

<400> SEQUENCE: 75

Met Lys Arg Val Leu Val Leu Asn Val Asp Ser Phe Val Gly Arg Glu
1               5                   10                  15

Val Cys Arg Arg Phe Phe Asp Ala Lys Glu Tyr Leu Val Asp Gly Thr
            20                  25                  30

Leu Tyr His Ser Gln Ser Thr Arg Gly Asn Pro Glu Ala Lys Glu Ser
        35                  40                  45

Leu Arg Thr Asp Gly Leu Asp Ser Ala Gly Thr Met Lys Pro His Cys
    50                  55                  60

Ala Thr Ala Ser Thr Ser Ser Val Arg Leu Asp Val Pro Ala Asp Met
65                  70                  75                  80
```

-continued

Arg Pro Phe Leu Asn Ser Val Met Pro Arg His Gly Asp Ile Ser Asp
                    85                  90                  95

Glu Gln Phe Arg Ala Arg Val Leu Thr Tyr Asp Ile Ile Ala Ile
                100                 105                 110

Leu Glu Glu Asp Ala Phe Glu Ala Asp Cys Thr Ile Lys Val Leu Arg
                    115                 120                 125

Gly Thr His Tyr Glu Val Glu Lys Thr Phe Val Leu Val Ser Asn Val
                130                 135                 140

Phe Thr Trp Thr Gln Thr Asp Ala His Glu Arg Glu Leu Arg Arg Ala
145                 150                 155                 160

Ala Arg Arg Ala Glu Arg Glu Ala Arg Ala Gln Arg Tyr Glu Asp
                    165                 170                 175

Asp Val Ile Glu Glu Glu Glu Glu Glu Glu Glu Glu Glu Glu
                180                 185                 190

Glu Met Glu Gln Lys Val Trp Thr Glu Glu Asp Tyr Arg Gln Arg Tyr
                195                 200                 205

Ser Asp Leu Arg Tyr His Leu Trp Lys Asp Leu Glu His Ala Val Lys
                210                 215                 220

His Ala Asn Ser Glu Thr Leu His Thr Tyr Val Leu Trp Ala Gly Leu
225                 230                 235                 240

Pro Tyr Gly Arg Gly Glu Asp Leu Leu Ala Pro His Phe Asn Ala Ala
                    245                 250                 255

Trp Arg His Gln Glu Met Leu Gln Tyr Gly Asp Gly Ser Asn Tyr Ile
                    260                 265                 270

Pro Thr Ile His Val Lys Asp Leu Ala Arg Ile Ile Tyr Leu Val Gly
                275                 280                 285

Ser Ser Tyr Asp Thr Leu Glu Asp Arg Tyr Met Phe Ala Val Asp Gln
290                 295                 300

Gly Asn Asn Thr Gln Ser Asp Ile Leu Gln Gly Ile Lys Asp Phe Ile
305                 310                 315                 320

Gly Gly Val Val Ser Val Thr Ala Pro Glu Ile Asp Arg Lys Asn Gln
                    325                 330                 335

Val Val Ile Pro Gly Asn Gln Lys Lys Asp Ile Arg Glu Ala Asp Leu
                340                 345                 350

Lys Glu Asn Glu Ser Ala Glu Glu Ile Gln His Glu His Asp Val Leu
                355                 360                 365

Val Glu Leu Gly Met Arg Glu Ala Arg Val Leu Asp Glu Ala Lys Glu
                370                 375                 380

Glu Leu Ser Arg Ile Arg Glu Ile Ser Gln Arg Glu Lys Leu Leu Arg
385                 390                 395                 400

Leu Gly Leu Gly Val Gln Glu Ser Gly Asn Asp Asp Thr Asn His
                    405                 410                 415

Ala Leu Met Pro Glu Ala Ala Ser Lys Val Gly Ala Ser Leu Thr Ile
                420                 425                 430

Ala Pro Pro His Gly Leu Ala Asn Trp Phe Ser Ala Val Asp Met Arg
                435                 440                 445

Cys Glu Pro Gly Ala Val Leu Ala Leu Leu Glu Glu Glu Trp Val
                450                 455                 460

Ser Leu Gly Gly Phe Phe Ala Asn Val Asp Lys Ile Val Gln Glu Phe
465                 470                 475                 480

Lys Ala Ala Arg Gln Leu Arg Pro Met Arg Leu Val Leu Ser Gly Pro
                    485                 490                 495

Pro Leu Ser Lys Val Gly Glu Val Ala Gly Val Leu Ala Glu Leu Phe
                500                 505                 510

-continued

```
Asp Ile Pro His Leu Thr Leu Ala Asn Val Thr Ala Ala Tyr Glu Glu
            515                 520                 525
His Val Arg Ser Leu Arg Glu Glu Leu Ile Gly Ile Leu Val Ser Arg
        530                 535                 540
Gln Leu Arg Arg His Thr Ala Arg Glu Glu Arg Arg Arg Glu Lys
545                 550                 555                 560
Glu Arg Ala Lys Glu Ala Arg Lys Ala Arg Glu Glu Gly Glu
                565                 570                 575
Glu Gly Glu Glu Glu Glu Glu Glu Glu Gly Glu Glu Glu Gly
            580                 585                 590
Glu Glu Glu Gly Glu Gly Ala Glu Glu Glu Glu Lys Gly Glu
        595                 600                 605
Glu Gly Ser Pro Ala Ala Gln Asp Leu Asp Pro Ala Glu Arg Ile Arg
            610                 615                 620
Ala Ala Ile Thr Glu Ala Met Leu Leu His Leu Pro Glu Asp Glu Glu
625                 630                 635                 640
Glu Glu Glu Glu Asp Asp Ser His Tyr Asn Ala Asp Asp Glu Glu
                645                 650                 655
Val Asp Glu Lys Ala Ala Met Ala Gln Gln Val Asp Glu Ala Glu
            660                 665                 670
Arg Arg Ile Ala Thr Leu Arg Glu Glu Tyr Arg Phe Ala Thr Gln
        675                 680                 685
Leu Leu Ser Leu Arg Leu Leu Asn Gly Glu Phe Pro Arg Arg Pro Lys
            690                 695                 700
Ser Ala Asp Glu Glu Glu Gly Glu Glu Glu Glu Tyr Asp Glu
705                 710                 715                 720
Tyr Asp Asp Glu Glu Tyr Met Asn Arg Lys Lys Arg Arg Glu Gln
                725                 730                 735
Lys Lys Asp Val Lys Lys Asp Val Thr Glu Glu Pro Pro Thr Ile
            740                 745                 750
Arg Tyr Phe Asp Glu Val Met Ala Val Met Val Arg Trp Arg Leu Arg
            755                 760                 765
Gln Glu Asp Cys Lys Asn Gln Gly Tyr Ile Leu Glu Ala Phe Pro Glu
770                 775                 780
Thr Val Arg Gln Ala Trp Leu Thr Phe Leu Ala Asp Thr Glu Glu Gln
785                 790                 795                 800
Lys Glu Met Gln Arg Pro Lys Leu Gln Lys Val Arg Asp Glu Glu Ala
                805                 810                 815
Val Pro Gln Pro Leu Leu Asp Ala Asn Phe Pro Leu Pro Val Leu Ala
            820                 825                 830
Asp Leu Glu Glu Asp Arg Lys Gln Glu Ile Met Glu Leu Met Thr Gly
            835                 840                 845
Arg Arg Phe Ala Ser Ala Glu Glu Val Leu Val Pro Thr His Asp Thr
        850                 855                 860
Phe Phe Pro Asp Cys Phe Ile Ala Leu Thr Gly Asn Glu Val Thr Leu
865                 870                 875                 880
Arg Ser Gln Ile Tyr Ala Ala Ile Ala Thr Ala Pro Gly Asp Thr
                885                 890                 895
Thr Pro Asp Phe Ser Gln Phe Thr Arg Tyr Met Thr His Asn Arg
            900                 905                 910
Pro Gly Ala Pro Pro Thr Glu Ser Leu Ile Cys Trp Phe Gln Thr Val
        915                 920                 925
Val Ala Glu Arg Val Asp Glu Asp Gly Asp Val Ala Val Ala Thr Glu
```

```
                930           935           940
Gly Gly Glu Leu Arg Glu Lys Val Pro Arg Lys Ala Cys Val Leu Phe
945                 950                 955                 960

Val Pro Val Phe Ser Thr Phe Pro Ser Ala Val Leu Pro Lys Phe Phe
                965                 970                 975

Asn His Glu Glu Ile Ser Gly Met Lys Ala Tyr Cys Thr Phe Ile Arg
                980                 985                 990

Ser Glu Ile Leu Lys Asn Ile Gly Leu Asp Ser Cys Gly Ser Val Ile
                995                 1000                1005

Asp Ser Met Arg Ala Glu Ala Glu Thr Asn Lys Arg Arg Val Gln
        1010                1015                1020

Glu Leu Ala Ser Glu Lys Glu Lys Leu Glu Lys Leu Ser Thr Ser
        1025                1030                1035

Asp Lys Leu Phe Ala Ala Ala Ala Gln Lys Leu Glu Asp Asp Phe
        1040                1045                1050

Leu Glu Asn Glu Arg Arg Ala Leu Arg Phe Tyr Gln Ala Lys Glu
        1055                1060                1065

Glu Leu Ala Ser Ile Val Gly Ile Asp Ser Ile Pro Val Asp Val
        1070                1075                1080

Tyr Leu Met Arg Tyr Val Met Pro Ser Leu Thr Pro Leu Met Ala
        1085                1090                1095

Glu Val Val Arg Met Arg Pro Glu Asp Pro Val Thr Val Leu Ala
        1100                1105                1110

Asp Ala Leu Phe His His Lys Arg Gln Val Ser Leu
        1115                1120                1125

<210> SEQ ID NO 76
<211> LENGTH: 181
<212> TYPE: PRT
<213> ORGANISM: Trypanosoma cruzi

<400> SEQUENCE: 76

Met Ser Thr Thr Arg Ala Ala Gly Gly Arg Leu Thr Ala Pro Val Arg
1               5                   10                  15

Thr Ala Val Pro Ala Ala Leu Pro Arg Lys Arg Arg Phe Glu Leu Thr
                20                  25                  30

Asp Glu Gln Arg Gln Glu Ile Arg Glu Ala Phe Glu Leu Phe Asp Ser
                35                  40                  45

Asp Lys Asn Gly Leu Ile Asp Val His Glu Met Lys Val Ser Met Arg
        50                  55                  60

Ala Leu Gly Phe Asp Val Lys Lys Asp Glu Val Leu Arg Met Met Gln
65                  70                  75                  80

Asp Cys Ala Ala Arg Asp Gln His Asn Gln Pro Leu Met Asp Leu Ala
                85                  90                  95

Gly Phe Thr Asp Leu Met Thr Glu Arg Phe Ala Gln Arg Asp Pro Arg
                100                 105                 110

Gln Glu Met Ile Lys Ala Phe Gln Leu Phe Asp Glu Asn Asn Thr Gly
                115                 120                 125

Lys Ile Ser Leu Arg Ser Leu Arg Arg Val Ala Arg Glu Leu Gly Glu
        130                 135                 140

Asn Met Thr Asp Glu Glu Leu Gln Ala Met Ile Asp Glu Phe Asp Thr
145                 150                 155                 160

Asp Gln Asp Gly Glu Ile Asn Leu Asp Glu Phe Leu Ala Ile Met Leu
                165                 170                 175

Glu Asp Glu Asp Tyr
```

180

<210> SEQ ID NO 77
<211> LENGTH: 734
<212> TYPE: PRT
<213> ORGANISM: Trypanosoma cruzi

<400> SEQUENCE: 77

Met Tyr Pro Arg Gln Asp Asp Val Ser Leu Leu Gln Arg Tyr Ile Asn
1               5                   10                  15

Asp Asn Lys Leu Glu Glu Lys Gly Val Pro Leu Thr Glu Leu Arg Arg
            20                  25                  30

Leu Glu Gly Thr Gly Gln Val Met Leu Gly Val Asp Gly Thr Lys Ile
        35                  40                  45

Ile Asp Leu Ile Thr Gln Ala Val Arg Glu Lys Glu Lys Met Ala Ile
    50                  55                  60

Tyr Thr Tyr Thr Thr Pro Phe Thr Val Tyr Asp Lys Ile Thr Asp Val
65                  70                  75                  80

Cys Lys Thr Leu Arg Ser Leu Lys Asn Cys Thr Pro Val Leu Val Phe
                85                  90                  95

Asn Gly Ile Pro Phe Tyr Pro Asp Pro Ser Asp Asp Asn Cys Arg Glu
            100                 105                 110

Lys Asn Met Val Pro Pro Asp Val Ala Ala Leu Asn Gly Thr Asp Ser
        115                 120                 125

Ser Arg Leu Cys Asn Met His Ser Met Arg Ala Val Asp Ile Gln Lys
    130                 135                 140

Lys Ser Ser Ser Arg Phe Phe Val Glu Glu Asp Val Glu Asn Gln Ile
145                 150                 155                 160

Val Lys Leu Phe Arg Ser Glu Phe Lys Asp Thr Met Arg Ala Pro Tyr
                165                 170                 175

Leu Ala Trp Ala Gln Leu Ser Ala Phe Cys His Pro Lys Asn Arg His
            180                 185                 190

Ile Ser Glu Val Tyr Gly Cys Leu Glu Leu Leu Ala Phe Pro Gly Ile
        195                 200                 205

Asp Arg Val Ile Thr Asn Ile Asn Val Met Lys Gly Thr Val Asp Met
    210                 215                 220

Val Arg Lys Ser Arg Leu Leu Glu Leu Arg Ile Ser Glu Asp Asp
225                 230                 235                 240

Leu Gly Ser Leu Ile Val Val Asp Ser Arg Asn Arg Val Met Arg Thr
                245                 250                 255

Val Gly Pro Lys Phe Ser Ser Phe Asp Asp Met Cys Lys Lys Ile Thr
            260                 265                 270

Arg Val Asn Asp Leu Ser Leu Gly Ala Ser Tyr Val His Gln Leu His
        275                 280                 285

Gln Glu Ala Met His Leu Ser Glu Gln Ala Arg Asn Arg Thr Leu Asn
    290                 295                 300

Leu Lys Ser Ala Val Leu Arg Asn Leu Ala Ala Leu Gly Cys Pro Val
305                 310                 315                 320

Leu Thr Leu Val Pro Pro Tyr Cys Thr Leu Leu Thr Arg Leu Tyr Glu
                325                 330                 335

Ser Arg Arg Gln Leu Pro Ile Asp Pro Lys Met Val Met Gly Cys Pro
            340                 345                 350

Leu Pro Pro Val Met Tyr Tyr Met Phe Thr Ala Gly Leu Leu Ser Pro
        355                 360                 365

Ser Leu Phe Gly Ala Leu Cys Gln Gly Ser Leu Val Asp Asp Trp Pro

```
            370             375             380
Leu Val Asp Ser Ile Lys Tyr Arg Asp Val Ala Glu Thr Val Leu Pro
385                 390                 395                 400

Leu Arg Val Gln Thr Leu His Gln Leu Ala Ala Ser Leu Arg Met Ser
                405                 410                 415

Asp Phe Gly Met Thr Trp Phe Arg Arg Tyr Asn Ala Phe Leu Ser Arg
            420                 425                 430

Val Ser Lys Val His Ala Pro Pro Glu Ile Gly Leu Asp Ser Trp Asn
                435                 440                 445

Leu Ala Gly Glu Thr Ile Ser Glu Asn Leu Phe Leu Val Asp Val Met
            450                 455                 460

Glu Phe Ser His Leu Ala Val Ser Ser Arg His Ile Ile Tyr Glu Thr
465                 470                 475                 480

Ala Glu Glu Thr Cys Ala Ala Val Leu Leu Gln Ser Leu Asp Leu Leu
                485                 490                 495

Gly Tyr Leu Thr His Glu Thr Arg Asp Asp Gly Glu Asp Val Gln Val
                500                 505                 510

Ser Glu Pro Ser Pro Phe Gly Arg Ala Leu Lys Leu Cys Gly Val Pro
            515                 520                 525

Thr Leu Ser Glu Tyr Val Val Leu Leu Ile Glu Leu Ser Arg Thr Gly
530                 535                 540

Ala Ile Thr Thr Glu Gln Phe Arg Met Thr Ser Glu Glu Ile Ile Pro
545                 550                 555                 560

Arg Asp Ile Pro Pro Glu Ile Val Leu Ala Ser Arg Ile Leu Ser Ile
                565                 570                 575

Ile Pro Leu Asn Val Ser Ser Ser Trp Ser Gly Pro Ile Asp Pro Glu
            580                 585                 590

Leu Ala Ala Phe Ser Met Ile Ser Arg Met Ile Ser Arg Ser Ile Arg
            595                 600                 605

His Leu Leu Glu Ala Met Leu Ala Ile Ile Phe Tyr Gln Gly Arg Thr
            610                 615                 620

Leu Val Pro Leu His Arg Ile Cys Ala Ile Gln Gln Ala Leu Pro Phe
625                 630                 635                 640

Ser Thr Pro Val Glu Phe Gly Gly Val Leu Ile Glu Tyr Val Leu
                645                 650                 655

Met Lys Glu Lys Cys Thr Leu Ser Asp Ile Glu Ala Ala Phe Pro Glu
                660                 665                 670

Cys Asn Tyr Leu Arg His Asp Leu Ala Thr Leu Phe Tyr Phe Trp Glu
                675                 680                 685

Leu Ala Val Cys Val Leu Asn Ser Ile Ala Cys Lys Asp Val Pro Leu
            690                 695                 700

Asp Val Gly Cys Leu His Lys Ala Asn Glu Arg Met Lys Glu Leu Gln
705                 710                 715                 720

Arg Asn Leu Asp Ile Asn Thr Gly Val Arg Glu Thr Tyr Tyr
                725                 730

<210> SEQ ID NO 78
<211> LENGTH: 447
<212> TYPE: PRT
<213> ORGANISM: Trypanosoma cruzi

<400> SEQUENCE: 78

Met Ile Thr Leu Ser Glu Gly Arg Ser Lys Phe Ile Ser Asn Glu Lys
1               5                   10                  15

Phe Gln Glu Val Leu Glu Trp Val Lys Ser Ala Gly Val Asp Arg Arg
```

-continued

```
            20                  25                  30
Ser Asp Gln Glu Ser Thr Ser Cys Ile Leu Phe His Arg Gly Trp Arg
            35                  40                  45
Ala Asp Lys Leu Tyr Leu Leu Asp Gly Ala Asp Val His Cys Leu Ser
            50                  55                  60
His Leu Asn Lys Ser Val Arg Met Ser Val Leu Glu Lys Ser Glu Trp
65                  70                  75                  80
Glu Arg Asp Gln His Arg Gln Lys Arg Glu Gln Ile Lys Glu Arg Met
                    85                  90                  95
Lys Glu Lys Glu Met Arg Tyr Val Leu Thr Lys Tyr Ser Gly Val Phe
                100                 105                 110
Ser Ala Cys Val Ala Val Leu Gly Val Val Ser Val Phe Gly Trp Asn
                115                 120                 125
Phe Lys Asn Tyr Lys Lys Gln Gln Arg Ser Tyr Gln Leu Ala Ile Ala
            130                 135                 140
Ala Ser Ala Leu Ser Gln Pro His Ser Lys Arg Pro Ile Lys Asp Tyr
145                 150                 155                 160
Val His Arg Glu Asp Glu Glu Gln Arg Leu Arg Gln Thr Leu Arg Gln
                165                 170                 175
Gln Asp Leu Ser His Pro Arg Ile Leu Val Phe Ala Gly Phe Tyr Gly
                180                 185                 190
Cys Gly Lys Ser Ile Leu Phe Arg Ser Ala Ile Arg Lys Glu Lys Met
                195                 200                 205
Ala Ala Ala Phe Val Asp Ile Arg Pro Asn Glu Asp Pro Leu Arg Ser
            210                 215                 220
Ile Val Lys Ser Leu Asn Val Gln Asn Ile Asp Ala Cys Gly Asp Leu
225                 230                 235                 240
Leu Asn Phe Ile Gly Glu Ala Ser Asp Arg Ala Arg Lys Ala Met His
                245                 250                 255
Gly Val Thr Pro Leu Phe Val Leu Lys Ile Arg Asp Gly Ser Ser Leu
                260                 265                 270
Leu Arg Ile Tyr Asn Glu Val Val Ala Leu Ala Cys Asp Arg Arg Leu
            275                 280                 285
Cys His Val Ile Ile Glu Val Pro Ile Glu Ser Leu Thr Ile Ala Met
            290                 295                 300
Thr Ala Leu Pro Arg Leu Asp Phe His Leu Val Pro Asn Phe Ser Val
305                 310                 315                 320
Ser Glu Ala Phe Arg Tyr Thr His His Leu Ile Asp Pro Leu Glu Leu
                325                 330                 335
Thr His Phe Val Glu Val Val Gly Thr Asn Ser Asn Asp Leu Asp Glu
                340                 345                 350
Leu Leu Ala Ala Val Arg His Ala His Met Ser Ala Thr Thr Tyr Thr
            355                 360                 365
Asn Gln Lys Leu Val Lys Ala Met Arg Gln Leu Gln Ala Ala Trp Ala
            370                 375                 380
Lys Asp Pro Ser Leu Arg Glu Ala Val Ile Lys Leu Ala Arg Phe Pro
385                 390                 395                 400
Phe Glu Glu Gly Gln Ser Glu Gly Tyr Asp Tyr Ser Ser Leu Arg Asn
                405                 410                 415
Glu Ala Leu Arg Asp Ile Val Met Tyr Asn Ala Val Ala Asp Val Trp
                420                 425                 430
Met Phe Gln Gln Lys Val Phe His Thr Ala Ala Cys Cys Trp Gln
            435                 440                 445
```

-continued

```
<210> SEQ ID NO 79
<211> LENGTH: 565
<212> TYPE: PRT
<213> ORGANISM: Trypanosoma cruzi

<400> SEQUENCE: 79
```

Met His Ser Arg Val Ala Ala Val Lys Ala Pro Arg Thr His Asn Arg
1               5                   10                  15

Arg Arg Val Thr Gly Ser Ser Gly Arg Gly Glu Gly Gly Glu Ser
            20                  25                  30

Glu Pro Pro Arg Pro Asn Met Ser Arg Arg Val Phe Thr Ser Ala Val
            35                  40                  45

Leu Leu Leu Leu Phe Val Leu Met Cys Gly Ala Ala Gly Pro Val Gln
        50                  55                  60

Ala Gln Ser Phe Gly Ala Gly Val Asp Asp Ser Tyr Gly Arg Gln Gly
65                  70                  75                  80

Ser Arg Gln Leu Pro Arg Glu His Gln Ala Ala Asn Pro Pro Ile Pro
                85                  90                  95

Gly His Ile Phe Arg Asn Pro His Leu Val Asn Val Asn Gly Met Leu
            100                 105                 110

Leu Ala Ile Ala Gly Ala Gln Phe Asn Arg Thr Val Gly Ser Gly Ser
        115                 120                 125

Ala Ser Met Gln Leu Thr Ala Gln Leu Ser Val Asn Arg Gly Val Asn
130                 135                 140

Trp Ser Pro Tyr Pro Arg Pro Gly Asp Ile Asp Cys Phe Ala Ala His
145                 150                 155                 160

Pro Tyr Trp Met Ser Phe Pro Ser Ser Phe Gly Pro Phe Gly Ser Leu
                165                 170                 175

Phe Ala Phe Val Glu Gly Tyr Asp Leu Arg Lys Gly Val Arg Pro His
            180                 185                 190

Tyr Ala Asn Arg Trp Gly Gly Ser Gly Val Glu Pro Val Ile His Phe
        195                 200                 205

Leu Asp Thr Arg Pro Gly Gln Ser Gly Gly Leu Ser Met Ser Ser Val
    210                 215                 220

Ser Met Ser Ile Leu Leu Pro Tyr Pro His Lys Ser Gly Asp Met Ile
225                 230                 235                 240

Gly Phe Leu Asn Asp Ala Ser Thr Pro Ile Thr Lys Met Thr Asp Gly
                245                 250                 255

Thr Leu Val Phe Pro Val Gln Phe Leu Thr Met Gly Gly Asp Thr Ala
            260                 265                 270

Ser Thr Ile Met Tyr Met Asn Phe Thr Gln Gln His Trp Thr Phe Ala
        275                 280                 285

Lys Ser Ala Thr His Ala Gly Cys Thr Asn Pro Ser Ile Leu Glu Trp
    290                 295                 300

Glu Asp Gly Lys Ile Ile Met Ile Thr Ser Cys Glu Tyr Gly Arg Arg
305                 310                 315                 320

Arg Val Tyr Glu Ser Thr Asp Lys Gly Asn Thr Trp Thr Glu Ala Leu
                325                 330                 335

Gly Thr Leu Ser Arg Val Trp Ser Asn Pro Leu Ala Arg Ser Gly Leu
            340                 345                 350

His Ile Gln Gly Gly Phe Ile Thr Ala Thr Ile Asp Gly Lys Lys Val
        355                 360                 365

Ile Leu Leu Thr Gln Leu Glu Tyr Phe Gly Asp Lys Glu Arg Ser Glu
    370                 375                 380

```
Ile His Leu Trp Leu Thr Asp Thr Asn Arg Ile Tyr His Val Gly Leu
385                 390                 395                 400

Leu Pro Thr Gly Tyr Gly Ala Thr Ser Ser Ser Leu Leu Tyr Ala Asn
            405                 410                 415

Asp Lys Leu Tyr Cys Leu Tyr Glu Ala Gly Val Gly Ser Ser Ser Gly
        420                 425                 430

Ala Phe Phe Leu Asp Leu Thr His Glu Leu Gln Arg Ile Arg His Ala
    435                 440                 445

Leu Ser Thr Trp Ala Val Lys Asp Asn Ala Leu Arg Arg Cys Ser Thr
450                 455                 460

Gly Ala Ala Asp Ala Ala Leu Ser Arg Trp Asp Cys Ser Val Pro Ile
465                 470                 475                 480

Pro Thr Ala Gly Leu Val Gly His Leu Ala Asp Thr Leu Arg Gly Asp
            485                 490                 495

Lys Trp Glu Asp Glu Tyr Leu Gly Val Asn Ala Val Arg Gly Ala
        500                 505                 510

Thr Lys Lys Val Pro Ser Gly Leu Thr Phe Glu Gly Arg Ser Ala Gly
        515                 520                 525

Ala Glu Trp Pro Val Cys Lys Gln Trp Pro Lys Met Pro Phe His Phe
530                 535                 540

Ala Asn Tyr Gly Phe Thr Leu Ala Ala Thr Val Ser Ile Gln Glu Val
545                 550                 555                 560

Pro Thr Gly Ile Thr
            565

<210> SEQ ID NO 80
<211> LENGTH: 467
<212> TYPE: PRT
<213> ORGANISM: Trypanosoma cruzi

<400> SEQUENCE: 80

Met Ser Gly Trp Ala Arg Ala Leu Leu Ala Ala Val Leu Val Val
1               5                   10                  15

Met Ala Cys Leu Val Pro Ala Ala Thr Ala Ser Leu His Ala Glu Glu
            20                  25                  30

Thr Leu Thr Ser Gln Phe Ala Glu Phe Lys Gln Lys His Gly Arg Val
        35                  40                  45

Tyr Glu Ser Ala Ala Glu Glu Ala Phe Arg Leu Ser Val Phe Arg Glu
    50                  55                  60

Asn Leu Phe Leu Ala Arg Leu His Ala Ala Asn Pro His Ala Thr
65                  70                  75                  80

Phe Gly Val Thr Pro Phe Ser Asp Leu Thr Arg Glu Glu Phe Arg Ser
            85                  90                  95

Arg Tyr His Asn Gly Ala Ala His Phe Ala Ala Gln Glu Arg Ala
        100                 105                 110

Arg Val Pro Val Lys Val Glu Val Val Gly Ala Pro Ala Ala Val Asp
        115                 120                 125

Trp Arg Ala Arg Gly Ala Val Thr Ala Val Lys Asp Gln Gly Gln Cys
130                 135                 140

Gly Ser Cys Trp Ala Phe Ser Ala Ile Gly Asn Val Glu Cys Gln Trp
145                 150                 155                 160

Phe Leu Ala Gly His Pro Leu Thr Asn Leu Ser Glu Gln Met Leu Val
            165                 170                 175

Ser Cys Asp Lys Thr Asp Phe Gly Cys Ser Gly Gly Leu Met Asn Asn
        180                 185                 190
```

Ala Phe Glu Trp Ile Val Gln Glu Asn Asn Gly Ala Val Tyr Thr Glu
        195                 200                 205

Asp Ser Tyr Pro Tyr Ala Ser Gly Glu Gly Ile Ser Pro Pro Cys Thr
    210                 215                 220

Thr Ser Gly His Thr Val Gly Ala Thr Ile Thr Gly His Val Glu Leu
225                 230                 235                 240

Pro Gln Asp Glu Ala Gln Ile Ala Ala Trp Leu Ala Val Asn Gly Pro
            245                 250                 255

Val Ala Val Ala Val Asp Ala Ser Ser Trp Met Thr Tyr Thr Gly Gly
        260                 265                 270

Val Met Thr Ser Cys Val Ser Glu Gln Leu Asp His Gly Val Leu Leu
    275                 280                 285

Val Gly Tyr Asn Asp Ser Ala Ala Val Pro Tyr Trp Ile Ile Lys Asn
        290                 295                 300

Ser Trp Thr Thr Gln Trp Gly Glu Glu Gly Tyr Ile Arg Ile Ala Lys
305                 310                 315                 320

Gly Ser Asn Gln Cys Leu Val Lys Glu Glu Ala Ser Ser Ala Val Val
            325                 330                 335

Gly Gly Pro Gly Pro Thr Pro Glu Pro Thr Thr Thr Thr Thr Thr Ser
        340                 345                 350

Ala Pro Gly Pro Ser Pro Ser Tyr Phe Val Gln Met Ser Cys Thr Asp
    355                 360                 365

Ala Ala Cys Ile Val Gly Cys Glu Asn Val Thr Leu Pro Thr Gly Gln
        370                 375                 380

Cys Leu Leu Thr Thr Ser Gly Val Ser Ala Ile Val Thr Cys Gly Ala
385                 390                 395                 400

Glu Thr Leu Thr Glu Glu Val Phe Leu Thr Ser Thr His Cys Ser Gly
            405                 410                 415

Pro Ser Val Arg Ser Ser Val Pro Leu Asn Lys Cys Asn Arg Leu Leu
        420                 425                 430

Arg Gly Ser Val Glu Phe Phe Cys Gly Ser Ser Ser Gly Arg Leu
    435                 440                 445

Ala Asp Val Asp Arg Gln Arg Arg His Gln Pro Tyr His Ser Arg His
    450                 455                 460

Arg Arg Leu
465

<210> SEQ ID NO 81
<211> LENGTH: 704
<212> TYPE: PRT
<213> ORGANISM: Trypanosoma cruzi

<400> SEQUENCE: 81

Met Thr Glu Thr Phe Ala Phe Gln Ala Glu Ile Asn Gln Leu Met Ser
1               5                   10                  15

Leu Ile Ile Asn Thr Phe Tyr Ser Asn Lys Glu Ile Phe Leu Arg Glu
            20                  25                  30

Leu Ile Ser Asn Ser Ser Asp Ala Cys Asp Lys Ile Arg Tyr Gln Ser
        35                  40                  45

Leu Thr Asn Gln Ala Val Leu Gly Asp Glu Ser His Leu Arg Ile Arg
    50                  55                  60

Val Ile Pro Asp Lys Ala Asn Lys Thr Leu Thr Val Glu Asp Thr Gly
65                  70                  75                  80

Ile Gly Met Thr Lys Ala Glu Leu Val Asn Asn Leu Gly Thr Ile Ala
            85                  90                  95

-continued

```
Arg Ser Gly Thr Lys Ala Phe Met Glu Ala Leu Glu Ala Gly Asp
                100                 105                 110

Met Ser Met Ile Gly Gln Phe Val Gly Phe Tyr Ser Ala Tyr Leu
            115                 120                 125

Val Ala Asp Arg Val Thr Val Ser Lys Asn Asn Asp Asp Glu Ala
        130                 135                 140

Tyr Thr Trp Glu Ser Ser Ala Gly Gly Thr Phe Thr Val Thr Pro Thr
145                 150                 155                 160

Pro Asp Cys Asp Leu Lys Arg Gly Thr Arg Ile Val Leu His Leu Lys
                165                 170                 175

Glu Asp Gln Gln Glu Tyr Leu Glu Glu Arg Arg Leu Lys Asp Leu Ile
                180                 185                 190

Lys Lys His Ser Glu Phe Ile Gly Tyr Asp Ile Glu Leu Met Val Glu
            195                 200                 205

Lys Ala Thr Glu Lys Glu Val Thr Asp Glu Asp Glu Asp Glu Ala Ala
        210                 215                 220

Ala Ala Lys Asn Glu Glu Gly Glu Glu Pro Lys Val Glu Glu Val Lys
225                 230                 235                 240

Asp Asp Ala Glu Glu Gly Glu Lys Lys Lys Thr Lys Lys Val Lys
                245                 250                 255

Glu Val Thr Gln Glu Phe Val Val Gln Asn Lys His Lys Pro Leu Trp
                260                 265                 270

Thr Arg Asp Pro Lys Asp Val Thr Lys Glu Glu Tyr Ala Ala Phe Tyr
            275                 280                 285

Lys Ala Ile Ser Asn Asp Trp Glu Glu Pro Leu Ser Thr Lys His Phe
        290                 295                 300

Ser Val Glu Gly Gln Leu Glu Phe Arg Ala Ile Leu Phe Val Pro Lys
305                 310                 315                 320

Arg Ala Pro Phe Asp Met Phe Glu Pro Ser Lys Lys Arg Asn Asn Ile
                325                 330                 335

Lys Leu Tyr Val Arg Arg Val Phe Ile Met Asp Asn Cys Glu Asp Leu
            340                 345                 350

Cys Pro Glu Trp Leu Ala Phe Val Arg Gly Val Val Asp Ser Glu Asp
        355                 360                 365

Leu Pro Leu Asn Ile Ser Arg Glu Asn Leu Gln Gln Asn Lys Ile Leu
370                 375                 380

Lys Val Ile Arg Lys Asn Ile Val Lys Lys Ala Leu Glu Leu Phe Glu
385                 390                 395                 400

Glu Ile Ala Glu Asn Lys Glu Asp Tyr Lys Lys Phe Tyr Glu Gln Phe
                405                 410                 415

Gly Lys Asn Val Lys Leu Gly Ile His Glu Asp Ser Ala Asn Arg Lys
            420                 425                 430

Lys Leu Met Glu Leu Leu Arg Phe His Ser Ser Glu Ser Gly Glu Asp
        435                 440                 445

Met Thr Thr Leu Lys Asp Tyr Val Thr Arg Met Lys Glu Gly Gln Lys
450                 455                 460

Cys Ile Tyr Tyr Val Thr Gly Asp Ser Lys Lys Lys Leu Glu Thr Ser
465                 470                 475                 480

Pro Phe Ile Glu Gln Ala Arg Arg Gly Phe Glu Val Leu Phe Met
                485                 490                 495

Thr Glu Pro Ile Asp Glu Tyr Val Met Gln Gln Val Lys Asp Phe Glu
            500                 505                 510

Asp Lys Lys Phe Ala Cys Leu Thr Lys Glu Gly Val His Phe Glu Glu
        515                 520                 525
```

```
Thr Glu Glu Glu Lys Lys Gln Arg Glu Glu Lys Thr Ala Tyr Glu
    530                 535                 540

Arg Leu Cys Lys Ala Met Lys Asp Val Leu Gly Asp Lys Val Glu Lys
545                 550                 555                 560

Val Val Val Ser Glu Arg Leu Ala Thr Ser Pro Cys Ile Leu Val Thr
                565                 570                 575

Ser Glu Phe Gly Trp Ser Ala His Met Glu Gln Ile Met Arg Asn Gln
            580                 585                 590

Ala Leu Arg Asp Ser Ser Met Ser Ala Tyr Met Met Ser Lys Lys Thr
        595                 600                 605

Met Glu Ile Asn Pro Ala His Pro Ile Val Lys Glu Leu Lys Arg Arg
    610                 615                 620

Val Glu Ala Asp Glu Asn Asp Lys Ala Val Lys Asp Leu Val Tyr Leu
625                 630                 635                 640

Leu Phe Asp Thr Ala Leu Leu Thr Ser Gly Phe Thr Leu Asp Asp Pro
                645                 650                 655

Thr Ser Tyr Ala Glu Arg Ile His Arg Met Ile Lys Leu Gly Leu Ser
            660                 665                 670

Leu Asp Asp Glu Asp Asn Gly Asn Glu Glu Ala Glu Pro Ala Ala Ala
        675                 680                 685

Val Pro Ala Glu Pro Val Ala Gly Thr Ser Ser Met Glu Gln Val Asp
    690                 695                 700

<210> SEQ ID NO 82
<211> LENGTH: 677
<212> TYPE: PRT
<213> ORGANISM: Trypanosoma cruzi

<400> SEQUENCE: 82

Met Thr Tyr Glu Gly Ala Ile Gly Ile Asp Leu Gly Thr Thr Tyr Ser
1               5                   10                  15

Cys Val Gly Val Trp Gln Asn Glu Arg Val Glu Ile Ile Ala Asn Asp
                20                  25                  30

Gln Gly Ser Arg Thr Thr Pro Ser Tyr Val Ala Phe Thr Asp Thr Glu
            35                  40                  45

Arg Leu Ile Gly Asp Ala Ala Lys Asn Gln Val Ala Met Asn Pro Thr
        50                  55                  60

Asn Thr Val Phe Asp Ala Lys Arg Leu Ile Gly Arg Lys Phe Ser Asp
65                  70                  75                  80

Pro Val Val Gln Ser Asp Met Lys His Trp Pro Phe Lys Val Ile Thr
                85                  90                  95

Lys Gly Asp Asp Lys Pro Val Ile Gln Val Gln Phe Arg Gly Glu Thr
            100                 105                 110

Lys Thr Phe Asn Pro Glu Glu Val Ser Ser Met Val Leu Ser Lys Met
        115                 120                 125

Lys Glu Ile Ala Glu Ser Tyr Leu Gly Lys Gln Val Lys Lys Ala Val
    130                 135                 140

Val Thr Val Pro Ala Tyr Phe Asn Asp Ser Gln Arg Gln Ala Thr Lys
145                 150                 155                 160

Asp Ala Gly Thr Ile Ala Gly Met Glu Val Leu Arg Ile Ile Asn Glu
                165                 170                 175

Pro Thr Ala Ala Ala Ile Ala Tyr Gly Leu Asp Lys Val Glu Asp Gly
            180                 185                 190

Lys Glu Arg Asn Val Leu Ile Phe Asp Leu Gly Gly Gly Thr Phe Asp
        195                 200                 205
```

```
Val Thr Leu Leu Thr Ile Asp Gly Gly Ile Phe Glu Val Lys Ala Thr
    210                 215                 220
Asn Gly Asp Thr His Leu Gly Gly Glu Asp Phe Asp Asn Arg Leu Val
225                 230                 235                 240
Ser His Phe Thr Asp Glu Phe Lys Arg Lys Asn Lys Gly Lys Asp Leu
                    245                 250                 255
Thr Thr Ser Gln Arg Ala Leu Arg Arg Leu Arg Thr Ala Cys Glu Arg
                260                 265                 270
Ala Lys Arg Thr Leu Ser Ser Ala Ala Gln Ala Thr Ile Glu Ile Asp
            275                 280                 285
Ala Leu Phe Asp Asn Val Asp Phe Gln Ala Thr Ile Thr Arg Ala Arg
        290                 295                 300
Phe Glu Glu Leu Cys Gly Asp Leu Phe Arg Gly Thr Leu Gln Pro Val
305                 310                 315                 320
Glu Arg Val Leu Gln Asp Ala Lys Met Asp Lys Arg Ala Val His Asp
                325                 330                 335
Val Val Leu Val Gly Gly Ser Thr Arg Ile Pro Lys Val Met Gln Leu
                340                 345                 350
Val Ser Asp Phe Phe Gly Gly Lys Glu Leu Asn Lys Ser Ile Asn Pro
            355                 360                 365
Asp Glu Ala Val Ala Tyr Gly Ala Ala Val Gln Ala Phe Ile Leu Thr
        370                 375                 380
Gly Gly Lys Ser Lys Gln Thr Glu Gly Leu Leu Leu Leu Asp Val Thr
385                 390                 395                 400
Pro Leu Thr Leu Gly Ile Glu Thr Ala Gly Gly Val Met Thr Ser Leu
                405                 410                 415
Ile Lys Arg Asn Thr Thr Ile Pro Thr Lys Lys Ser Gln Ile Phe Ser
                420                 425                 430
Thr Tyr Ala Asp Asn Gln Pro Gly Val His Ile Gln Val Phe Glu Gly
            435                 440                 445
Glu Arg Ala Met Thr Lys Asp Cys His Leu Leu Gly Thr Phe Asp Leu
        450                 455                 460
Ser Gly Ile Pro Pro Ala Pro Arg Gly Val Pro Gln Ile Glu Val Thr
465                 470                 475                 480
Phe Asp Leu Asp Ala Asn Gly Ile Leu Asn Val Ser Ala Glu Glu Lys
                485                 490                 495
Gly Thr Gly Lys Arg Asn Gln Ile Val Ile Thr Asn Asp Lys Gly Arg
                500                 505                 510
Leu Ser Lys Ala Asp Ile Glu Arg Met Val Ser Glu Ala Ala Lys Tyr
            515                 520                 525
Glu Ala Gln Asp Lys Glu Gln Arg Glu Arg Ile Asp Ala Lys Asn Gly
        530                 535                 540
Leu Glu Asn Tyr Ala Phe Ser Met Lys Asn Thr Val Asn Glu Pro Asn
545                 550                 555                 560
Val Ala Gly Lys Ile Glu Glu Ala Asp Lys Asn Thr Ile Thr Ser Ala
                565                 570                 575
Val Glu Glu Ala Leu Gln Trp Leu Asn Asn Asn Gln Glu Ala Ser Lys
                580                 585                 590
Glu Glu Tyr Glu His Arg Gln Lys Glu Leu Glu Asn Leu Cys Thr Pro
            595                 600                 605
Ile Met Thr Lys Met Tyr Gln Gly Met Gly Ala Gly Gly Gly Met Pro
        610                 615                 620
Gly Gly Met Pro Gly Gly Met Pro Gly Gly Met Pro Gly Gly Met Pro
```

```
                625                 630                 635                 640
Gly Gly Met Pro Gly Gly Met Pro Gly Gly Met Pro Gly Gly Met Pro
                        645                 650                 655

Gly Gly Met Pro Gly Gly Ala Asn Pro Ser Ser Ser Gly Pro Lys
                        660                 665                 670

Val Glu Glu Val Asp
            675

<210> SEQ ID NO 83
<211> LENGTH: 280
<212> TYPE: PRT
<213> ORGANISM: Trypanosoma cruzi

<400> SEQUENCE: 83

Met Thr Ala Phe Glu Ala Arg Glu Leu Pro Pro Phe Leu Phe Phe Ser
1               5                   10                  15

Phe Leu Phe Phe Ser Lys Thr Thr Lys Thr Thr Lys Arg Leu Leu Thr
                20                  25                  30

Ala Asn Asn Ile Lys Lys Gly Val Lys Lys Lys Glu Lys Lys Lys
                35                  40                  45

Lys Glu Lys Lys Glu Lys Lys Gln Lys Glu Phe Thr Cys Val Gly Met
    50                  55                  60

Gln Val Pro Ser Thr Ser Asp Cys Val Ala Thr Phe Lys Leu Ile Leu
65                  70                  75                  80

Val Gly Asp Gly Gly Thr Gly Lys Thr Thr Phe Val Lys Arg His Leu
                85                  90                  95

Thr Gly Glu Phe Glu Lys Arg Tyr Val Ala Thr Val Gly Val Asp Val
                100                 105                 110

His Pro Leu Thr Phe His Thr Asn Arg Gly Lys Ile Cys Phe Asn Cys
                115                 120                 125

Trp Asp Thr Ala Gly Gln Glu Lys Phe Gly Gly Leu Arg Asp Gly Tyr
    130                 135                 140

Tyr Ile Glu Gly Gln Cys Ala Ile Ile Met Phe Asp Val Thr Ser Arg
145                 150                 155                 160

Asn Thr Tyr Lys Asn Val Pro Asn Trp His Arg Asp Ile Thr Arg Val
                165                 170                 175

Cys Asp Asn Ile Pro Ile Val Leu Val Gly Asn Lys Val Asp Cys Ala
                180                 185                 190

Asp Arg Gln Val Lys Ala Lys Met Ile Thr Phe His Arg Lys Lys Gly
            195                 200                 205

Leu Gln Tyr Tyr Asp Ile Ser Ala Lys Ser Asn Tyr Asn Phe Glu Lys
    210                 215                 220

Pro Phe Leu Trp Leu Ala Lys Lys Leu Ala Asn Asp Pro Asn Leu Thr
225                 230                 235                 240

Leu Val Glu Ala Pro Leu Leu Asp Pro Asn Val Gln Pro Leu Ser Ala
                245                 250                 255

Glu Gln Leu Gln Ala Leu Gln Glu Glu Ala Arg Ala Val Glu Asn Ala
            260                 265                 270

Pro Leu Pro Met Gly Asp Asp Glu
    275                 280
```